US012139723B2

(12) United States Patent
Stice et al.

(10) Patent No.: US 12,139,723 B2
(45) Date of Patent: *Nov. 12, 2024

(54) NEURAL CELL EXTRACELLULAR VESICLES

(71) Applicants: University of Georgia Research Foundation, Inc., Athens, GA (US); Aruna Bio, Inc., Athens, GA (US)

(72) Inventors: Steven L. Stice, Athens, GA (US); Robin Lynn Webb, Winterville, GA (US); Tracey A. Stice, Athens, GA (US)

(73) Assignees: UNIVERSITY OF GEORGIA RESEARCH FOUNDATION, INC., Athens, GA (US); ARUNA BIO, INC., Athens, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/238,760

(22) Filed: Apr. 23, 2021

(65) Prior Publication Data

US 2022/0356444 A1 Nov. 10, 2022

Related U.S. Application Data

(63) Continuation of application No. 16/414,576, filed on May 16, 2019, now Pat. No. 11,111,475, which is a continuation of application No. 15/770,881, filed as application No. PCT/US2016/062245 on Nov. 16, 2016, now Pat. No. 11,993,787.

(60) Provisional application No. 62/256,823, filed on Nov. 18, 2015.

(51) Int. Cl.
| | | |
|---|---|---|
| *A61K 35/12* | (2015.01) | |
| *A61K 9/51* | (2006.01) | |
| *A61K 35/30* | (2015.01) | |
| *A61K 35/545* | (2015.01) | |
| *A61P 25/28* | (2006.01) | |
| *C12N 5/079* | (2010.01) | |
| *C12N 5/0793* | (2010.01) | |
| *C12N 5/0797* | (2010.01) | |
| *A61K 9/50* | (2006.01) | |
| *G01N 33/569* | (2006.01) | |

(52) U.S. Cl.
CPC .......... *C12N 5/0619* (2013.01); *A61K 9/5176* (2013.01); *A61K 35/12* (2013.01); *A61K 35/545* (2013.01); *C12N 5/0622* (2013.01); *C12N 5/0623* (2013.01); *A61K 9/5068* (2013.01); *A61K 35/30* (2013.01); *A61P 25/28* (2018.01); *C12N 2506/02* (2013.01); *C12N 2506/45* (2013.01); *C12N 2533/30* (2013.01); *G01N 33/56966* (2013.01)

(58) Field of Classification Search
CPC .... A61K 35/545; A61K 35/12; A61K 9/5176; A61K 35/30; A61K 9/5068; C12N 2506/45; A61P 25/28
See application file for complete search history.

(56) References Cited

U.S. PATENT DOCUMENTS

| | | | |
|---|---|---|---|
| 4,188,373 | A | 2/1980 | Krezanoski et al. |
| 4,352,883 | A | 10/1982 | Lim |
| 4,440,921 | A | 4/1984 | Allcock et al. |
| 4,474,751 | A | 10/1984 | Haslam et al. |
| 4,474,752 | A | 10/1984 | Haslam et al. |
| 4,474,753 | A | 10/1984 | Haslam et al. |
| 4,478,822 | A | 10/1984 | Haslam et al. |
| 4,880,622 | A | 11/1989 | Allcock et al. |
| 5,410,016 | A | 4/1995 | Hubbel et al. |
| 5,843,780 | A | 12/1998 | Thomson |
| 7,531,354 | B2 | 5/2009 | Stice et al. |
| 9,919,011 | B2 | 3/2018 | Chang et al. |
| 10,240,127 | B2 | 3/2019 | Larocca et al. |
| 10,308,959 | B2 | 6/2019 | Liu et al. |
| 10,329,561 | B2 | 6/2019 | Seow et al. |
| 11,111,475 | B2 | 9/2021 | Stice et al. |
| 2014/0356382 | A1* | 12/2014 | Wood ............... A61K 35/36 424/178.1 |
| 2015/0079046 | A1 | 3/2015 | Sinden et al. |
| 2016/0137716 | A1 | 5/2016 | El Andaloussi et al. |
| 2016/0235788 | A1 | 8/2016 | Hicks et al. |
| 2016/0370265 | A1 | 12/2016 | Ott et al. |
| 2017/0183685 | A1 | 6/2017 | Wells et al. |
| 2017/0183686 | A1 | 6/2017 | Khvorova et al. |
| 2017/0360842 | A1 | 12/2017 | Kreke et al. |
| 2018/0066307 | A1 | 3/2018 | Ter-Ovanesyan et al. |
| 2018/0327714 | A1 | 11/2018 | Stice et al. |

(Continued)

FOREIGN PATENT DOCUMENTS

| | | |
|---|---|---|
| CN | 103740645 A | 4/2014 |
| EP | 3336190 A1 | 6/2018 |

(Continued)

OTHER PUBLICATIONS

Yuan et al. Cell-Surface Marker Signatures for the Isolation of Neural Stem Cells, Glia and Neurons Derived from Human Pluripotent Stem Cells 2011. PLoS ONE. vol. 6, Issue 3. e17540. p. 1-16 (Year: 2011).*
Martínez-Cerdeño et al. Neural Progenitor Cell Terminology. Front. Neuroanat. 12:104, p. 1-8 (Year: 2018).*
Lai et al. Dynamic Biodistribution of Extracellular Vesicles In Vivo Using a Multimodal Imaging Reporter. ACS Nano. Jan. 28, 2014; 8(1): 483-494 (Year: 2014).*
Alvarez-Erviti et al. Delivery of siRNA to the mouse brain by systemic injection of targeted exosomes. nature biotechnology vol. 29 No. 4 Apr. 2011. p. 341-345 (Year: 2011).*

(Continued)

*Primary Examiner* — Taeyoon Kim
(74) *Attorney, Agent, or Firm* — WOMBLE BOND DICKINSON (US) LLP; Danielle L. Herritt; Seiko Okada

(57) ABSTRACT

Disclosed herein are neural extracellular vesicles (EVs) and methods of using these EVs in the treatment of spinal cord injury, stroke, and traumatic brain injury and neurodegenerative disease.

26 Claims, 23 Drawing Sheets

(56) References Cited

U.S. PATENT DOCUMENTS

| | | | |
|---|---|---|---|
| 2019/0093105 A1 | 3/2019 | Gibbings et al. | |
| 2019/0144830 A1 | 5/2019 | Cha et al. | |
| 2019/0167732 A1 | 6/2019 | Shiels et al. | |

FOREIGN PATENT DOCUMENTS

| | | | | |
|---|---|---|---|---|
| JP | 2015-513906 A | 5/2015 | | |
| JP | 2015-524849 A | 8/2015 | | |
| WO | WO-2006087233 A2 | 8/2006 | | |
| WO | WO-2013150303 A1 | * 10/2013 | ............... | A61P 43/00 |
| WO | WO-2014028763 A1 | * 2/2014 | ............ | C12N 15/113 |
| WO | WO-2015038065 A1 | 3/2015 | | |
| WO | WO-2015038075 A1 | 3/2015 | | |
| WO | WO-2015058148 A1 | * 4/2015 | ............ | A61K 38/177 |
| WO | WO-2018085587 A1 | 5/2018 | | |

OTHER PUBLICATIONS

Drago Denise et al., "The stem cell secretome and its role in brain repair", Biochimie, 95(12): 2271-2285 (2013).
Pluchino, Stefano et al., "How Stem Cells Speak with Host Immune Cells in Inflammatory Brain Diseases", Glia, 61(9): 1379-1401 (2013).
UniProtKB-P21926 (CD9_HUMAN); downloaded from www.uniprot.org/P21926 on Apr. 21, 2021; pp. 1-16 (2021).
Yong Yuluo et al., "Neural stem cell-derived small extracellular vesicles attenuate apoptosis and neuroinflammation after traumatic spinal cord injury by activating autophagy", Cell Death & Disease; pp. 1-18 (2019).
Endres, et al., "Improving Outcome after Stroke: Overcoming the Translational Roadblock", Cerebrov asc Disc, 225:268-278 (2008).
Fluri, et al., "Animal models of ischemic stroke and their application in clinical research", Drug Design, Developmental and Therapy, 9:3445-3454 (2015).
Sommer, et al., "Ischemic stroke: experimental models and reality", Acta Neuropathol, 133:245-261 (2017).
Huuskonen MT, et al., "Bexarotene targets autophagy and is protective against thromboembolic stroke in aged mice with tauopathy", Scientific Reports, 6:33176 DOI: 10.1038/srep33176 (2016).
Lemarchand E, et al., "Extent of Ischemic Brain Injury After Thrombotic Stroke is Independent of the NLRP3 Nacht, LRR and PYO Domains-Containing Protein 3)", Inflammasome, Stroke, 50:1232-1239 (2019).
Garcia-Yebenes I, et al., "Iron Overload Exacerbates the Risk of Hemorrhagic Transformation After tPA (Tissue-Wype Plasminogen Activator)", Administration in Thromboembolic Stroke Mice, Stroke, 49:2163-2172 (2018).
Ansar S, et al., "Pro-Inflammatory Mediators and Apoptosis Correlate to rt-PA Response in a Novel Mouse Model of Whromboembolic Stroke", PLOS ONE, 9(1):e85849 p. 1-8 (2014).
Hoda MN, et al., "Sex-independent neuroprotection with minocycline after experimental thromboembolic stroke", Experimental & Translational Stroke Medicine, 3:16 (2011).
Ishrat T, et al., "Thioredoxin interacting protein: a novel target for neuroprotection in experimental thromboembolic stroke in mice", Mol Neurobiol, 51(2):766-778 (2015).
Marzesco AM, et al., "Release of extracellular membrane particles carrying the stem cell marker prominin-1 (CD133) from neural progenitors and other epithelial cells", Journal of Cell Science, 118:2849-2858 (2005).
Fruhbeis C, et al., "Extracellular vesicles as mediators of neuron-glia communication", Frontiers in Cellular Neuroscience, 7(182):1-6 (2013).
Zhang Shuchen, et al., "Sox2, a key factor in the regulation of pluripotency and neural differentiation", World J Stem Cells, 6(2):305-311 (2014).
Doeppner TR, et al., "Extracellular Vesicles Improve Post-Stroke Neuroregeneration and Prevent Postischemic Immunosuppression", Stem Cells Translational Medicine, 4:1131-1143 (2015).
Li N, et al., "Prosaposin in the secretome of marrow stroma-derived neural progenitor cells protects neural cells from apoptotic death", Journal of Neurochemistry, 112:1527-1538 (2010).
Cossetti C, et al., "Extracellular membrane vesicles and immune regulation in the brain", Frontiers in Physiology, 3(117):1-14 (2012).
Bansai, et al., "Drug Treatment of Acute Ischemic Stroke", Am J Cardiovasc Drugs, 13(1): p. 1-22 (2013).
Xin, et al., "Systemic administration of exosomes released from mesenchymal stromal cells promote functional recovery and neurovascular plasticity after stroke in rats", Journal of Cerebral Blood Flow & Metabolism, 33, 1711-1715 (2013).
"Stroke. Symptoms and causes-Mayo Clinic", downloaded on Sep. 17, 2019 from www.mayoclinic.org/diseases-conditions/stroke/ <http://www.mayoclinic.org/diseases-conditions/stroke/> symptoms-causes/syc-20350113?p=1. p. 1-7 (2019.
Dhara SK, Majumder A, Dodia MC and Stice SL, "Nonviral gene delivery in neural progenitors derived from human pluripotent stem cells", Methods Mal. Biol., 767:343-354, doi: 10:1007/978-1-61779-201-4 25 (2011).
Setlow JL and Hollaender A (EDS), Genetic Engineering Principles and Methods, vol. I; Plenum Press, New York (1979).
Boing An, et al., "Single-step isolation of extracellular vesicles by size-exclusion chromatography", Journal of ExtracellularVesicles, vol. 3:1, 23430, doi: 10.3402/jev.v3.23430 (2014).
Boyd NL, et al., "Human embryonic stem cell-deprived mesoderm-like epithelium transitions to mesenchymal progenitor cells", issue Engineering, vol. 15, nr. 8, pp. 1897+. doi: 10.1089/ten/tea.2008/0351 (2009).
Chambers SM, et al., "Highly efficient neuraql conversion of human ES and iPS cells by dual inhibition of SMAD signaling", Nat. Biotechnol, vol. 27, nr 3, pp. 275-280, doi: 10.1038/nbt.1529 (2009).
Dodia M C, et al., "Differing lectin binding profiled among human embryonic stem cells and derivativesx aid in the isolation of neural progenitor cells", PLos ONE, vol. 6, nr. 8, pp. e23266+. doi: 10.1371/journal.pone.0023266 (2011).
Folkerth R D, "Abnormalities of developing white matter in lysosomal storage diseases", Journal of Neuropathology and Experimental Neurology, vol. 58, nr. 9, pp. 887-902 (1999).
Majumder A, et al., "Inhibition of DNA methyltransferases and histone deacylaces induces astrocytic differentiation of neural progenitors", Stem Cell Research, vol. 11, pp. 574-586 (2013).
Mumaw J L, et al., "Neural differentiation of human embryonic stem cells at the ultrastructural level", Microscopy and Microanalysis, vol. 10, pp. 80-90 (2010).
Palm T, et al., "Rapid and robust generation of long-term self-renewing human neural stem cells with the ability to generate mature astroglia", Scientific Reports, vol. 5, pp. 16321+. doi:10.1038/srep16321 (2015).
Shin S, et al., "Long-term proliferation of human embryonic stem cell-derived neuroepithelial cells using defined adherent culture conditions", Stem Cells, vol. 24, pp. 125-138 (2006).
Sokolova V, et al.,, "Characterization of exosomes derived from human cells by nanoparticule tracking analysis and scanning electron microscopy", Colloids and Surfaces B: Biointerfaces, doi: 10.1016/j.colsurfb.2011.05.013 (2011).
Thomson J A, et al., "Isolation of a primate embryonic stem cell line", Proc. Natl. Acad. Sci. USA, vol. 92, pp. 7844-7848 (1995).
Thomson J A, et al., "Embryonic stem cell lines derived from human blastomas", Science, vol. 282, pp. 1145+ (1998).
Thery C, et al., "Isolation and characterization of exosomes from cell culture supernatants and biological fluids", Current Protocols in Cell biology, 3.22.1-3.22.29 ; supplement 30 (2006).
Wiklander O P M, et al., "Extracellular vesicle in vivo biodistribution is determined by cell sourcs, route of administration and targeting", Journal of Extracellular Vesicles, vol. 4:1, 26316, doi: 10.3402/jev. v4.26316 (2015).
Young A, et al., "Ion channels and ionotrophic receptors in human embryonic stem cell derived neural progenitors", Neuroscience, vol. 192, pp. 793-805. doi: 10.1016/j.neuroscience.2011.04.039 (2011).
Dunn AS, "Book Review of Concise encyclopedia of polymer science and engineering", Edited by J.I. Kroschwitz, John Wiley &

(56) References Cited

OTHER PUBLICATIONS

Sons, New York New York, p. xxiv + 1341, ISBN 0-471-51253-2. book review appears in Polymer International 1991; vol. 25, nr. 1, p. 64 (1990).

Zhou J, et al., "High-efficiency induction of neural conversion in human ESCs and human induced pluripotent stem cells with a single chemical inhibitor of transforming growth factor beta superfamily receptors", Stem Cells; vol. 28, pp. 1741-1750 (2010).

Glover D M (Ed.), "DNA cloning a practical approach", vols. I; and II; IRL Press Limited (UK), Oxford England United Kingdom (1985).

Hames B D and Higgins Sj (Eds), "Nucleic acid hybridization a practical approach", IRL Press Limited (UK), Washington DC (1985).

Maniatis T, Fritsche F, and Sambrook J, "Molecular Cloning a Laboratory Manual", Cold Spring Harbor Laboratory (Press); Cold Spring Harbor New York (1982).

Miller J H, "Experiments in Molecular Genetics", Cold Spring Harbor Laboratory (Press); Cold Spring Harbor New York (1972).

Old R Wand, Primroses B, "Principles of Genetic Manipulation an Introduction to Genetic Engineering", University of California Press, Berkeley California USA (1980).

Gennaro AR, et al. (Eds.), "Remington's Pharmaceutical Sciences Seventeenth Edition", Mack Publishing Company, Easton Pennsylvania 18042 USA (1985).

Sambrook J, Fritsche F and Maniatis T, "Molecular Cloning a Laboratory Manual", Second Edition, Cold Spring Harbor Laboratory Press, Cold Spring Harbor New York USA (1989).

Schleif R F and Wensink P C, "Practical Methods in Molecular Biology", Springer-Verlag (Press), New York New York USA (1981).

Setlow JL and Hollaender A (Eds.), "Genetic Engineering Principles and Methods", vols. 2-4, Plenum Press, New York New York USA (1980-1982).

Pedersen RA and Schatten GP (Eds.), "Current Topics in Developmental Biology", vol. 38, Academic Press a division of Harcourt Brace & Company, San Diego, California USA (1988).

Grossman L (Ed.), "Methods in Enzymology", vol. 65, Academic Press.Inc., New York New York USA (1980).

Wu, Ray (Ed.), "Methods in Enzymology vol. 68 Recombinant DNA", Academic Press A subsidiary of Harcourt Brace Jovanovich Publishers, New York New York USA (1979).

Wu Ray, Grossman Lawrence and Moldave Kivie (Eds.), "Methods in Enzymology vol. 100 Recombinant DNA Part B", Academic Press A Subsidiary of Harcourt Brace Jovanovich Publishers, New York New York USA (1983).

Wu Ray, Grossman Lawrence and Moldave Kivie (Eds.), "Methods in Enzymology vol. 101 Recombinant DNA Part C", Academic Press A Subsidiary of Harcourt Brace Jovanovich Publishers; New York New York USA (1983).

Wu Ray (Ed.), "Methods in Enzymology vol. 218 Recombinant DNA Part I", Academic Press Inc. Harcourt Brace & Company; San Diego, California USA (1993).

Rong, et al., "Neural stem cell-derived small extracellular vesicles attenuate apoptosis and neuroinflammation after traumatic spinal cord injury by activating autophagy", Cell Death and Disease, 10:340 (2019).

Bala, et al., "Biodistribution and function of extracellular miRNA-155 in mice", Sci. Rep. 5, 10721, doi: 10.1038/srep10721 (2015).

Zhou, et al., "Collection, storage, preservation, and normalization of human urinary exosomes for biomarker discovery", Kidney Int., 69(8): 1471-1476 (2006).

Cossetti C, et al., "Extracellular Vesicles from Neural Stem Cells Transfer IFN-y via Ifngr1 to Activate Stat1 Signaling in Target Cells", Mol Cell, 56(2):193-204 (2014).

\* cited by examiner

FIG. 2A
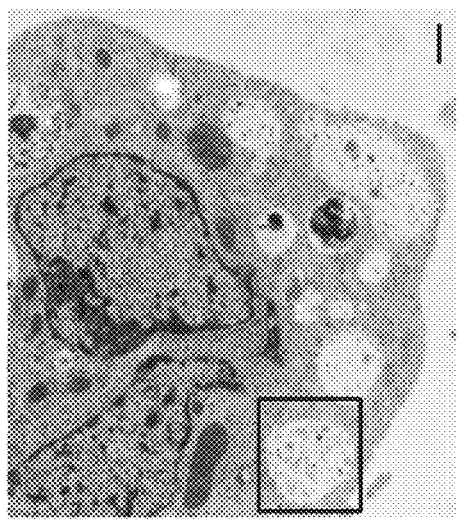
FIG. 2B
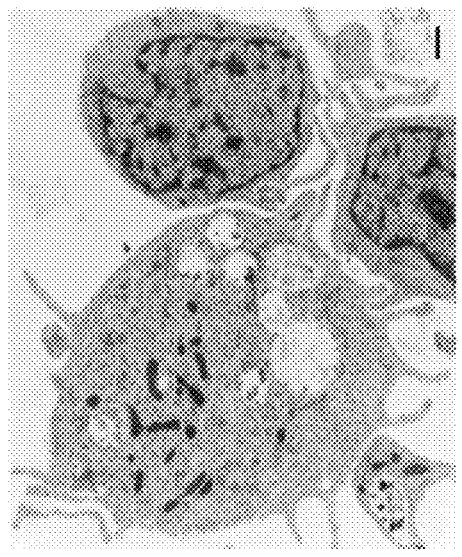
FIG. 2C
FIG. 2G
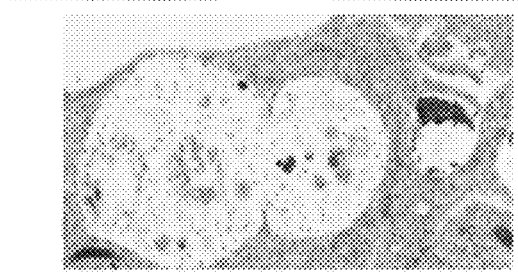
FIG. 2H
FIG. 2F
FIG. 2E
FIG. 2D

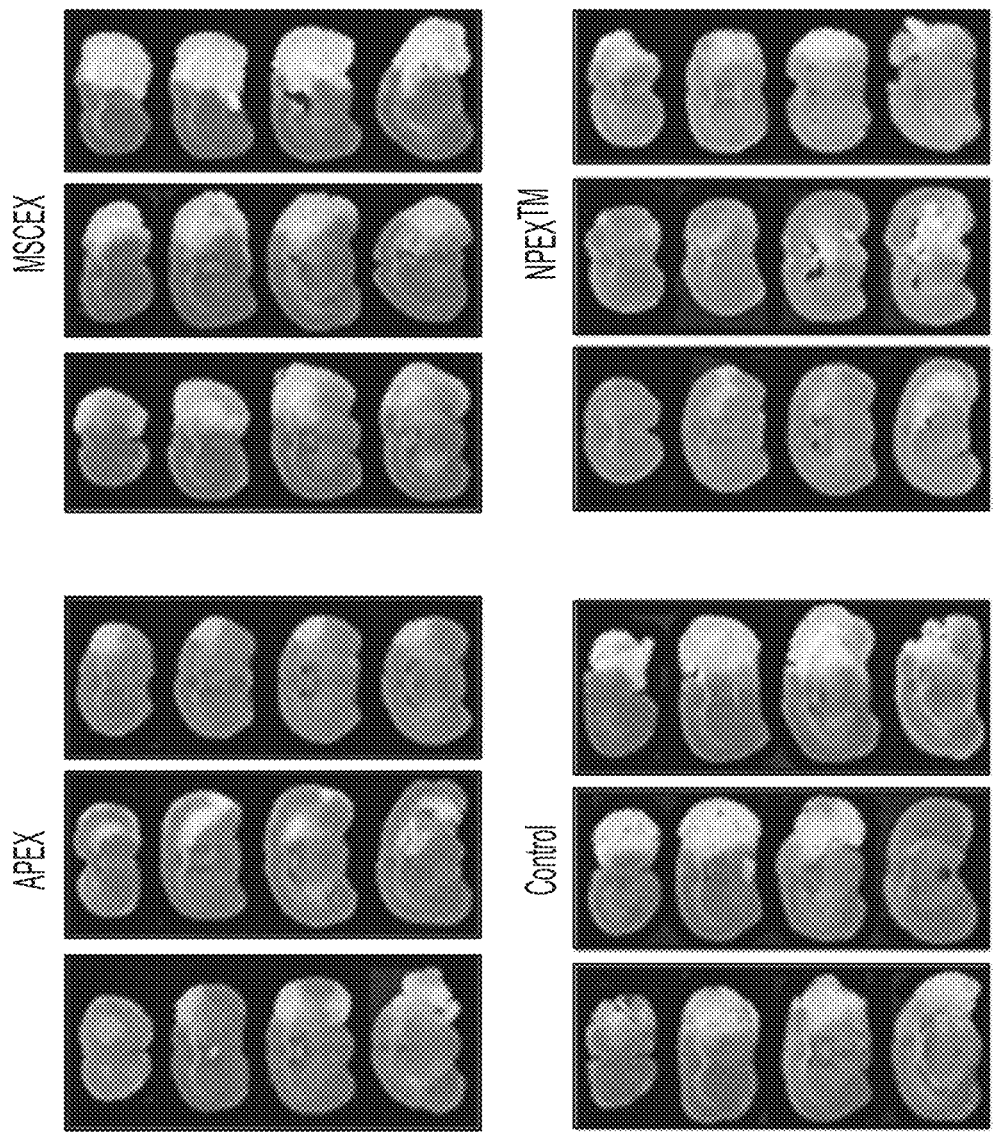

NEURAL CELL EXTRACELLULAR VESICLES

CROSS-REFERENCE TO RELATED APPLICATIONS

This application is a continuation of U.S. patent application Ser. No. 16/414,576, filed May 16, 2019; which is a continuation of U.S. patent application Ser. No. 15/770,881, filed Apr. 25, 2018; which is a 371 National Stage Application of International Application No. PCT/US2016/062245, filed Nov. 16, 2016; which claims the benefit of U.S. Provisional Application No. 62/256,823, filed Nov. 18, 2015. Each of the foregoing applications are hereby incorporated herein by reference in their entirety.

STATEMENT REGARDING FEDERALLY SPONSORED RESEARCH OR DEVELOPMENT

This invention was made with government support under grant number CBET0939511 awarded by the NSF and grant number EP-D-13-018 awarded by the EPA. The government has certain rights in the invention. 37 CFR 401.14 f (4).

BACKGROUND

Diseases and injuries to the nervous system, including congenital disorders, cancers, degenerative diseases, and spinal cord injury, affect millions of people of all ages. Congenital disorders occur when the brain or spinal cord does not form correctly during development. Cancers of the nervous system result from the uncontrolled spread of aberrant cells. Degenerative diseases occur when the nervous system loses functioning of nerve cells. There is evidence that damage can be reversed by replacing lost cells with new ones derived from cells that can mature into nerve cells, called neural stem cells. However, transplanted stem cells may and often do migrate from the site of implantation and undergo some cell transformation that lead to a teratoma formation. In addition, due to their size, stem cells are often directly injected into the CNS which can induce complications. Invasive CNS surgeries place the patient at risk due to complication that occur during and after delivery, including but not limited to hemorrhages and edema. Stem cells administered systemically often end up being lodged in small capillaries which can induce undesired effects in the lung and may not even reach the disease or injury. Stem cell therapy can also trigger an elicit and adverse immune response.

SUMMARY

Disclosed herein are neural extracellular vesicles (EVs) and methods of using these EVs in the treatment of spinal cord injury, stroke, and traumatic brain injury and neurodegenerative diseases.

The disclosed EVs can be obtained in some embodiments, by culturing neural progenitor (NP) cells that were produced from pluripotent stem cells (e.g. human embryonic stem cells (ESCs) or induced pluripotent stem cells (iPSCs)) in cell culture medium under conditions and for a time sufficient for the NP cells to produce EVs, and isolating said EVs from the culture medium. In some embodiments, the NP cells are SOX 1+, SOX 2+, OCT4−, and NESTIN+.

The disclosed EVs can be obtained in some embodiments by culturing neural cells derived directly or indirectly from pluripotent stem cells (PSCs) (e.g. ESCs or iPSCs) in cell culture medium under conditions and for a time sufficient to produce EVs, and isolating said EVs from the culture medium. In some embodiments, the PSC-derived neural cell comprises a glial cell, such as an astrocyte or oligodendrocyte. In some embodiments, the PSC-derived neural cell comprises a neuron. In some embodiments, the PSC-derived neural cell are differentiated from NP cells derived from the hES cells. In some embodiments, the PSC-derived neural cells are differentiated directly from PSCs.

Also disclosed are EVs obtained by culturing astrocytes of any origin in cell culture medium under conditions and for a time sufficient for the astrocytes to produce EVs, and isolating said EVs from the culture medium.

The disclosed EVs can alternatively be obtained in some embodiments, by culturing mesenchymal stem cells (MSCs) that were produced from PSCs in cell culture medium under conditions and for a time sufficient for the MSC cells to produce EVs, and isolating said EVs from the culture medium.

As disclosed herein, EVs produced from hNP cells (also referred to herein as NPEX) had 1653 proteins (see Table 9) that were not identified in EVs from stem-cell-derived astrocytes (also referred to herein as APEX) or mesenchymal stem cells (also referred to herein as MSCEX). Therefore, in some embodiments, the EVs comprises 1, 2, 3, 4, 5, 6, 7, 8, 9, 10, 20, 30, 40, 50, 60, 70, 80, 90, 100, 200, 300, 400, 500, 600, 700, 800, 900, 1000, 1100, 1200, 1300, 1400, 1500, 1600 or more protein biomarkers listed in Table 9.

As disclosed herein, EVs produced from APEX had 596 proteins (see Table 8) that were not identified in NPEX or MSCEX. Therefore, in some embodiments, the EVs comprises 1, 2, 3, 4, 5, 6, 7, 8, 9, 10, 20, 30, 40, 50, 60, 70, 80, 90, 100, 200, 300, 400, 500 or more protein biomarkers listed in Table 8.

As disclosed herein, EVs produced from MSCEX had 536 proteins (see Table 7) that were not identified in APEX or MSCEX. Therefore, in some embodiments, the EVs comprises 1, 2, 3, 4, 5, 6, 7, 8, 9, 10, 20, 30, 40, 50, 60, 70, 80, 90, 100, 200, 300, 400, or more protein biomarkers listed in Table 7.

In some embodiments, the disclosed EVs are produced from a substantially homogeneous population of cells. In some embodiments, the disclosed EVs are produced from non-transformed cells.

Also disclosed are compositions containing the disclosed EVs. In some embodiments, the composition comprises the disclosed EVs in a biocompatible scaffold, such as a hydrogel. Suitable hydrogels include temperature dependent hydrogels that solidify or set at body temperature, e.g., PLURONICS™; hydrogels crosslinked by ions, e.g., sodium alginate; hydrogels set by exposure to either visible or ultraviolet light, e.g., polyethylene glycol polylactic acid copolymers with acrylate end groups; and hydrogels that are set or solidified upon a change in pH, e.g., TETRONICS™. The hydrogel can, for example, include any of the following: polysaccharides, proteins, polyphosphazenes, poly(oxyethylene)-poly(oxypropylene) block polymers, poly(oxyethylene)-poly(oxypropylene) block polymers of ethylene diamine, poly(acrylic acids), poly(methacrylic acids), copolymers of acrylic acid and methacrylic acid, poly(vinyl acetate), and sulfonated polymers.

In some embodiments, the composition comprising the disclosed EVs further comprises one more neurotrophic agents. The composition can further comprises one or more agents selected from the group consisting of leukemia inhibitory factor (LIF), brain-derived neurotrophic factor (BDNF), ciliary neurotrophic factor (CTNF), epidermal growth factor receptor (EGF), basic fibroblast growth factor (bFGF), FGF-6, glial-derived neurotrophic factor (GDNF), ciliary neurotrophic factor (CTNF), granulocyte colony-stimulating factor (GCSF), hepatocyte growth factor (HGF), IFN-γ, insulin-like growth factor binding protein (IGFBP-2), IGFBP-6, IL-1ra, IL-6, IL-8, monocyte chemotactic protein (MCP-1), mononuclear phagocyte colony-stimulating factor (M-CSF), neurotrophic factors (NT3), tissue inhibitor of metalloproteinases (TIMP-1), TIMP-2, tumor necrosis factor (TNF-β), vascular endothelial growth factor (VEGF), VEGF-D, urokinase plasminogen activator receptor (uPAR), bone morphogenetic protein 4 (BMP4), IL1-a, IL-3, leptin, stem cell factor (SCF), stromal cell-derived factor-1 (SDF-1), platelet derived growth factor-BB (PDGFBB), transforming growth factors beta (TGFβ-1) and TGFβ-3.

In some embodiments, the composition comprising the disclosed EVs further comprises a protease inhibitor, RNAse inhibitor, or combination thereof.

Also disclosed is a method of treating a subject with a with a spinal cord injury, stroke, traumatic brain injury or a neurodegenerative disease comprising administering to the subject an effective amount of a composition containing a neural EVs disclosed herein. In some embodiments, the neurodegenerative disease is Alzheimer's disease, Parkinson's disease, a Parkinson's-related disorder, Huntington's disease, prion disease, motor neuron disease (MND), spinocerebellar ataxia (SCA) or spinal muscular atrophy (SMA).

There are several protein families represented in the contents of the disclosed EV that could be beneficial in the context of several age related diseases. These include catalytically active enzymes like metalloproteases, several calcium-mediated signaling proteins, and other ion channels. Several DNA and RNA polymerase subunits are present as well as ubiquitin ligases, and proteasome subunits. Therefore, also disclosed is a method of treating a subject with a protein homeostasis disorder or a proteinopathy comprising administering to the subject an effective amount of a composition containing a neural EVs disclosed herein.

Also disclosed is the use of a composition containing a neural EVs in the manufacture of a medicament for treating a patient or subject with a spinal cord injury, who has suffered a stroke or traumatic brain injury or has a neurodegenerative disease.

The details of one or more embodiments of the invention are set forth in the accompa-nying drawings and the description below. Other features, objects, and advantages of the invention will be apparent from the description and drawings, and from the claims.

DESCRIPTION OF DRAWINGS

FIG. 2 is an ultrastructural analysis indicating that multivesicular bodies (MVBs) which contain EVs are common in neural progenitors (NPs). Traditionally described as "vesicles containing smaller spherical and ellipsoidal vesicles and other inclusions described as filaments, granules, irregular dense masses, and membrane components", are apparent near the limiting membrane of NPs. Also as reported, the vesicles were frequently found in clusters of 3 or more vesicles (panels A, B). The inset from panel B is shown in panel C and this MVB actual has a vesicle budding inward into the larger multivesicular body, supporting a role for these vesicles in protein recycling from the plasma membrane. These vesicles do appear to bind with the plasma membrane, releasing EVs into the extracellular space (panels D, E). Previous reports indicate that the vesicles can coalesce, and this seems common in NPs, and can be seen in most cells with clusters of MVBs (panels A, F, G). Panel H is a transmission electron microscopic (TEM) image of purified EVs from NPs.

FIG. 3A shows proteins from exosomes separated by SDS-PAGE and gels stained with coomassie stain. Protein profiles from EVs overlapped but was distinctive from the cell pellet, supporting that cargoes are specifically trafficked to EVs. FIG. 3B shows that protein content when compared by BCA Assay reveals that amount of protein in the profile changes when cells are exposed to stressful conditions, like nutrient deprivation. FIGS. 3C and 3D show NanoSight analysis of purified EVs from neural progenitor cells (FIG. 3C) and astrocytes (FIG. 3D). These EVs show overlapping but different size profiles, with both types of cells producing a peak indicating 55 nm vesicles, and ranging from 25-250 nm.

FIG. 5A shows EVs harvested by ultrafiltration from neural progenitor cells (NPs), astrocytes, or human umbilical MSCs. Protein content was measured by BCA, and EVs were serially diluted and transferred in equal volumes phosphate buffered serum (PBS) into wells containing NeuroNet cells (6-8 week differentiated). Cells were subjected to starvation stress for 10 days, when cells were fixed, and stained for β-III tubulin (Tuj). The center 20 fields of view per well were imaged using the Cellomics Arrayscan (representative images from 4 technical reps shown). FIG. 5B shows NP and Astrocyte EVs protected the cells from starvations stress, and largely maintained integrity of the monolayer and extensions. While more cells and debris are present in the MSC treated wells, the cells had largely lost their neural morphology. Few cells were still detectable in the wells that received only PBS. NP and Astrocyte EVs samples had higher protein concentrations, so were treated with 50 μg protein/well. Protein was limiting in the MSC samples, so 6.25 was the highest concentration possible, but still appeared to kill the cells in a concentration dependent way, so it is unlikely that the higher doses (50, 25, or 12.5 μg/well) would produce a different result.

FIGS. 6A to 6C show biodistribution of indium-111 labeled EVs (FIG. 6B, 6C) compared to free indium (FIG. 6A), which indicates that EVs are present in the brain in proximity of the stroke within 1 hour of injection either when injected immediately following stroke (FIG. 6B circles, left panels), or 24 hours after the stroke occurred (FIG. 6C, circles, left panels). Regardless of the timing of the initial injection, EVs were largely cleared from the area 24 hours after injection (FIGS. 6B, 6C; circles, right panels) although a smaller amount of radioactivity was still detectable, likely indicating EVs were metabolized by surrounding tissues.

FIGS. 8A to 8E show treatment using EVs derived from neural cells improves infarct size and functional outcomes in the mouse embolic stroke model. APEX, MSCEX, PBS, and NPEX aliquots were provided to blinded investigators for injection into mice following induction of embolic stroke (3 repeated doses of approximately $2.7 \times 10^{11}$ vesicles/kg at 2, 14, and 28 hours after stroke). TTC staining of brains harvested 96 hours post-stroke revealed substantially decreased infarct size following NPEX or APEX treatment while MSCEX had no effect (FIG. 8A, 8C). NPEX and APEX also decreased mortality over the course of the study with over 40% of control and MSCEX treated mice succumbing to complications over the course of the study while approximately 25-30% of APEX and NPEX treated animals were lost (FIG. 8B). Phenotypic benefits including improved sensory capacity detected by adhesive tape test (FIG. 8E), and fewer neurological deficits as summarized by neurological deficit score (FIG. 8D) were also noted in APEX and NPEX treated animals.

DETAILED DESCRIPTION

Definitions

Figure 1:
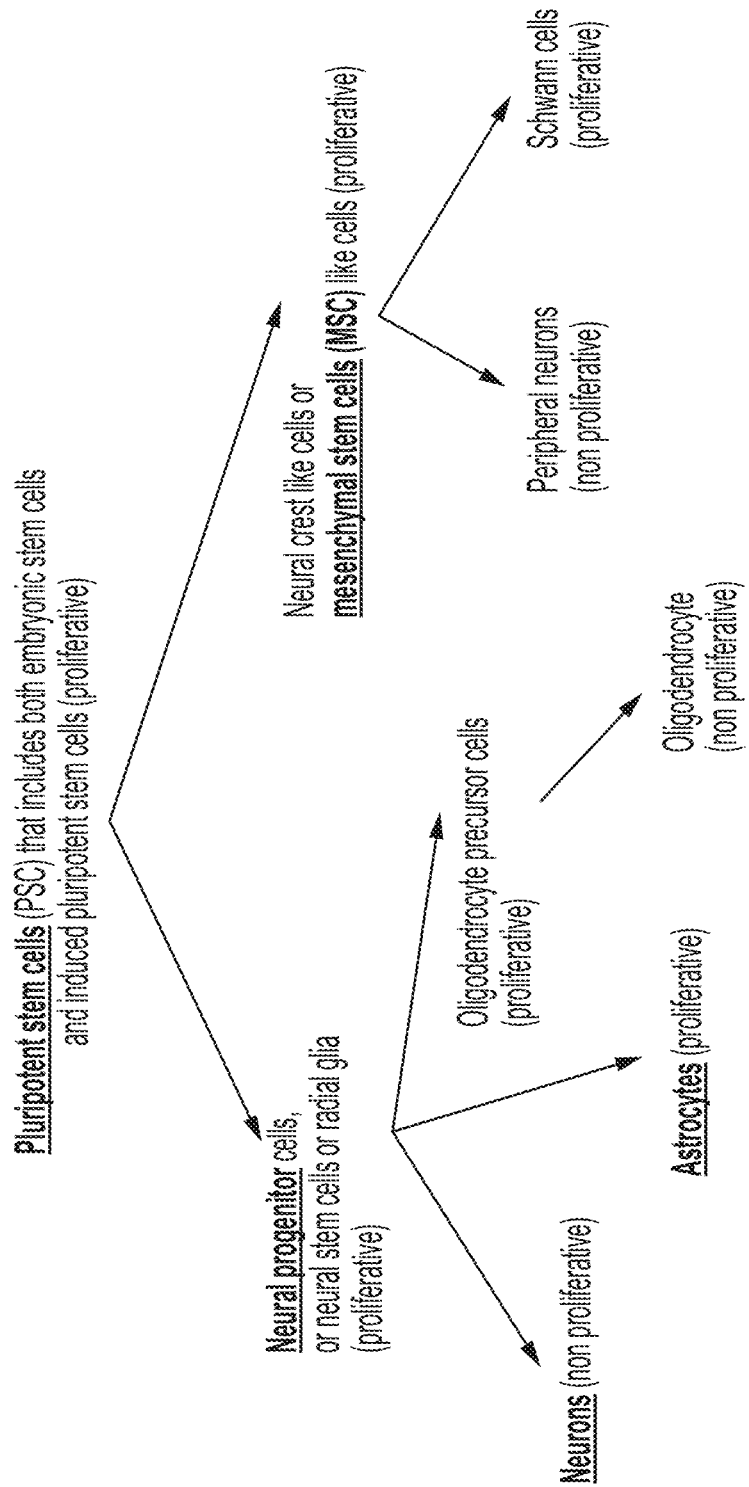
FIG. 1 illustrates potential sources of cells from which extracellular vesicles (EVs) (e.g. exosomes) may be obtained.

In accordance with the present invention there may be employed conventional cell culture methods, chemical synthetic methods and other biological and pharmaceutical techniques within the skill of the art. Such techniques are well-known and are otherwise explained fully in the literature.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It is to be noted that as used herein and in the appended claims, the singular forms "a," "and" and "the" include plural references unless the context clearly dictates otherwise. Furthermore, the following terms shall have the definitions set out below. It is understood that in the event a specific term is not defined herein below, that term shall have a meaning within its typical use within context by those of ordinary skill in the art.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The terms "treat", "treating", and "treatment", etc., as used herein, refer to any action providing a benefit to a patient at risk for or afflicted by a disease state, condition or deficiency which may be improved using cellular compositions according to the present invention. Treating a condition includes improving the condition through lessening or suppression of at least one symptom, delay in progression of the effects of the disease state or condition, including the prevention or delay in the onset of effects of the disease state or condition, etc. In the present application, treatment can involve reducing the impact of a spinal cord injury or stroke, including reversing and/or inhibiting the effects of such injury, reversing, improving, inhibiting and/or stabilizing a neurodegenerative disease such that the disease improves and/or does not progress or worsen. The term "prophylactic" is used to describe a method which "reduces the likelihood" that a particular result will occur, often the progression and/or worsening of a disease state and/or condition.

Standard techniques for growing cells, separating cells, and where relevant, cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, New York; Maniatis et al., 1982 Molecular Cloning, Cold Spring Harbor Laboratory, Plainview, New York; Wu (Ed.) 1993 Meth. Enzymol. 218, Part I; Wu (Ed.) 1979 Meth. Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, New York; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

The term "human Pluripotent Stem Cells", of which "human Embryonic Stem Cells" (hESCs) and human induced pluripotent stem cells (hiPSCs) are a subset, are derived from pre-embryonic, embryonic, fetal tissue or adult stem cells (in the case of human induced pluripotent stem cells) at any time after fertilization, and have the characteristic of being capable under appropriate conditions of producing progeny of several different cell types, especially including neuronal stem and progenitors, neural crest cells, mesenchymal stem cells (MSCs) and related proliferative and non-proliferative neural cells. The term includes both established lines of stem cells of various kinds, and cells obtained from primary tissue that are pluripotent in the manner described.

The term "embryonic stem cell" refers to pluripotent cells, preferably of primates, including humans, which are isolated from the blastocyst stage embryo.

The term "neural progenitor cell" refers to cells capable of dividing a limited number of times that have the capacity to differentiate into neuronal and glial cell types.

The terms "extracellular vesicle" and "EV" are used herein to refer to a vesicle of about 10 nm to 10 µm in size consisting of fluid, macro-molecules, solutes, and metabolites from a cell contained by a lipid bilayer or micelle. In some cases, the EV is a cell-derived EV. The term "EV" also includes lipid vesicle engineered to contain bioactive molecules found in a cell-derived EVs, such as a neural EVs. These terms encompass both exosomes and ectosomes. Exosomes are released on the exocytosis of multivesicular bodies (MVBs). Ectosomes are vesicles assembled at and released from the plasma membrane. In some cases, the EV is about 20 nm to 10 µm, 20 nm to 1 µm, 20 nm-500 nm, 30 nm-100 nm, 30 nm-160 nm, or 80-160 nm in size. In some embodiments, the EVs are exosomes that are about 20 to 150 nm in size.

The term "autologous EV" is used to describe a population of EVs which are obtained from cells from a subject or patient to whom the EVs are to be administered.

The term "neural EV" is used to refer to a cell-derived EV produced from neural progenitor cells derived in vitro from pluripotent stem cells or neural cells derived in vitro from said neural progenitor cells or from pluripotent stem cells. The term also refers to vesicles engineered to contain a sufficient number of the bioactive molecules found in the cell-derived neural EV to have substantially the same bioactivity.

Compositions

Disclosed herein are neural EVs (e.g. exosomes) and methods of using these EVs in the treatment of spinal cord injury, stroke, and traumatic brain injury and neurodegenerative diseases.

The disclosed EVs can be obtained in some embodiments, by culturing neural progenitor (NP) cells or mesenchymal stem cells (MSCs) that were produced in vitro from pluripotent stem cells (e.g. human embryonic stem cells (hESCs) or induced pluripotent stem cells (iPSCs)) in cell culture medium under conditions and for a time sufficient for the NP cells or MSCs to produce EVs.

Methods for the production of human neural progenitor (hNP) cells from human embryonic stem cells (ESCs) are described, for example, in U.S. Pat. No. 7,531,354, which is hereby incorporated by reference in its entirety for the teaching of these cells. Human neuroprogenitor cells (hNPs) are known to express markers associated with the earliest multipotent neural stem cells, including Nestin, Musashi-1, Sox1, Sox2 and Sox3. It is noted that although feeder cell free neural progenitor cells may be used to produce EVs, any neuroprogenitor cell as otherwise described herein may also be used. Preferred neuroprogenitor cells are produced according to the methods presented in U.S. Pat. No. 7,531,354, are adherent feeder cell free as well as free from embryoid bodies.

The disclosed EVs can be obtained in some embodiments by culturing differentiated neural cells, such as astrocytes, derived directly or indirectly from pluripotent stem cells in cell culture medium under conditions and for a time sufficient to produce EVs, and isolating said EVs from the culture medium. In some embodiments, the differentiated neural cells are hN2™ neuronal cells (ArunA Biomedical), NeuroNet™ neurons, or AstroPro™ astrocytes (ArunA Biomedical Inc).

Pluripotent stem cells used to produce the EV-producing NP cells, neural cells, or MSCs include human embryonic stem cells (hESCs) and human induced pluripotent stem cells (hiPSCs).

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra-1-60, and Tra-1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame Calif.) Undifferentiated pluripotent stem cells also typically express Oct-4 and TERT, as detected by RT-PCR.

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established ethical lines of human embryonic stem cells or human embryonic germ cells, such as, for example the human embryonic stem cell lines WA01, WA07, and WA099 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.), as well as normal human embryonic stem cell lines such as WA01, WA07, WA09 (WiCell) and BG01, BG02 (BresaGen, Athens, Ga.).

Human embryonic stem cells (hESCs) may be prepared by methods which are described in the in the art as described for example, by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995). Alternatively, they may be obtained commercially.

Epiblast stem cells (EpiScs) and induced pluripotent stem cells (iPSCs) isolated from early post-implantation stage embryos. They express Oct4 and are pluripotent. iPSCs are made by dedifferentiating adult somatic cells back to a pluripotent state by retroviral transduction of four genes (c-myc, Klf4, Sox2, Oct4).

As described in U.S. Patent Application Document No. 20140356382, "[e]xosomes produced from cells can be collected from the culture medium and/or cell tissue by any suitable method. Typically a preparation of EVs can be prepared from cell culture or tissue supernatant by centrifugation, filtration or combinations of these methods. For example, EVs can be prepared by differential centrifugation, that is low speed (<2,0000 g) centrifugation to pellet larger particles followed by high speed (>100,000 g) centrifugation to pellet EVs, size filtration with appropriate filters (for example, 0.22 μm filter), gradient ultracentrifugation (for example, with sucrose gradient) or a combination of these methods." It is noted that the contents of EVs, i.e., EVs in which the lipid bilayer has been removed or eliminated and the contents obtained may also be used to engineer artificial EVs.

Further, as described in U.S. Patent Application Document No. 20140356382, exogenous protein and/or peptide and other cargo can be introduced into the EVs by a number of different techniques including electroporation or the use of a transfection reagent. Electroporation conditions may vary depending on the charge and size of the biotherapeutic cargo. Typical voltages are in the range of 20V/cm to 1,000V/cm, such as 20V/cm to 100V/cm with capacitance typically between 25 μF and 250 μF, such as between 25 μF and 125 μF. A voltage in the range of 150 mV to 250 mV, particularly a voltage of 200 mV is preferred for loading EVs with an antibody. Alternatively, the EVs may be loaded with exogenous protein and/or peptide using a transfection reagent. Despite the small size of the EVs, conventional transfection agents may be used for transfection of EVs with protein and/or peptide. EVs may also be loaded by transforming or transfecting a host cell with a nucleic acid construct which expresses therapeutic protein or peptide of interest, such that the therapeutic protein or peptide is taken up into the EVs as the EVs are produced from the cell.

In illustrative embodiments, the EV-producing NP cells and/or neural cells disclosed herein are cultured for about 1, 2, 3, 4, 5, 6, 7, 8, 9, 10, 11, 12, 13 or 14 days or for as long as about 1, 2, 3, 4, 5, 6, 7, 8 weeks or about 1, 2, 3, 4, 5, or 6 months, depending on the cell and its ability to produce EVs. The EV-producing cells may be cultured in suitable media and grown under conditions that are readily determined by one of ordinary skill in the art. Cell culture conditions may vary with cell type and the examples presented hereinafter illustrate suitable media and conditions. For example, CMRL 1066 medium (from Invitrogen) with fetal bovine serum (e.g., at 10%) and optionally supplemented with glutamine or glutamine-containing mixtures and antibiotics could be used. Cells can be grown on a surface (feeder cells) in some embodiments, e.g. they can be grown as a monolayer on the surface (feeder cell free) and may be grown until 30, 40, 50, 60, 70, 80, 90, 95 or 100% confluent.

Cell growth media are well known in the art and comprise at least a minimum essential medium plus one or more optional components such as growth factors, ascorbic acid, glucose, non-essential amino acids, salts (including trace elements), glutamine, insulin (where indicated and not excluded), Activin A, transferrin, beta mercaptoethanol, and other agents well known in the art and as otherwise described herein. A preferred media is a low protein, serum-free based growth medium that supports neural cells. The growth factor used can be fibroblast growth factor 2 (FGF2), alone or preferably in combination with leukemia inhibitor factor (LIF). Depending on the NP or neural cells to be grown in the growth media, the inclusion of LIF is preferred but may not be required. Additional media includes basal cell media which may contain serum, for example, between about 0.1% and 20% (preferably, about 2-10%) fetal calf serum, or for defined medium, an absence of fetal calf serum and KSR, and optionally including bovine serum albumin (about 1-5%, preferably about 2%). Preferred medium is defined and is serum-free and low protein. The components of the growth media depends on the type of neural cell to be grown, all of which are well known in the art. Particularly preferred media is media and supplement from ArunA. The AB2™ Neural Cell Culture Media Kit contains AB2™ Basal Neural Medium and ANS™ Neural Medium Supplement. The medium and supplement are specifically engineered for versatility to meet all neural cell culture needs. The AB2™ Basal Neural Medium and ANS™ Neural Medium Supplement can be used as the base for specialized mediums to direct differentiation of the hNP1™ line toward various neural phenotypes. Each lot of medium and supplement is pre-qualified for use by testing for cell growth, sterility, pH, osmolarity, and endotoxins.

Formulations from ArunA allow neural cultures to maintain a stable karyotype over multiple passages without the need for feeder cells, making them an excellent choice for a wide variety of research applications including early stage drug discovery.

Other agents which optionally may be added to the medium include, depending on the cell type grown in the media, for example, any one or more of nicotinamide, members of TGF-β family, including TGF-β 1, 2, and 3, Activin A, nodal, Bone Morphogen Proteins (BMP 2 to 7) serum albumin, members of the fibroblast growth factor (FGF) family, platelet-derived growth factor-AA, and -BB, platelet rich plasma, insulin growth factor (IGF-I, II, LR-IGF), growth differentiation factor (GDF-5, -6, -8, -10, 11), glucagon like peptide-I and II (GLP-I and II), GLP-1 and GLP-2 mimetobody, Exendin-4, parathyroid hormone, insulin, progesterone, aprotinin, hydrocortisone, ethanolamine, epidermal growth factor (EGF), gastrin I and II, copper chelators such as, for example, triethylene pentamine, forskolin, Na-Butyrate, betacellulin, ITS, noggin, neurite growth factor, nodal, valporic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, heregulin, or combinations thereof, among a number of other components. Each of these components, when included, are included in effective amounts.

By way of further example, suitable media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029.

Cell media are commercially available and can be supplemented with commercially available components, including defined xeno-free components, such as those available from Invitrogen Corp. (GIBCO), Cell Applications, Inc., Biological Industries, Beth HaEmek, Israel, and Calbiochem. One of ordinary skill in the art will be able to readily modify the cell media to produce any one or more of the target cells pursuant to the present invention.

The disclosed EV-producing cells may be cultured on a layer of feeder cells that support the cells in various ways. Approaches for culturing cells on a layer of feeder cells are well known in the art. The cells may be grown on a cellular support or matrix, as adherent monolayers, rather than as embryoid bodies or in suspension. In certain embodiments, the use of a cellular support may be preferred, depending upon the cells used to produce the EVs. When used, cellular supports preferably comprise at least one substrate protein. Substrate proteins include, for example, an extracellular matrix protein, which is a protein found in the extracellular matrix, such as laminin, tenascin, thrombospondin, and mixtures thereof, which exhibit growth promoting and contain domains with homology to epidermal growth factor (EGF) and exhibit growth promoting activity. Other substrate proteins which may be used include for example, collagen, fibronectin, vibronectin, polylysine, polyornithine and mixtures thereof. In addition, gels and other materials such as methylcellulose of other gels which contain effective concentrations of one or more of these embryonic stem cell differentiation proteins may also be used. Exemplary differentiation proteins or materials which include these differentiation proteins include, for example, laminin, BD Cell-Tak™ Cell and Tissue Adhesive, BD™ FIBROGEN Human Recombinant Collagen I, BD™ FIBROGEN Human Recombinant Collagen III, BD Matrigel™ Basement Membrane Matrix, BD Matrigel™ Basement Membrane Matrix High Concentration (HC), BD™ PuraMatrix™ Peptide Hydrogel, Collagen I, Collagen I High Concentration (HC), Collagen II (Bovine), Collagen III, Collagen IV, Collagen V, and Collagen VI, among others.

Alternatively, these cells may be cultured in a culture system that is essentially free of feeder cells, but nonetheless supports proliferation of the cells to produce EVs. The growth of cells in feeder-free culture can be supported using a medium conditioned by culturing previously with another cell type. Alternatively, the growth of EV-producing cells in feeder-free culture without differentiation can be supported using a chemically defined medium. These approaches are well known in the art. In certain embodiments of the present invention, the cells are grown in feeder cell free medium.

EVs can be harvested at various time intervals (e.g. at about 2, 4, 6, 8 or 3, 6, 9, 12 day or longer intervals, depending upon the rate of production of EVs). Exemplary yields of EVs can range from at least about 1 ng EVs/1 million cells, at least about 10 ng EVs/1 million cells, at least about 50 ng EVs/1 million cells, at least about 100 ng EVs/1 million cells, at least about 500 ng EVs/1 million cells, at least about 750 ng EVs/1 million cells, at least about 800 ng EVs/1 million cells, at least about 900 ng EVs/1 million cells, at least about 1.0 µg EVs/1 million cells, at least about 1.5 µg EVs/1 million cells, at least about 2.0 µg EVs/1 million cells, at least about 2.5 µg EVs/1 million cells, at least e.g. about 3.0 µg EVs/1 million cells, at least about 5.0 µg EVs/1 million cells, and at least about 10.0 µg EVs/1 million cells, during a time period of about 24 hours to seven days of culture of proliferative and non-proliferative neural cells as otherwise described herein.

In certain embodiments, EVs are harvested and collected by ultracentrifugation or differential centrifugation or any combination thereof, pelleted EVs are collected, and, optionally, collected pelleted EVs are washed with a suitable medium. For example, a preparation of EVs can be prepared from cell culture or tissue supernatant by centrifugation, filtration or combinations of these methods. In some embodiments, the EVs can be prepared by differential centrifugation, that is low speed (<2,0000 g) centrifugation to pellet larger particles followed by high speed (>100,000 g) centrifugation to pellet EVs, size filtration with appropriate filters (for example, 0.22 µm filter), gradient ultracentrifugation (for example, with sucrose gradient) or a combination of these methods. EVs may be purified by differential centrifugation, micro and ultra-filtration, polymeric precipitation, microfluidic separation, immunocapture and size-exclusion chromatography. These and/or related methods for isolating and purifying EVs are described by Théry, et al., *Current Protocols in Cell Biology*, (2006) 3.221-3.22.29, copyright 2006 by John Wiley & Sons, Inc.; Sokolova, et al., *Colloids and Surfaces* B: Biointerfaces, 2011, 87, 146-150; Wiklander, et al., *Journal of Extracellular Vesicles*, 2015, 4, 26316, pp. 1-13; and Böing, et al., *Journal of Extracellular Vesicles*, 2014, 3, 23430, pp. 1-11. Other methods for isolation may be developed such as electrical field radiofrequency and acoustics.

Pharmaceutical Compositions

Disclosed is a pharmaceutical compositions containing therapeutically effective amounts of one or more of the disclosed EVs and a pharmaceutically acceptable carrier. Formulations containing the disclosed EVs may take the form of liquid, solid, semi-solid or lyophilized powder forms, such as, for example, solutions, suspensions, emulsions, sustained-release formulations, tablets, capsules, powders, suppositories, creams, ointments, lotions, aerosols, patches or the like, preferably in unit dosage forms suitable for simple administration of precise dosages.

Pharmaceutical compositions typically include a conventional pharmaceutical carrier and/or excipient and may additionally include other medicinal agents, carriers, adjuvants, additives and the like. The weight percentage ratio of the EVs to the one or more excipients can be between about 20:1 to about 1:60, or between about 15:1 to about 1:45, or between about 10:1 to about 1:40, or between about 9:1, 8:1, 7:1, 6:1, 5:1, 4:1, 3:1, 2:1 or 1:1 to about 1:2, 1:3, 1:4, 1:5, 1:6, 1:7, 1:8, 1:9, 1:10, 1:15, 1:20, 1:25, 1:30, or 1:35, and preferably is about 20:1, 19:1, 18:1, 17:1, 16:1, 15:1, 14:1, 13:1, 12:1, 11:1, 10:1, 9:1, 8:1, 7:1, 6:1 or 5:1. In some embodiments, the disclosed composition comprises between about 1 µg to about 1 g or more of total EVs, about 500 µg about 500 mg, about 1 mg to about 500 mg of total EVs, about 5 to about 500 mg, about 10 to about 500 mg, about 25 to about 500 mg, about 50 mg to about 350 mg, about 75 mg to about 450 mg, about 50 mg to about 450 mg, or about 75 mg to about 325 mg or about 100 mg to about 650 mg of total EVs and may optionally contain one or more suitable pharmaceutical carriers, additives and/or excipients.

An injectable composition for parenteral administration (e.g. intravenous, intramuscular, intrathecal intracerebrospinal fluid, or intranasal), will typically contain the EVs and optionally additional components in a suitable i.v. solution, such as sterile physiological salt solution. The composition may also be formulated as a suspension in an aqueous emulsion.

Liquid compositions can be prepared by dissolving or dispersing the pharmaceutical composition comprising the EVs, and optional pharmaceutical adjuvants, in a carrier, such as, for example, aqueous saline, aqueous dextrose, glycerol, or ethanol, to form a solution or suspension. For use in an oral liquid preparation, the composition may be prepared as a solution, suspension, emulsion, or syrup, being supplied either in liquid form or a dried form suitable for hydration in water or normal saline. In the case of intranasal, intratracheal or intrapulmonary administration, the compositions may be provided as liquid composition which can be sprayed into the nose, trachea and/or lungs.

For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

Methods for preparing such dosage forms are known or are apparent to those skilled in the art; for example, see Remington's Pharmaceutical Sciences (17th Ed., Mack Pub. Co. 1985). The composition to be administered will contain a quantity of the selected compound in a pharmaceutically effective amount for therapeutic use in a biological system, including a patient or subject according to the present invention.

Intravenous formulations can comprise the EVs described herein, an isotonic medium and one or more substances preventing aggregation of the EVs. Example intravenous/intrathecal/intracerebrospinal fluid formulations may contain saline solutions (e.g. normal saline (NS); about 0.91% w/v of NaCl, about 300 mOsm/L) and/or dextrose 4% in 0.18% saline, and optionally 1%, 2% or 3% human serum albumin. In addition, the EVs may be disrupted to obtain the contents and the contents used in compositions according to the present invention.

In exemplary embodiments, formulations of the invention may comprise about 50 ng EVs/ml intravenous/intrathecal/intracerebrospinal fluid medium, including about 100 ng, 200 ng, 300 ng, 400 ng, 500 ng, 600 ng, 700 ng, 800 ng, 900 ng, 1.0 µg, 1.5 µg, 2.0 µg, 2.5 µg, 3.0 µg, 5.0 µg, 10.0, 15.0 µg, 20.0 µg, 100 µg, or more EVs/ml intravenous/intrathecal/intracerebrospinal fluid medium for use in treating spinal cord injury, stroke, traumatic brain injury and/or neurodegenerative diseases.

In some embodiments, intravenous formulations may comprise about 0.1 µg EVs/ml medium, about 0.2 µg EVs/ml intravenous medium, about 0.3 µg EVs/ml intravenous medium, about 0.4 µg EVs/ml intravenous medium, about 0.5 µg EVs/ml intravenous medium, about 0.6 µg EVs/ml intravenous medium, about 0.7 µg EVs/ml intravenous medium, about 0.8 µg EVs/ml intravenous medium, about 0.9 µg EVs/ml intravenous medium, about 1.0 µg EVs/ml intravenous medium, about 1.5 µg EVs/ml intravenous medium, about 2.0 µg EVs/ml intravenous medium, about 2.5 µg EVs/ml intravenous medium, such as at least e.g. about 3.0 µg EVs/ml intravenous medium, such as e.g. at least about 5.0 µg EVs/ml intravenous medium, about 10.0 µg EVs/ml intravenous medium, 15.0 µg EVs/ml intravenous medium or about 20.0 µg or more EVs/ml intravenous medium.

In some embodiments, the pharmaceutical composition is in a dosage form comprising at least 25 mg of EVs, at least 50 mg of EVs, at least 60 mg of EVs, at least 75 mg of EVs, at least 100 mg of EVs, at least 150 mg of EVs, at least 200 mg of EVs, at least 250 mg of EVs, at least 300 mg of EVs, about 350 mg of EVs, about 400 mg of EVs, about 500 mg of EVs, about 750 mg of EVs, about 1 g (1,000 mg) or more of EVs, alone or in combination with a therapeutically effective amount of at least one additional bioactive agent, which agent may be useful in the treatment of spinal cord injury, stroke, traumatic brain injury and/or neurodegenerative disease. In some embodiments, the pharmaceutical composition comprises between about 10 mg to about 750 mg, about 25 mg to about 650 mg, or between about 30 mg to about 500 mg, or about 35 mg to about 450 mg, most often about 50 to about 500 mg of EVs.

In some embodiments, an intravenous formulation comprises the EVs described herein, an isotonic medium, and one or more substances preventing aggregation of the EVs. Intravenous formulations may therefore contain saline solutions (e.g. normal saline (NS); about 0.91% w/v of NaCl, about 300 mOsm/L) and/or dextrose 4% in 0.18% saline, and optionally 1%, 2% or 3% human serum albumin.

In some embodiments, the composition comprising the disclosed EVs further comprises one more neurotrophic agents. The composition can further comprises one or more agents selected from the group consisting of leukemia inhibitory factor (LIF), brain-derived neurotrophic factor (BDNF), epidermal growth factor receptor (EGF), basic fibroblast growth factor (bFGF), FGF-6, glial-derived neurotrophic factor (GDNF), granulocyte colony-stimulating factor (GCSF), hepatocyte growth factor (HGF), IFN-γ, insulin-like growth factor binding protein (IGFBP-2), IGFBP-6, IL-1ra, IL-6, IL-8, monocyte chemotactic protein (MCP-1), mononuclear phagocyte colony-stimulating factor (M-CSF), neurotrophic factors (NT3), tissue inhibitor of metalloproteinases (TIMP-1), TIMP-2, tumor necrosis factor (TNF-β), vascular endothelial growth factor (VEGF), VEGF-D, urokinase plasminogen activator receptor (uPAR), bone morphogenetic protein 4 (BMP4), IL1-a, IL-3, leptin, stem cell factor (SCF), stromal cell-derived factor-1 (SDF-1), platelet derived growth factor-BB (PDGFBB), transforming growth factors beta (TGFβ-1) and TGFβ-3.

In some embodiments, the disclosed EVs are contained in or on a biocompatible scaffold, such as a hydrogel. Suitable hydrogels include temperature dependent hydrogels that solidify or set at body temperature, e.g., PLURONICS™; hydrogels crosslinked by ions, e.g., sodium alginate; hydrogels set by exposure to either visible or ultraviolet light, e.g., polyethylene glycol polylactic acid copolymers with acrylate end groups; and hydrogels that are set or solidified upon a change in pH, e.g., TETRONICS™. Examples of materials that can be used to form these different hydrogels include polysaccharides such as alginate, polyphosphazenes, and polyacrylates, which are cross-linked ionically, or block copolymers such as PLURONICS™ (also known as POLOXAMERS™), which are poly(oxyethylene)-poly(oxypropylene) block polymers solidified by changes in temperature, or TETRONICS™ (also known as POLOXAMINES™), which are poly(oxyethylene)-poly(oxypropylene) block polymers of ethylene diamine solidified by changes in pH.

Suitable hydrogels also include undefined extracellular matrix derived hydrogels that originated from tissues including but not limited to bladder intestine, blood and brain.

In some embodiments, the disclosed EVs are contained in or on a biocompatible scaffold comprising collagen, fibrin, silk, agarose, alginate, hyaluronan, chitosan, a biodegradable polyester such as polylactic-co-glycolic acid, polylacic acid, or polyglycolic acid, polyethylene glycol, polyvinylpyrrolidone, polyethersulfone, a peptide-based biomaterial, glycose amino glycan, fibronectin, laminin, or any combination thereof.

In some cases, the hydrogel is produced by cross-linking the anionic salt of alginic acid, a carbohydrate polymer isolated from seaweed, with ions, such as calcium cations. The strength of the hydrogel increases with either increasing concentrations of calcium ions or alginate. For example, U.S. Pat. No. 4,352,883 describes the ionic cross-linking of alginate with divalent cations, in water, at room temperature, to form a hydrogel matrix.

EVs are mixed with an alginate solution, the solution is delivered to an already implanted support structure and then solidifies in a short time due to the presence in vivo of physiological concentrations of calcium ions. Alternatively, the solution is delivered to the support structure prior to implantation and solidified in an external solution containing calcium ions.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly(phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

Polyphosphazenes are polymers with backbones consisting of nitrogen and phosphorous atoms separated by alternating single and double bonds. Each phosphorous atom is covalently bonded to two side chains. Polyphosphazenes that can be used have a majority of side chains that are acidic and capable of forming salt bridges with di- or trivalent cations. Examples of acidic side chains are carboxylic acid groups and sulfonic acid groups.

Bioerodible polyphosphazenes have at least two differing types of side chains, acidic side groups capable of forming salt bridges with multivalent cations, and side groups that hydrolyze under in vivo conditions, e.g., imidazole groups, amino acid esters, glycerol, and glucosyl. Bioerodible or biodegradable polymers, i.e., polymers that dissolve or degrade within a period that is acceptable in the desired application (usually in vivo therapy), will degrade in less than about five years and most preferably in less than about one year, once exposed to a physiological solution of pH 6-8 having a temperature of between about 25° C. and 38° C. Hydrolysis of the side chain results in erosion of the polymer. Examples of hydrolyzing side chains are unsubstituted and substituted imidizoles and amino acid esters in which the side chain is bonded to the phosphorous atom through an amino linkage.

Methods for synthesis and the analysis of various types of polyphosphazenes are described in U.S. Pat. Nos. 4,440,921, 4,495,174, and 4,880,622. Methods for the synthesis of the other polymers described above are known to those skilled in the art. See, for example Concise Encyclopedia of Polymer Science and Engineering, J. I. Kroschwitz, editor (John Wiley and Sons, New York, N.Y., 1990). Many polymers, such as poly(acrylic acid), alginates, and PLURONICS™, are commercially available.

Water soluble polymers with charged side groups are cross-linked by reacting the polymer with an aqueous solution containing multivalent ions of the opposite charge, either multivalent cations if the polymer has acidic side groups, or multivalent anions if the polymer has basic side groups. Cations for cross-linking the polymers with acidic side groups to form a hydrogel include divalent and trivalent cations such as copper, calcium, aluminum, magnesium, and strontium. Aqueous solutions of the salts of these cations are added to the polymers to form soft, highly swollen hydrogels.

Anions for cross-linking the polymers to form a hydrogel include divalent and trivalent anions such as low molecular weight dicarboxylate ions, terepthalate ions, sulfate ions, and carbonate ions. Aqueous solutions of the salts of these anions are added to the polymers to form soft, highly swollen hydrogels, as described with respect to cations.

For purposes of preventing the passage of antibodies into the hydrogel, but allowing the entry of nutrients, a useful polymer size in the hydrogel is in the range of between 10,000 D and 18,500 D.

Temperature-dependent, or thermosensitive, hydrogels have so-called "reverse gelation" properties, i.e., they are liquids at or below room temperature, and gel when warmed to higher temperatures, e.g., body temperature. Thus, these hydrogels can be easily applied at or below room temperature as a liquid and automatically form a semi-solid gel when warmed to body temperature. As a result, these gels are especially useful when the support structure is first implanted into a patient, and then filled with the hydrogel-EV composition. Examples of such temperature-dependent hydrogels are PLURONICS™ (BASF-Wyandotte), such as polyoxyethylene-polyoxypropylene F-108, F-68, and F-127, poly(N-isopropylacrylamide), and N-isopropylacrylamide copolymers.

These copolymers can be manipulated by standard techniques to affect their physical properties such as porosity, rate of degradation, transition temperature, and degree of rigidity. For example, the addition of low molecular weight saccharides in the presence and absence of salts affects the lower critical solution temperature (LCST) of typical thermosensitive polymers. In addition, when these gels are prepared at concentrations ranging between 5 and 25% (W/V) by dispersion at 4° C., the viscosity and the gel-sol transition temperature are affected, the gel-sol transition temperature being inversely related to the concentration.

U.S. Pat. No. 4,188,373 describes using PLURONIC™ polyols in aqueous compositions to provide thermal gelling aqueous systems. U.S. Pat. No. 4,474,751, '752, '753, and U.S. Pat. No. 4,478,822 describe drug delivery systems which utilize thermosetting polyoxyalkylene gels; with these systems, both the gel transition temperature and/or the rigidity of the gel can be modified by adjustment of the pH and/or the ionic strength, as well as by the concentration of the polymer.

pH-dependent hydrogels are liquids at, below, or above specific pH values, and gel when exposed to specific pHs, e.g., 7.35 to 7.45, the normal pH range of extracellular fluids within the human body. Thus, these hydrogels can be easily delivered to an implanted support structure as a liquid and automatically form a semi-solid gel when exposed to body pH. Examples of such pH-dependent hydrogels are TETRONICS™ (BASF-Wyandotte) polyoxyethylene-polyoxypropylene polymers of ethylene diamine, poly(diethyl aminoethyl methacrylate-g-ethylene glycol), and poly(2-hydroxymethyl methacrylate). These copolymers can be manipulated by standard techniques to affect their physical properties.

Hydrogels that are solidified by either visible or ultraviolet light can be made of macromers including a water soluble region, a biodegradable region, and at least two polymerizable regions as described in U.S. Pat. No. 5,410,016. For example, the hydrogel can begin with a biodegradable, polymerizable macromer including a core, an extension on each end of the core, and an end cap on each extension. The core is a hydrophilic polymer, the extensions are biodegradable polymers, and the end caps are oligomers capable of cross-linking the macromers upon exposure to visible or ultraviolet light, e.g., long wavelength ultraviolet light.

Examples of such light solidified hydrogels include polyethylene oxide block copolymers, polyethylene glycol polylactic acid copolymers with acrylate end groups, and 10K polyethylene glycol-glycolide copolymer capped by an acrylate at both ends. As with the PLURONIC™ hydrogels, the copolymers comprising these hydrogels can be manipulated by standard techniques to modify their physical properties such as rate of degradation, differences in crystallinity, and degree of rigidity.

Methods of Treatment

Also disclosed is a method of treating a subject with a with a spinal cord injury, stroke, traumatic brain injury or a neurodegenerative disease comprising administering to the subject an effective amount of a composition containing a population of neural EVs disclosed herein. In some embodiments, the neurodegenerative disease is Alzheimer's disease, Parkinson's disease, a Parkinson's-related disorder, Huntington's disease, prion disease, motor neuron disease (MND), spinocerebellar ataxia (SCA) or spinal muscular atrophy (SMA).

The term "spinal cord injury" is used to describe a spinal cord injury which results in a temporary or permanent change in the normal motor, autonomic or sensory function of the cord. The damage often results from physical trauma, such as sports injuries, slip and fall accidents or motor vehicular accidents but can also result from diseases such as spina bifida, Friedrich's ataxis and/or transverse myelitis. Injury to the spinal cord resulting in a loss of function does not have to be the result of complete severing of the spinal cord. Depending on where the spinal cord and its nerve roots are damaged, the symptoms and degree of injury can vary widely, from pain to incontinence to paralysis. Spinal cord injuries are described at various levels of incomplete to complete injury, resulting in a total loss of function. The spinal cord injury can result in paraplegia or tetraplegia.

Traditional treatment of spinal cord injuries starts with stabilizing the spine and controlling inflammation associated with the spin cord damage to prevent further damage. Other interventions can vary widely depending on the location and extent of the injury. In many cases, using conventional therapy, spinal cord injuries require substantial, long-term physical therapy and rehabilitation, especially if the injury interferes with activities of daily life.

Spinal cord injury can be classified into three types based on its cause: mechanical forces, toxic, and ischemic, from lack of blood flow. Spinal cord damage can also be divided into primary and second injury. Primary injury is caused by the cell death that occurs immediately in the original injury (physical trauma, exposure to toxins, or ischemia), and secondary injury is caused by the resultant cascades that are caused by the original insult and cause further tissue damage. These secondary injury pathways include inflammation, swelling, neurotransmitter deficiencies/imbalances, the results of ischemia and cell suicide. The present invention may be used to treat all forms of spinal cord injury, including complete and incomplete injuries, ischemia, spinal cord injury without radiographic abnormality, central cord syndrome, anterior cord syndrome, Brown-Séquard syndrome, posterior cord syndrome, tabes dorsalis and conus medullaris, among others.

The term "stroke" is used to describe a cerebrovascular accident (CVA), cerebrovascular insult (CVI), or brain attack, occurs when poor blood flow to the brain results in cell death. There are two main types of stroke: ischemic, due to lack of blood flow, and hemorrhagic, due to bleeding. Both of these types of stroke result in part of the brain not functioning properly. Signs and symptoms of a stroke may include an inability to move or feel on one side of the body, problems understanding or speaking, a sense of spinning, or loss of vision to one side, among others. Signs and symptoms often appear soon after the stroke has occurred. If symptoms last less than one or two hours it is known as a transient ischemic attack. Hemorrhagic strokes may also be associated with a severe headache. The symptoms of a stroke can be permanent. Long term complications of stroke may include pneumonia or loss of bladder control The main risk factor for stroke is high blood pressure. Other risk factors include tobacco smoking, obesity, high blood cholesterol, diabetes mellitus, previous transient ischemic attack (TIA), and atrial fibrillation, among others. An ischemic stroke is typically caused by blockage of a blood vessel. A hemorrhagic stroke is caused by bleeding either directly into the brain or into the space surrounding the brain. Bleeding may occur due to a brain aneurysm. Both ischemic and hemorrhagic stroke are treated pursuant to the present invention.

The term "traumatic brain injury" (TBI) is used to describe an injury to the brain caused by movement of the brain within the skill or an injury to the brain caused by a foreign object. Causes of TBI may include falls, a motor vehicle crash or being struck by or with an object. TBI may also be caused by a penetrating object—an injury to the brain caused by a foreign object entering the skull. Causes may include firearm injuries or being struck with a sharp object. TBI may cause a concussion, a period of unconsciousness (coma) or amnesia. TBI may impair one or more of cognitive function (e.g., attention and memory), motor function (e.g., extremity weakness, impaired coordination and balance), sensation (e.g., hearing, vision, impaired perceptin and touch and emotion (e.g., depression, anxiety, aggression, impulse control, personality changes).

The term "neurodegenerative disease" is used throughout the specification to describe a disease which is caused by damage to the central nervous system and which damage can be reduced and/or alleviated through transplantation of neural cells according to the present invention to damaged areas of the brain and/or spinal cord of the patient. Exemplary neurodegenerative diseases which may be treated using the neural cells and methods according to the present invention include for example, Parkinson's disease, Huntington's disease, amyotrophic lateral sclerosis (Lou Gehrig's disease), Alzheimer's disease, lysosomal storage disease ("white matter disease" or glial/demyelination disease, as described, for example by Folkerth, *J. Neuropath. Exp. Neuro.*, 58, 9, September 1999), Tay Sachs disease (beta hexosamimidase deficiency), other genetic diseases, multiple sclerosis, brain injury or trauma caused by ischemia, accidents, environmental insult, etc., spinal cord damage, ataxia and alcoholism. In addition, the present invention may be used to reduce and/or eliminate the effects on the central nervous system of a stroke or a heart attack in a patient, which is otherwise caused by lack of blood flow or ischemia to a site in the brain of said patient or which has occurred from physical injury to the brain and/or spinal cord. The term neurodegenerative diseases also includes neurodevelopmental disorders including for example, autism and related neurological diseases such as schizophrenia, among numerous others.

The herein disclosed compositions, including pharmaceutical composition, may be administered in a number of ways depending on whether local or systemic treatment is desired, and on the area to be treated.

Methods of treating subjects involve administration of a pharmaceutical composition comprising an effective amount of EVs described herein and optionally at least one additional bioactive (e.g. an agent which is useful in the treatment of a neurodegenerative disease, stroke and/or spinal cord injury) agent. For example, the compositions could be formulated so that a therapeutically effective dosage of between about 0.01, 0.1, 1, 5, 10, 15, 20, 25, 30, 35, 40, 45, 50, 55, 60, 65, 70, 75, 80, 85, 90 or 100 mg/kg of patient/day or in some embodiments, greater than 100, 110, 120, 130, 140, 150, 160, 170, 180, 190 or 200 mg/kg of the disclosed EVs can be administered to a patient receiving these compositions.

The dose of EVs administered to a subject can be less than 10 µg, less than 25 µg, less than 50 µg, less than 75 µg, less than 0.10 mg, less than 0.25 mg, less than 0.5 mg, less than 1 mg, less than 2.5 mg, less than 5 mg, less than 10 mg, less than 15 mg, less than 20 mg, less than 50 mg, less than 75 mg, less than 100 mg, less than 500 mg, less than 750 mg, less than 1 g or more than 1 g. Administration may be by numerous routes of administration, but intravenous, intrathecal, intranasal and/or intracerebrospinal fluid are often used as routes of administration.

In some embodiments, the disclosed EVs are administered within 24 after a stroke or trauma. However, in some embodiments, the EVs are administered at least 1, 2, 3, or 4 weeks after a stroke or trauma. In some embodiments, the disclosed EVs are administered in multiple doses 1, 2, 3, or more days apart. In some cases, such as cases of neurodegenerative disease, the EVs are administered continuously (e.g., once every 1, 2, 3, or 4 weeks) over the course of the disease.

EVs may be loaded with small molecules, antisense oligonucleotides, siRNAs, peptides, proteins or antibodies that target, peptides or peptide translation products which are involved in neurodegenerative processes.

In certain embodiments, the disclosed EVs are loaded with additional bioactive agents or are co-administered with additional bioactive agents, especially agents which are useful in the treatment of neurodegenerative diseases.

The term "coadministered", "coadministration" or "combination therapy" is used to describe a therapy in which at least two active compounds/compositions in effective amounts are used to treat neural injury and/or a neurodegenerative disease. Although the term co-administration preferably includes the administration of EVs and at least one additional active compound to the subject at the same time, it is not necessary that the compounds/compositions be administered to the patient simultaneously, only that effective amounts of the individual compounds/compositions be present in the patient at the same time. Thus, the term co-administration includes an administration in which the EVs and the bioactive agent(s) are administered at approximately the same time (contemporaneously), or from about one to several minutes to about eight hours, about 30 minutes to about 6 hours, about an hour to about 4 hours, or even much earlier than the other compound/composition as otherwise described herein including up to a day or substantially more.

Agents which may be loaded or coadministered along with EVs may include, for example aricept, namenda, donepezil, excelon, razadyne, glantamine, rivastigmine, memantine, ergoloid, namzaric and mixtures thereof for Alzheimer's disease, biperiden, apomorphine, trihexyphenidyl, carbidopa/levodopa, rasagline, belladona, levodopa, benztropine, entacapone, selegiline, rivastigmine, pramipexole, rotigotine, bromocriptine, pergolide, ropinirole, carbidopa/entacapone/levodopa, amantadine, tolcopone, trihexiphenidyl and mixtures thereof, for Parkinson's disease, tetrabenazine, haloperidol, chlorpromazine, olanzapine, fluoxetine, sertraline, nortriptyline, benzodiazpines, paroxetine, venlafaxin, beta-blockers, lithium, valproate, carbamazepine, botulinum toxin and mixtures thereof for the treatment of Huntington's disease, anticholinergic drugs, anticonvulsants, antidepressants, benzodiazepines, decongestants, muscle relaxants, pain medications, stimulants and mixtures thereof for the treatment of motor neuron disease, selective serotonin reuptake inhibitors (SSRI's), selective norepinephrine-serotoning reuptake inhibitors (SNRI's), acetazolamide, baclofen, clonazepam, flunarizine, gabapentin, meclizine, memantine, ondansetron, scopolamine, modafinil, armodafinil, amantadine, atomoxetine, buproprion, carnitine, creatine, modafinil, armodafinil, pyrudistigmine, selegiline, venlafaxine, desvenlafaxine, buspirone, riluzole, verenicline, memantine, baclofen, tizanidine, cymbalta, lyrica, acetazolamide, carbamazepine, clonazepam, isoniazid, droxidopa, ephedrine, fludrocortisones, midodrine, levodopa, pramipexole, fluoxetine, n-acetylcysteine, baclofen, dantrolene sodium, diazepam, ropinirole, tizanidine, trihexylphenidyl, clonazepine, flunarizine, levetiracetam, primidone, topiramate, valproic acid, phenytoin, 4-aminopyridine and mixtures thereof for the treatment of spinocerebellar ataxia and riluzole for the treatment of spinal muscular atrophy. Agents for the treatment of stroke include salicylates, such as aspirin, a thrombolytic agent (alteplase) and a platelet aggregation inhibitor (clopidogrel), among others.

More generally, non-steroidal anti-inflammatory drugs (NSAIDS) and other anti-inflammatory agents may be used in the treatment of neurodegenerative diseases as described herein.

The activities of EVs described herein can be evaluated by methods known in the art. The amount of EVs required for use in treatment can vary not only with the particular cell from which the EVs are prepared, but also with the route of administration, the nature of the condition being treated and the age and condition of the patient and can be ultimately at the discretion of the attendant physician or clinician. In general, however, a dose can be in the range of from about 0.01 mg/kg to about 10 mg/kg of body weight per day.

Identifying EVs useful in the present methods for treating a spinal cord injury, stroke, traumatic brain injury and/or a neurodegenerative disease which occurs by modulating the activity and expression of a disease-related protein and biologically active fragments thereof can be made by screening EV activity in any of a variety of screening techniques. The screening can be made for whole EVs or their contents. Fragments employed in such screening tests may be free in solution, affixed to a solid support, borne on a cell surface, or located intracellularly. The blocking or reduction of biological activity or the formation of binding complexes between the disease-related protein, the EVs and/or one or more components of the EVs may be measured by methods available in the art.

A number of embodiments of the invention have been described. Nevertheless, it will be understood that various modifications may be made without departing from the spirit and scope of the invention. Accordingly, other embodiments are within the scope of the following claims.

EXAMPLES

Studies were conducted to determine whether EVs confer paracrine benefits on neural stem cells and play a role in both optimal in vitro neural cultures conditions and in therapeutic outcomes of neural stem cell treatments. The objective of the study was to determine if it was possible to isolate EVs from human stem cells of a neural lineage, specifically neural progenitor cells and/or differentiated post-mitotic neuronal cells. EVs were purified from neural progenitor cells (SOX 1+ and 2+, OCT4−; hNP1™ ArunA Biomedical), derived from human pluripotent stem cell lines or differentiated neuronal cells (β-III tubulin (Tuj1)+, MAP2+, Oct4−); hN2™ ArunA Biomedical).

Example 1

Human pluripotent stem cells [see, Chambers, et al., Methods Mol Biol, 2016. 1307: p. 329-43] lines were cultured in media absent of serum such as MTeSR or E8 which is commercially available from vendors such Stem Cell Technology using feeder free conditions or media composed of knock-out serum replacement (KSR) media (DMEM=F12, 2 mM L-glutamine, 0.1 mM MEM nonessential amino acids, 50 U/mL penicillin, 50 mg/mL streptomycin, and 20% KSR) (all from Gibco, Carlsbad, CA) and 4 ng/ml basic fibroblast growth factor bFGF; R&D Systems, Minneapolis, MN). Cells were cultured on Mitomycin-C (Sigma, St. Louis, MO) mitotically inactivated murine embryonic fibroblasts (MEF) or without feeders, manually or enzymatically dissociated, and passaged to new feeder layers every 2-5 days. For feeder-free culture of hPSC in Conditioned media, cells grown on MEF were washed once with PBS (without Ca2+ and Mg2+), and then incubated with 0.25% trypsin (Gibco) until the MEF layer began to lift off the dish. The floating MEF layer was discarded after agitating it to release adherent stem cells that were collected, centrifuged, and resuspended in MEF-conditioned media (CM). CM was prepared by placing 20% KSR media on MEF for 24 h and then supplementing the collected media with an additional 4 ng/ml of bFGF. Cells were plated on tissue culture dishes coated with laminin substrate (1 mg/cm2; Sigma) and grown to ~90% confluence. The cells were passaged at least three times to minimize MEF contamination [see, Boyd, et al., Tissue Eng Part A, 2009. 15(8): p. 1897-907, Mumaw, et al., Microsc Microanal, 2010. 16(1): p. 80-90 and Young, et al., Neuroscience, 2011. 192: p. 793-805,]. Regardless of the culture method all media is collected and EVs are collected from the media and used to treat patients After manual passage onto fresh feeder cells, hESCs were allowed to proliferate in ES medium for 7 days (stage 1). Cell differentiation was then induced with either DN2, MEDII, or ES medium for another 7 days (stage 2). DN2 medium is DMEM/F12-based medium supplemented with $N_2$ (Gibco), L-glutamine, penicillin/streptomycin (P/S), and 4 ng/ml bFGF. MEDII medium for this study is DN2 medium supplemented at 50% (unless otherwise noted) with conditioned medium. To understand and follow the differentiation steps applied here, phenotype marker expression was examined at various time intervals. At stages 1, 2, and 3, populations were harvested and the markers Musashi-1, Nestin, and Oct-4 were observed. Immunocytochemical analysis was also performed on the adherent cell population. The cells at both stages were double-stained with Nestin and Oct-4 and observed under the fluorescence microscope for immunocytochemical examination associated with morphology. Groups that displayed phenotypic difference were then subjected to quantitative analysis for these same markers using flow cytometry. All experiments were replicated three times unless otherwise noted. After manual passage onto fresh feeder cells, hESCs were allowed to proliferate in ES medium for 7 days (stage 1). Cell differentiation was then induced with either DN2, MEDII, or ES medium for another 7 days (stage 2). DN2 medium is DMEM/F12-based medium supplemented with N2 (Gibco), L-glutamine, penicillin/streptomycin (P/S), and 4 ng/ml bFGF. MEDII medium for this study is DN2 medium supplemented at 50% (unless otherwise noted) with conditioned medium (described above). Stages 1, 2, and 3, populations were harvested and the markers Musashi-1, Nestin, and Oct-4 were observed. Immunocyto-chemical analysis was also performed on the adherent cell population. The cells at both stages were double-stained with Nestin and Oct-4 and observed under the fluorescence microscope for immunocytochemical examination associated with morphology. Groups that displayed phenotypic difference were then subjected to quantitative analysis for these same markers using flow cytometry. All experiments were replicated three times unless otherwise noted.

After manual passage onto fresh feeder cells, hESCs were allowed to proliferate in ES medium for 7 days (stage 1). Cell differentiation was then induced with either DN2, MEDII, or ES medium for another 7 days (stage 2). DN2 medium is DMEM/F12-based medium supplemented with N2 (Gibco), L-glutamine, penicillin/streptomycin (P/S), and 4 ng/ml bFGF. MEDII medium for this study is DN2 medium supplemented at 50% (unless otherwise noted) with conditioned medium (described above). At stages 1, 2, and 3, populations were harvested and the markers Musashi-1, Nestin, and Oct-4 were observed. Immunocytochemical analysis was also performed on the adherent cell population. The cells at both stages were double-stained with Nestin and Oct-4 and observed under the fluorescence microscope for immunocytochemical examination associated with morphology. Groups that displayed phenotypic difference were then subjected to quantitative analysis for these same markers using flow cytometry. All experiments were replicated three times unless otherwise noted.

hPSC were allowed to proliferate in hPSC medium (any of those described above) for approximately 5 to 10 days (stage 1) as a monolayer or as embryoid bodies. Cell differentiation was then induced with medium typically DMEM/F12-based medium supplemented with N2 (Gibco), L-glutamine, penicillin/streptomycin (P/S), and usually 4 ng/ml bFGF. Nestin, and Oct-4 were observed and neural rosettes form. Neural rosettes are isolated (manually or enzymatically and are immunocytochemical analysis was also performed on the adherent rosette population. The cells at both stages were double-stained and are Nestin+ and Oct-4- and observed under the fluorescence microscope for immunocytochemical examination associated with morphology [Shin, et al., Stem Cells, 2006. 24(1): p. 125-38]. The rosettes when isolated from most of the contaminating cells are considered human neural progenitor cells. Briefly, hNP cells were grown on poly-ornithine (20 mg/mL)/laminin (Sigma-Aldrich, Inc.) (5 mg/mL) coated plates or other ECM such as Matrigel, and maintained and expanded in media with 2 mM L-glutamine and 20 ng/ml b-FGF. hNP Cells were passaged approximately every 48 h and split 1:2 following manual dissociation [see, Mumaw, et al., Id., Young, et al. Id. and Dhara, et al., Methods Mol Biol, 2011. 767: p. 343-54].

Alternatively, neural induction may be stimulated by inhibition of SMAD signaling using inhibitors of Activin/Nodal pathway, and/or BMP signaling (examples of inhibitors might be Noggin, SB431542 [Chambers, et al. Nat Biotechnol, 2009. 27(3): p. 275-80], Compound C [Zhou, et al., Stem Cells, 2010. 28(10): p. 1741-508], or other strategies alone or in combination). Cells may be cultured on matrigel or other extracellular matrices, in AB2, Neurobasal, or other mediums listed above, in the presence of absence of Sonic Hedgehog [Chambers, et al., Id., and Zhou, et al., Id.].

hNP cells differentiated into neurons on poly-ornithine and laminin coated plates or other ECM such as Matrigel under maintenance media described above without bFGF and LIF. Alternatively LIF or EGF are added hNP cells were allowed to differentiate under these two conditions for 1 to 7 weeks [Mumaw, et al., Id., and Dodia, et al., PLOS One, 2011. 6(8): p. e232669].

After 1 to 4 weeks of neuronal differentiation such as hNP cells differentiated into neurons on poly-ornithine and laminin coated plates (under two conditions in maintenance media without bFGF or bFGF and LIF or EGF), astrocytic differentiation was induced by switching the neural to cells from hNSC Maintenance Medium to the basic medium (DMEM HAM's F12 medium, glutamine, Penicillin/Streptomycin) supplemented with 1% FCS (Gibco). See Mumaw, et al., Id. and Young, et al., Id. Finally, multilinear differentiation was achieved by replacing the maintenance medium by the basic medium containing 10% of FCS. After 45-50 days cultures were nearly 100% positive for glial markers S100β and vimentin [Palm, et al., Sci Rep, 2015. 5: p. 1632110].

Alternatively, hNP cells were propagated as adherent monolayer cultures in a proliferation media (such as AB2™, ANS™ Neurobasal™, 1×B27, 1×Glutamax™, P/S, FGF2 (10 ng/mL) as described (Shin et al., Id.), and differentiated by removal of FGF. For astrocytic differentiation of hNP cells, neuronal differentiation media were supplemented with recombinant proteins, such as BMP2 and combinations of chemicals such as Azacytidine, Trichostatin A, or similar molecules for 1-5 days, with complete media changes in between, followed by differentiation media supplemented with the molecules separately or in combination. Cells were harvested prior to analysis at 5, 15 or 30 days of treatment or for cryopreservation at d6 or d10 of differentiation. For cryopreservation, cells were dissociated with Accutase™ and frozen in differentiation media containing 10% DMSO [Majumder, et al., Stem Cell Res, 2013. 11(1): p. 574-86].

When hPSC cultured without feeders as described above reached approximately 90% confluence, the 100 mm dishes were washed with PBS++(with Ca2+ and Mg2+) and replaced with 10 mL of fresh endothelial growth media 2 microvascular (EGM2-MV) (Lonza; 5% FBS, proprietary endothelial basal media 2 (EBM2) basal media and concentrations of bFGF, VEGF, EGF, and R3-IGF-125). The media was changed every 2-3 days over a period of 20-30 days. After transition from hESC to epithelial sheet was completed, the cells were trypsin passaged to a T75 flask and grown to confluence. To expand the initial cell culture, cells were passaged and seeded at a target density of approximately $4\times10^4$ cells/cm$_2$ per flasks. For subsequent culture for experimentation, cells were subcultured at $10^6$ cells-T75 flask (approximately $1.3\times10^5$ cells/cm$_2$) and grown to confluence over 5-7 days [Boyd, et al., Id].

Example 2

Methods

Cell medium was collected from confluent cultures 24 hours post media change and frozen at −20° C. Medium was thawed at 4° C. overnight and filtered through a 0.22 μm Steriflip unit prior to EV purification.

Extracellular Vesicle Purification by Ultracentrifugation.

Isolation of extracellular vesicles from cell culture media was performed according to the protocols published by Théry, C., et al., Isolation and Characterization of EVs from Cell Culture Supernatants and Biological Fluids, in Current Protocols in Cell Biology. 2001, John Wiley & Sons, Inc. Briefly, filtered media was serially centrifuged at 300×g for 10 minutes, and supernatant was transferred to a fresh tube for centrifugation at 2,000×g for 10 minutes. Collected supernatants were then centrifuged at 10,000×g for 30 minutes, and resultant supernatant collected into a fresh tube. To label EVs, DiI was added to the purified supernatants at a final concentration of 10 UM and incubated at room temperature for 30 minutes. Supernatants were distributed into 11.5 ml Sorvall Ultracrimp tubes and sealed before transfer into a Sorvall T880 fixed angle rotor for centrifugation at 100,000×g for 70 minutes at 4° C. Supernatant was carefully removed and pelleted material resuspended in PBS and transferred into another ultracrimp tube, and again centrifuged at 100,000×g for 70 minutes at 4° C. The PBS was removed and pelleted material from each tube was resuspended in 100 μl PBS. All purified EVs from the same cell type were pooled, triturated, and aliquoted into DNase/RNase free tubes (20-50 μl aliquots) for storage at −20° C.

Extracellular Vesicle Purification by Ultrafiltration

Ultrafiltration of extracellular vesicles was performed according to the procedure developed for purification of cardiomyocyte derived extracellular vesicles. Amicon Ultra-15 100 kDa molecular weight cutoff filters were wetted with 10 ml PBS and centrifuged in a swinging bucket rotor at 4,000×g for 10 minutes. The PBS was discarded and the cell culture medium was added to the filter approximately 15 ml/tube and centrifuged at 4,000×g for 10 minutes. Another 15 ml culture medium was added to the filter when filtering stem cell derived extracellular vesicles, because less media was retained in the filter from the first run through, so approximately 30 ml of medium total was filtered for the H9 derived NP, Astrocyte, and MSC lines, while only 15 ml of medium was filtered for SH SY5Y cells; the media in the filter was centrifuged at 4,000×g in 5 minute increments to obtain approximately 1 ml of retentate. This was then either moved to a 1.5 ml tube for DiI labeling (at 10 UM for 30 minutes) or for unlabeled purification diluted to 15 ml with PBS and washed twice before repeating 5 minute centrifugation increments until a final volume of 1-1.5 ml was obtained. The purified extracellular vesicle preparation was then pooled from the same cell type and dispersed into approximately 100 µl aliquots (DNase/RNase free tubes) and stored at −20° C.

DiI-Labeling Vesicles

Labeled vesicles were generated by ultrafiltration. After the ultrafiltration was complete, the filter retentate was moved to a centrifuge tube, and 10 µM DiI was added to the supernatant for 30 min. PBS was added to the filtration unit during this time to prevent the filter from drying out. After incubation with the labeling agent, supernatant was transferred back into the filtration device and washed three times with PBS (approximately 45 ml) to remove free label. After the final wash the retentate was concentrated to approximately 1 ml, which was aliquoted and stored at −20° C.

Electron Microscopy

Vesicle preparations were mixed 1:1 with 4% paraformaldehyde (PFA) (to yield 2% PFA final) and incubated for 15 minutes. 5 µl droplets of fixed vesicle suspensions were transferred to Formvar-coated grids for 20 min., and then washed by transferring to drops of PBS. Grids were transferred onto drops of 1% glutaraldehyde for 5 min, and then moved over several drops of water to remove residual glutaraldehyde before transferring to uranyl-oxylate. Grids were imaged by electron microscopy at 80 kV.

Results

While initial reports indicate that neural progenitor cells secrete fewer EVs than other cell types, ultrastructural analysis of the cells revealed prominent vesicles of endocytic origin (FIGS. 2A-2C), and many were in close proximity or associated with the outer limiting membrane of the cell (FIG. 2D, 2E). Cargoes within the multivesicular bodies (MVBs) vary in size (FIG. 2B, 2C) and are occasionally visualized budding off into the vesicle (arrow). Smaller vesicles seem to coalesce into larger MVBs as they move to the periphery of the cell (FIG. 2F, 2G). It was possible to purify and visualize vesicles from the media of neural progenitor cells (FIG. 2H). These data suggest that neural progenitor cells do release extracellular vesicles into the cellular medium, and these vesicles can be purified using published EV purification protocols. All scale bars are 500 nm.

Figure 3A:
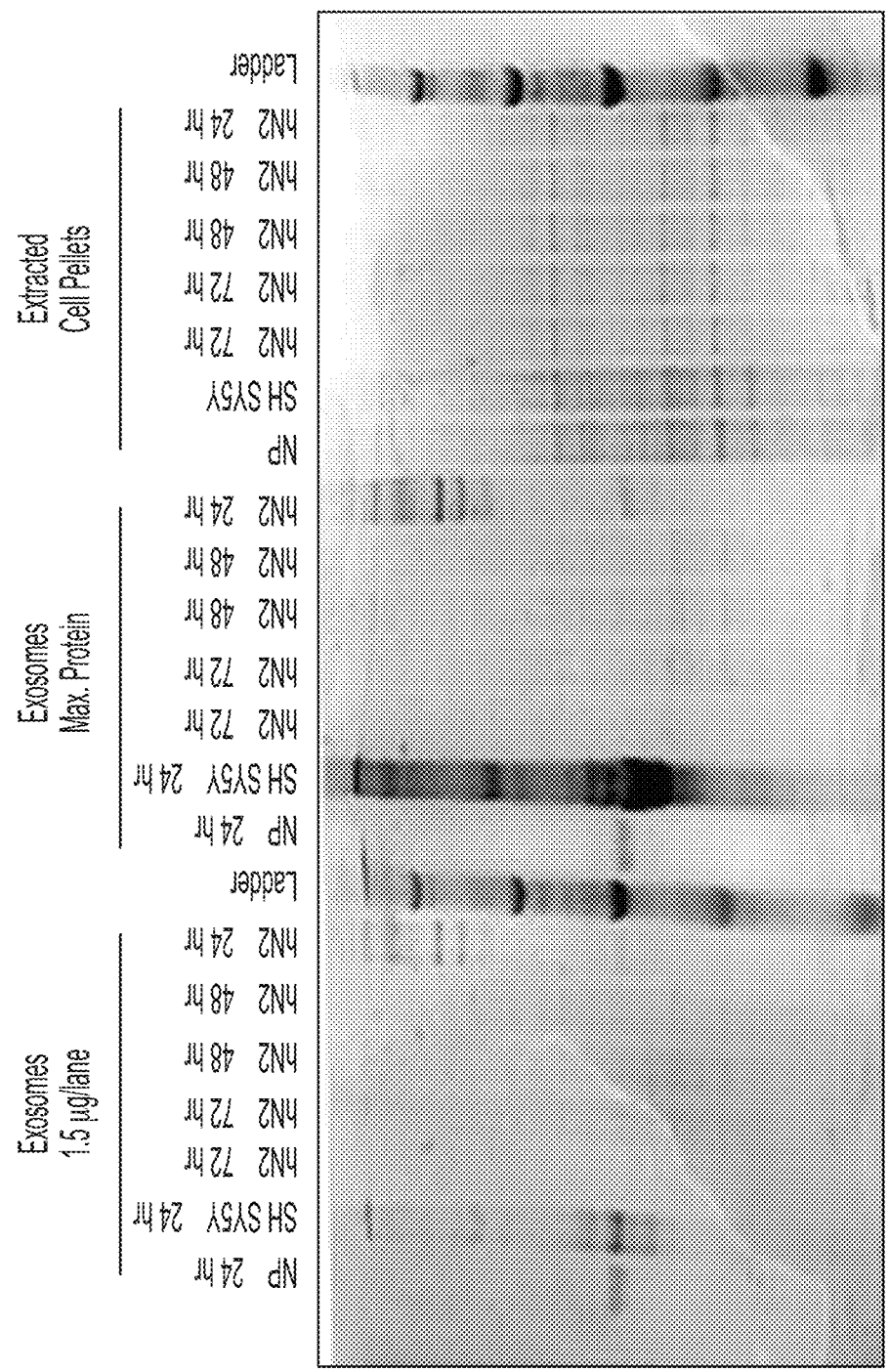
FIGS. 3A to 3D show that EVs can be purified and detected by nanoparticle tracking analysis.
Figure 3B:
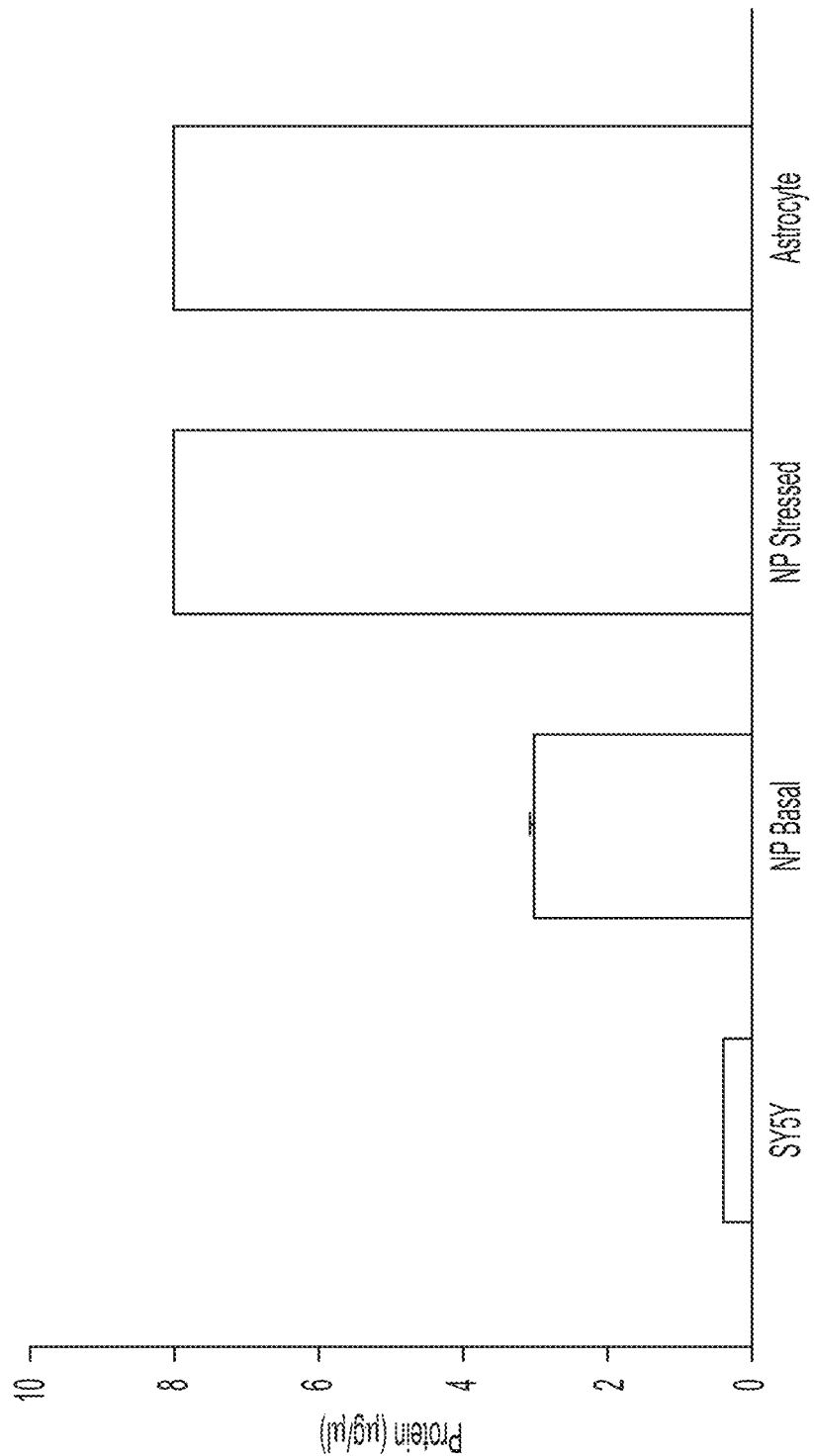
Figure 3C:
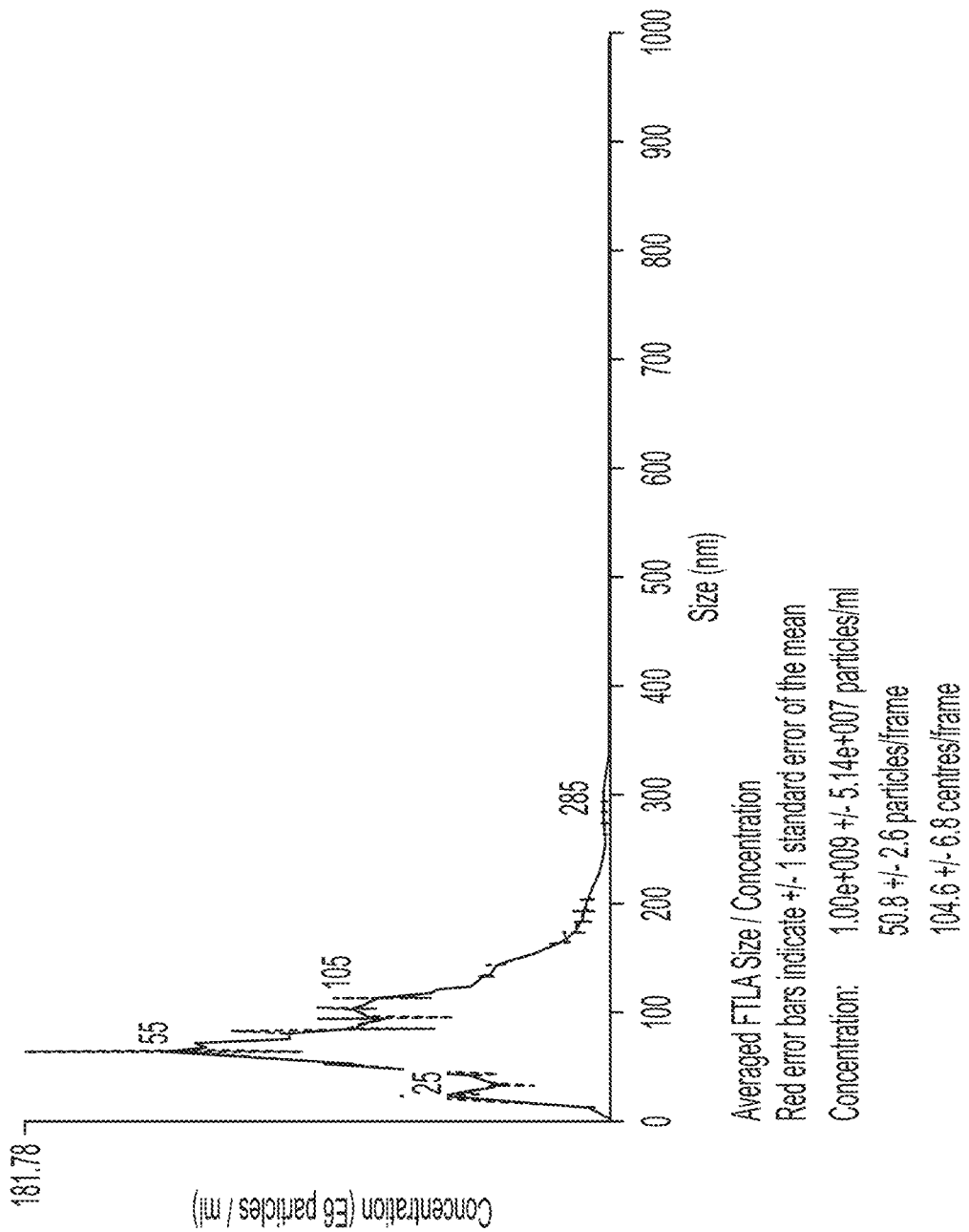
Figure 3D:
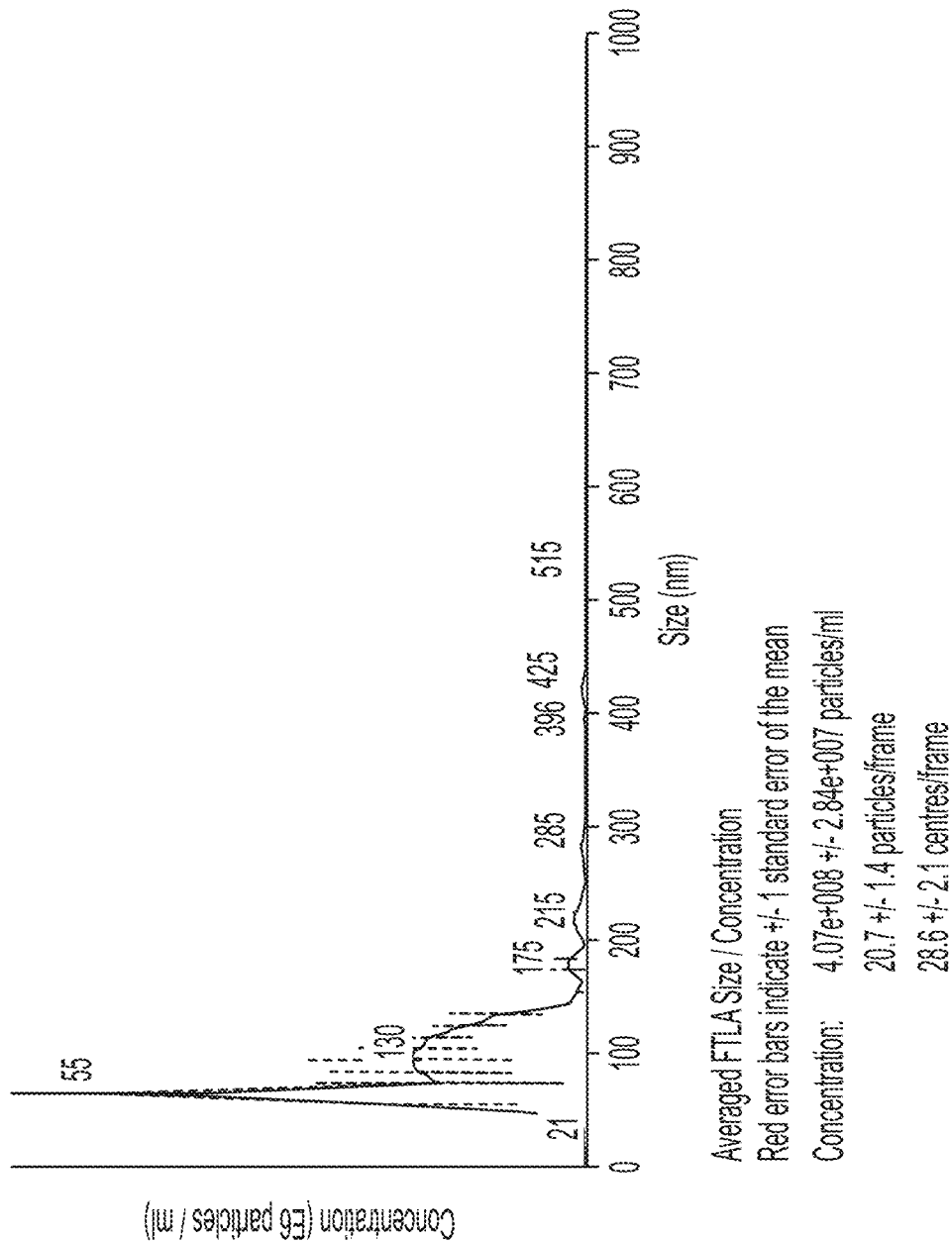

After realizing that neural progenitor cells have the capability of producing EVs that could be purified and visualized by electron microscopy, the process of characterizing the purified vesicles from multiple cell types began with protein profiling by Coomassie stain (FIG. 3A), and BCA Analysis of total protein content (FIG. 3B). The protein profiles were compared from neural progenitor cells, differentiated neural cells, and astrocytes, all derived from the same ES cell line, and SH SY5Y cells, a human neuroblastoma cell line used as a positive control. Early experiments indicate that the protein profile overlaps, but there are distinct proteins in the neural progenitor and differentiated neural cells, even though the cells are of the same genetic origin. Similarly, comparing the size profiles of the vesicles from neural progenitors, and astrocyte cells from the same genetic origin indicates that the size of vesicles from the 2 cell types overlap (including a large percentage of 55 nm vesicles), but there are distinct subpopulations that vary between the two cell types, with astrocytes showing unique vesicle sizes including a 25 nm population, and slightly larger 135 nm population (FIGS. 3C, 3D). Taken together, these data indicate that cargoes are specifically targeted into MVBs, and these cargoes change in the differentiation process, supporting a role for EVs in cell to cell communication throughout the process of development.

Figure 4:
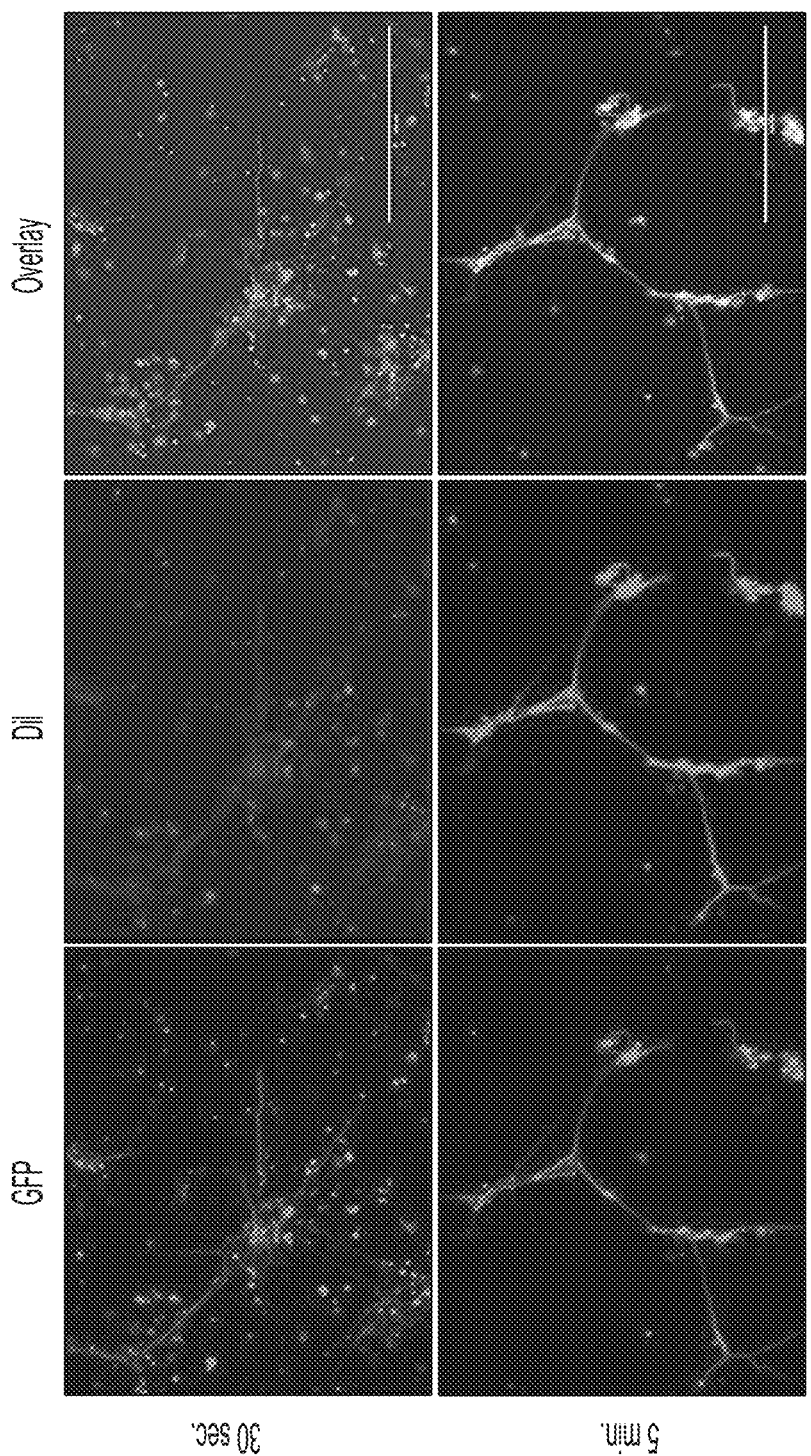
FIG. 4 shows differentiated neural cells internalize DiI-labeled EVs from neural progenitor cells. By adding 10 uM DiI to the cellular supernatant for 30 minutes prior to the final EVs spin and PBS wash, it was possible to label EVs. When added into the culture medium of differentiated cells, uptake of EVs was evident within 5 minutes.

In order to determine if it was possible to label EVs, and visualize their uptake by another cell, differentiated neural cells (6-8 weeks in differentiation medium without fibroblast growth factor (FGF) were treated with astrocyte derived vesicles at timepoints ranging from 30 seconds through 30 minutes, after which, cells were fixed, and stained for β-III tubulin. At the earliest time points, few vesicles were found in the cells, (FIGS. 4A-4C). By 5 minutes in the culture it was possible to find neural cells with prominent red fluorescence, indicating vesicle uptake in these cells (FIGS. 4D-4F).

Figure 5A:
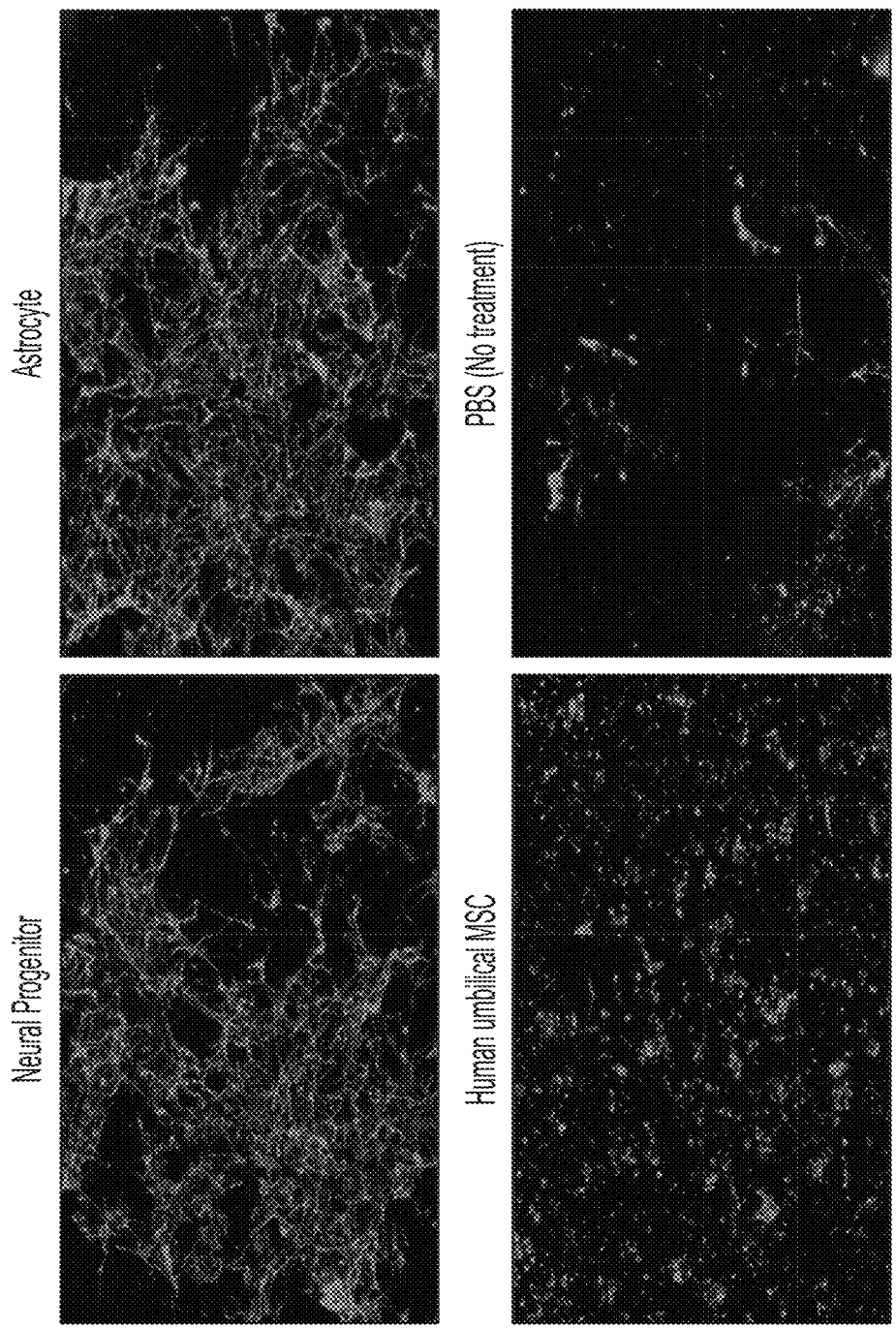
FIGS. 5A and 5B show EVs from neural progenitors protect more differentiated neural cells from starvation stress.
Figure 5B:
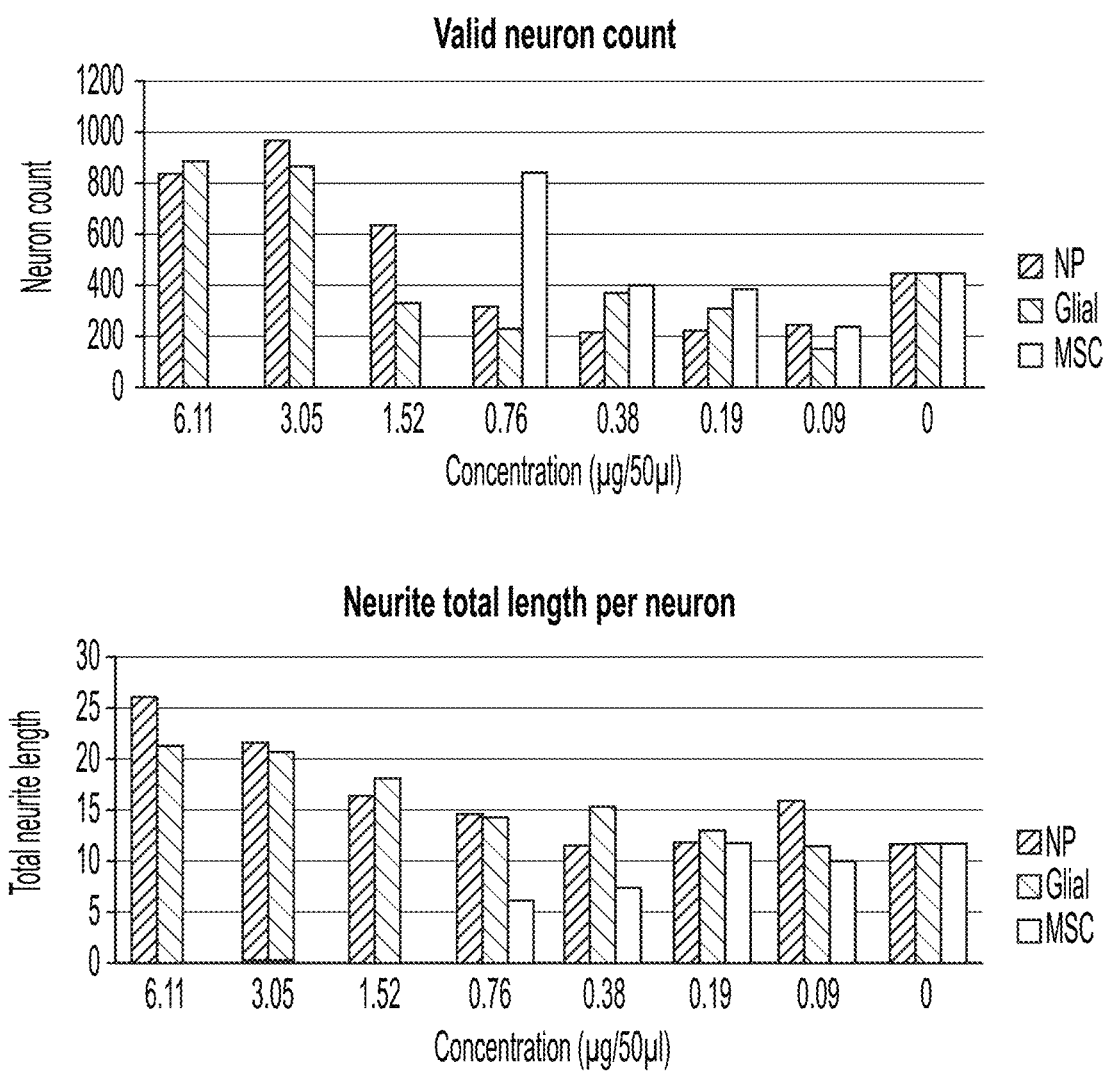
Figure 5B:
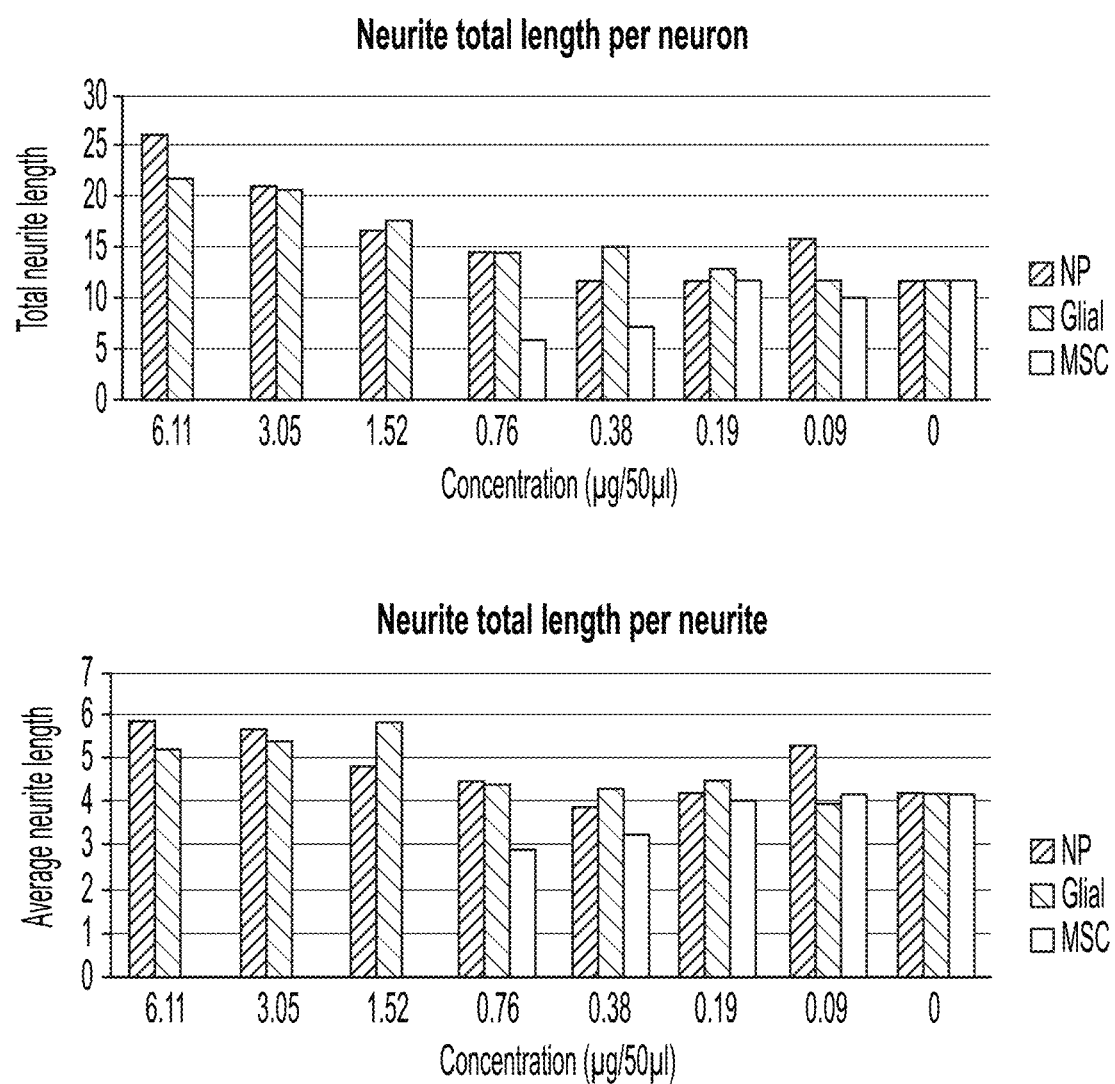

To determine if these vesicles could elicit an effect in recipient cells, differentiated neural cells were treated with serially diluted concentrations of vesicles derived from neural progenitors, astrocytes, or MSCs all derived from the same ES cell line, or SH SY5Y cells. These cells were then subjected to nutrient deprivation over 10 days and analyzed for neurite outgrowth. As expected, in wells that received only PBS the monolayer was disrupted and few cells were left (FIG. 5. D). However, cells that received the highest concentrations of EVs from either neural progenitors or astrocytes were able to survive this nutrient deprivation, and the monolayer of cells with intact neurites were largely still intact (FIG. 5. A, B). Wells treated with MSC derived EVs contained more cells than untreated wells, but the monolayer was no longer intact and neurites were largely lost (FIG. 5. C). These data indicate that vesicle treatment protected the recipient cells from nutrient deprivation, and importantly, indicate that cells respond differently to vesicles that originate from different cell types, even if the vesicles are from an isogenic or autologous source.

Taken together, these data support the idea that the parental source of origin has an impact on the vesicles that result. This has huge implications for considering extracellular vesicles as a therapeutic source that can potentially be exploited for regenerative medicine, and highlights the need for vesicles derived from neural sources for the treatment of CNS injuries and/or disease. Importantly, these data also indicate that not only neuron derived vesicles, but also glial vesicles provide benefit in vitro.

Example 3

Biodistribution Methods: Rodent biodistribution by single-photon emission spectroscopy. 1.5-2 mCi of Indium-111-oxine in PBS was added to 200 µl doses containing EVs ($\sim 2.7 \times 10^{11}$ vesicles/kg) and incubated at 37° C. for 20 minutes. Free indium was removed by three repeated PBS washes through an Amicon 100 kDa ultrafiltration device. Collected EVs were diluted to 200 µCi of radioactivity per dose, and injected intravenously into the mouse tail vein, either 1 hour or 24 hours post-stroke. Control animals received injection of free indium-111-oxine. Whole body and head single photon emission spectroscopy (SPECT) images were acquired by Mediso's nanoScan microSPECT/CT system 1 and 24 hours after injection, and projection images were reconstructed according to maximum intensity to determine radioactivity in the brain and throughout the body.

Piglet biodistribution: EVs were concentrated by ultrafiltration using Centricon units as previously described and then moved to 50 ml falcon tubes for DiR labeling (5 µM) in the dark for 30 minutes. Labeled EVs were collected by ultracentrifugation at 100,000×g for 4 hours. Pelleted EVs were washed with PBS and again collected by ultracentrifugation. EVs were resuspended in PBS and diluted into $2.7 \times 10^{10}$ vesicle/kg body weight (in 200 µl PBS) doses for individual piglets based on NanoSightNS 300 nanoparticle tracking analysis. Piglets were anesthetized with isoflourane for intravenous injection (tail vein), intranasal delivery, cerebrospinal fluid EV injection into the subarachnoid cistern, or injection directly into the brain parenchyma. For intraparenchymal injection EVs were delivered at a flow rate of 5 µl per minute. Animals were euthanized by isoflourane followed by $CO_2$ asphyxiation 30 minutes after completion of EV delivery. Brain, heart, liver, kidneys, lungs, and spleen were removed and imaged using Lumina IVIS (model) to detect DiR fluorescence.

Figure 6A:
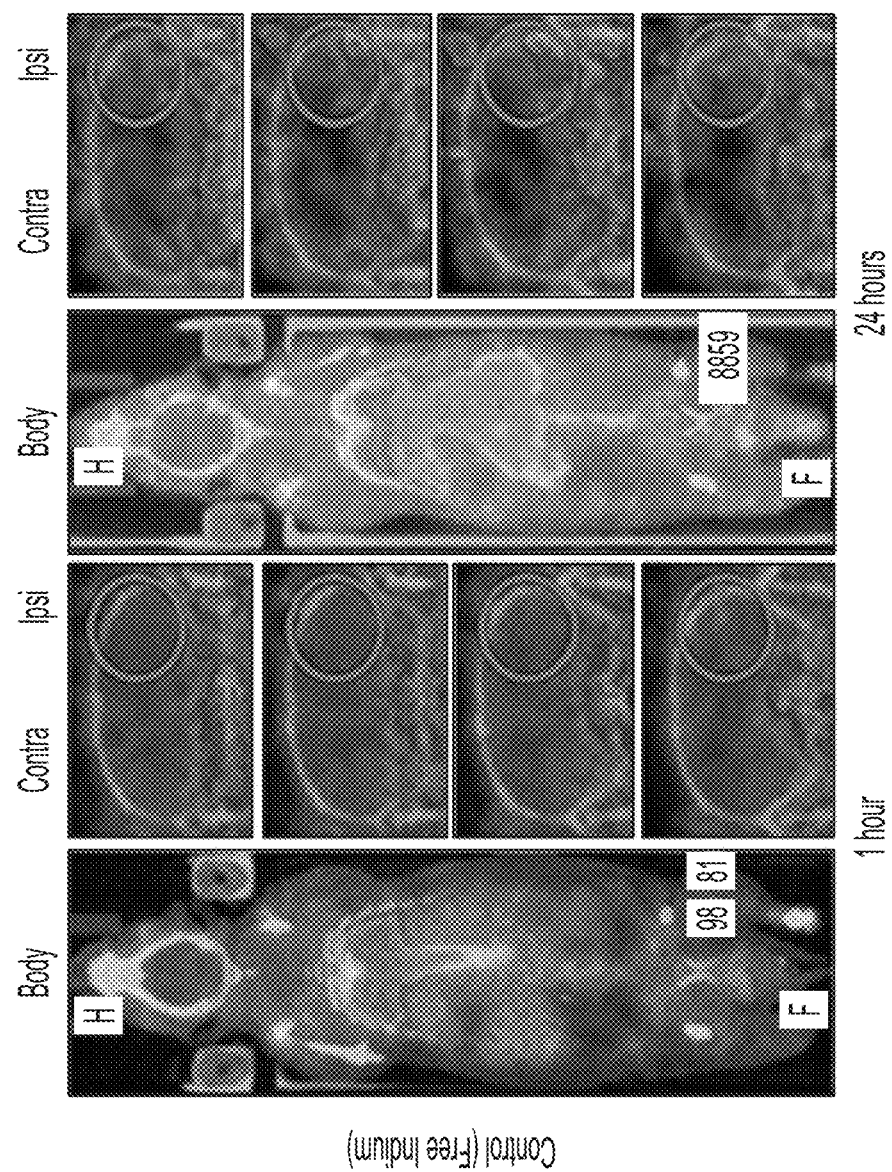
FIGS. 6A to 6C show indium-111 labeled EVs can be found in proximity of stroke tissue within 1 hour of injection.
Figure 6B:
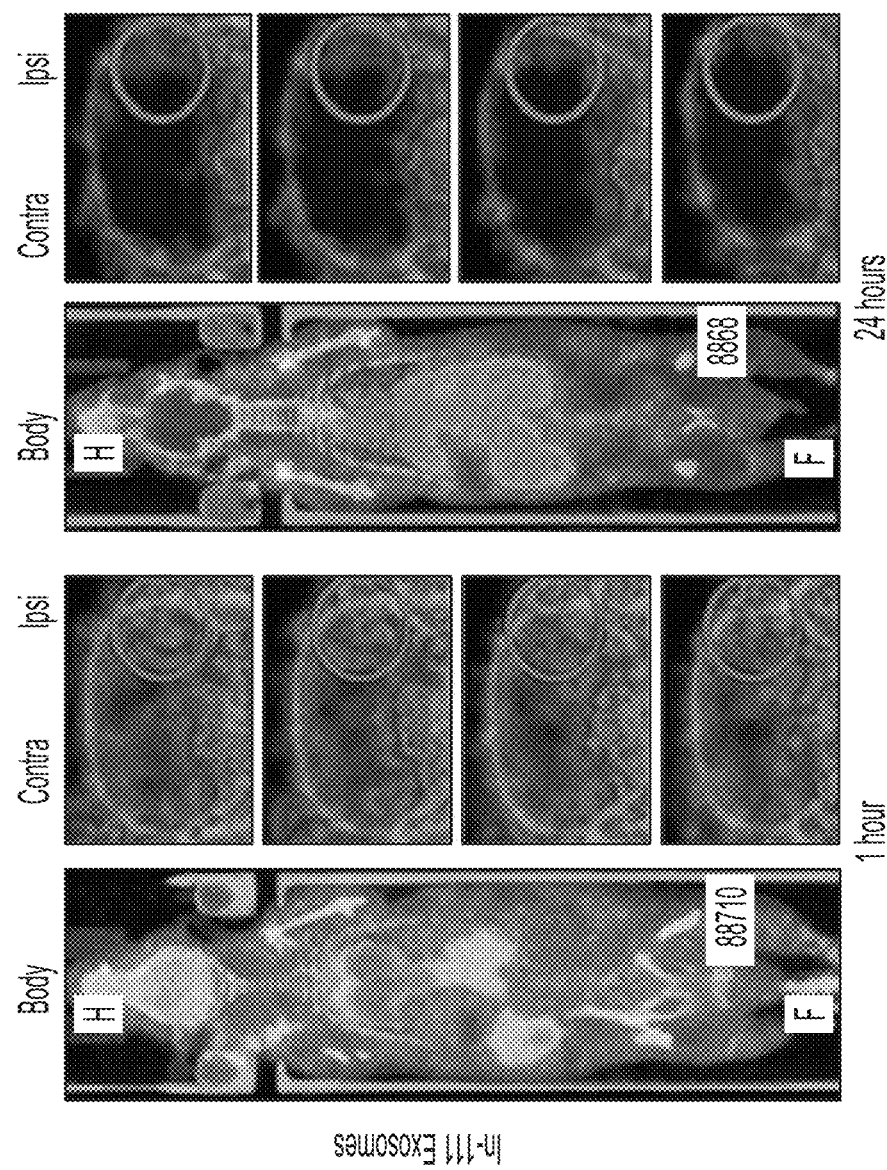
Figure 6C:
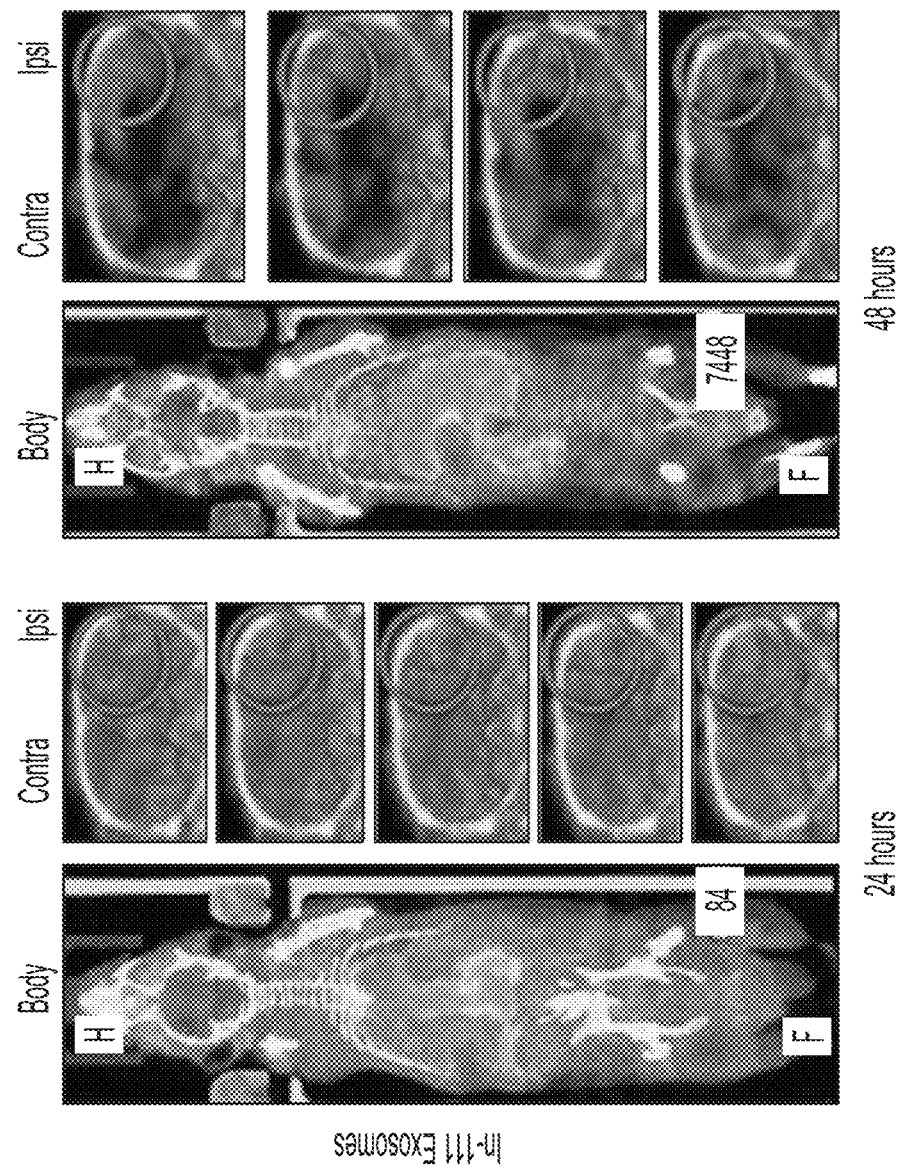

Mouse: EV biodistribution was evaluated after either free indium-111 or indium-111 labeled EVs were injected into the mouse tail vein either immediately (FIG. 6B), or 24 hours post-stroke (FIG. 6C). SPECT scans were performed 1 hour after injection (FIG. 6A, 6B, 6C, left panels), and again 24 hours after injection (FIG. 6A, 6B, 6C, right panels). Images reconstructed by maximum intensity indicate that indium-111 labeled EVs are distributed throughout the bodies filtration organs in lungs, liver, spleen, and kidneys at both the initial timepoint, and 24 hours later (FIG. 6B, 6C; whole body scans) while free indium-111 is initially localized mostly to the lungs before disbursing into the liver, spleen, and kidneys 24 hours later (FIG. 6A; whole body scans) likely indicating clearance through the renal system. Uniquely, labeled EVs were present in the brain in proximity of the stroke within 1 hour of injection when injected either immediately or 24 hours after stroke (FIG. 6B, 6C; circles), indicating either access from the circulation due to disruption of the blood brain barrier, homing to the damaged tissue, or some combination of the two. Free indium did not localize to the stroked tissue at either time point assessed (FIG. 6A, circles).

Uniqueness: This is the first time that anyone has shown that IV injection of EVs are actually distributed in and around the infarcted brain following stroke. The majority of the EVs were distributed in other organs such as heart, liver, lung, and kidney, and we have data to suggest that the EVs for the first time have a systemic effect on the immune response post stroke (data in other sections). Thus it is likely that systemic effects of peripheral EVs have a positive effect on molecular and phenotypic benefits following stroke. Thus the EVs may have a direct effect at the site of injury, could be via local immune cells or via direct effect on the neurons, as well as a system effect on the immune system. This is the first data showing biodistribution in a large animal brain.

Figure 7:
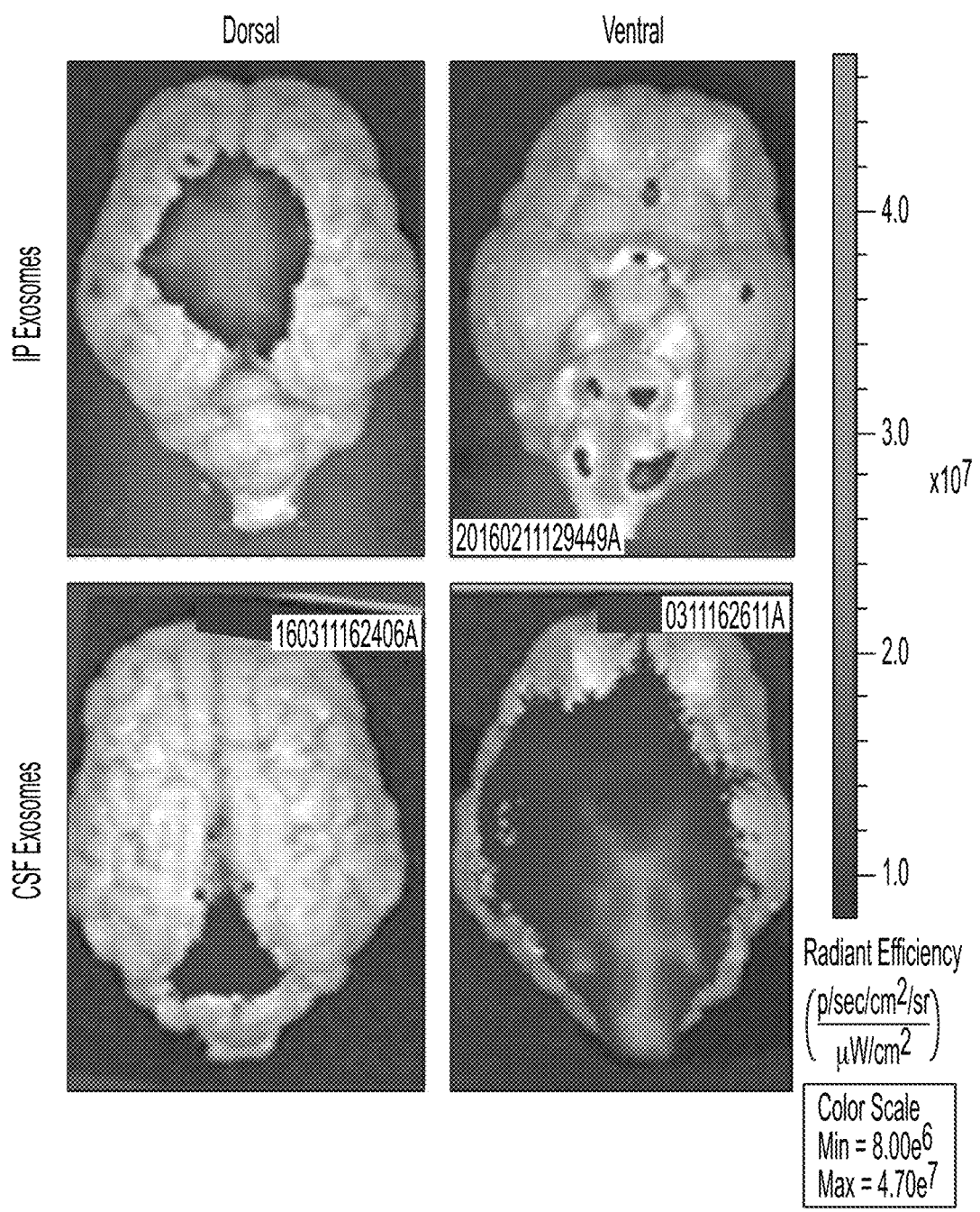
FIG. 7 shows biodistribution of DiR labeled EVs in piglet brain. DiR labeled EVs (approximately $2.7 \times 10^{10}$ vesicles/kg) were detectable from both the dorsal and ventral via direct delivery into the brain parenchyma by stereotaxic injection (top panels), and into the CSF in the subarachnoid space (lower panels). Fluorescence was detectable in the dorsal and ventral aspects of the brain in both instances, but more pronounced in the dorsal region when injected IP (top panels), and ventral areas of the brain following CSF injection (lower panels).

Piglet: In order to optimize EV delivery to the brain following stroke, biodistribution of fluorescently labeled (DiR, 5 µM) was evaluated in uninjured piglets. Labeled EVs were detected in the brain after injection directly into the parenchyma (FIG. 7, top panels), or into the CSF of the subarachnoid cistern at the base of the skull (FIG. 7, lower panels). This is the first demonstration of EV biodistribution in a large animal study.

Example 4

Methods
Mouse Model

Middle-aged C57/B6 male mice (retired breeders of 9-11 months) were pre-trained for adhesive tape test (ATT) for 3 days prior to the stroke surgery (3 trials/day). Mice were marked for identity, numbered, and randomized for therapy after stroke in a block size of 4 (4 animals from the same cage) to different treatment groups following induction of embolic stroke. The surgeon performing the stroke surgery and cerebral blood flow (CBF), and the investigator performing neurobehavior and neurologic deficit scoring remained blinded to the identity of the groups. All four therapies received were thawed and injected intravenously at 2, 14 and 38 hrs post stroke with doses 1, 2 and 3, respectively. Relative cerebral blood flow (CBF) was measured at 6 and 48 hrs post stroke. Neurologic deficit score (NDS) was assessed at 48 hrs post stroke; the ATT that reflects the somatosensory function was performed at 96 hrs post stroke just prior to euthanasia. Mortality was monitored daily and recorded until day 4 and prior to euthanasia.

Embolic Stroke

Mice were sedated with Buprenorphine (0.05 mg/kg SC) 20 min prior to stroke surgery, and anesthetized with 3.5% isoflourane. Surgical plain of anesthesia was maintained with 1.5-2.0% during the surgery. Body temperature was maintained at 37° C. by a thermo-regulated surgery pad. By a midline incision on the ventral side of the neck, the right common carotid artery (CCA), external carotid artery (ECA), and the internal carotid artery (ICA) were assessed. A temporary atraumatic clip was placed on the CCA to prevent loss of blood during catheter insertion. A modified PE-10 catheter containing a single fibrin rich clot (9±0.5 mm length) was introduced into the ECA and advanced into the ICA. The clot was gently injected with 100 µL of PBS, the catheter was removed immediately after embolization, and the arterial wound was secured to prevent blood loss. Induction of stroke was confirmed using on-site portable single point cortical laser Doppler flowmetry (PeriMed Inc.). Finally, the temporary clip was removed and the blood flow in the CCA was reinstated. The site of surgery was closed using #6 sterile monofilament nylon suture, and Buprenorphine (0.05 mg/kg SC) was again injected. Mice were transferred to clean recovery cages and animal temperature was maintained. Conscious mice were transferred to clean regular cages with free access to food and water. NAPA gel and lactated ringers solution were provided as needed, in case of any sign of dehydration; otherwise 1 ml of regular sterile saline pre-warmed at 37° C. was injected SC every 12 hours.

Laser Speckle Contrast Imaging:

Briefly, 6 hrs after stroke, mice were anesthetized using isoflourane, while body temperature was maintained at 37±0.5° C. The skull was shaved and a midline skin incision was made to expose the middle cerebral region. Perfusion images were acquired using PeriCam high resolution Laser Speckle Contrast Imager (LSCI; PSI system, Perimed) with a 70 mW built-in laser diode for illumination and 1388× 1038 pixels CCD camera installed 10 cm above the skull (speed 19 Hz, and exposure time 6 mSec, 1.3×1.3 cm). Acquired video and images were analyzed for dynamic changes in CBF. Overall perfusion of the ischemic region will be compared to an equally sized region of interest from the uninjured contralateral hemisphere to estimate relative CBF. The skin wound was closed using tissue glue. At 48 hrs post-stroke, the skin wound was again opened, cleaned, and the middle cerebral artery region was exposed to repeat the LSCI procedure as previously described.

Neurologic Deficit Score (NDS):

Neurologic deficits in mice were assessed by investigators blinded to the therapeutic group at 48 hr post stroke on a 5-point scale with the highest number indicating the worst outcomes and lower number indicating better neurological outcomes according to the following criteria: 0, no deficit (normal mice); 1, forelimb flexion deficit on contralateral side; 2, flexion deficit along with decreased resistance to lateral push and torso turning to the ipsilateral side when held by tail; 3, All deficits as in Score 2, including very significant circling to the affected side during the move inside the cage, and reduced capability to bear weight on the affected side; 4, All deficits as above but rarely willing to move spontaneously, and prefer to stay in rest; 5, considered terminal and euthanized in accordance with animal care requirements.

ATT for Somatosensory Test:

Adhesive tape test (ATT) was used as a test of somatosensory motor function, and was performed at 96 hrs post-stroke immediately prior to euthanasia. Briefly, naïve mice were acclimatized to the procedure of the test for 3 days prior to surgery by placing them in a transparent acrylic box (15 cm×25 cm). Two pieces of adhesive tape (0.3 cm×0.4 cm) were used as bilateral tactile stimuli after they were attached at the distal-radial region on each forelimb such that it covered the hairless part (3 pads, thenar and hypothenar). Within 180 seconds, the tape removal time was recorded as the sensorimotor function. If a mouse failed to remove the tape within 180 seconds, it was given a score of 180 seconds. Therefore, a shorter time score indicates a better outcome while longer time indicates an outcome with higher deficit.

Euthanasia and 2,3,5-Triphenyltetrazolium Chloride (TTC)-Staining:

TTC-stain differentiates between metabolically active (live or penumbra) and inactive (dead or core) tissues after stroke. TTC is a colorless solution, which is reduced to red 1,3,5-triphenylformazan (TPF) by the enzymatic action of various dehydrogenases primarily mitochondrial dehydrogenase from the living tissues, while the core (dead tissue) remains white. Therefore, larger white area indicates higher injury and infarction volume. At 96 hrs post stroke and after performing ATT, mice were deeply anesthetized with isofluorane (5%). Blood was collected via direct cardiac puncture to isolate and obtain serum later. Brains were very quickly perfused with 25 mls of cold 0.01 M phosphate-buffered saline (PBS), harvested fresh, and immediately transferred to a metallic mouse brain matrix. Looking at the infarcted area, 5-blades were placed in alternate gaps to obtain 2-mm coronal slices (4 sections per brain). Sections were individually placed in a 35-mm dish containing pre-warmed (37° C.) 3 ml of 5% TTC in PBS (Sigma) for 20-30 minutes at 37° C., followed by 2× washing with cold PBS and fixation with 10% formalin. In order to image, fixed sections were taken out of the dish and placed in order on a high-resolution Cannon Scanner. Images were cropped and saved for analysis. Corrected infarct volume was estimated using gray scale image and Scion Image software, and presented as the % volume of the uninjured side.

Blood Sample Flow Cytometry (Th17, Treg, M2)

Prior to euthanasia blood was collected and purified cells were subjected to fluorescence activated cell sorting to identify populations of immune cells present systemically including T-helper (CD4+/FOX3P+) populations, regulatory T-cells (CD4+/IL17+), and M2 macrophage (IL10+/CD206+) populations.

Results

Figure 8C:
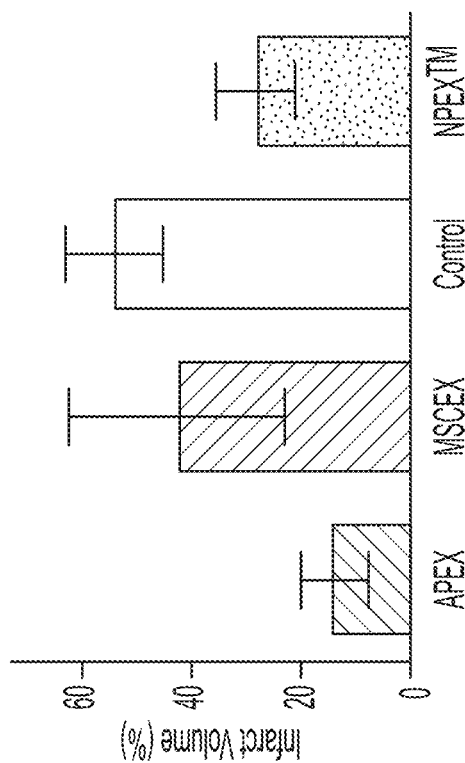
Figure 8B:
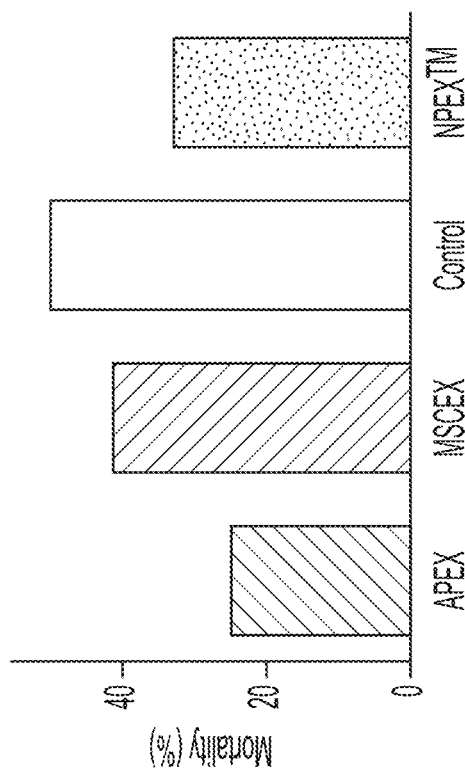
Figures 8D, 8E:
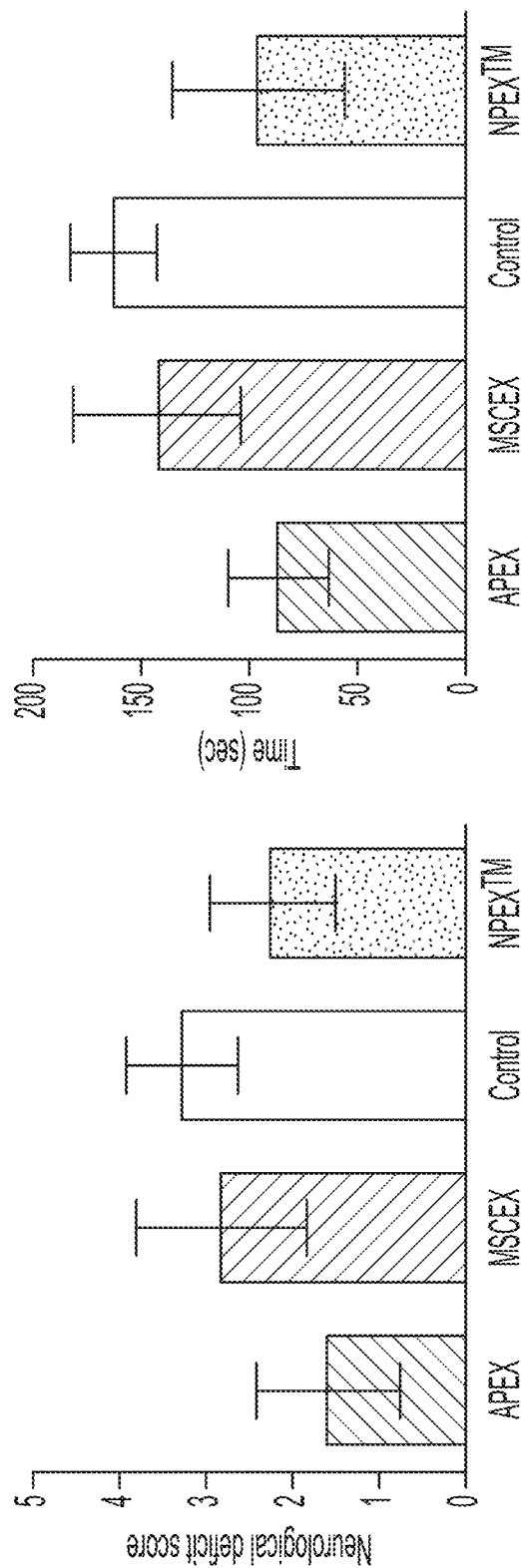

EVs were purified from isogenically derived astrocyte progenitors (APEX), MSCs (MSCEX), and neural progenitor (NPEX) cells using standard methods (see manufacturing section), evaluated by nanoparticle tracking analysis (NanoSight-NS300) and stored in individual dose aliquots at −20° C. until they were thawed at room temperature immediately prior to tail vein injection following embolic stroke. The 3 EV types and PBS were administered by blinded investigators following embolic stroke, in 3 doses of approximately $2.7 \times 10^{11}$ vesicles/kg (or vehicle) at 2, 14, and 28 hours post-stroke. In all parameters evaluated both APEX and NPEX outperformed the vehicle treated controls as well as the MSCEX treatment group. Immediately after euthanasia, 2,3,5-Triphenyltetrazolium Chloride (TTC) was used to differentiate metabolically active (live, red) and inactive (dead, colorless) tissues. Importantly, TTC indicates decreased injury and infarction volume following APEX or NPEXIM treatment (FIG. 8A), while MSCEX treatment was comparable to control. Within the 96 hrs following stroke APEX and NPEX treatments decreased mortality by 20 and 17% respectively (FIG. 8B). Neurologic deficits evaluated 48 hrs post stroke (on a 5-point scale from no deficit [0] with increasing severity through terminal deficits [5]) indicated significantly better behavioral outcomes for mice that received APEX or NPEX (FIG. 8D). Ability to remove adhesive tape used as bilateral tactile stimuli attached at the distal-radial region of each forelimb indicated improved sensorimotor function as well (FIG. 8E). Taken together, these data indicate improved survival, molecular, and functional outcomes in NPEX treated thromboembolic stroke rodent models compared to contemporary vehicle controls.

Figure 9A:
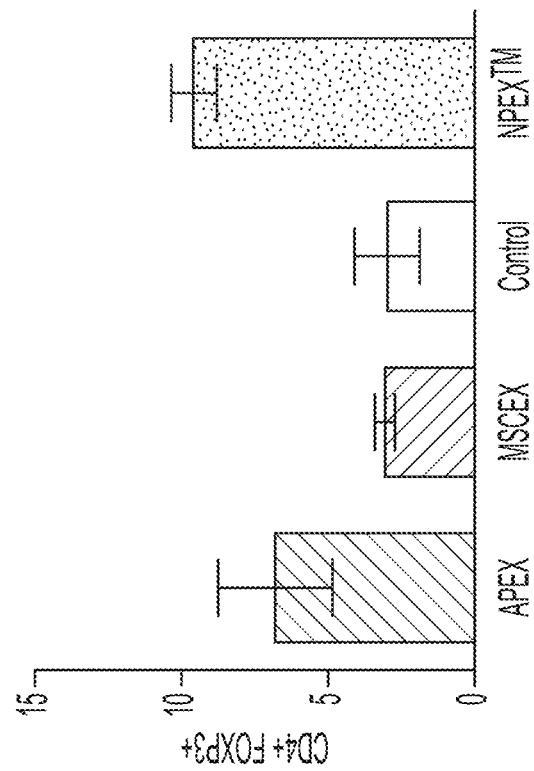
FIGS. 9A to 9C show EVs derived from neural cells modulate the immune response following stroke. Blood sample flow cytometry 96 hours post-stroke indicates that APEX and NPEX increase regulatory T-cells relative to MSCEX and control (vehicle) treated groups (FIG. 9A), decrease inflammatory T-helper cells (FIG. 9B), and increase anti-inflammatory M2 macrophages in the circulation (FIG. 9C).
Figure 9B:
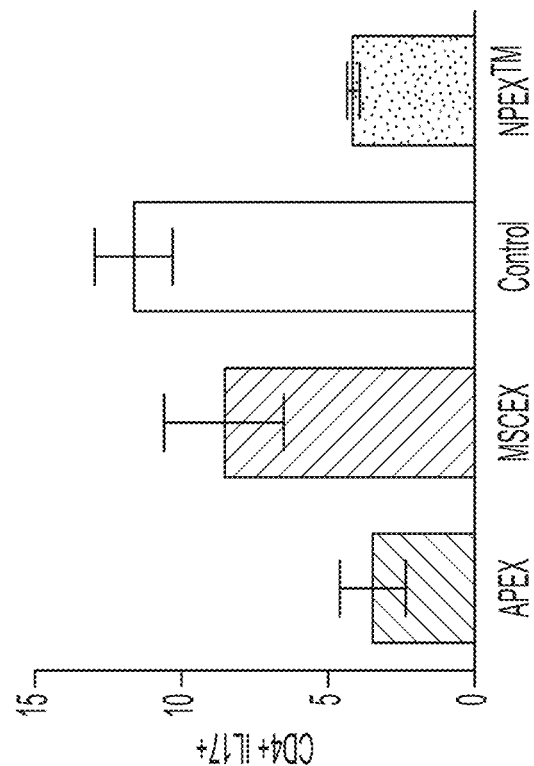
Figure 9C:
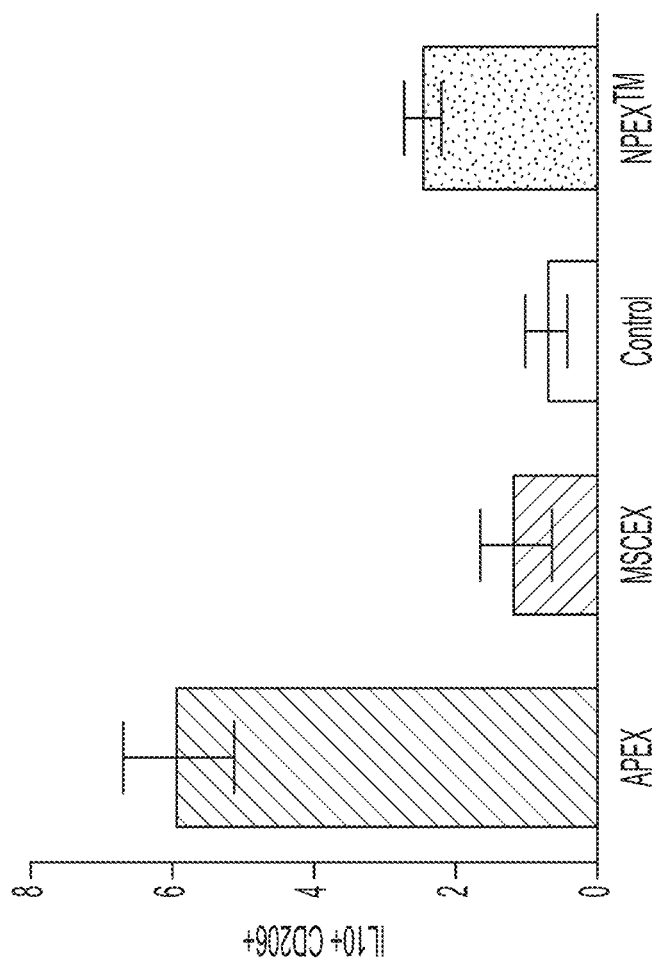

Flow cytometric analysis of blood cells at the 96 hour time point just prior to euthanasia indicates that neural cell type derived EVs, APEX and NPEX treatment resulted in an increase in the presence of protective regulatory T cells in circulation (FIG. 9A), while MSCEX were indistinguishable from controls. Pro-inflammatory T-helper cells were reduced in the APEX and NPEX groups (FIG. 9B), while anti-inflammatory M2 macrophages were increased in these groups (FIG. 9C). Taken together, these data indicate that neural cell type derived EVs exert part or all of their effects by modulating the immune response following stroke.

The production and quality control methods used to produce isogenically (genetically identical) derived neural progenitor, astrocyte progenitor, and MSC cells from the same ES cell line produce a unique opportunity to compare the EVs from these 3 cell types without the confounding variable of genetic variation due to source of the donor material. The vast majority of stem cell derived EV literature centers on use of MSC derived EVs. Here, for the first time neural cell derived EVs (APEX and NPEX) were evaluated and compared directly with MSC-derived EVs. There is a substantial improvement in molecular benefit (infarct volume), also increased survival and improved functional outcomes of neural derived EVs (APEX and NPEX) over the MSCEX. These improvements were immediate in older animals which is more prone to death. Thus no other group has shown that any EV (MSC or neural) therapy has such stark and immediate improvements in a mouse model that replicates the human stroke condition (embolic stroke) and factors in co-morbidly factors such as age (middle age mice). It appears that these early strong effects can only be obtained with a neural EV as disclosed herein.

These studies suggest that the mechanism of action in part may be through immune modulation suppressing the inflammatory M1 response including but not limited to suppressing IL17 cytokine while enhancing the M2 response perhaps through IL10 or other cytokines.

Example 5

Pig Model, Ischemic Injury Induced by Middle Cerebral Artery (MCA) Occlusion.

Landrace barrows (5-6 months, 150-170 lbs) were subjected to injury as previously described using the only fully developed porcine stroke model [1]. Briefly, a portion of the zygomatic arch was resected and the underlying muscle was elevated dorsally revealing the parietal bone. A window was generated in the bone surface exposing the dura mater. The proximal MCA was permanently occluded resulting in infarction spanning the most caudal aspect of the frontal lobe as well as significant portions of the temporal, parietal, and occipital lobes.

Magnetic Resonance Spectroscopy

Magnetic resonance imaging (MRI) was performed 24 hours and 90 days post-MCAO surgery on a GE 16-channel fixed-site Twin gradient Signa HDx 3.0 Tesla MRI system. Under anesthesia, MRI of the neurocranium was performed using a multichannel phase array spine coil, with the patient in dorsal recumbency. Standard multiplanar MR brain imaging series were acquired. These included T2-weighted (T2w), T2-weighted fluid attenuated inversion recovery (FLAIR), and T1-weighted (T1w) FLAIR, as well as diffusion-weighted imaging (DWI) series. DWI was acquired with b=0 and b=1000. DWI, apparent diffusion coefficient (ADC) maps and T1w-FLAIR images were evaluated using Osirix® software for presence of cerebral infarction and changes in cerebral hemisphere volume. Specifically, the volume of the ischemic area was manually derived from the ADC maps generated from DWI sequences. The ischemic area was defined by two levels of ADC number reduction, with the ADC number from the contralateral cerebral hemisphere providing normal ADC values. Ischemic areas, defined by those with 80% and 40% ADC values of normal, were manually traced on the sequential ADC images. Each area was multiplied by slice thickness to produce a volume of ischemic tissue. This method was chosen because it has been demonstrated to strongly correlate with histologically defined areas. The cerebral hemisphere volume was determined through a similar process, whereby the cerebral hemisphere volume was quantified (excluding sulci and the lateral ventricular spaces) on T1w FLAIR images. The T2w FLAIR images were used for reference to differentiate areas filled with CSF and parenchymal areas of hyperintensity (Platt, S. R., et al., Experimental & Translational Stroke Medicine, 2014. 6:5).

EV Dosage and Administration

NPEX EVs containing ~2.7×10$^{10}$ vesicles/kg in 50-60 ml PBS were thawed at 4° C. and transferred into a 60 cc syringe using aseptic technique while in a biological safety cabinet. Samples were inverted a minimum of 25 times immediately prior to intravenous injection via an ear vein catheter. Pigs received either 3 doses (50-60 ml) of NPEX or PBS (vehicle) at 2, 14, and 24 hours post-MCAO.

Animal Evaluation and Recovery

Following surgery, animals were moved to a clean recovery pen and monitored continuously until extubation. Rectal temperature, heart rate, and respiration rate (TPR) were recorded every 15 minutes until the pig was awake and vital signs were stable within normal limits. Thereafter, TPR measurements were initially reduced to 1-2 hour intervals unless vital signs deviated from normal (for example, a fever), then to longer intervals over the next 48 hours as the pig recovered. During the first 36 hours, pigs were never left for more than 4 hours without observation, and generally for no more than 2 hours. In addition to TPR, other observations recorded included time from arrival in recovery until the animal first stood up on its own, time to drink and eat with assistance, and time to eat and drink unassisted. Events such as fevers (rectal temperature 103° F. or greater), circling behavior, and seizures were also monitored and documented.

As seen in Table 1, routine evaluation indicates improved survival and functional outcomes in immediate recovery post-stroke with NPEX treatment. Survival was substantially better in the NPEX treatment group, with 7/7 pigs surviving more than 72 hours post-stroke, while only 5/8 survived in the control group. Time until the animals could stand unassisted was reduced by about 2 hours with NPEX treatment. Fevers, which are very common within 72 hours post-stroke, were reduced in the NPEX treatment group where 4/7 animals had one or more fever episodes as compared to control group where 6/8 animals had at least one fever. Time to eat and drink unassisted, number of animals exhibiting circling behavior, and number of animals with documented seizure activity were similar between groups.

TABLE 1

|  | Percent Survival (72 hrs) | Time to stand (hrs) | Fevers (%) | Time to eat (days) | Assisted drinking (days) | Unassisted Drinking (days) |
| --- | --- | --- | --- | --- | --- | --- |
| Treated | 100 | 4.21 | 57.14 | 1.24 | 1.56 | 3.13 |
| Control | 62.5 | 6.28 | 75.00 | 1.36 | 0.96 | 3.12 |

As seen in Table 2, gait analysis indicates improved motor function in NPEX treated pigs compared to controls. At 7 days post-stroke, NPEX treated pigs move faster and with more cadence (rhythmicity) as they move throughout their stride. Due to stroke in the right hemisphere, the left side specific deficits were more pronounced. Left side specific measurements indicate greater step length, shorter cycle time, greater stride length, and swing percent of cycle time. Treated animals placed more pressure on each foot as they moved through their stride and displayed more pronounced movement of the hind limbs past the front limb evidenced by the reach, indicating a more natural movement compared to controls.

TABLE 2

|  | Velocity | Cadence | Step Length (cm) | Cycle Time (sec) | Stride Length (cm) | Swing % of Cycle | Foot Pressure | Hind Reach |
| --- | --- | --- | --- | --- | --- | --- | --- | --- |
| NPEX | 131.45 | 91.99 | 41.43 | 0.79 | 80.89 | 41.06 | 62.87 | −12.34 |
| Control | 106.63 | 79.99 | 38.60 | 0.83 | 77.14 | 38.28 | 57.18 | −9.55 |

Results

Figure 10B:
FIGS. 10A to 10D show NPEX treatment results in decreased infarct volume within 28±4 hours post-stroke as measured by MRI. Animals subjected to stroke received either NPEX (approximately $2.7 \times 10^{10}$ vesicles/kg) or PBS (vehicle) at 2, 14, and 24 hours post-stroke. While anesthetized, animals were also subjected to MRI analysis. NPEX treated animals had substantially reduced infarct volume compared to those that received PBS (FIGS. 10A-10C). When the size difference between the ipsilateral and contralateral sides was evaluated, there was less difference between hemispheres in the NPEX group, indicating less edema and swelling as compared to controls (FIG. 10D).
Figure 10A:
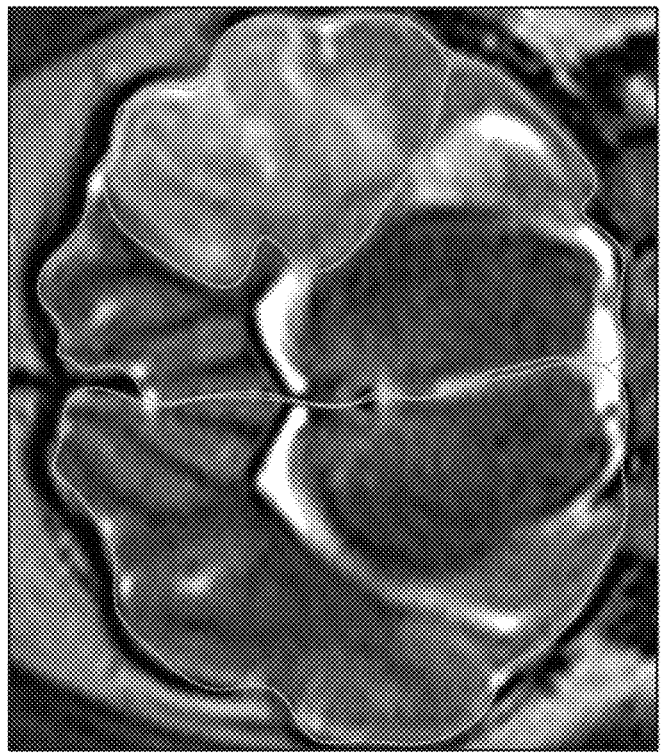
Figure 10C:
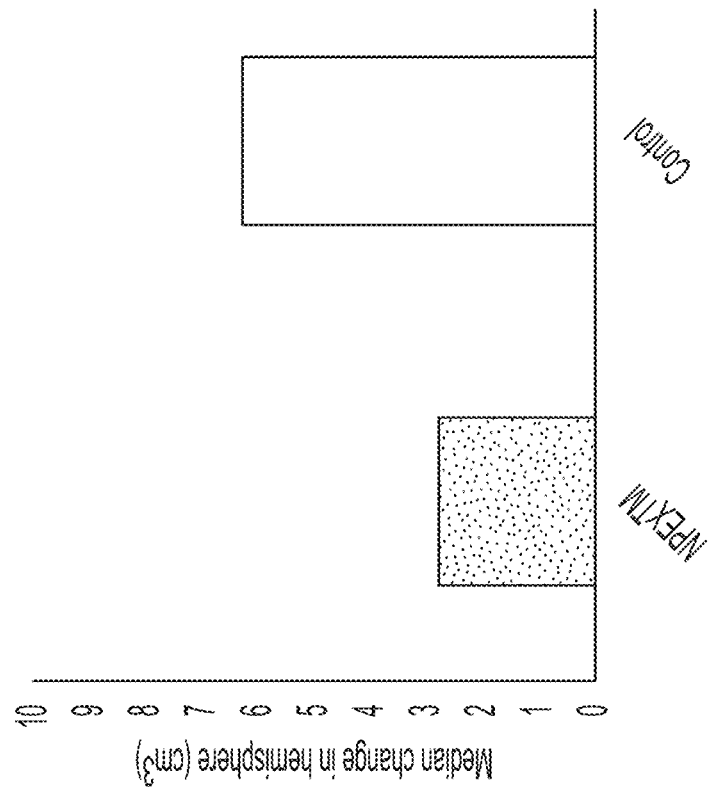
Figure 10D:
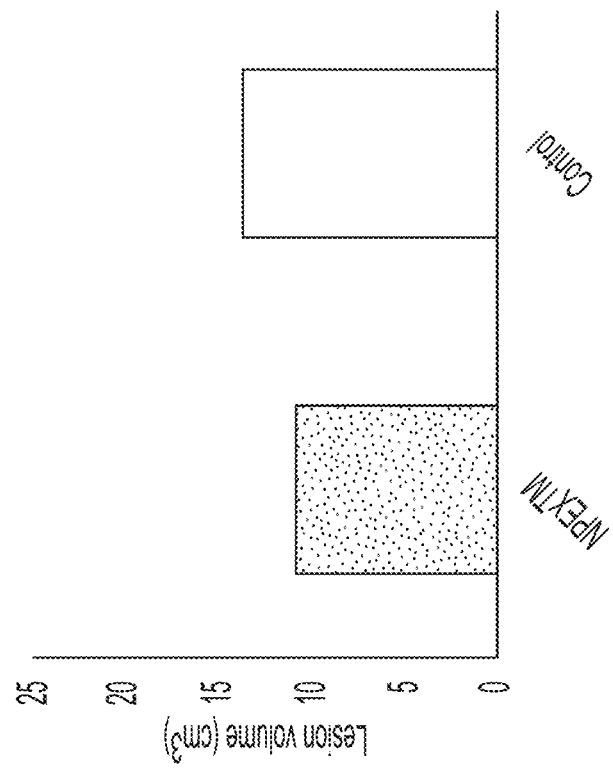

Initial MRI analysis at 28±4 hours indicated a smaller lesion volume in NPEX treated pigs compared to controls (FIG. 10A-10C). Volume measurements of the ipsilateral and contralateral hemispheres indicate less change in volume after stroke with NPEX treatment (FIG. 10D), indicating less swelling in the ipsilateral hemisphere in the first 24 hours after stroke, consistent with the rodent data indicating an early modulation of the immune response and indicative of a neuroprotective effect in the porcine model as well. Physiological parameters, most notably survival, was also increased in the 72 hours following induction of stroke. Treated animals were also able to stand unassisted ~2 hours faster than controls. Gait analysis at 7 days post-stroke indicated improved motor function as detected by increased velocity and cadence (rhythmicity), more pressure being applied to each foot throughout the motion, as well as increased step and stride length, an increased percentage of time in swing stance (foot off of ground) per cycle, and a more pronounced reach with the rear limb extending past the fore-limb, as is expected in quadrupeds.

Figure 11:
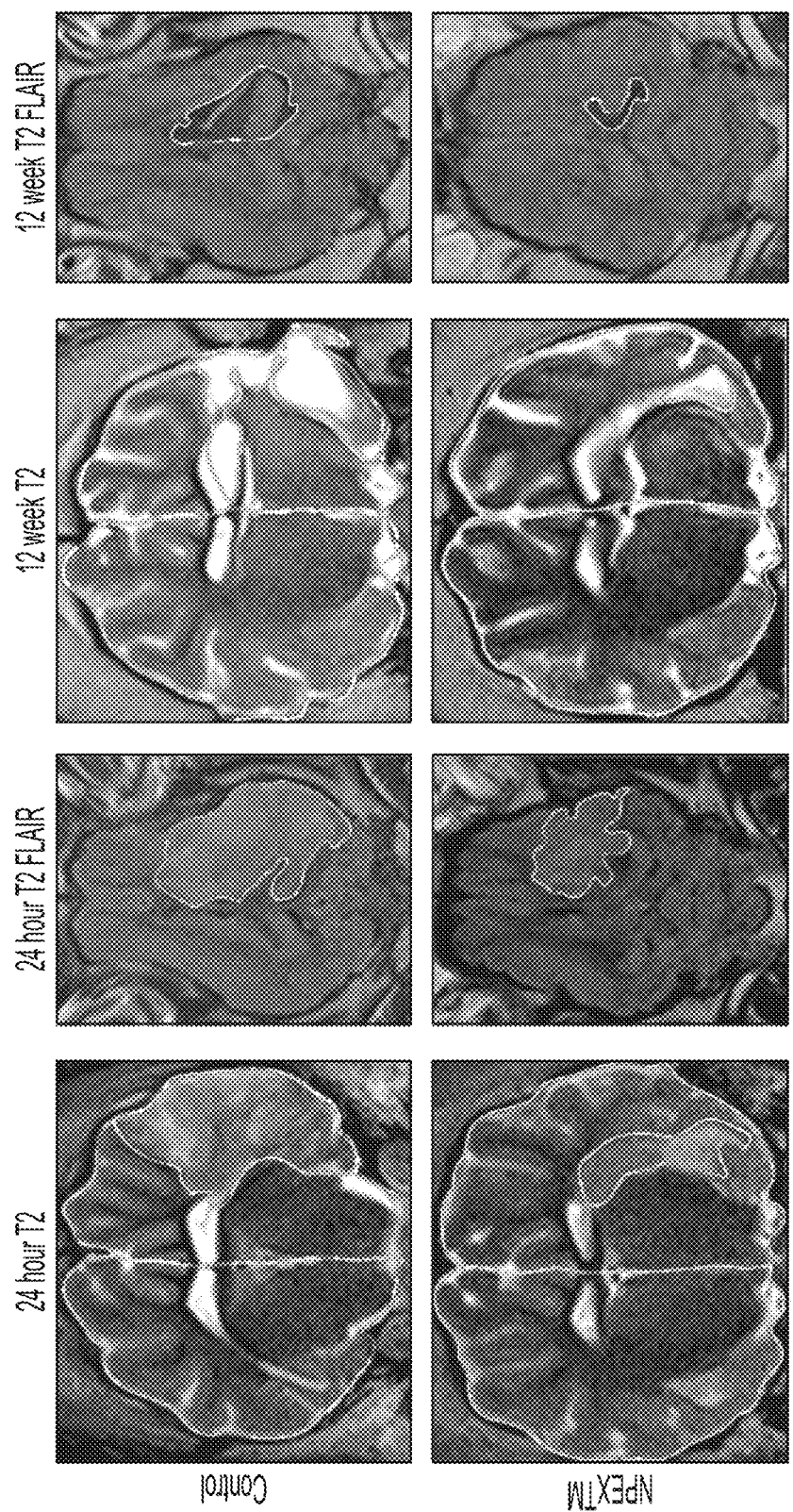
FIG. 11 shows NPEX treatment improves molecular deficits 12 weeks after stroke. T2 and T2 flair images both indicate less detectable damage in NPEX treated pigs 12 weeks post-stroke. The absence (death) of tissue was significantly reduced at the 12 week timepoint and areas of density incongruent with host tissue were far less evident in treated animals.

NPEX treatment also had a profound effect on molecular benefit in the animals 12 weeks post-stroke as detected by MRI T2 and T2 FLAIR images (FIG. 11). Dead/dying tissue was reduced by treatment and damaged tissue (green traces) were far reduced, involving mainly cortical tissue while largely preserving integrity of the ventricle compared to the control. Animals that received NPEX were able to survive larger infarct sizes (as much as 3.8 cm3 larger at 24 hours post-stroke) over the 12 week study than those that received control treatment. This is probably due to the anti-inflammatory properties of NPEX leading to decreased stroke severity and promoting better long-term outcomes including integrity of brain tissue, as well as behavioral and motor function.

Never before have EVs of any kind improved the outcome of stroke or for that matter any neural deficit in a large animal. Consistent with the small animal we show that NPEX effects the brain immediately, thus NPEX is fast acting in the pig and the mouse. We do not know of any other study that has suggested such and immediate effect of EVs on a stroked animal. Immediately NPEX improved survival and motor function (speed in which animals recover, time to stand, balance, etc). Molecular and phenotypic outcomes in a large animal species expand upon previously described rodent data, indicating that EVs exert a likely neuroprotective effect that is longer lasting. This effect is likely due in part to modulation of the secondary injury cascade by muting the immune response that occurs following stroke, as molecular and phenotypic differences are detectable as early as 24 hours post-stroke and a later effect on the enhanced M2 response, which is neuro-reparative. The longer lasting effects are observed throughout, with improved gait of the NPEX treated animals.

In summary, this is the first stroke study to suggest to mechanisms of action are consistent across animals and includes a study in a more complex brain with a structure that is similar to humans. Our in vitro human cell studies suggest neuroprotective action directly on the damaged neural cells, and the mouse and pig studies suggest protection through the immune system. The longer acting effects on neuro-reparative mechanisms in both species were observed and could be in part due to up regulation of Treg cells (mouse only to date).

Importantly, the porcine brain unlike the mouse shares many homologies with the human brain including white matter ratio, presence of gyrencephalic cortex, cytoarchitecture, and size. Due to these similarities, the pig is considered a superior model system compared to rodents, and is likely more representative of anticipated benefits in human treatment of ischemic stroke with therapeutically produced neural progenitor derived EVs.

This is possible due to an ability to produce a large quantity of EVs from neural progenitor cultures, approximately 5 times greater than yields obtained from MSCs. The ability to generate EVs on a commercial scale consistently from cultures will require that EV-producing cells be dependent on a rigorous quality control process for handling the cells and purifying the resultant EVs.

Example 6

Primary Filtration (Step 1, Used for all Purification Methods)

Media is harvested from plates or flasks containing cultured cells. The harvested media was frozen at −20° C. before or after the primary filtration and thawed at 4° C. Filtration is completed in a sterile laminar flow hood to minimize contamination. The harvested media was filtered via dead end filtration through a 0.22 μm filter (EMD Millipore Stericup). This primary filtration removes any cellular debris and/or dead cells from the harvested media. This allows for the EVs and microvesicles to pass through to the filtrate for further purification.

Centricon Ultrafiltration

Having undergone primary filtration, the media is ready for secondary filtration. This step utilizes a system including Centricon centrifuge units, which can process up to 70 ml culture medium per spin. This filtration process uses a 100 kDa filter to collect enriched EVs. During this process the media is forced through the filter discs via centrifugation at 4,000×g. Once the retentate reaches approximately 250 μL to 5 mL per unit, a buffer exchange is then performed using approximately 90% of the starting media volume of PBS+/+. The PBS+/+ is passed through the Centricon filters by centrifugation at 2,000×g until the retentate reaches 250 μL to 1 mL of volume per filter unit. At this point the retentate is collected for EV analysis. A sample is taken for immediate nanoparticle tracking analysis, and purified EVs from the same cell type were pooled, triturated, and aliquoted into DNase/RNase free tubes for storage at −20° C.

Amicon Stirred-Cell Ultrafiltration

For larger volume ultrafiltrations, Amicon stirred-cell ultrafiltration units were used, connected 3 units in tandem. Each base unit held 400 ml medium, which was further expanded using a reservoir to increase throughput. This step utilizes a system including a pressure vessel, and three EMD Millipore Stirred Cell Units (Fisher Scientific, USA) working in sequence. This step utilizes dead end filtration as well with media passing through a 100 kDa filter disc (Fisher Scientific, USA). During this process the media is forced through the filter discs using 25 psi of positive pressure supplied by compressed nitrogen gas. Once the retentate reaches 50 ml/stirred cell unit the system is de-pressurized. A buffer exchange is then performed using 50% of the starting media volume of PBS+/+. The PBS+/+ is passed through the stirred cell filters until the retentate reaches 50 mL of volume per filter unit. At this point the retentate is collected for EV analysis. A sample is taken for immediate nanoparticle tracking analysis, and purified EVs from the same cell type were pooled, triturated, and aliquoted into DNase/RNase free tubes for storage at −20° C.

Fibroblast Growth Factor ELISA

To determine hFGF2 content, cryopreserved samples of NPEX™, APEX, and MSCEX EVs were thawed at 4° C. and lysed with an equal volume of EV lysis buffer to release exosomal content. The lysate was analyzed for human FGF2 using a commercially available human FGF2 ELISA assay kit (Thermo Scientific-Catalog number KHG0021) following manufacturers protocol. FGF2 standards provided with the kit were used to generate a standard curve and quantitated FGF2 in the test sample. FGF2 was detected in NPEX™ sample at 490 pG/mL. No FGF2 could be detected either in APEX™ or in MSCEX™ samples.

Mass Spectroscopy

To compare proteins unique to neural EVs versus MSC derived EVs, purified EV proteins were subjected to mass spectroscopy by Bioproximity, LLC.

Results

Ultracentrifugation and ultrafiltration methods were used as previously described. Large volume purifications utilized the Amicon stirred-cell system to purify over 24 liters of cell culture medium in a single work week.

Fibroblast Growth Factor ELISA Results

The protein human Fibroblast Growth Factor 2 (hFGF2) is added to hNP1™ culture media to maintain the proliferative state of hNP1™ cells. EVs produced by hNP1™ cells (NPEX) cultured in hFGF2 supplemented media may accumulate/contain any of this hFGF2 protein as part of the exosomal protein content. NPEX EVs, harvested from hNP1™ culture media collected from live hNP1™ cell cultures were tested for the presence of hFGF2. These purified and cryopreserved NPEX™ EVs contained detectable levels of hFGF2 after thaw. On the other hand, EVs from hAstroPro™ human astrocytes (APEX), and from mesenchymal stem cells (MSCEX), where the cell culture media is not supplemented with hFGF2, did not contain any detectable hFGF2. Taken together, these data indicate that proteins supplemented in the medium are taken up by the cells and are present in the enriched EV sample even in the absence of transfection or other techniques to overexpress proteins in the cells.

Mass Spectroscopy

Figure 12:
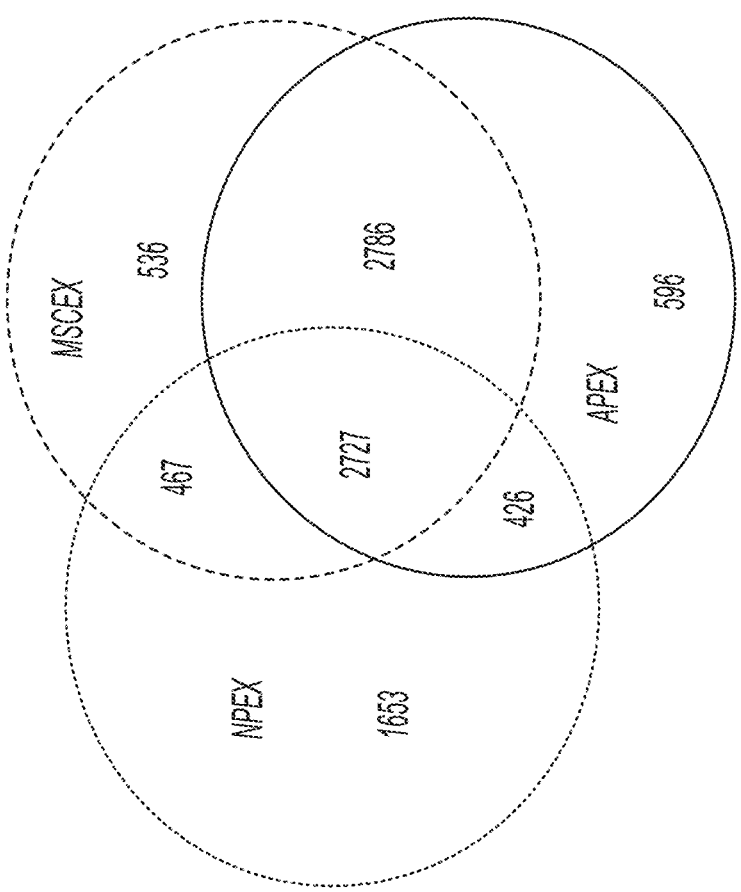
FIG. 12 is a Venn diagram showing the number of proteins unique to, and shared by NPEX, APEX, and MSCEX EVs.

FIG. 12 is a Venn diagram showing the number of proteins unique to, and shared by NPEX, APEX, and MSCEX vesicles. A total of 2727 proteins were shared by all of these vesicles (Table 3). APEX and MSCEX shared 2786 proteins that were not in NPEX vesicles (Table 4). NPEX shared 467 proteins only with MSCEX (Table 5) and 426 proteins only with APEX vesicles (Table 6). MSCEX had 536 unique proteins that were not identified in APEX or NPEX vesicles (Table 7). APEX had 596 proteins that were not identified in NPEX or MSCEX vesicles (Table 8). NPEX had 1653 proteins that were not identified in APEX or MSCEX vesicles (Table 9).

TABLE 3

Protein codes found in NPEX, APEX, and MSCEX

| | |
|---|---|
| 1 | A0A023UFG1 |
| 2 | A0A024QZ30 |
| 3 | A0A024R0R4 |
| 4 | A0A024R1Q5 |
| 5 | A0A024R269 |
| 6 | A0A024R294 |
| 7 | A0A024R2A8 |
| 8 | A0A024R3H6 |
| 9 | A0A024R3W5 |
| 10 | A0A024R473 |
| 11 | A0A024R4U7 |
| 12 | A0A024R663 |
| 13 | A0A024R6C6 |
| 14 | A0A024R7F1 |
| 15 | A0A024R816 |
| 16 | A0A024R900 |
| 17 | A0A024R972 |
| 18 | A0A024R9G7 |
| 19 | A0A024RA85 |
| 20 | A0A024RAB6 |
| 21 | A0A024RB27 |
| 22 | A0A024RB49 |
| 23 | A0A024RBR1 |
| 24 | A0A024RC42 |
| 25 | A0A024RD01 |
| 26 | A0A024RDU6 |
| 27 | A0A087WTT9 |
| 28 | A0A087WTY7 |
| 29 | A0A087WU72 |
| 30 | A0A087WUP3 |
| 31 | A0A087WUR9 |
| 32 | A0A087WUZ8 |
| 33 | A0A087WV01 |
| 34 | A0A087WV58 |
| 35 | A0A087WVQ9 |
| 36 | A0A087WVY5 |
| 37 | A0A087WX41 |
| 38 | A0A087X1N7 |
| 39 | A0A087X208 |
| 40 | A0A087X270 |
| 41 | A0A088AWP7 |
| 42 | A0A090N7U3 |
| 43 | A0A090N8G0 |
| 44 | A0A090N8I2 |
| 45 | A0A090N8Z3 |
| 46 | A0A096LNH2 |
| 47 | A0A096LP10 |
| 48 | A0A096LPK6 |
| 49 | A0A0A0MQZ3 |
| 50 | A0A0A0MR11 |
| 51 | A0A0A0MRA3 |
| 52 | A0A0A0MRA8 |
| 53 | A0A0A0MT16 |
| 54 | A0A0A7NZX2 |
| 55 | A0A0B4J262 |
| 56 | A0A0C4DG44 |
| 57 | A0A0C4DGP4 |
| 58 | A0A0C4DGQ0 |
| 59 | A0A0C4DGR9 |
| 60 | A0A0C4DGV7 |
| 61 | A0A0C4DH10 |
| 62 | A0A0C4DH26 |
| 63 | A0A0C4DH32 |
| 64 | A0A0C4DH71 |
| 65 | A0A0D9SF05 |
| 66 | A0A0D9SF53 |
| 67 | A0A0D9SFF0 |
| 68 | A0A0E3SU01 |
| 69 | A0A0F7TC28 |
| 70 | A0A0G2JQ57 |
| 71 | A0A0J9YWL9 |
| 72 | A0A0J9YY17 |
| 73 | A0A0J9YY65 |
| 74 | A0A0K0K1J1 |
| 75 | A0A0K2FPC8 |
| 76 | A0A0R4J2G5 |
| 77 | A0A0S2Z3C0 |
| 78 | A0A0S2Z3H6 |
| 79 | A0A0S2Z3N2 |
| 80 | A0A0S2Z4F6 |
| 81 | A0A0S2Z4K6 |
| 82 | A0A0S2Z4S4 |
| 83 | A0A0U1RQF0 |
| 84 | A0A0U1RQK4 |
| 85 | A0A0U1RR05 |
| 86 | A0A0U1RRH6 |

TABLE 3-continued

Protein codes found in NPEX, APEX, and MSCEX

| | |
|---|---|
| 87 | A0A0U4BW16 |
| 88 | A0A0U4DR30 |
| 89 | A0A0U5Q0I5 |
| 90 | A0A0X7YLB8 |
| 91 | A0A0X9T0I7 |
| 92 | A0A0X9TDD0 |
| 93 | A0A0X9UWM4 |
| 94 | A0A109PSY4 |
| 95 | A0A126GVT4 |
| 96 | A0A126GVV9 |
| 97 | A0A126GVY4 |
| 98 | A0A126GW97 |
| 99 | A0A126LAV0 |
| 100 | A0A126LAW8 |
| 101 | A0A140VJG3 |
| 102 | A0A140VJM5 |
| 103 | A0A140VJZ1 |
| 104 | A0A140VJZ4 |
| 105 | A0A140VK24 |
| 106 | A0A142K0N8 |
| 107 | A0N7J6 |
| 108 | A1A5C4 |
| 109 | A1L0U7 |
| 110 | A1YZK0 |
| 111 | A2IPH5 |
| 112 | A2J1M8 |
| 113 | A2MYD2 |
| 114 | A2N0U1 |
| 115 | A2RRE5 |
| 116 | A2RTY3 |
| 117 | A3KMF7 |
| 118 | A3KMG4 |
| 119 | A4D0R5 |
| 120 | A4D1F6 |
| 121 | A4D263 |
| 122 | A4D2F6 |
| 123 | A4FU99 |
| 124 | A5XEJ8 |
| 125 | A6NCJ1 |
| 126 | A6NDG6 |
| 127 | A6NHK2 |
| 128 | A6NMH8 |
| 129 | A8K1Z4 |
| 130 | A8K2Q7 |
| 131 | A8K2X9 |
| 132 | A8K4L4 |
| 133 | A8K580 |
| 134 | A8K5W7 |
| 135 | A8K646 |
| 136 | A8K674 |
| 137 | A8K6Q8 |
| 138 | A8K6R3 |
| 139 | A8K889 |
| 140 | A8K941 |
| 141 | A8K948 |
| 142 | A8KA19 |
| 143 | A8KAM8 |
| 144 | A8KAQ0 |
| 145 | A8MQ14 |
| 146 | A8MSG4 |
| 147 | A8MUM1 |
| 148 | A8MYJ1 |
| 149 | B0AZV0 |
| 150 | B0I1R4 |
| 151 | B0I1R7 |
| 152 | B0I1R8 |
| 153 | B0I1S0 |
| 154 | B1AH62 |
| 155 | B2R604 |
| 156 | B2R6E3 |
| 157 | B2R8C2 |
| 158 | B2R8R5 |
| 159 | B2RAG9 |
| 160 | B2RAK1 |
| 161 | B2RD27 |
| 162 | B2RDG9 |
| 163 | B2RDV2 |
| 164 | B2RP65 |
| 165 | B2ZZ86 |
| 166 | B3KMD3 |
| 167 | B3KMX8 |
| 168 | B3KNH6 |
| 169 | B3KNH8 |
| 170 | B3KNJ3 |
| 171 | B3KR88 |
| 172 | B3KS22 |
| 173 | B3KS78 |
| 174 | B3KT94 |
| 175 | B3KUL2 |
| 176 | B3KV04 |
| 177 | B3KVE3 |
| 178 | B3KVJ2 |
| 179 | B3KW39 |
| 180 | B3KX05 |
| 181 | B3KXG9 |
| 182 | B4DE59 |
| 183 | B4DEA8 |
| 184 | B4DEN3 |
| 185 | B4DGW2 |
| 186 | B4DGX3 |
| 187 | B4DH09 |
| 188 | B4DHQ3 |
| 189 | B4DHR1 |
| 190 | B4DHV2 |
| 191 | B4DI57 |
| 192 | B4DJ98 |
| 193 | B4DJM8 |
| 194 | B4DK16 |
| 195 | B4DK41 |
| 196 | B4DKE0 |
| 197 | B4DKG5 |
| 198 | B4DKL5 |
| 199 | B4DL04 |
| 200 | B4DL67 |
| 201 | B4DLV7 |
| 202 | B4DM31 |
| 203 | B4DMC6 |
| 204 | B4DMD7 |
| 205 | B4DMI9 |
| 206 | B4DMK9 |
| 207 | B4DMS8 |
| 208 | B4DMY4 |
| 209 | B4DN39 |
| 210 | B4DN66 |
| 211 | B4DN96 |
| 212 | B4DNS4 |
| 213 | B4DPB7 |
| 214 | B4DPF0 |
| 215 | B4DPS3 |
| 216 | B4DQF8 |
| 217 | B4DQJ9 |
| 218 | B4DRF2 |
| 219 | B4DRV4 |
| 220 | B4DRZ1 |
| 221 | B4DRZ5 |
| 222 | B4DSD8 |
| 223 | B4DSI2 |
| 224 | B4DSK2 |
| 225 | B4DTD5 |
| 226 | B4DTF5 |
| 227 | B4DTI4 |
| 228 | B4DTV0 |
| 229 | B4DUV1 |
| 230 | B4DVQ8 |
| 231 | B4DVY2 |
| 232 | B4DXJ3 |
| 233 | B4DXW6 |
| 234 | B4DXX8 |
| 235 | B4DYE2 |
| 236 | B4DYM1 |
| 237 | B4DYQ3 |
| 238 | B4DYV9 |
| 239 | B4DZ96 |
| 240 | B4DZD8 |
| 241 | B4DZK5 |
| 242 | B4DZL0 |

TABLE 3-continued

Protein codes found in NPEX, APEX, and MSCEX

| | |
|---|---|
| 243 | B4DZX5 |
| 244 | B4DZY9 |
| 245 | B4E0C3 |
| 246 | B4E116 |
| 247 | B4E1Z8 |
| 248 | B4E2C9 |
| 249 | B4E310 |
| 250 | B4E358 |
| 251 | B4E396 |
| 252 | B4E3S1 |
| 253 | B5BUB5 |
| 254 | B5MC96 |
| 255 | B7SXT3 |
| 256 | B7WPN9 |
| 257 | B7Z1C7 |
| 258 | B7Z1Y1 |
| 259 | B7Z208 |
| 260 | B7Z225 |
| 261 | B7Z2P6 |
| 262 | B7Z395 |
| 263 | B7Z3F9 |
| 264 | B7Z3I3 |
| 265 | B7Z425 |
| 266 | B7Z4S3 |
| 267 | B7Z5R5 |
| 268 | B7Z5U1 |
| 269 | B7Z6G1 |
| 270 | B7Z6T9 |
| 271 | B7Z865 |
| 272 | B7ZAS5 |
| 273 | B7ZKX2 |
| 274 | B7ZKY2 |
| 275 | B7ZL41 |
| 276 | B7ZL68 |
| 277 | B7ZMC8 |
| 278 | B7ZVX0 |
| 279 | C0JYZ2 |
| 280 | C4P0A0 |
| 281 | C8CHS3 |
| 282 | C9IYI4 |
| 283 | C9IZK7 |
| 284 | C9J0E9 |
| 285 | C9J6F5 |
| 286 | C9J8V2 |
| 287 | C9J9C4 |
| 288 | C9JBI4 |
| 289 | C9JG87 |
| 290 | C9JKM5 |
| 291 | C9JKM9 |
| 292 | C9JSJ3 |
| 293 | C9JX31 |
| 294 | D3DPG0 |
| 295 | D3DQH8 |
| 296 | D3DTX7 |
| 297 | D3DUZ3 |
| 298 | D3DV53 |
| 299 | D3DWL0 |
| 300 | D3DX49 |
| 301 | D3VVE1 |
| 302 | D3VVP9 |
| 303 | D4YW75 |
| 304 | D6RCE4 |
| 305 | D6RCP5 |
| 306 | D6RCQ3 |
| 307 | D6RGX4 |
| 308 | D6RHD5 |
| 309 | D6RHJ5 |
| 310 | D6W573 |
| 311 | D9ZGF2 |
| 312 | E2QRN8 |
| 313 | E5RFF8 |
| 314 | E5RG49 |
| 315 | E7EMW7 |
| 316 | E7EQW5 |
| 317 | E7ESB3 |
| 318 | E7ETY2 |
| 319 | E7EUH7 |
| 320 | E7EX80 |
| 321 | E9PB28 |
| 322 | E9PDD2 |
| 323 | E9PFQ4 |
| 324 | E9PJ15 |
| 325 | E9PJG1 |
| 326 | E9PKH2 |
| 327 | E9PKQ0 |
| 328 | E9PS68 |
| 329 | F1LLU8 |
| 330 | F5GZB4 |
| 331 | F5H7Y6 |
| 332 | F6X3N5 |
| 333 | F8VBW7 |
| 334 | F8VPD4 |
| 335 | F8VQY3 |
| 336 | F8VY01 |
| 337 | F8VYK9 |
| 338 | F8W6H2 |
| 339 | F8W883 |
| 340 | F8WEI7 |
| 341 | G3V1C3 |
| 342 | G3V1Y7 |
| 343 | G3V2J9 |
| 344 | H0Y390 |
| 345 | H0Y3V5 |
| 346 | H0Y5A2 |
| 347 | H0Y720 |
| 348 | H0Y8I2 |
| 349 | H0Y935 |
| 350 | H0Y991 |
| 351 | H0Y9B6 |
| 352 | H0Y9P3 |
| 353 | H0Y9Z7 |
| 354 | H0YA40 |
| 355 | H0YAA7 |
| 356 | H0YDK7 |
| 357 | H0YDZ4 |
| 358 | H0YF10 |
| 359 | H0YFH1 |
| 360 | H0YHN7 |
| 361 | H0YJ21 |
| 362 | H0YJI8 |
| 363 | H0YM90 |
| 364 | H3BM60 |
| 365 | H3BMQ8 |
| 366 | H3BPI1 |
| 367 | H3BPK7 |
| 368 | H3BPS8 |
| 369 | H3BQK9 |
| 370 | H3BQQ2 |
| 371 | H3BQT0 |
| 372 | H3BRQ0 |
| 373 | H3BS19 |
| 374 | H3BS34 |
| 375 | H3BT13 |
| 376 | H3BV16 |
| 377 | H7BYH4 |
| 378 | H7BZ70 |
| 379 | H7BZ95 |
| 380 | H7BZL8 |
| 381 | H7BZY4 |
| 382 | H7C0I3 |
| 383 | H7C0I1 |
| 384 | H7C0Q9 |
| 385 | H7C132 |
| 386 | H7C1F8 |
| 387 | H7C1W1 |
| 388 | H7C3P6 |
| 389 | H7C446 |
| 390 | H7C4N3 |
| 391 | H7C4W1 |
| 392 | H7C557 |
| 393 | H7C5G5 |
| 394 | H9E7H3 |
| 395 | I3L174 |
| 396 | I3L1P4 |
| 397 | I3L3B3 |
| 398 | I3L3U6 |

TABLE 3-continued

Protein codes found in NPEX, APEX, and MSCEX

| | |
|---|---|
| 399 | I6L965 |
| 400 | J3KNJ2 |
| 401 | J3KP25 |
| 402 | J3KQ96 |
| 403 | J3KRF1 |
| 404 | J3KTA9 |
| 405 | J3KTL8 |
| 406 | J3QQK7 |
| 407 | J3QQP2 |
| 408 | J3QR51 |
| 409 | J3QRM5 |
| 410 | J3QS68 |
| 411 | J3QS89 |
| 412 | J3QS93 |
| 413 | J3QSE7 |
| 414 | K7EIX3 |
| 415 | K7EKG3 |
| 416 | K7EMJ3 |
| 417 | K7ENJ9 |
| 418 | K7EPV5 |
| 419 | K7EQA8 |
| 420 | K7EQP5 |
| 421 | K7EQQ3 |
| 422 | K7EQV0 |
| 423 | K7ERC0 |
| 424 | K7ERL1 |
| 425 | K7ERP4 |
| 426 | K7ES39 |
| 427 | K7N7B3 |
| 428 | K9JJH7 |
| 429 | L0R6L1 |
| 430 | L8E9M8 |
| 431 | L8E9T4 |
| 432 | L8EA98 |
| 433 | M0QYS6 |
| 434 | M0R0R9 |
| 435 | M0R0Z7 |
| 436 | M0R248 |
| 437 | M1VKI3 |
| 438 | M4N8S7 |
| 439 | O00629 |
| 440 | O00716 |
| 441 | O15034 |
| 442 | O15049 |
| 443 | O15230 |
| 444 | O15327 |
| 445 | O43149 |
| 446 | O43697 |
| 447 | O60248 |
| 448 | O60284 |
| 449 | O60568 |
| 450 | O75095 |
| 451 | O75197 |
| 452 | O75874 |
| 453 | O94804 |
| 454 | O94905 |
| 455 | O95185 |
| 456 | O95608 |
| 457 | P02769 |
| 458 | P04040 |
| 459 | P04206 |
| 460 | P04207 |
| 461 | P04434 |
| 462 | P05543 |
| 463 | P06312 |
| 464 | P08779 |
| 465 | P09382 |
| 466 | P0C1S8 |
| 467 | P0C7M3 |
| 468 | P10909 |
| 469 | P11055 |
| 470 | P14543 |
| 471 | P16152 |
| 472 | P16930 |
| 473 | P17039 |
| 474 | P17301 |
| 475 | P19838 |
| 476 | P21359 |
| 477 | P22059 |
| 478 | P22314 |
| 479 | P22680 |
| 480 | P25054 |
| 481 | P25398 |
| 482 | P26641 |
| 483 | P28325 |
| 484 | P31689 |
| 485 | P35527 |
| 486 | P43251 |
| 487 | P46531 |
| 488 | P53621 |
| 489 | P55291 |
| 490 | P56589 |
| 491 | P59510 |
| 492 | P59923 |
| 493 | P60602 |
| 494 | P61160 |
| 495 | P78407 |
| 496 | P86434 |
| 497 | P98066 |
| 498 | P98168 |
| 499 | Q02952 |
| 500 | Q03188 |
| 501 | Q04741 |
| 502 | Q05CY8 |
| 503 | Q0ZCI6 |
| 504 | Q10471 |
| 505 | Q12789 |
| 506 | Q13707 |
| 507 | Q14402 |
| 508 | Q14517 |
| 509 | Q14789 |
| 510 | Q15050 |
| 511 | Q15198 |
| 512 | Q15293 |
| 513 | Q15645 |
| 514 | Q15917 |
| 515 | Q16696 |
| 516 | Q16706 |
| 517 | Q17R55 |
| 518 | Q2NNQ8 |
| 519 | Q2TAC2 |
| 520 | Q2TAC6 |
| 521 | Q2VWP7 |
| 522 | Q32MA5 |
| 523 | Q3B776 |
| 524 | Q3B836 |
| 525 | Q3MJ16 |
| 526 | Q3ZTS6 |
| 527 | Q4G0T1 |
| 528 | Q4G112 |
| 529 | Q4KWH8 |
| 530 | Q4R9M8 |
| 531 | Q4VCS5 |
| 532 | Q4VNC0 |
| 533 | Q4W4X9 |
| 534 | Q52LW3 |
| 535 | Q53EK6 |
| 536 | Q53FV4 |
| 537 | Q53G58 |
| 538 | Q53G89 |
| 539 | Q53H47 |
| 540 | Q53H80 |
| 541 | Q53HL1 |
| 542 | Q53SS8 |
| 543 | Q53TC2 |
| 544 | Q562X7 |
| 545 | Q562Z6 |
| 546 | Q56G89 |
| 547 | Q58FF8 |
| 548 | Q58G82 |
| 549 | Q59EE5 |
| 550 | Q59FP8 |
| 551 | Q59FR6 |
| 552 | Q59FV9 |
| 553 | Q59G96 |
| 554 | Q59GU6 |

TABLE 3-continued

Protein codes found in NPEX, APEX, and MSCEX

| | |
|---|---|
| 555 | Q5CZA6 |
| 556 | Q5CZI2 |
| 557 | Q5DT02 |
| 558 | Q5FWF6 |
| 559 | Q5H9P2 |
| 560 | Q5HY92 |
| 561 | Q5HYM0 |
| 562 | Q5JB40 |
| 563 | Q5JRB0 |
| 564 | Q5JVX6 |
| 565 | Q5JVX7 |
| 566 | Q5JXB8 |
| 567 | Q5JY77 |
| 568 | Q5JYT4 |
| 569 | Q5MJQ3 |
| 570 | Q5NV78 |
| 571 | Q5PT55 |
| 572 | Q5SNW4 |
| 573 | Q5T2N8 |
| 574 | Q5T566 |
| 575 | Q5T7F5 |
| 576 | Q5TB80 |
| 577 | Q5TBG1 |
| 578 | Q5TZA2 |
| 579 | Q5U077 |
| 580 | Q5UGI6 |
| 581 | Q5VSQ6 |
| 582 | Q5VTT2 |
| 583 | Q5VYL4 |
| 584 | Q5VYM1 |
| 585 | Q5VZP5 |
| 586 | Q5W064 |
| 587 | Q5XKE5 |
| 588 | Q5XUM6 |
| 589 | Q5ZEZ4 |
| 590 | Q658Z1 |
| 591 | Q66GS9 |
| 592 | Q687X5 |
| 593 | Q68CY5 |
| 594 | Q68DE6 |
| 595 | Q69YJ3 |
| 596 | Q6A162 |
| 597 | Q6AW98 |
| 598 | Q6B823 |
| 599 | Q6FH49 |
| 600 | Q6FH59 |
| 601 | Q6FHU2 |
| 602 | A0A024R0A8 |
| 603 | A0A024R104 |
| 604 | A0A024R1U8 |
| 605 | A0A024R842 |
| 606 | A0A024RAC0 |
| 607 | A0A024RAQ9 |
| 608 | A0A024RB03 |
| 609 | A0A024RBK0 |
| 610 | A0A024RBS1 |
| 611 | A0A067ZXG4 |
| 612 | A0A087WUL2 |
| 613 | A0A087WX34 |
| 614 | A0A087WZE4 |
| 615 | A0A087X2G6 |
| 616 | A0A024R2U9 |
| 617 | A0A024R3L9 |
| 618 | A0A024R4E9 |
| 619 | A0A075B6S5 |
| 620 | A0A075B747 |
| 621 | A0A087WV66 |
| 622 | A0A087WW06 |
| 623 | A0A087WWT3 |
| 624 | A0A090N8N3 |
| 625 | A0A090N8Y2 |
| 626 | A0A0A0MQU5 |
| 627 | A0A0B4J1W6 |
| 628 | A0A0C4DFU3 |
| 629 | A0A0G2JMD7 |
| 630 | A0A0K1H1B1 |
| 631 | A0A0S1TL27 |
| 632 | A0A0S2Z4R7 |
| 633 | A0A0U1RQQ4 |
| 634 | A0A0U1RR20 |
| 635 | A0A120HF61 |
| 636 | A0A126GVJ4 |
| 637 | A0A126LAV1 |
| 638 | A0A126LAY0 |
| 639 | A0A140VJM3 |
| 640 | A0A140VK19 |
| 641 | A0A142CHG9 |
| 642 | A0N8J1 |
| 643 | A2RU48 |
| 644 | A4D0Y5 |
| 645 | A4D110 |
| 646 | A4D189 |
| 647 | A4FU11 |
| 648 | A4UCU1 |
| 649 | A5PL16 |
| 650 | A5X2V1 |
| 651 | A5XEH9 |
| 652 | A6NFK2 |
| 653 | A6NMD2 |
| 654 | A6NNH2 |
| 655 | A7MBM2 |
| 656 | A8K243 |
| 657 | A8K3A8 |
| 658 | A8K491 |
| 659 | A8K6K2 |
| 660 | A8K7J3 |
| 661 | A8K7K7 |
| 662 | A8K8Q0 |
| 663 | A8MQ27 |
| 664 | B0AZS5 |
| 665 | B1AHM9 |
| 666 | B1AMG5 |
| 667 | B2R742 |
| 668 | B2R9V7 |
| 669 | B2RCE6 |
| 670 | B3KNP2 |
| 671 | B3KPR2 |
| 672 | B3KQ86 |
| 673 | B3KRC4 |
| 674 | B3KRR7 |
| 675 | B3KSP5 |
| 676 | B3KT66 |
| 677 | B3KTN0 |
| 678 | B3KUG8 |
| 679 | B3KWB1 |
| 680 | B3KWZ6 |
| 681 | B4DEH2 |
| 682 | B4DEI5 |
| 683 | B4DEI9 |
| 684 | B4DFW5 |
| 685 | B4DGL0 |
| 686 | B4DI08 |
| 687 | B4DIS3 |
| 688 | B4DJI1 |
| 689 | B4DJQ8 |
| 690 | B4DJS2 |
| 691 | B4DLD1 |
| 692 | B4DM56 |
| 693 | B4DMC3 |
| 694 | B4DMR0 |
| 695 | B4DN86 |
| 696 | B4DP97 |
| 697 | B4DQG2 |
| 698 | B4DRY1 |
| 699 | B4DS24 |
| 700 | B4DS65 |
| 701 | B4DSN3 |
| 702 | B4DTV8 |
| 703 | B4DTZ8 |
| 704 | B4DUN3 |
| 705 | B4DWC4 |
| 706 | B4DWK8 |
| 707 | B4DXZ7 |
| 708 | B4DZE2 |
| 709 | B4DZL4 |
| 710 | B4E216 |

TABLE 3-continued

Protein codes found in NPEX, APEX, and MSCEX

| | |
|---|---|
| 711 | B4E2V9 |
| 712 | B4E3P1 |
| 713 | B5BU24 |
| 714 | B7Z1V9 |
| 715 | B7Z2B4 |
| 716 | B7Z5V6 |
| 717 | B7Z7Y3 |
| 718 | B7ZKR9 |
| 719 | B7ZW01 |
| 720 | B9A6J8 |
| 721 | C0IMJ3 |
| 722 | C9J1E7 |
| 723 | C9J4I9 |
| 724 | C9J5G4 |
| 725 | C9J634 |
| 726 | C9J9K3 |
| 727 | C9JDQ2 |
| 728 | C9JEJ9 |
| 729 | C9JKR2 |
| 730 | C9JR82 |
| 731 | C9JWV4 |
| 732 | D3VVC2 |
| 733 | D6NKH9 |
| 734 | D6RA67 |
| 735 | D6RDA2 |
| 736 | D6RF03 |
| 737 | D6RIA3 |
| 738 | D6W5C0 |
| 739 | E2PU09 |
| 740 | E5KBQ3 |
| 741 | E5RFG5 |
| 742 | E5RHT6 |
| 743 | E7EPA6 |
| 744 | E7ET48 |
| 745 | E7EU81 |
| 746 | E9PE82 |
| 747 | E9PEB9 |
| 748 | E9PEZ1 |
| 749 | E9PGT3 |
| 750 | E9PIK2 |
| 751 | E9PK47 |
| 752 | E9PNH1 |
| 753 | E9PP05 |
| 754 | E9PP73 |
| 755 | E9PR23 |
| 756 | F2X0U9 |
| 757 | F2YYR6 |
| 758 | F5GWJ4 |
| 759 | F5H1K7 |
| 760 | F5H1Y4 |
| 761 | F5H2D5 |
| 762 | F5H793 |
| 763 | F5H7J8 |
| 764 | F6L6N6 |
| 765 | F6WFU6 |
| 766 | F8VPW2 |
| 767 | F8VPW9 |
| 768 | F8VRS4 |
| 769 | F8VWZ8 |
| 770 | F8VXB0 |
| 771 | F8W712 |
| 772 | F8W7L3 |
| 773 | F8W8Y7 |
| 774 | F8WB06 |
| 775 | F8WBZ7 |
| 776 | F8WCD0 |
| 777 | F8WD89 |
| 778 | F8WE06 |
| 779 | F8WE86 |
| 780 | F8WER7 |
| 781 | F8WEY3 |
| 782 | G3V217 |
| 783 | G3V2N2 |
| 784 | G3V433 |
| 785 | G3V534 |
| 786 | G3V5A9 |
| 787 | G3V5N8 |
| 788 | G3V5X1 |
| 789 | G3XAI2 |
| 790 | G5CCM8 |
| 791 | G5EA29 |
| 792 | G8FPZ9 |
| 793 | H0Y2W2 |
| 794 | H0Y797 |
| 795 | H0Y8U6 |
| 796 | H0Y9U5 |
| 797 | H0Y9Y7 |
| 798 | H0YDI0 |
| 799 | H0YFB2 |
| 800 | H0YGR4 |
| 801 | H0YJ57 |
| 802 | H0YM23 |
| 803 | H3BMT2 |
| 804 | H3BQ82 |
| 805 | H3BRX6 |
| 806 | B3BUU8 |
| 807 | H7BXT3 |
| 808 | H7BZ55 |
| 809 | H7BZT5 |
| 810 | H7BZX5 |
| 811 | H7C218 |
| 812 | H7C296 |
| 813 | H7C2B3 |
| 814 | H7C2G8 |
| 815 | H7C3Y8 |
| 816 | H7C5N9 |
| 817 | H9ZYJ2 |
| 818 | I3L2W4 |
| 819 | I3L4Z0 |
| 820 | I3NI05 |
| 821 | J3KQF5 |
| 822 | J3KSB5 |
| 823 | J3KT75 |
| 824 | J3QR77 |
| 825 | J3QSD7 |
| 826 | J7M2B1 |
| 827 | K7EJ66 |
| 828 | K7EJX9 |
| 829 | K7EK80 |
| 830 | K7EK91 |
| 831 | K7EMF0 |
| 832 | K7EQK5 |
| 833 | K7EQN3 |
| 834 | L0L6C1 |
| 835 | L8E855 |
| 836 | L8E9G8 |
| 837 | M0QYR7 |
| 838 | M0R196 |
| 839 | M0R1T2 |
| 840 | O00391 |
| 841 | O43680 |
| 842 | O60882 |
| 843 | O75074 |
| 844 | O75193 |
| 845 | O94888 |
| 846 | P01023 |
| 847 | P02462 |
| 848 | P02489 |
| 849 | P02753 |
| 850 | P02774 |
| 851 | P10244 |
| 852 | P11047 |
| 853 | P12270 |
| 854 | P12882 |
| 855 | P13645 |
| 856 | P14616 |
| 857 | P16234 |
| 858 | P20248 |
| 859 | P27987 |
| 860 | P40227 |
| 861 | P62068 |
| 862 | P78509 |
| 863 | Q01970 |
| 864 | Q05C57 |
| 865 | Q05CW6 |
| 866 | Q09666 |

TABLE 3-continued

Protein codes found in NPEX, APEX, and MSCEX

| | |
|---|---|
| 867 | Q0VD83 |
| 868 | Q12841 |
| 869 | Q13092 |
| 870 | Q13129 |
| 871 | Q13202 |
| 872 | Q13219 |
| 873 | Q13428 |
| 874 | Q13740 |
| 875 | Q13753 |
| 876 | Q13946 |
| 877 | Q14204 |
| 878 | Q14697 |
| 879 | Q14DG7 |
| 880 | Q15046 |
| 881 | Q15436 |
| 882 | Q15516 |
| 883 | Q16658 |
| 884 | Q1RMG2 |
| 885 | Q1T7F5 |
| 886 | Q1WWL2 |
| 887 | Q29939 |
| 888 | Q3LIF4 |
| 889 | Q3MIR4 |
| 890 | Q3SY84 |
| 891 | Q3YL85 |
| 892 | Q3ZCV2 |
| 893 | Q49A69 |
| 894 | Q4G163 |
| 895 | Q53FX3 |
| 896 | Q53GE2 |
| 897 | Q53GK6 |
| 898 | Q53GV6 |
| 899 | Q53QD5 |
| 900 | Q53SV8 |
| 901 | Q53TJ8 |
| 902 | Q53ZX9 |
| 903 | Q562L3 |
| 904 | Q57Z91 |
| 905 | Q58FF7 |
| 906 | Q59EM6 |
| 907 | Q59EZ3 |
| 908 | Q59F15 |
| 909 | Q59FP5 |
| 910 | Q59G95 |
| 911 | Q59GG8 |
| 912 | Q5H8Y1 |
| 913 | Q5I947 |
| 914 | Q5NV64 |
| 915 | Q5QGS0 |
| 916 | Q5SZK8 |
| 917 | Q5T0Z6 |
| 918 | Q5T114 |
| 919 | Q5T4Y8 |
| 920 | Q5T699 |
| 921 | Q5THK1 |
| 922 | Q5W0B1 |
| 923 | Q68CT4 |
| 924 | Q6FI37 |
| 925 | Q6FI52 |
| 926 | Q6GMV8 |
| 927 | Q6GV28 |
| 928 | Q6IAT9 |
| 929 | Q6ICQ8 |
| 930 | Q6JH02 |
| 931 | Q6KB66 |
| 932 | Q6MZI7 |
| 933 | Q6MZL5 |
| 934 | Q6MZM7 |
| 935 | Q6MZQ3 |
| 936 | Q6MZR7 |
| 937 | Q6MZT3 |
| 938 | Q6MZU1 |
| 939 | Q6N022 |
| 940 | Q6N065 |
| 941 | Q6NTE1 |
| 942 | Q6NWM3 |
| 943 | Q6NWP5 |
| 944 | Q6P047 |
| 945 | Q6P0N0 |
| 946 | Q6P2Q9 |
| 947 | Q6P2S7 |
| 948 | Q6P5S8 |
| 949 | Q6P6D3 |
| 950 | Q6PEY2 |
| 951 | Q6PG47 |
| 952 | Q6PI78 |
| 953 | Q6PID2 |
| 954 | Q6PJ55 |
| 955 | Q6PKG0 |
| 956 | Q6RFH8 |
| 957 | Q6S381 |
| 958 | Q6V0I7 |
| 959 | Q6YL47 |
| 960 | Q6ZN28 |
| 961 | Q6ZNP9 |
| 962 | Q6ZNS0 |
| 963 | Q6ZNX7 |
| 964 | Q6ZP46 |
| 965 | Q6ZP98 |
| 966 | Q6ZQN7 |
| 967 | Q6ZQV5 |
| 968 | Q6ZRW4 |
| 969 | Q6ZRX8 |
| 970 | Q6ZSK9 |
| 971 | Q6ZSW5 |
| 972 | Q6ZT24 |
| 973 | Q6ZTI3 |
| 974 | Q6ZU72 |
| 975 | Q6ZUU7 |
| 976 | Q6ZVV6 |
| 977 | Q6ZWB6 |
| 978 | Q71SM9 |
| 979 | Q7KYN0 |
| 980 | Q7Z2R7 |
| 981 | Q7Z3C9 |
| 982 | Q7Z3W2 |
| 983 | Q7Z3Y7 |
| 984 | Q7Z4Y9 |
| 985 | Q7Z5J4 |
| 986 | Q7Z6A0 |
| 987 | Q7Z6J9 |
| 988 | Q7Z6M2 |
| 989 | Q7Z6V2 |
| 990 | Q7Z6V5 |
| 991 | Q7Z7L0 |
| 992 | Q86SJ6 |
| 993 | Q86T79 |
| 994 | Q86UQ8 |
| 995 | Q86VZ2 |
| 996 | Q86W24 |
| 997 | Q86WP2 |
| 998 | Q86X73 |
| 999 | Q86Y38 |
| 1000 | Q86Y46 |
| 1001 | Q86YY7 |
| 1002 | Q8IUD6 |
| 1003 | Q8IVF1 |
| 1004 | Q8IVL0 |
| 1005 | Q8IWJ7 |
| 1006 | Q8IWU5 |
| 1007 | Q8IX07 |
| 1008 | Q8IXF7 |
| 1009 | Q8IYA2 |
| 1010 | Q8IYS3 |
| 1011 | Q8IZ60 |
| 1012 | Q8N112 |
| 1013 | Q8N1L4 |
| 1014 | Q8N1N0 |
| 1015 | Q8N1N4 |
| 1016 | Q8N3T9 |
| 1017 | Q8N4C7 |
| 1018 | Q8N4L1 |
| 1019 | Q8N4T0 |
| 1020 | Q8N5L1 |
| 1021 | Q8N604 |
| 1022 | Q8N6Y2 |

TABLE 3-continued

Protein codes found in NPEX, APEX, and MSCEX

| | |
|---|---|
| 1023 | Q8N7C6 |
| 1024 | Q8N7K0 |
| 1025 | Q8N7P1 |
| 1026 | Q8N7U2 |
| 1027 | Q8N8K9 |
| 1028 | Q8N9P6 |
| 1029 | Q8N9U2 |
| 1030 | Q8NAL2 |
| 1031 | Q8NAN9 |
| 1032 | Q8NAY4 |
| 1033 | Q8NBI3 |
| 1034 | Q8NBT9 |
| 1035 | Q8NC95 |
| 1036 | Q8NCK5 |
| 1037 | Q8NDA2 |
| 1038 | Q8NDB2 |
| 1039 | Q8NDL6 |
| 1040 | Q8NDQ6 |
| 1041 | Q8NEG7 |
| 1042 | Q8NF11 |
| 1043 | Q8NFC6 |
| 1044 | Q8NH37 |
| 1045 | Q8NHB0 |
| 1046 | Q8NHC0 |
| 1047 | Q8NHP1 |
| 1048 | Q8NIA0 |
| 1049 | Q8TB40 |
| 1050 | Q8TBB6 |
| 1051 | Q8TBP5 |
| 1052 | Q8TCF0 |
| 1053 | Q8TDJ5 |
| 1054 | Q8TDY2 |
| 1055 | Q8TE27 |
| 1056 | Q8TE59 |
| 1057 | Q8TE67 |
| 1058 | Q8TER0 |
| 1059 | Q8WUK0 |
| 1060 | Q8WW38 |
| 1061 | Q8WY74 |
| 1062 | Q8WYY5 |
| 1063 | Q92859 |
| 1064 | Q92908 |
| 1065 | Q92935 |
| 1066 | Q93034 |
| 1067 | Q93098 |
| 1068 | Q96BD5 |
| 1069 | Q96C96 |
| 1070 | Q96CT2 |
| 1071 | Q96D15 |
| 1072 | Q96DU3 |
| 1073 | Q96E76 |
| 1074 | Q96EN8 |
| 1075 | Q96F82 |
| 1076 | Q96H53 |
| 1077 | Q96I82 |
| 1078 | Q96IT0 |
| 1079 | Q96J92 |
| 1080 | Q96JU8 |
| 1081 | Q96LP0 |
| 1082 | Q96LW6 |
| 1083 | Q96MT7 |
| 1084 | Q96N23 |
| 1085 | Q96SP7 |
| 1086 | Q96T58 |
| 1087 | Q99772 |
| 1088 | Q9BQ22 |
| 1089 | Q9BQH9 |
| 1090 | Q9BQJ3 |
| 1091 | Q9BQS8 |
| 1092 | Q9BS06 |
| 1093 | Q9BTB7 |
| 1094 | Q9BTY2 |
| 1095 | Q9BUD9 |
| 1096 | Q9BUM6 |
| 1097 | Q9BV73 |
| 1098 | Q9BZU2 |
| 1099 | Q9C029 |
| 1100 | Q9C0B2 |
| 1101 | Q9C0B6 |
| 1102 | Q9GZP0 |
| 1103 | Q9GZS3 |
| 1104 | Q9H1B5 |
| 1105 | Q9H1L0 |
| 1106 | Q9H2I9 |
| 1107 | Q9H3I5 |
| 1108 | Q9H4S2 |
| 1109 | Q9H572 |
| 1110 | Q9H5H6 |
| 1111 | Q9H5T3 |
| 1112 | Q9H6V3 |
| 1113 | Q9H6X9 |
| 1114 | Q9H707 |
| 1115 | Q9H729 |
| 1116 | Q9H773 |
| 1117 | Q9H8X2 |
| 1118 | Q9H981 |
| 1119 | Q9H999 |
| 1120 | Q9H9J1 |
| 1121 | Q9HAP6 |
| 1122 | Q9HAT8 |
| 1123 | Q9HBF5 |
| 1124 | Q9HBJ3 |
| 1125 | Q9HBQ5 |
| 1126 | Q9HBV3 |
| 1127 | Q9HCB6 |
| 1128 | Q9NPD8 |
| 1129 | Q9NPG1 |
| 1130 | Q9NPI3 |
| 1131 | Q9NQ82 |
| 1132 | Q9NQW5 |
| 1133 | Q9NR99 |
| 1134 | Q9NRC3 |
| 1135 | Q9NRJ2 |
| 1136 | Q9NS63 |
| 1137 | Q9NSI4 |
| 1138 | Q9NTQ3 |
| 1139 | Q9NTQ5 |
| 1140 | Q9NTS0 |
| 1141 | Q9NTU8 |
| 1142 | Q9NVR5 |
| 1143 | Q9NWG8 |
| 1144 | Q9NWI5 |
| 1145 | Q9NX80 |
| 1146 | Q9NXG0 |
| 1147 | Q9NY61 |
| 1148 | Q9NY94 |
| 1149 | Q9NYI0 |
| 1150 | Q9NZK4 |
| 1151 | Q9P109 |
| 1152 | Q9P1A2 |
| 1153 | Q9P217 |
| 1154 | Q9P225 |
| 1155 | Q9P272 |
| 1156 | Q9P2P6 |
| 1157 | Q9UEG4 |
| 1158 | Q9UEJ6 |
| 1159 | Q9UFC7 |
| 1160 | Q9UG16 |
| 1161 | Q9UHU7 |
| 1162 | Q9UJ20 |
| 1163 | Q9UJQ4 |
| 1164 | Q9UKK3 |
| 1165 | Q9UKY7 |
| 1166 | Q9UL77 |
| 1167 | Q9UL82 |
| 1168 | Q9ULD0 |
| 1169 | Q9ULQ1 |
| 1170 | Q9UM06 |
| 1171 | Q9UMS4 |
| 1172 | Q9UPA5 |
| 1173 | Q9UPR0 |
| 1174 | Q9UPT9 |
| 1175 | Q9Y336 |
| 1176 | Q9Y349 |
| 1177 | Q9Y432 |
| 1178 | Q9Y490 |

TABLE 3-continued

Protein codes found in NPEX, APEX, and MSCEX

| | |
|---|---|
| 1179 | Q9Y594 |
| 1180 | Q9Y5F8 |
| 1181 | Q9Y5Z1 |
| 1182 | Q9Y678 |
| 1183 | Q9Y694 |
| 1184 | Q9Y6B5 |
| 1185 | Q9Y6C5 |
| 1186 | Q9Y6G4 |
| 1187 | Q9Y6L7 |
| 1188 | Q9Y6R7 |
| 1189 | Q9Y6T0 |
| 1190 | Q9Y6Y9 |
| 1191 | R4GMN1 |
| 1192 | R4GMT4 |
| 1193 | R4GMU0 |
| 1194 | R4GMY9 |
| 1195 | R4GMZ7 |
| 1196 | R4GN13 |
| 1197 | R4GN99 |
| 1198 | S4R3C4 |
| 1199 | S6BAQ9 |
| 1200 | S6E000 |
| 1201 | U3KQ32 |
| 1202 | U6C5D7 |
| 1203 | U6FVB0 |
| 1204 | V9GY82 |
| 1205 | A0A024R2W0 |
| 1206 | A0A068LN11 |
| 1207 | Q9Y3B8 |
| 1208 | A0A024R2Y4 |
| 1209 | A0A024R3C7 |
| 1210 | A0A024R610 |
| 1211 | A0A068F753 |
| 1212 | A0A075B6F3 |
| 1213 | A0A087X151 |
| 1214 | A0A0A0MQS9 |
| 1215 | A0A0A0MSF2 |
| 1216 | A0A0A0WDA6 |
| 1217 | A0A0A6YYF7 |
| 1218 | A0A0C4DGN2 |
| 1219 | A0A0G2JN42 |
| 1220 | A0A0K0K1H8 |
| 1221 | A0A0S2Z3Y1 |
| 1222 | A0A0U1RR22 |
| 1223 | A0A0U1RRB6 |
| 1224 | A0A125U0V4 |
| 1225 | A0A126LAY2 |
| 1226 | A0A140VKC0 |
| 1227 | A1L0W4 |
| 1228 | A4D1I1 |
| 1229 | A4D275 |
| 1230 | A4D2D2 |
| 1231 | A6NE02 |
| 1232 | A7E2D5 |
| 1233 | A7MBN3 |
| 1234 | A8K0D3 |
| 1235 | A8K2T0 |
| 1236 | A8K7E4 |
| 1237 | A8K7F6 |
| 1238 | A8K8N7 |
| 1239 | A8MQB8 |
| 1240 | B1ALU3 |
| 1241 | B1AQP2 |
| 1242 | B2RDN9 |
| 1243 | B2RWP0 |
| 1244 | B2RXH2 |
| 1245 | B3KRN2 |
| 1246 | B3KUD3 |
| 1247 | B3KW75 |
| 1248 | B3KW81 |
| 1249 | B3KXS7 |
| 1250 | B3KYA4 |
| 1251 | B3Y1X6 |
| 1252 | B4DDF8 |
| 1253 | B4DEC7 |
| 1254 | B4DER6 |
| 1255 | B4DET5 |
| 1256 | B4DH02 |
| 1257 | B4DH43 |
| 1258 | B4DHS0 |
| 1259 | B4DHZ6 |
| 1260 | B4DKR1 |
| 1261 | B4DM50 |
| 1262 | B4DPF7 |
| 1263 | B4DPR2 |
| 1264 | B4DSH6 |
| 1265 | B4DTD3 |
| 1266 | B4DUY3 |
| 1267 | B4DWR5 |
| 1268 | B4DYL8 |
| 1269 | B4E0A4 |
| 1270 | B4E123 |
| 1271 | B4E1L0 |
| 1272 | B4E1N8 |
| 1273 | B4E1Q0 |
| 1274 | B4E2H9 |
| 1275 | B4E2S2 |
| 1276 | B4E3R1 |
| 1277 | B7Z4A4 |
| 1278 | B7Z4R3 |
| 1279 | B7Z4V1 |
| 1280 | B7Z5C0 |
| 1281 | B7Z5M1 |
| 1282 | B7Z7Z9 |
| 1283 | B7Z829 |
| 1284 | B7Z983 |
| 1285 | B7ZA86 |
| 1286 | B7ZLS9 |
| 1287 | C0LLI5 |
| 1288 | C8CH86 |
| 1289 | C9IZN7 |
| 1290 | C9JBW9 |
| 1291 | C9JSD3 |
| 1292 | C9K0F9 |
| 1293 | D6RD73 |
| 1294 | D6RFI7 |
| 1295 | D6W603 |
| 1296 | D6W636 |
| 1297 | E3UVQ2 |
| 1298 | E3RIS7 |
| 1299 | E7ERW7 |
| 1300 | E9PCX8 |
| 1301 | E9PMT9 |
| 1302 | E9PPW0 |
| 1303 | E9PSE1 |
| 1304 | F5H077 |
| 1305 | F5H3S5 |
| 1306 | F5H571 |
| 1307 | F6KPG5 |
| 1308 | F6TH74 |
| 1309 | F8VZK3 |
| 1310 | F8W775 |
| 1311 | G3V1W5 |
| 1312 | H0Y638 |
| 1313 | H0Y8P0 |
| 1314 | H0YCI1 |
| 1315 | H0YI55 |
| 1316 | H0YJW3 |
| 1317 | H3BMJ1 |
| 1318 | H7C1D4 |
| 1319 | H7C2J6 |
| 1320 | H7C2Y5 |
| 1321 | H7C4F6 |
| 1322 | H7C4J7 |
| 1323 | H7C5W5 |
| 1324 | I3L4N8 |
| 1325 | J3KRN5 |
| 1326 | J3QR93 |
| 1327 | K7EKL5 |
| 1328 | O00245 |
| 1329 | O00468 |
| 1330 | O00755 |
| 1331 | O43304 |
| 1332 | P00792 |
| 1333 | P10253 |
| 1334 | P15924 |

TABLE 3-continued

Protein codes found in NPEX, APEX, and MSCEX

| | |
|---|---|
| 1335 | P17021 |
| 1336 | P23526 |
| 1337 | P43378 |
| 1338 | Q13332 |
| 1339 | Q13867 |
| 1340 | Q14353 |
| 1341 | Q14DE1 |
| 1342 | Q16271 |
| 1343 | Q2M3D2 |
| 1344 | Q2NKN3 |
| 1345 | Q2Q1W2 |
| 1346 | Q2UVF0 |
| 1347 | Q308M2 |
| 1348 | Q3C1V9 |
| 1349 | Q3KNT6 |
| 1350 | Q3ZCS4 |
| 1351 | Q4ZG05 |
| 1352 | Q53G71 |
| 1353 | Q53G75 |
| 1354 | Q53G76 |
| 1355 | Q53H01 |
| 1356 | Q53RS6 |
| 1357 | Q59ES2 |
| 1358 | Q5H9K5 |
| 1359 | Q5QPV1 |
| 1360 | Q5TEC6 |
| 1361 | Q5VWG9 |
| 1362 | Q6DN12 |
| 1363 | Q6GMP2 |
| 1364 | Q6NUL1 |
| 1365 | Q6YN16 |
| 1366 | Q7Z7J9 |
| 1367 | Q8IZJ3 |
| 1368 | Q8N0U2 |
| 1369 | Q8N9M3 |
| 1370 | Q8NAV9 |
| 1371 | Q8NB77 |
| 1372 | Q8NCL6 |
| 1373 | Q8NDH2 |
| 1374 | Q8NEI1 |
| 1375 | Q96HC0 |
| 1376 | Q96JR4 |
| 1377 | Q9BZ72 |
| 1378 | Q9H155 |
| 1379 | Q9H1R3 |
| 1380 | Q9H2Q8 |
| 1381 | Q9HB00 |
| 1382 | Q9P058 |
| 1383 | Q9UBG0 |
| 1384 | Q9UFH2 |
| 1385 | Q9UM07 |
| 1386 | Q9UM47 |
| 1387 | Q9UN91 |
| 1388 | Q9UNA0 |
| 1389 | U4PP31 |
| 1390 | V9GY66 |
| 1391 | Q9Y3F4 |
| 1392 | A0A024R8R4 |
| 1393 | A0A0X9V9D6 |
| 1394 | A6NHQ4 |
| 1395 | A8K6K7 |
| 1396 | B2R870 |
| 1397 | B3KTY7 |
| 1398 | B3KUC1 |
| 1399 | B3KXR5 |
| 1400 | B4DH61 |
| 1401 | B4DHZ3 |
| 1402 | B4DM44 |
| 1403 | B4DUF1 |
| 1404 | B4DWE1 |
| 1405 | B7Z3D8 |
| 1406 | C9JIJ3 |
| 1407 | C9JSN9 |
| 1408 | C9JYB8 |
| 1409 | D6RC11 |
| 1410 | D6RDA5 |
| 1411 | D6REC8 |
| 1412 | E7EUF1 |
| 1413 | E9PMJ5 |
| 1414 | E9PMP3 |
| 1415 | E9PNQ4 |
| 1416 | F8WE21 |
| 1417 | G3V0E5 |
| 1418 | H3BMT0 |
| 1419 | P31947 |
| 1420 | P50454 |
| 1421 | Q8WTX7 |
| 1422 | Q8WW34 |
| 1423 | Q8WY22 |
| 1424 | Q96A83 |
| 1425 | Q96LP2 |
| 1426 | Q96PE2 |
| 1427 | Q96RW4 |
| 1428 | Q9BVQ7 |
| 1429 | Q9H0A9 |
| 1430 | G5EA40 |
| 1431 | H0Y3Q4 |
| 1432 | H0Y6J8 |
| 1433 | H0Y849 |
| 1434 | H0YBC4 |
| 1435 | H0YJD8 |
| 1436 | H7C313 |
| 1437 | I3L188 |
| 1438 | L0R6N9 |
| 1439 | M0QYC8 |
| 1440 | M0QZD8 |
| 1441 | O60880 |
| 1442 | O95393 |
| 1443 | O96009 |
| 1444 | P06315 |
| 1445 | P61576 |
| 1446 | Q07092 |
| 1447 | Q15075 |
| 1448 | Q15818 |
| 1449 | Q4VXU2 |
| 1450 | Q4ZG84 |
| 1451 | Q53GD1 |
| 1452 | Q5T447 |
| 1453 | Q6IMJ0 |
| 1454 | Q6P5U3 |
| 1455 | Q6UWC4 |
| 1456 | Q6ZMX3 |
| 1457 | Q71DI3 |
| 1458 | Q7L553 |
| 1459 | Q7Z2K8 |
| 1460 | Q7Z535 |
| 1461 | Q7Z7B8 |
| 1462 | Q86SK3 |
| 1463 | Q8IUD5 |
| 1464 | Q8IX30 |
| 1465 | Q8IZ63 |
| 1466 | Q8N5R8 |
| 1467 | Q8N9W8 |
| 1468 | Q8NAA4 |
| 1469 | Q8NDQ8 |
| 1470 | Q8NG06 |
| 1473 | Q8TC36 |
| 1472 | Q8TE47 |
| 1473 | Q9NRG7 |
| 1474 | Q9NS39 |
| 1475 | Q9NVW7 |
| 1476 | Q9P0K7 |
| 1477 | Q9P0U3 |
| 1478 | Q9P1C0 |
| 1479 | Q9UBG5 |
| 1480 | Q9UFC3 |
| 1481 | Q9ULE4 |
| 1482 | Q9ULV4 |
| 1483 | Q9UMS0 |
| 1484 | Q9Y5T4 |
| 1485 | S6AWE3 |
| 1486 | U3KPS5 |
| 1487 | V9GYJ9 |
| 1488 | A0A024R2E1 |
| 1489 | A0A024R2M2 |
| 1490 | A0A087WZM7 |

TABLE 3-continued

Protein codes found in NPEX, APEX, and MSCEX

| | |
|---|---|
| 1491 | A0A0A0MRE3 |
| 1492 | A0A0A0MSB3 |
| 1493 | A0A0A0MTR1 |
| 1494 | A0A0F7G8J1 |
| 1495 | A0A0H4PJU9 |
| 1496 | A0A0S2Z4Z5 |
| 1497 | A0A125SXV9 |
| 1498 | A0A126LB06 |
| 1499 | A0A126LB27 |
| 1500 | A0N4Z6 |
| 1501 | A8K2X4 |
| 1502 | A8K3Q2 |
| 1503 | A8K486 |
| 1504 | A8K9U1 |
| 1505 | A9Z1X1 |
| 1506 | B1ANH7 |
| 1507 | B2R950 |
| 1508 | B2R9K6 |
| 1509 | B2RBG2 |
| 1510 | B2RCP4 |
| 1511 | B3KTN4 |
| 1512 | B3KVW6 |
| 1513 | B4DH07 |
| 1514 | B4DHB3 |
| 1515 | B4DI28 |
| 1516 | B4DIG0 |
| 1517 | B4DJG5 |
| 1518 | B4DMW8 |
| 1519 | B4DMX4 |
| 1520 | B4DNA0 |
| 1521 | B4DTV9 |
| 1522 | B4DW33 |
| 1523 | B4E1P8 |
| 1524 | B4E3Q1 |
| 1525 | B7WNR0 |
| 1526 | B7Z920 |
| 1527 | B7ZAA5 |
| 1528 | B7ZBP3 |
| 1529 | C9J6G3 |
| 1530 | C9JC84 |
| 1531 | C9JI87 |
| 1532 | E5RIL7 |
| 1533 | E7EQM8 |
| 1534 | E7EUJ7 |
| 1535 | E9PK10 |
| 1536 | E9PM35 |
| 1537 | E9PMF0 |
| 1538 | F8VS81 |
| 1539 | F8VTR5 |
| 1540 | F8W696 |
| 1541 | F8WEP4 |
| 1542 | H0Y596 |
| 1543 | H0YM50 |
| 1544 | H3BRJ5 |
| 1545 | H7BZ61 |
| 1546 | H7C0E2 |
| 1547 | H7C185 |
| 1548 | H7C3P7 |
| 1549 | H7C3S6 |
| 1550 | I0J9E2 |
| 1551 | J3KP97 |
| 1552 | J3KSC1 |
| 1553 | K7EKZ1 |
| 1554 | K9MS24 |
| 1555 | M0R0S9 |
| 1556 | O60701 |
| 1557 | O95613 |
| 1558 | P06331 |
| 1559 | P07737 |
| 1560 | P08253 |
| 1561 | P11021 |
| 1562 | P25391 |
| 1563 | P30041 |
| 1564 | P31267 |
| 1565 | P32238 |
| 1566 | P46093 |
| 1567 | P53618 |
| 1568 | P55786 |
| 1569 | P58397 |
| 1570 | P60174 |
| 1571 | P62304 |
| 1572 | Q05DH4 |
| 1573 | Q0IIN9 |
| 1574 | Q1HW68 |
| 1575 | Q49SQ1 |
| 1576 | Q4LE45 |
| 1577 | Q59FG0 |
| 1578 | Q5H9N7 |
| 1579 | Q5VW36 |
| 1580 | Q6AZ94 |
| 1581 | A0A024QZJ6 |
| 1582 | A0A024R1X2 |
| 1583 | A0A024R2J4 |
| 1584 | A0A024R4X7 |
| 1585 | A0A024R524 |
| 1586 | A0A024R694 |
| 1587 | A0A024R6R4 |
| 1588 | A0A024R8F8 |
| 1589 | A0A024RAR5 |
| 1590 | A0A024RC65 |
| 1591 | A0A024RDJ4 |
| 1592 | A0A024RDP2 |
| 1593 | A0A024RDY0 |
| 1594 | A0A075B6U6 |
| 1595 | A0A087WTA2 |
| 1596 | A0A087WW31 |
| 1597 | A0A087WXI0 |
| 1598 | A0A087WXI2 |
| 1599 | A0A087WY71 |
| 1600 | A0A087WYL6 |
| 1601 | A0A087WYS6 |
| 1602 | A0A087WZE5 |
| 1603 | A0A087X115 |
| 1604 | A0A087X1P2 |
| 1605 | A0A087X2A5 |
| 1606 | A0A096LP50 |
| 1607 | A0A096LPG1 |
| 1608 | A0A0A0MSK6 |
| 1609 | A0A0A0MSW5 |
| 1610 | A0A0A0MT87 |
| 1611 | A0A0A0MTS7 |
| 1612 | A0A0A0N0L5 |
| 1613 | A0A0A8WIM0 |
| 1614 | A0A0C4DG40 |
| 1615 | A0A0C4DGG6 |
| 1616 | A0A0C4ZLG8 |
| 1617 | A0A0D9SF38 |
| 1618 | A0A0E3DD76 |
| 1619 | A0A0G2JH42 |
| 1620 | A0A0G2JKA5 |
| 1621 | A0A0G2JS76 |
| 1622 | A0A0H4IV28 |
| 1623 | A0A0S2Z3F5 |
| 1624 | A0A0S2Z421 |
| 1625 | A0A0S2Z4Q2 |
| 1626 | A0A0S2Z4Y8 |
| 1627 | A0A0S2Z500 |
| 1628 | A0A0S2Z592 |
| 1629 | A0A0U1RQE8 |
| 1630 | A0A0U1RR70 |
| 1631 | A0A126GW51 |
| 1632 | A0A126LAX2 |
| 1633 | A0A126LB21 |
| 1634 | A0A126LB25 |
| 1635 | A0A126LB36 |
| 1636 | A0A140VK10 |
| 1637 | A0A140VK26 |
| 1638 | A0A140VK66 |
| 1639 | A0A140VKE5 |
| 1640 | A0A158RFU5 |
| 1641 | A0JLU2 |
| 1642 | A0PJZ3 |
| 1643 | A2IPH7 |
| 1644 | A2JA19 |
| 1645 | A2V663 |
| 1646 | A4D1E4 |

TABLE 3-continued

Protein codes found in NPEX, APEX, and MSCEX

| | |
|---|---|
| 1647 | A4D233 |
| 1648 | A5PKX5 |
| 1649 | A6H8X0 |
| 1650 | A6N865 |
| 1651 | A6NCN8 |
| 1652 | A6NCT7 |
| 1653 | A6NEC2 |
| 1654 | A6NFI3 |
| 1655 | A6NHR9 |
| 1656 | A6NL46 |
| 1657 | A6NLG9 |
| 1658 | A6NMY6 |
| 1659 | A6NMZ7 |
| 1660 | A6PVY3 |
| 1661 | A7E2F9 |
| 1662 | A8K2P8 |
| 1663 | A8K343 |
| 1664 | A8K394 |
| 1665 | A8K468 |
| 1666 | A8K4W7 |
| 1667 | A8K6K9 |
| 1668 | A8K6T3 |
| 1669 | A8K9T5 |
| 1670 | A8KA30 |
| 1671 | A8KAJ9 |
| 1672 | A8MZI9 |
| 1673 | B0AZV7 |
| 1674 | B0LPE5 |
| 1675 | B1AML2 |
| 1676 | B1N7G3 |
| 1677 | B1WB49 |
| 1678 | B2R4Q7 |
| 1679 | B2R5M9 |
| 1680 | B2R6N0 |
| 1681 | B2R6N6 |
| 1682 | B2R7N9 |
| 1683 | B2R926 |
| 1684 | B2RAH7 |
| 1685 | B2RB89 |
| 1686 | B2RBF5 |
| 1687 | B2RD36 |
| 1688 | B2RD79 |
| 1689 | B2RDX5 |
| 1690 | B2RG98 |
| 1691 | B3CJD3 |
| 1692 | B3KNV5 |
| 1693 | B3KP07 |
| 1694 | B3KPN7 |
| 1695 | B3KQG6 |
| 1696 | B3KQK3 |
| 1697 | B3KQT2 |
| 1698 | B3KRN6 |
| 1699 | B3KRS1 |
| 1700 | B3KSV8 |
| 1701 | B3KTA3 |
| 1702 | B3KTH9 |
| 1703 | B3KTQ9 |
| 1704 | B3KU00 |
| 1705 | B3KUB1 |
| 1706 | B3KUX9 |
| 1707 | B3KWK3 |
| 1708 | B3KXJ7 |
| 1709 | B3KYA0 |
| 1710 | B3W6G7 |
| 1711 | B4DDK9 |
| 1712 | B4DDQ4 |
| 1713 | B4DG76 |
| 1714 | B4DGF9 |
| 1715 | B4DI39 |
| 1716 | B4DIQ8 |
| 1717 | B4DJD3 |
| 1718 | B4DKU3 |
| 1719 | B4DM05 |
| 1720 | B4DMF0 |
| 1721 | B4DNE9 |
| 1722 | B4DNI5 |
| 1723 | B4DPM5 |
| 1724 | B4DPV4 |
| 1725 | B4DR01 |
| 1726 | B4DR16 |
| 1727 | B4DR46 |
| 1728 | B4DSR6 |
| 1729 | B4DSU7 |
| 1730 | B4DT39 |
| 1731 | B4DU16 |
| 1732 | B4DUD7 |
| 1733 | B4DUZ6 |
| 1734 | B4DVQ0 |
| 1735 | B4DW60 |
| 1736 | B4DXM0 |
| 1737 | B4DYJ4 |
| 1738 | B4DZ36 |
| 1739 | B4DZP6 |
| 1740 | B4DZQ7 |
| 1741 | B4E1P9 |
| 1742 | B4E3R4 |
| 1743 | B5MCY1 |
| 1744 | B5MD39 |
| 1745 | B5MEF5 |
| 1746 | B6ZGT4 |
| 1747 | B7Z2B7 |
| 1748 | B7Z3I1 |
| 1749 | B7Z3R6 |
| 1750 | B7Z3V1 |
| 1751 | B7Z4S2 |
| 1752 | B7Z5H8 |
| 1753 | B7Z6I6 |
| 1754 | B7Z6K5 |
| 1755 | B7Z704 |
| 1756 | B7Z7Z0 |
| 1757 | B7Z938 |
| 1758 | B7Z9B7 |
| 1759 | B7Z9J7 |
| 1760 | B7Z9W3 |
| 1761 | B7ZKM7 |
| 1762 | B7ZLE5 |
| 1763 | C1K3N0 |
| 1764 | C6KIA6 |
| 1765 | C9JPF8 |
| 1766 | C9JQ82 |
| 1767 | C9JQI7 |
| 1768 | C9JSP6 |
| 1769 | C9JTC5 |
| 1770 | C9JTN7 |
| 1771 | C9JY46 |
| 1772 | D2X9V0 |
| 1773 | D3DN94 |
| 1774 | D3DPF9 |
| 1775 | D3DR43 |
| 1776 | D3DU04 |
| 1777 | D3DVC4 |
| 1778 | D3DW55 |
| 1779 | D3DX93 |
| 1780 | D3VVD3 |
| 1781 | D3WYY9 |
| 1782 | D6R9T4 |
| 1783 | D6REL0 |
| 1784 | D6RIE4 |
| 1785 | D6RJB7 |
| 1786 | D6W5C2 |
| 1787 | D7RTA7 |
| 1788 | E5RFV7 |
| 1789 | E5RHN3 |
| 1790 | E5RIY1 |
| 1791 | E5RJA3 |
| 1792 | E7ENR6 |
| 1793 | E7EQ34 |
| 1794 | E7ER60 |
| 1795 | E7ERF0 |
| 1796 | E7ESF5 |
| 1797 | E7EWS1 |
| 1798 | E9PAL5 |
| 1799 | E9PBB1 |
| 1800 | E9PC41 |
| 1801 | E9PDN5 |
| 1802 | E9PII3 |

TABLE 3-continued

Protein codes found in NPEX, APEX, and MSCEX

| | |
|---|---|
| 1803 | E9PJ29 |
| 1804 | E9PKB8 |
| 1805 | E9PKI9 |
| 1806 | E9PLK6 |
| 1807 | E9PM30 |
| 1808 | E9PMQ3 |
| 1809 | E9PMV1 |
| 1810 | E9PNF1 |
| 1811 | E9PNZ6 |
| 1812 | E9PPM7 |
| 1813 | E9PQ56 |
| 1814 | E9PQL1 |
| 1815 | E9PRA7 |
| 1816 | F4ZW64 |
| 1817 | F5GXA0 |
| 1818 | F5GY56 |
| 1819 | F5H423 |
| 1820 | F5H7E5 |
| 1821 | F5H8I3 |
| 1822 | F8VSC5 |
| 1823 | F8VUZ7 |
| 1824 | F8VWV6 |
| 1825 | F8W1S1 |
| 1826 | F8WAM2 |
| 1827 | F8WBI5 |
| 1828 | F8WBJ2 |
| 1829 | F8WCF2 |
| 1830 | F8WD09 |
| 1831 | F8WDF1 |
| 1832 | F8WDM8 |
| 1833 | F8WEK9 |
| 1834 | G3V1N2 |
| 1835 | G3V2D8 |
| 1836 | G3V5L2 |
| 1837 | H0Y3T6 |
| 1838 | H0Y592 |
| 1839 | H0Y938 |
| 1840 | H0Y9K1 |
| 1841 | H0YA55 |
| 1842 | H0YAD3 |
| 1843 | H0YAM0 |
| 1844 | H0YAS1 |
| 1845 | H0YBNS |
| 1846 | H0YCL7 |
| 1847 | H0YCP4 |
| 1848 | H0YEX9 |
| 1849 | H0YFA9 |
| 1850 | H0YFT1 |
| 1851 | H0YIA0 |
| 1852 | H0YIC5 |
| 1853 | H0YJP0 |
| 1854 | H0YJV3 |
| 1855 | H0YL56 |
| 1856 | H0YM11 |
| 1857 | H0YNY7 |
| 1858 | H3BM10 |
| 1859 | H3BNR2 |
| 1860 | H3BPD2 |
| 1861 | H3BTE9 |
| 1862 | H6VRF9 |
| 1863 | H7BXN1 |
| 1864 | H7BYJ3 |
| 1865 | H7BZ08 |
| 1866 | H7BZI1 |
| 1867 | H7C0D8 |
| 1868 | H7C0Y8 |
| 1869 | H7C0Z9 |
| 1870 | H7C269 |
| 1871 | H7C435 |
| 1872 | H7C4A7 |
| 1873 | H7C4G9 |
| 1874 | H7C505 |
| 1875 | H7C519 |
| 1876 | H7C5R4 |
| 1877 | H9MHK7 |
| 1878 | I0CMK6 |
| 1879 | I1SRC5 |
| 1880 | I3L192 |
| 1881 | I3L202 |
| 1882 | I3L2B0 |
| 1883 | I3L454 |
| 1884 | I6U4P1 |
| 1885 | J3KNM9 |
| 1886 | J3KRI7 |
| 1887 | J3KRQ5 |
| 1888 | J3KRS3 |
| 1889 | J3KRZ0 |
| 1890 | J3KSI7 |
| 1891 | J3QKM3 |
| 1892 | J3QR31 |
| 1893 | J3QR90 |
| 1894 | K7EKP8 |
| 1895 | K7EQJ8 |
| 1896 | K7ES02 |
| 1897 | K7ES57 |
| 1898 | L0B1V4 |
| 1899 | L0R8A8 |
| 1900 | L7RXH0 |
| 1901 | L8E775 |
| 1902 | L8E7T8 |
| 1903 | L8E872 |
| 1904 | L8E935 |
| 1905 | L8EA23 |
| 1906 | L8EC78 |
| 1907 | L8ECD0 |
| 1908 | L8ECG5 |
| 1909 | L8ECJ9 |
| 1910 | L8ECM9 |
| 1911 | M0QX38 |
| 1912 | M0QZ52 |
| 1913 | M0QZH0 |
| 1914 | M0QZL2 |
| 1915 | M0R0B6 |
| 1916 | M0R0I5 |
| 1917 | M0R1Y0 |
| 1918 | M0R265 |
| 1919 | M0R2B8 |
| 1920 | M0R2G8 |
| 1921 | M0R2X8 |
| 1922 | O00186 |
| 1923 | O00228 |
| 1924 | O00231 |
| 1925 | O00300 |
| 1926 | O00370 |
| 1927 | O00602 |
| 1928 | O15031 |
| 1929 | O15061 |
| 1930 | O15379 |
| 1931 | O15389 |
| 1932 | O15400 |
| 1933 | O43298 |
| 1934 | O43313 |
| 1935 | O60318 |
| 1936 | O60687 |
| 1937 | O60806 |
| 1938 | O60869 |
| 1939 | O60888 |
| 1940 | O75037 |
| 1941 | O75051 |
| 1942 | O75054 |
| 1943 | O75230 |
| 1944 | O75294 |
| 1945 | O77727 |
| 1946 | O94933 |
| 1947 | O95073 |
| 1948 | O95396 |
| 1949 | O95459 |
| 1950 | O95622 |
| 1951 | O95760 |
| 1952 | P00761 |
| 1953 | P01024 |
| 1954 | P01031 |
| 1955 | P01716 |
| 1956 | P01782 |
| 1957 | P04264 |
| 1958 | P05388 |

TABLE 3-continued

Protein codes found in NPEX, APEX, and MSCEX

| | |
|---|---|
| 1959 | P07996 |
| 1960 | P08572 |
| 1961 | P09544 |
| 1962 | P09619 |
| 1963 | P0C091 |
| 1964 | P0C671 |
| 1965 | P0C7M7 |
| 1966 | P0C7V6 |
| 1967 | P0CG21 |
| 1968 | P0DKB5 |
| 1969 | P10745 |
| 1970 | P12109 |
| 1971 | P12268 |
| 1972 | P13196 |
| 1973 | P15531 |
| 1974 | P15621 |
| 1975 | P19174 |
| 1976 | P20783 |
| 1977 | P22760 |
| 1978 | P23471 |
| 1979 | P25786 |
| 1980 | P25788 |
| 1981 | P25940 |
| 1982 | P27694 |
| 1983 | P30050 |
| 1984 | P30101 |
| 1985 | P31152 |
| 1986 | P33908 |
| 1987 | P35555 |
| 1988 | P35606 |
| 1989 | P35908 |
| 1990 | P36955 |
| 1991 | P38570 |
| 1992 | P38606 |
| 1993 | P38935 |
| 1994 | P45974 |
| 1995 | P47989 |
| 1996 | P49419 |
| 1997 | P49454 |
| 1998 | P49588 |
| 1999 | P49788 |
| 2000 | P49792 |
| 2001 | P50570 |
| 2002 | P51160 |
| 2003 | P51884 |
| 2004 | P53708 |
| 2005 | P54136 |
| 2006 | P56537 |
| 2007 | P61221 |
| 2008 | P62318 |
| 2009 | P62805 |
| 2010 | P69905 |
| 2011 | P82987 |
| 2012 | P98160 |
| 2013 | Q01959 |
| 2014 | Q02388 |
| 2015 | Q02779 |
| 2016 | Q04721 |
| 2017 | Q05BT5 |
| 2018 | Q05BU1 |
| 2019 | Q05BV1 |
| 2020 | Q05C82 |
| 2021 | Q05CV2 |
| 2022 | Q06210 |
| 2023 | Q07954 |
| 2024 | Q08211 |
| 2025 | Q0VGA3 |
| 2026 | Q0ZAJ2 |
| 2027 | Q0ZAJ7 |
| 2028 | Q12813 |
| 2029 | Q12965 |
| 2030 | Q13118 |
| 2031 | Q13136 |
| 2032 | Q13162 |
| 2033 | Q13537 |
| 2034 | Q14127 |
| 2035 | Q14315 |
| 2036 | Q14423 |
| 2037 | Q14543 |
| 2038 | Q14917 |
| 2039 | Q14C87 |
| 2040 | Q14CE9 |
| 2041 | Q15058 |
| 2042 | Q15113 |
| 2043 | Q15247 |
| 2044 | Q15296 |
| 2045 | Q16394 |
| 2046 | Q16761 |
| 2047 | Q2I009 |
| 2048 | Q2M1Z3 |
| 2049 | Q2M2I5 |
| 2050 | Q2M3M2 |
| 2051 | Q2PT48 |
| 2052 | Q2WEN9 |
| 2053 | Q2WGN9 |
| 2054 | Q3T906 |
| 2055 | Q494V2 |
| 2056 | Q494X3 |
| 2057 | Q496A9 |
| 2058 | Q496Y1 |
| 2059 | Q499G7 |
| 2060 | Q4KMG9 |
| 2061 | Q4LE48 |
| 2062 | Q4VBP4 |
| 2063 | Q53H82 |
| 2064 | Q53HC2 |
| 2065 | Q53HI2 |
| 2066 | Q53HQ4 |
| 2067 | Q53HU6 |
| 2068 | Q562R1 |
| 2069 | Q562V5 |
| 2070 | Q562Z4 |
| 2071 | Q59E18 |
| 2072 | Q59FG2 |
| 2073 | Q59FM3 |
| 2074 | Q59FS8 |
| 2075 | Q59GB4 |
| 2076 | Q59GM9 |
| 2077 | Q59GN1 |
| 2078 | Q59H94 |
| 2079 | Q59HE3 |
| 2080 | Q5CZB5 |
| 2081 | Q5F1R6 |
| 2082 | Q5H9M0 |
| 2083 | Q5H9S0 |
| 2084 | Q5HYC2 |
| 2085 | Q5J875 |
| 2086 | Q5JPB2 |
| 2087 | Q5JXI3 |
| 2088 | Q5JY65 |
| 2089 | Q5JZ02 |
| 2090 | Q5K684 |
| 2091 | Q5R2U7 |
| 2092 | Q5RI53 |
| 2093 | Q5SQS7 |
| 2094 | Q5SR54 |
| 2095 | Q5T6X5 |
| 2096 | Q5T7P6 |
| 2097 | Q5T8A7 |
| 2098 | Q5TCT4 |
| 2099 | Q5TFJ7 |
| 2100 | Q5U0K8 |
| 2101 | Q5VWW1 |
| 2102 | Q5VZB9 |
| 2103 | Q5XKR4 |
| 2104 | Q63HL4 |
| 2105 | Q641R5 |
| 2106 | Q659F9 |
| 2107 | Q68CZ6 |
| 2108 | Q68D85 |
| 2109 | Q68VJ5 |
| 2110 | Q6EMK4 |
| 2111 | Q6FGB3 |
| 2112 | Q6IBG1 |
| 2113 | Q6IBZ4 |
| 2114 | Q6IPQ0 |

TABLE 3-continued

Protein codes found in NPEX, APEX, and MSCEX

| | |
|---|---|
| 2115 | Q6MZX7 |
| 2116 | Q6NVY8 |
| 2117 | Q6NXN2 |
| 2118 | Q6NXP6 |
| 2119 | Q6P2D8 |
| 2120 | Q6P461 |
| 2121 | Q6PGP7 |
| 2122 | Q6TFL4 |
| 2123 | Q6U717 |
| 2124 | Q6UVK1 |
| 2125 | Q6UW63 |
| 2126 | Q6UWF9 |
| 2127 | Q6UWP8 |
| 2128 | Q6UWX4 |
| 2129 | Q6DXR4 |
| 2130 | Q6UXS9 |
| 2131 | Q6Y2K9 |
| 2132 | Q6ZNE2 |
| 2133 | Q6ZP05 |
| 2134 | Q6ZQP0 |
| 2135 | Q6ZTY9 |
| 2136 | Q6ZUX1 |
| 2137 | Q6ZUZ3 |
| 2138 | Q70Z35 |
| 2139 | Q71V99 |
| 2140 | Q75MY8 |
| 2141 | Q75N88 |
| 2142 | Q7RTY8 |
| 2143 | Q7Z3A2 |
| 2144 | Q7Z4Q2 |
| 2145 | Q7Z5P9 |
| 2146 | Q7Z5Y4 |
| 2147 | Q86VH2 |
| 2148 | Q86W28 |
| 2149 | Q86X55 |
| 2150 | Q86XX4 |
| 2151 | Q8IX54 |
| 2152 | Q8IY85 |
| 2153 | Q8IYV9 |
| 2154 | Q8IYX0 |
| 2155 | Q8IZ13 |
| 2156 | Q8N0Y7 |
| 2157 | Q8N2E1 |
| 2158 | Q8N3G4 |
| 2159 | Q8N5C1 |
| 2160 | Q8N609 |
| 2161 | Q8N7E2 |
| 2162 | Q8N7U5 |
| 2163 | Q8N944 |
| 2164 | Q8N9V7 |
| 2165 | Q8NB66 |
| 2166 | Q8ND82 |
| 2167 | Q8NEN9 |
| 2168 | Q8NFX7 |
| 2169 | Q8NHP8 |
| 2170 | Q8TBP0 |
| 2171 | Q8TD16 |
| 2172 | Q8TD90 |
| 2173 | Q8TDV0 |
| 2174 | Q8TEY7 |
| 2175 | Q8WUG5 |
| 2176 | Q8WUH2 |
| 2177 | Q8WUJ3 |
| 2178 | Q8WUM6 |
| 2179 | Q8WWU8 |
| 2180 | Q8WXI7 |
| 2181 | Q8WY44 |
| 2182 | Q8WZ18 |
| 2183 | Q8WZ31 |
| 2184 | Q8WZB3 |
| 2185 | Q92626 |
| 2186 | Q92630 |
| 2187 | Q92743 |
| 2188 | Q92833 |
| 2189 | Q969Y0 |
| 2190 | Q96AW0 |
| 2191 | Q96BN2 |
| 2192 | Q96BY6 |
| 2193 | Q96DJ8 |
| 2194 | Q96FN9 |
| 2195 | Q96HJ3 |
| 2196 | Q96IT5 |
| 2197 | Q96JQ0 |
| 2198 | Q96KQ4 |
| 2199 | Q96L96 |
| 2200 | Q96LM5 |
| 2201 | Q96LQ0 |
| 2202 | Q96MK8 |
| 2203 | Q96MX6 |
| 2204 | Q96N75 |
| 2205 | Q96PD2 |
| 2206 | Q96PD5 |
| 2207 | Q96PQ9 |
| 2208 | Q96Q15 |
| 2209 | Q96QH0 |
| 2210 | Q96RS6 |
| 2211 | Q96RW7 |
| 2212 | Q99985 |
| 2213 | Q9BQK8 |
| 2214 | Q9BRH9 |
| 2215 | Q9BS26 |
| 2216 | Q9BUG9 |
| 2217 | Q9BWV1 |
| 2218 | Q9BXJ3 |
| 2219 | Q9BXX0 |
| 2220 | Q9BY89 |
| 2221 | Q9BYX7 |
| 2222 | Q9BZT5 |
| 2223 | Q9C055 |
| 2224 | Q9C071 |
| 2225 | Q9C0G0 |
| 2226 | Q9CSP3 |
| 2227 | Q9H1B7 |
| 2228 | Q9H224 |
| 2229 | Q9H2M8 |
| 2230 | Q9H3U1 |
| 2231 | Q9H3U2 |
| 2232 | Q9H526 |
| 2233 | Q9H557 |
| 2234 | Q9H7T9 |
| 2235 | Q9H7U1 |
| 2236 | Q9H814 |
| 2237 | Q9H863 |
| 2238 | Q9H993 |
| 2239 | Q9H996 |
| 2240 | Q9HAR7 |
| 2241 | Q9HBV4 |
| 2242 | Q9HBW1 |
| 2243 | Q9HC10 |
| 2244 | Q9HD43 |
| 2245 | Q9NQL0 |
| 2246 | Q9NQX0 |
| 2247 | Q9NRN1 |
| 2248 | Q9NS98 |
| 2249 | Q9NSF5 |
| 2250 | Q9NT48 |
| 2251 | Q9NU22 |
| 2252 | Q9NUL7 |
| 2253 | Q9NVD3 |
| 2254 | Q9NXD9 |
| 2255 | Q9NYQ8 |
| 2256 | Q9NYU2 |
| 2257 | Q9NZ56 |
| 2258 | Q9NZI8 |
| 2259 | Q9NZJ4 |
| 2260 | Q9NZQ3 |
| 2261 | Q9P0K0 |
| 2262 | Q9P0Z3 |
| 2263 | Q9P104 |
| 2264 | Q9P186 |
| 2265 | Q9P1F0 |
| 2266 | Q9P266 |
| 2267 | Q9P2C8 |
| 2268 | Q9P2R9 |
| 2269 | Q9UBK8 |
| 2270 | Q9UBW8 |

TABLE 3-continued

Protein codes found in NPEX, APEX, and MSCEX

| | |
|---|---|
| 2271 | Q9UCR1 |
| 2272 | Q9UE50 |
| 2273 | Q9UF29 |
| 2274 | Q9UGK2 |
| 2275 | Q9UIY3 |
| 2276 | Q9UJX5 |
| 2277 | Q9UKE0 |
| 2278 | Q9UKX2 |
| 2279 | Q9UL97 |
| 2280 | Q9ULH4 |
| 2281 | Q9ULI3 |
| 2282 | Q9ULL8 |
| 2283 | Q9UMG4 |
| 2284 | Q9UMJ0 |
| 2285 | Q9UML5 |
| 2286 | Q9UMR3 |
| 2287 | Q9UN70 |
| 2288 | Q9UPX8 |
| 2289 | Q9UPY3 |
| 2290 | Q9UPZ3 |
| 2291 | Q9UQR0 |
| 2292 | Q9Y277 |
| 2293 | Q9Y2K3 |
| 2294 | Q9Y3A2 |
| 2295 | Q9Y3D6 |
| 2296 | Q9Y3I0 |
| 2297 | Q9Y4K0 |
| 2298 | Q9Y574 |
| 2299 | Q9Y5G4 |
| 2300 | Q9Y5Q9 |
| 2301 | Q9Y680 |
| 2302 | Q9Y6C2 |
| 2303 | R4GMQ5 |
| 2304 | R4GN15 |
| 2305 | S4R3C7 |
| 2306 | S4R3Q3 |
| 2307 | U3KQG5 |
| 2308 | U5IRJ4 |
| 2309 | V9GY54 |
| 2310 | V9GZ55 |
| 2311 | V9GZG2 |
| 2312 | V9H0A6 |
| 2313 | V9H102 |
| 2314 | V9HW11 |
| 2315 | V9HW34 |
| 2316 | V9HW62 |
| 2317 | V9HW88 |
| 2318 | V9HWB4 |
| 2319 | V9HWB5 |
| 2320 | V9HWE1 |
| 2321 | V9HWF2 |
| 2322 | V9HWI6 |
| 2323 | V9TNI8 |
| 2324 | W8YM35 |
| 2325 | X5DNI9 |
| 2326 | X5DP31 |
| 2327 | X5DPA6 |
| 2328 | X5DR62 |
| 2329 | X6R647 |
| 2330 | X6RE28 |
| 2331 | A0A024R3N3 |
| 2332 | A0A024R456 |
| 2333 | A0A024R462 |
| 2334 | A0A024R6P6 |
| 2335 | A0A024R7W9 |
| 2336 | A0A024R893 |
| 2337 | A0A024R9I0 |
| 2338 | A0A024R9Q1 |
| 2339 | A0A024RAA7 |
| 2340 | A0A024RC00 |
| 2341 | A0A087WTA8 |
| 2342 | A0A087WUA7 |
| 2343 | A0A087WVP1 |
| 2344 | A0A087WYF9 |
| 2345 | A0A087X163 |
| 2346 | A0A087X1V8 |
| 2347 | A0A0A0MRD2 |
| 2348 | A0A0A0MRS2 |
| 2349 | A0A0A0MSD0 |
| 2350 | A0A0C4DFM7 |
| 2351 | A0A0C4DG73 |
| 2352 | A0A0D9SFA9 |
| 2353 | A0A0E3DCV7 |
| 2354 | A0A0J9YVW2 |
| 2355 | A0A0J9YVW5 |
| 2356 | A0A0J9YX90 |
| 2357 | A0A0S2Z4B5 |
| 2358 | A0A0X9UWJ6 |
| 2359 | A0A126GVE6 |
| 2360 | A0A126LB13 |
| 2361 | A1L4H1 |
| 2362 | A6NEQ2 |
| 2363 | A6PVK5 |
| 2364 | A8K0K1 |
| 2365 | A8K0P8 |
| 2366 | A8K0R7 |
| 2367 | A8K2P0 |
| 2368 | A8K7T4 |
| 2369 | A8K874 |
| 2370 | A8K8X0 |
| 2371 | A8K964 |
| 2372 | A8MTJ3 |
| 2373 | B0AZS6 |
| 2374 | B3KM36 |
| 2375 | B3KNK5 |
| 2376 | B3KPZ8 |
| 2377 | B3KQU2 |
| 2378 | B3KWQ8 |
| 2379 | B3KX74 |
| 2380 | B4DEB0 |
| 2381 | B4DEG1 |
| 2382 | B4DFY0 |
| 2383 | B4DGQ7 |
| 2384 | B4DGQ8 |
| 2385 | B4DIP4 |
| 2386 | B4DJ30 |
| 2387 | B4DL30 |
| 2388 | B4DM84 |
| 2389 | B4DMV8 |
| 2390 | B4DP50 |
| 2391 | B4DPV2 |
| 2392 | B4DPY2 |
| 2393 | B4DRQ4 |
| 2394 | B4DU77 |
| 2395 | B4DW52 |
| 2396 | B4E0D8 |
| 2397 | B4E2L2 |
| 2398 | B4E2M7 |
| 2399 | B4E2Y4 |
| 2400 | B7Z1H7 |
| 2401 | B7Z2V6 |
| 2402 | B7Z4C0 |
| 2403 | B7Z6W4 |
| 2404 | B7ZLW8 |
| 2405 | B7ZMN7 |
| 2406 | C6GLW5 |
| 2407 | C9JH44 |
| 2408 | C9JR58 |
| 2409 | C9JW04 |
| 2410 | D6R9I8 |
| 2411 | D6REZ4 |
| 2412 | E1A689 |
| 2413 | E5RJI5 |
| 2414 | E9PAV3 |
| 2415 | E9PL83 |
| 2416 | E9PPG5 |
| 2417 | F1T0E5 |
| 2418 | F2Z2U4 |
| 2419 | F6QYI9 |
| 2420 | F8W0W6 |
| 2421 | F8W8H5 |
| 2422 | G3V471 |
| 2423 | H0Y645 |
| 2424 | H0YAB8 |
| 2425 | H0YB13 |
| 2426 | H0YJ11 |

TABLE 3-continued

Protein codes found in NPEX, APEX, and MSCEX

| | |
|---|---|
| 2427 | H3BRX4 |
| 2428 | H3BT74 |
| 2429 | B3BUH4 |
| 2430 | H7BZH1 |
| 2431 | H7C149 |
| 2432 | H7C2W8 |
| 2433 | I6L894 |
| 2434 | I6L957 |
| 2435 | J3KQU2 |
| 2436 | J3QLS9 |
| 2437 | K0P793 |
| 2438 | K4DIA0 |
| 2439 | K4K7V6 |
| 2440 | K7EQ63 |
| 2441 | L0CQ38 |
| 2442 | M0QZR9 |
| 2443 | M0R261 |
| 2444 | M0R315 |
| 2445 | O00420 |
| 2446 | O14980 |
| 2447 | O15240 |
| 2448 | O43854 |
| 2449 | O75691 |
| 2450 | O95243 |
| 2451 | P00800 |
| 2452 | P01833 |
| 2453 | P05109 |
| 2454 | P0C869 |
| 2455 | P0CB47 |
| 2456 | P0CG39 |
| 2457 | P0DKL9 |
| 2458 | P12757 |
| 2459 | P26022 |
| 2460 | P28070 |
| 2461 | P35442 |
| 2462 | P35558 |
| 2463 | P43652 |
| 2464 | P54753 |
| 2465 | P55089 |
| 2466 | Q05CW1 |
| 2467 | Q09028 |
| 2468 | Q0VAS5 |
| 2469 | Q14455 |
| 2470 | Q16281 |
| 2471 | Q32MQ0 |
| 2472 | Q53HB3 |
| 2473 | Q53TR0 |
| 2474 | Q59EG0 |
| 2475 | Q59F22 |
| 2476 | Q59FG6 |
| 2477 | Q59H91 |
| 2478 | Q5BKT1 |
| 2479 | Q5FBY7 |
| 2480 | Q5T1R4 |
| 2481 | Q5TBK7 |
| 2482 | Q5TH58 |
| 2483 | Q658L2 |
| 2484 | Q658N2 |
| 2485 | Q684P5 |
| 2486 | Q69YM0 |
| 2487 | Q6IC83 |
| 2488 | Q6L9N1 |
| 2489 | Q6N097 |
| 2490 | Q6NUJ9 |
| 2491 | Q6NUN2 |
| 2492 | Q6NUP7 |
| 2493 | Q6NXR7 |
| 2494 | Q6P0Q1 |
| 2495 | Q6P2I0 |
| 2496 | Q6P5R7 |
| 2497 | Q6PJ72 |
| 2498 | Q6PK65 |
| 2499 | Q6QE20 |
| 2500 | Q6TCJ2 |
| 2501 | Q6TFL3 |
| 2502 | A0A075B6H0 |
| 2503 | A0A0A0MSY2 |
| 2504 | A0A0B4J1Z7 |
| 2505 | A0A0B4J2E5 |
| 2506 | A0A0J9YXN7 |
| 2507 | A0A0S2Z4J7 |
| 2508 | A4D2H0 |
| 2509 | A5PLN9 |
| 2510 | A8K2M0 |
| 2511 | A8K7H1 |
| 2512 | A8K9P0 |
| 2513 | B2R769 |
| 2514 | B2RA94 |
| 2515 | B3KMG3 |
| 2516 | B3KNF6 |
| 2517 | B3KSB9 |
| 2518 | B3KSG0 |
| 2519 | B3KSJ0 |
| 2520 | B3KU66 |
| 2521 | B4DJB9 |
| 2522 | B4DN12 |
| 2523 | B4DNP9 |
| 2524 | B4DPX6 |
| 2525 | B4DQ18 |
| 2526 | B4DQL5 |
| 2527 | B4DTK1 |
| 2528 | B7Z1Z9 |
| 2529 | B7Z5P0 |
| 2530 | C7TPG7 |
| 2531 | C9J5J4 |
| 2532 | C9JYJ6 |
| 2533 | D3DPB7 |
| 2534 | D6RHV3 |
| 2535 | D7RF68 |
| 2536 | E0CX09 |
| 2537 | E1U340 |
| 2538 | E5RH59 |
| 2539 | E5RJV2 |
| 2540 | E7EPF0 |
| 2541 | E7ESP4 |
| 2542 | E7EW93 |
| 2543 | E9PQ73 |
| 2544 | F5GX09 |
| 2545 | F5GYN0 |
| 2546 | F5H4E5 |
| 2547 | F5H6Q4 |
| 2548 | F8VWA3 |
| 2549 | F8W1K8 |
| 2550 | G3V599 |
| 2551 | H0UI12 |
| 2552 | H0Y853 |
| 2553 | H0YAH0 |
| 2554 | H0YFK0 |
| 2555 | H3BPJ7 |
| 2556 | H3BPS9 |
| 2557 | H3BTH8 |
| 2558 | H7C0I7 |
| 2559 | H7C4L7 |
| 2560 | J3KS13 |
| 2561 | J3QS03 |
| 2562 | L0R5C4 |
| 2563 | O75603 |
| 2564 | P08588 |
| 2565 | P0CE72 |
| 2566 | P20742 |
| 2567 | P21453 |
| 2568 | P35251 |
| 2569 | P49720 |
| 2570 | Q14766 |
| 2571 | Q15333 |
| 2572 | Q15389 |
| 2573 | Q15631 |
| 2574 | Q17RW2 |
| 2575 | Q53RS3 |
| 2576 | Q53S27 |
| 2577 | Q53T09 |
| 2578 | Q5BN46 |
| 2579 | Q5RHP9 |
| 2580 | Q5T6X2 |
| 2581 | Q5TCI4 |
| 2582 | Q5VX52 |

TABLE 3-continued

Protein codes found in NPEX, APEX, and MSCEX

| | |
|---|---|
| 2583 | Q6AHZ7 |
| 2584 | Q6IBJ0 |
| 2585 | Q6NWP9 |
| 2586 | Q6P5T1 |
| 2587 | Q6PIP7 |
| 2588 | Q6U2F8 |
| 2589 | Q6UXN8 |
| 2590 | Q6UXQ0 |
| 2591 | Q6Y288 |
| 2592 | Q6ZMS2 |
| 2593 | Q6ZMU0 |
| 2594 | Q6ZMY6 |
| 2595 | Q6ZNI2 |
| 2596 | Q6ZNS1 |
| 2597 | Q6ZQQ2 |
| 2598 | Q6ZQY1 |
| 2599 | Q6ZRK5 |
| 2600 | Q6ZRK6 |
| 2601 | Q6ZRM8 |
| 2602 | Q6ZU10 |
| 2603 | Q6ZV46 |
| 2604 | Q6ZWC0 |
| 2605 | Q6ZWE2 |
| 2606 | Q6ZWG9 |
| 2607 | Q70JA7 |
| 2608 | Q71F56 |
| 2609 | Q71U70 |
| 2610 | Q75RY1 |
| 2611 | Q765P7 |
| 2612 | Q7LGC8 |
| 2613 | Q7Z418 |
| 2614 | Q7Z527 |
| 2615 | Q7Z528 |
| 2616 | Q7Z5A3 |
| 2617 | Q7Z5L7 |
| 2618 | Q7Z5P4 |
| 2619 | Q7Z5W6 |
| 2620 | Q7Z5Y7 |
| 2621 | Q7Z7L8 |
| 2622 | Q7Z7M0 |
| 2623 | Q7Z7M9 |
| 2624 | Q86SQ6 |
| 2625 | Q86SV6 |
| 2626 | Q86TJ9 |
| 2627 | Q86UD1 |
| 2628 | Q86V85 |
| 2629 | Q86VD1 |
| 2630 | Q86VY4 |
| 2631 | Q86WI1 |
| 2632 | Q86XP0 |
| 2633 | Q86YP6 |
| 2634 | Q8IUZ8 |
| 2635 | Q8IV28 |
| 2636 | Q8IV92 |
| 2637 | QSIVE3 |
| 2638 | Q8IWD5 |
| 2639 | Q8IXM7 |
| 2640 | Q8IY33 |
| 2641 | Q8IYA7 |
| 2642 | Q8IYF3 |
| 2643 | Q8IYP2 |
| 2644 | Q8IZ52 |
| 2645 | Q8IZD9 |
| 2646 | Q8IZK6 |
| 2647 | Q8IZQ8 |
| 2648 | Q8N1G2 |
| 2649 | Q8N2C7 |
| 2650 | Q8N397 |
| 2651 | Q8N4T4 |
| 2652 | Q8N715 |
| 2653 | Q8N7P7 |
| 2654 | Q8N7S3 |
| 2655 | Q8N8V4 |
| 2656 | Q8N904 |
| 2657 | Q8N987 |
| 2658 | Q8N9V6 |
| 2659 | Q8NA33 |
| 2660 | Q8NAV8 |

TABLE 3-continued

Protein codes found in NPEX, APEX, and MSCEX

| | |
|---|---|
| 2661 | Q8NAY8 |
| 2662 | Q8NB82 |
| 2663 | Q8NCD8 |
| 2664 | Q8ND61 |
| 2665 | Q8NE22 |
| 2666 | Q8NEZ4 |
| 2667 | Q8TA93 |
| 2668 | Q8TAS6 |
| 2669 | Q8TB82 |
| 2670 | Q8TD20 |
| 2671 | Q8TDY8 |
| 2672 | Q8TE73 |
| 2673 | Q8WUV3 |
| 2674 | Q8WXC6 |
| 2675 | Q8WXE0 |
| 2676 | Q92861 |
| 2677 | Q969F2 |
| 2678 | Q96AA8 |
| 2679 | Q96BY7 |
| 2680 | Q96JF0 |
| 2681 | Q96KN7 |
| 2682 | Q96KP6 |
| 2683 | Q96M27 |
| 2684 | Q96M95 |
| 2685 | Q96N28 |
| 2686 | Q96QE3 |
| 2687 | Q96QZ0 |
| 2688 | Q96S01 |
| 2689 | Q96T80 |
| 2690 | Q96TB4 |
| 2691 | Q99715 |
| 2692 | Q9BWG1 |
| 2693 | Q9C005 |
| 2694 | Q9H1K6 |
| 2695 | Q9H212 |
| 2696 | Q9H382 |
| 2697 | Q9H3R1 |
| 2698 | Q9H4L7 |
| 2699 | Q9HBR0 |
| 2700 | Q9HBU3 |
| 2701 | Q9HD29 |
| 2702 | Q9NQ33 |
| 2703 | Q9NQW1 |
| 2704 | Q9NR48 |
| 2705 | Q9NTB9 |
| 2706 | Q9NZ53 |
| 2707 | Q9P2B2 |
| 2708 | Q9UC91 |
| 2709 | Q9UDL0 |
| 2710 | Q9UHK0 |
| 2711 | Q9UL81 |
| 2712 | Q9ULI1 |
| 2713 | Q9ULL0 |
| 2714 | Q9ULL1 |
| 2715 | Q9ULM8 |
| 2716 | Q9UPU5 |
| 2717 | Q9UPU9 |
| 2718 | Q9Y3Q7 |
| 2719 | S4R3E2 |
| 2720 | U5XN63 |
| 2721 | U6FSN9 |
| 2722 | V9GYK6 |
| 2723 | V9H019 |
| 2724 | V9HW33 |
| 2725 | V9HW38 |
| 2726 | V9HW43 |
| 2727 | X2L7S8 |

TABLE 4

Proteins in both MSCEX and APEX

| | |
|---|---|
| 1 | A0A024R0P8 |
| 2 | A0A024R3G0 |
| 3 | A0A087WVV2 |

TABLE 4-continued

Proteins in both MSCEX and APEX

| | |
|---|---|
| 4 | A0A087WXZ2 |
| 5 | A0A0A0MR07 |
| 6 | A0A0A0MSZ4 |
| 7 | A0A0G2JIC2 |
| 8 | A0A0K0K1H9 |
| 9 | A0A0S2Z4G9 |
| 10 | A0A140VK05 |
| 11 | A0A140VK46 |
| 12 | A2RU30 |
| 13 | A2VCQ4 |
| 14 | A4PB67 |
| 15 | A8K3Y6 |
| 16 | A8KAQ8 |
| 17 | A8MXT8 |
| 18 | B1AKG0 |
| 19 | B2R7P8 |
| 20 | B2R8Z8 |
| 21 | B2RBJ8 |
| 22 | B3KMD9 |
| 23 | B3KQF9 |
| 24 | B3KQX9 |
| 25 | B3KVF9 |
| 26 | B4DDT3 |
| 27 | B4DE33 |
| 28 | B4DFP1 |
| 29 | B4DHX7 |
| 30 | A0A024RA75 |
| 31 | A0A024RDS3 |
| 32 | A0A087WV40 |
| 33 | A0A087WYY5 |
| 34 | A0A0C4DFX3 |
| 35 | A0A0J9YX34 |
| 36 | A1JUI8 |
| 37 | A1L4G8 |
| 38 | A6NHB5 |
| 39 | A7J1R1 |
| 40 | A8K2H9 |
| 41 | A8K3B0 |
| 42 | A8K4S1 |
| 43 | A8K5U9 |
| 44 | A8K7A4 |
| 45 | B1AKQ8 |
| 46 | B2R780 |
| 47 | B2RAQ9 |
| 48 | B3KNK9 |
| 49 | B3KVV5 |
| 50 | B3KXA5 |
| 51 | B4DH55 |
| 52 | B4DKZ3 |
| 53 | B4DL46 |
| 54 | B4DNX1 |
| 55 | B4DQF6 |
| 56 | B4DQQ9 |
| 57 | B4DRV9 |
| 58 | B4DS32 |
| 59 | B4DUQ1 |
| 60 | B4DUY7 |
| 61 | B4DVU1 |
| 62 | B4DWG4 |
| 63 | B4DWH5 |
| 64 | B4DZN3 |
| 65 | B4E047 |
| 66 | B4E3M5 |
| 67 | B7Z1I2 |
| 68 | B7Z2W3 |
| 69 | B7Z2Z8 |
| 70 | B7Z6U7 |
| 71 | B7ZMB3 |
| 72 | B8Y0L3 |
| 73 | B8ZZ80 |
| 74 | B9ZVT1 |
| 75 | C5HTY9 |
| 76 | C9J406 |
| 77 | C9J7H8 |
| 78 | C9J9E8 |
| 79 | C9JJV6 |
| 80 | C9JNG9 |
| 81 | C9JPM3 |
| 82 | D3DS95 |
| 83 | A0A087X1Q2 |
| 84 | A0A087X225 |
| 85 | A0A0A0MTC7 |
| 86 | A0A0S2Z430 |
| 87 | A8K2T9 |
| 88 | B4DE36 |
| 89 | B4DMR3 |
| 90 | B4E2A1 |
| 91 | B4E3S2 |
| 92 | B9EK61 |
| 93 | C9JEL4 |
| 94 | C9JXX4 |
| 95 | A0A087X0T3 |
| 96 | A0A0S2Z3J5 |
| 97 | B3KUJ8 |
| 98 | B4DM82 |
| 99 | B4DP93 |
| 100 | B4DS46 |
| 101 | B4DY39 |
| 102 | B7Z2Y4 |
| 103 | C9J673 |
| 104 | A0A024R8L6 |
| 105 | A0A024RBZ8 |
| 106 | A0A087WUI7 |
| 107 | A0A0B4J1Z4 |
| 108 | A0A0S2Z3L7 |
| 109 | A0A0S2Z4I7 |
| 110 | A0A0U1RQJ2 |
| 111 | A0A0U1RQK7 |
| 112 | A2A352 |
| 113 | A0A024R1N1 |
| 114 | A0A024R8F1 |
| 115 | A0A087WVD1 |
| 116 | A0A0C4DGF5 |
| 117 | A0A0C4DGS5 |
| 118 | A0A0S2Z542 |
| 119 | A0A140TA45 |
| 120 | A0A140VJW5 |
| 121 | A4FVC0 |
| 122 | A4QPE1 |
| 123 | A5PKV2 |
| 124 | A6NEM2 |
| 125 | A8K5S1 |
| 126 | A8K6S1 |
| 127 | A8K9T9 |
| 128 | B1AMW7 |
| 129 | B1Q3B3 |
| 130 | B2R577 |
| 131 | B2R7F8 |
| 132 | B2R7M3 |
| 133 | B2R7T2 |
| 134 | B2R8H4 |
| 135 | B3KN59 |
| 136 | B3KQT9 |
| 137 | B3KS79 |
| 138 | B3KSG1 |
| 139 | B3KSR8 |
| 140 | B3KTM9 |
| 141 | B3KTP2 |
| 142 | B3KTP9 |
| 143 | B3KW21 |
| 144 | B3KWF2 |
| 145 | B3KXY6 |
| 146 | B4DE00 |
| 147 | B4DF60 |
| 148 | B4DGH6 |
| 149 | B4DH24 |
| 150 | B4DI69 |
| 151 | B4DID5 |
| 152 | B4DK14 |
| 153 | B4DL98 |
| 154 | B4DLA1 |
| 155 | B4DLA3 |
| 156 | B4DNR7 |
| 157 | B4DPJ4 |
| 158 | B4DRT0 |
| 159 | B4DTX0 |

TABLE 4-continued

Proteins in both MSCEX and APEX

| | |
|---|---|
| 160 | B4E368 |
| 161 | B7Z1D9 |
| 162 | B7Z992 |
| 163 | B8ZZF3 |
| 164 | C9J4J8 |
| 165 | C9J4Z7 |
| 166 | C9JBE1 |
| 167 | C9JDW2 |
| 168 | CQJJP8 |
| 169 | CQJUM1 |
| 170 | C9JZG1 |
| 171 | C9JZW3 |
| 172 | C9K028 |
| 173 | D3DQB3 |
| 174 | D3DQI7 |
| 175 | D3DWY7 |
| 176 | D3DX70 |
| 177 | D3K0R1 |
| 178 | D6RAL9 |
| 179 | A0A024R0G8 |
| 180 | A0A024R1Y8 |
| 181 | A0A024RCZ4 |
| 182 | A0A087WTQ6 |
| 183 | A0A087X2E9 |
| 184 | A0A140VK29 |
| 185 | B1ALD0 |
| 186 | B2RBA0 |
| 187 | B3KWJ0 |
| 188 | B4DGD7 |
| 189 | B4DKI0 |
| 190 | B4DM67 |
| 191 | A6NE76 |
| 192 | A6NJA2 |
| 193 | A9LSU1 |
| 194 | B4DDL1 |
| 195 | B4DIV8 |
| 196 | B4DNH8 |
| 197 | B4DP22 |
| 198 | B4DR58 |
| 199 | B4DTN6 |
| 200 | B4DX99 |
| 201 | B4DYQ7 |
| 202 | B4E0S6 |
| 203 | B4E2M0 |
| 204 | B7Z2S7 |
| 205 | B7Z2V8 |
| 206 | B7Z864 |
| 207 | C9JPU9 |
| 208 | C9JZ53 |
| 209 | D6R972 |
| 210 | A0A024R0G0 |
| 211 | A0A024R4C5 |
| 212 | A0A024R7Z5 |
| 213 | A0A024RC72 |
| 214 | A0A087WUW5 |
| 215 | A0A087WVV1 |
| 216 | A0A087X1N8 |
| 217 | A0A087X232 |
| 218 | A0A0A0MT20 |
| 219 | A0A0N7A6P0 |
| 220 | A0A0U1RQV3 |
| 221 | A0A140TA54 |
| 222 | A0AV88 |
| 223 | A3KC71 |
| 224 | A4QPB0 |
| 225 | A7E2Y1 |
| 226 | A7LFP5 |
| 227 | A8K6I4 |
| 228 | B1ALC0 |
| 229 | B2R514 |
| 230 | B2R6L0 |
| 231 | B2R7J8 |
| 232 | B2RCM3 |
| 233 | B2ZZ90 |
| 234 | B3KM30 |
| 235 | B3KMW3 |
| 236 | B3KP89 |
| 237 | B3KR36 |
| 238 | B3KUS2 |
| 239 | B3KW84 |
| 240 | B4DFR3 |
| 241 | B4DG30 |
| 242 | A0A024R879 |
| 243 | A0A087WYV9 |
| 244 | A0A087X054 |
| 245 | A0A087X0S5 |
| 246 | A0A0D9SG88 |
| 247 | A0A0E3JSF5 |
| 248 | A0A0S2Z3W2 |
| 249 | A0A0S2Z6B4 |
| 250 | A0A0U1RRC9 |
| 251 | A0PJC9 |
| 252 | A1KY36 |
| 253 | A4UCT2 |
| 254 | A8K0G3 |
| 255 | A8K709 |
| 256 | A8K8Z1 |
| 257 | A8KAY3 |
| 258 | B2R8G9 |
| 259 | B2RBF8 |
| 260 | B3KWG6 |
| 261 | B3KY55 |
| 262 | B4DHT1 |
| 263 | B4DI54 |
| 264 | B4DKW1 |
| 265 | B4DL92 |
| 266 | B4DLZ2 |
| 267 | B4DMF7 |
| 268 | B4DPQ6 |
| 269 | B4DPS0 |
| 270 | B4DPU0 |
| 271 | B4DPU6 |
| 272 | B4DQ56 |
| 273 | B4E0N9 |
| 274 | B4E261 |
| 275 | B4E302 |
| 276 | B7Z273 |
| 277 | B7Z2M1 |
| 278 | B7Z4F6 |
| 279 | B7Z4W2 |
| 280 | B7Z856 |
| 281 | B7Z9M4 |
| 282 | B7ZAJ4 |
| 283 | B7ZB44 |
| 284 | B7ZLI7 |
| 285 | B7ZM04 |
| 286 | B9DI82 |
| 287 | B9EGI2 |
| 288 | C0JYZ1 |
| 289 | C1PHA2 |
| 290 | C4P0D4 |
| 291 | C9J315 |
| 292 | C9J9C1 |
| 293 | C9JKA9 |
| 294 | C9JN98 |
| 295 | D3DPK5 |
| 296 | D3DPU8 |
| 297 | D3DUK1 |
| 298 | A0A024R1A3 |
| 299 | A0A024RC58 |
| 300 | A0A0S2Z5A5 |
| 301 | A8K2R3 |
| 302 | A8K482 |
| 303 | A8K6V0 |
| 304 | B1ALD9 |
| 305 | B1B5R8 |
| 306 | B2RDG0 |
| 307 | B3KU23 |
| 308 | B3KUI4 |
| 309 | B4DGN8 |
| 310 | B4DIW7 |
| 311 | B4E3I6 |
| 312 | C9J539 |
| 313 | A0A087WX80 |
| 314 | A0A140VK07 |
| 315 | B3KUJ2 |

TABLE 4-continued

Proteins in both MSCEX and APEX

| | |
|---|---|
| 316 | B3KXN4 |
| 317 | B4DJF2 |
| 318 | B4DM34 |
| 319 | A0A087WZ85 |
| 320 | B2RCP7 |
| 321 | B3KNZ4 |
| 322 | A0A024R127 |
| 323 | A0A024R755 |
| 324 | A0A024RDT5 |
| 325 | A0A087WUV5 |
| 326 | A0A087WUZ3 |
| 327 | A0A0A0MSX9 |
| 328 | A0A0A7C7U2 |
| 329 | A0A0C4DG95 |
| 330 | A0A0C4DH07 |
| 331 | A0A0D9SG74 |
| 332 | A0A0J9YVZ6 |
| 333 | A0A0J9YWZ2 |
| 334 | A0A0S2Z3K0 |
| 335 | A0A0U1RRA4 |
| 336 | A0A140VJF9 |
| 337 | A4UCT0 |
| 338 | A8K7E0 |
| 339 | A8KA38 |
| 340 | A8KA74 |
| 341 | B1AH99 |
| 342 | B2RCA1 |
| 343 | B2RCJ7 |
| 344 | B2RDI7 |
| 345 | B3KN37 |
| 346 | B3KNG6 |
| 347 | B3KNX0 |
| 348 | B3KPI8 |
| 349 | B3KQH1 |
| 350 | B3KRC6 |
| 351 | B3KRN4 |
| 352 | B3KS36 |
| 353 | B3KS49 |
| 354 | B3KSB2 |
| 355 | B3KT90 |
| 356 | B3KTR9 |
| 357 | B3KUP0 |
| 358 | B3KY30 |
| 359 | B4DDH3 |
| 360 | B4DFM1 |
| 361 | B4DL06 |
| 362 | B4DM22 |
| 363 | B4DM79 |
| 364 | B4DQH6 |
| 365 | B4DUI5 |
| 366 | B4E0H8 |
| 367 | B7Z1H4 |
| 368 | B7Z213 |
| 369 | B7Z2N5 |
| 370 | B7Z5S9 |
| 371 | B7Z658 |
| 372 | B7Z7E5 |
| 373 | B9EIS5 |
| 374 | C9J1P7 |
| 375 | C9JC48 |
| 376 | C9JUP7 |
| 377 | C9K031 |
| 378 | D6R9L2 |
| 379 | D6RAF4 |
| 380 | D6RAX7 |
| 381 | D6RB21 |
| 382 | D6RBE9 |
| 383 | D6RBJ7 |
| 384 | D6RCL6 |
| 385 | D6RDP1 |
| 386 | D6RF19 |
| 387 | D6RF62 |
| 388 | D6RF77 |
| 389 | D6RF86 |
| 390 | D6RGK8 |
| 391 | D6RGV2 |
| 392 | D6RJ91 |
| 393 | D6RJ96 |
| 394 | D6RJA4 |
| 395 | D6RJI3 |
| 396 | D9ZGF4 |
| 397 | E2DRY6 |
| 398 | E5RGB0 |
| 399 | E5RGR6 |
| 400 | E5RGU3 |
| 401 | E5RH00 |
| 402 | E5RIV9 |
| 403 | E6Y3G0 |
| 404 | E7ERL0 |
| 405 | E7ETE2 |
| 406 | E7ETF9 |
| 407 | E7EX41 |
| 408 | E9PCM2 |
| 409 | E9PD92 |
| 410 | E9PFL9 |
| 411 | E9PGT6 |
| 412 | E9PJF7 |
| 413 | E9PKD5 |
| 414 | E9PKP4 |
| 415 | E9PKW6 |
| 416 | E9PMR6 |
| 417 | E9PNW4 |
| 418 | E9PQ82 |
| 419 | E9PRM1 |
| 420 | E9PS23 |
| 421 | E9PS78 |
| 422 | F5GX11 |
| 423 | F5GXD8 |
| 424 | F5GZN3 |
| 425 | F5H520 |
| 426 | F6MF51 |
| 427 | F8VUF6 |
| 428 | F8VYY9 |
| 429 | F8VZY9 |
| 430 | F8W7P5 |
| 431 | F8W943 |
| 432 | F8WBV3 |
| 433 | F8WCH0 |
| 434 | F8WD56 |
| 435 | F8WDR7 |
| 436 | F8WEQ7 |
| 437 | G3CIH8 |
| 438 | G3V1B5 |
| 439 | G3V1S6 |
| 440 | G3V210 |
| 441 | G3V281 |
| 442 | G3V4S5 |
| 443 | G3V5Z7 |
| 444 | G3XAM7 |
| 445 | G5E9W1 |
| 446 | H0Y409 |
| 447 | H0Y430 |
| 448 | H0Y465 |
| 449 | H0Y4A0 |
| 450 | H0Y5U1 |
| 451 | H0Y7G9 |
| 452 | H0Y7R7 |
| 453 | H0Y8M8 |
| 454 | H0Y9N2 |
| 455 | H0Y9Q9 |
| 456 | H0YAY4 |
| 457 | H0YCE1 |
| 458 | H0YCX6 |
| 459 | H0YCY8 |
| 460 | H0YD73 |
| 461 | H0YEL2 |
| 462 | H0YGK8 |
| 463 | H0YH82 |
| 464 | H0YI09 |
| 465 | H0YI26 |
| 466 | H0YJP3 |
| 467 | H0YM36 |
| 468 | H0YMB1 |
| 469 | H0YMP8 |
| 470 | H3BPX2 |
| 471 | H3BQU9 |

TABLE 4-continued

Proteins in both MSCEX and APEX

| | |
|---|---|
| 472 | H6UK83 |
| 473 | H6VRG2 |
| 474 | H7BXY6 |
| 475 | H7BZL4 |
| 476 | H7C063 |
| 477 | H7C064 |
| 478 | H7C0U5 |
| 479 | H7C1H6 |
| 480 | H7C1U0 |
| 481 | H7C2H5 |
| 482 | H7C410 |
| 483 | H7C5K4 |
| 484 | H7C5L4 |
| 485 | H7C5N8 |
| 486 | H7C5W6 |
| 487 | H7C5W8 |
| 488 | I1YAQ5 |
| 489 | I3L1Y9 |
| 490 | I3L392 |
| 491 | I3L3P5 |
| 492 | I3L425 |
| 493 | I3VM54 |
| 494 | J3KND3 |
| 495 | J3KNE3 |
| 496 | J3KPM9 |
| 497 | J3KRB5 |
| 498 | J3KRT5 |
| 499 | J3KRT8 |
| 500 | J3KSV6 |
| 501 | J3KTQ0 |
| 502 | J3QKR0 |
| 503 | J3QL20 |
| 504 | J3QQT0 |
| 505 | J3QQX2 |
| 506 | J3QR48 |
| 507 | J3QRS3 |
| 508 | J3QS32 |
| 509 | J3QS41 |
| 510 | J3QTA5 |
| 511 | J7HH10 |
| 512 | J7M3T8 |
| 513 | K7EJ01 |
| 514 | K7EJH8 |
| 515 | K7EKM4 |
| 516 | K7EKW4 |
| 517 | K7EL50 |
| 518 | K7ELI6 |
| 519 | K7EM20 |
| 520 | K7EP19 |
| 521 | K7EPB9 |
| 522 | K7ER62 |
| 523 | K7ERC6 |
| 524 | K7ESB6 |
| 525 | K7ESE8 |
| 526 | K7ESG6 |
| 527 | K7N7D6 |
| 528 | L7QJ95 |
| 529 | L8EAR0 |
| 530 | M0QZ17 |
| 531 | M0QZC5 |
| 532 | M0R0N8 |
| 533 | M0R0Q9 |
| 534 | M0R1H5 |
| 535 | M1TIV1 |
| 536 | M1VPF9 |
| 537 | O00267 |
| 538 | O00549 |
| 539 | O14562 |
| 540 | A0A0A0MSA0 |
| 541 | A0A0R4J2F3 |
| 542 | B4DHB6 |
| 543 | B4DHD2 |
| 544 | B7Z2F4 |
| 545 | A0A0S2Z4D6 |
| 546 | B4DXI1 |
| 547 | B4E1U3 |
| 548 | B7Z2B3 |
| 549 | B0YJC5 |
| 550 | B2R4D5 |
| 551 | A0A024R0E5 |
| 552 | A0A024R151 |
| 553 | A0A087WZ38 |
| 554 | B2R7B5 |
| 555 | B2RDZ9 |
| 556 | B3KN51 |
| 557 | B4DIJ6 |
| 558 | B4DNJ0 |
| 559 | B7Z4P8 |
| 560 | B7Z5V2 |
| 561 | B7Z5Z3 |
| 562 | C9IZA5 |
| 563 | C9J8I8 |
| 564 | D6RCL1 |
| 565 | E1P506 |
| 566 | E5RJR0 |
| 567 | E7EN95 |
| 568 | E9PI65 |
| 569 | E9PKA3 |
| 570 | E9PLE9 |
| 571 | E9PQ67 |
| 572 | F5H7C6 |
| 573 | F5H7T4 |
| 574 | F5H815 |
| 575 | G3CC15 |
| 576 | G3V4X5 |
| 577 | G5E9R9 |
| 578 | G8I2S9 |
| 579 | H0Y326 |
| 580 | H0YAP6 |
| 581 | H0YDN1 |
| 582 | H0YHV6 |
| 583 | H0YLD0 |
| 584 | H0YN28 |
| 585 | H3BQZ7 |
| 586 | H3BU13 |
| 587 | H3BUW1 |
| 588 | H7BZU1 |
| 589 | H7C1C2 |
| 590 | H7C1J5 |
| 591 | H7C248 |
| 592 | H7C3I4 |
| 593 | H7C5S0 |
| 594 | I3L155 |
| 595 | I3L1F7 |
| 596 | J9ZVQ3 |
| 597 | K7EL90 |
| 598 | K7EMN4 |
| 599 | M0QZ24 |
| 600 | M0R081 |
| 601 | O14660 |
| 602 | A0A024R0J4 |
| 603 | A0A024RDG1 |
| 604 | A0A024RDW7 |
| 605 | A0A075B730 |
| 606 | A0A087WTJ7 |
| 607 | A0A087WU44 |
| 608 | A0A087WUE6 |
| 609 | A0A087WZP6 |
| 610 | A0A0A0MSB2 |
| 611 | A0A0C4DFM8 |
| 612 | A0A0D9SFN7 |
| 613 | A0A0S2Z457 |
| 614 | A0A0S2Z486 |
| 615 | A0A0S2Z4C3 |
| 616 | A0A0S2Z5H3 |
| 617 | A0A0U1RQR6 |
| 618 | A0A0U1RRA7 |
| 619 | A0A140T9K1 |
| 620 | A0A140VJS6 |
| 621 | A0A158SIU0 |
| 622 | A0AVI4 |
| 623 | A2RQD9 |
| 624 | A6XMH5 |
| 625 | A7MBN2 |
| 626 | A8K224 |
| 627 | A8K3T5 |

TABLE 4-continued

Proteins in both MSCEX and APEX

| | |
|---|---|
| 628 | A8K668 |
| 629 | A8K6A5 |
| 630 | B1AHN3 |
| 631 | B1AKN5 |
| 632 | B2CNW3 |
| 633 | B2RCQ9 |
| 634 | B2RDL6 |
| 635 | B3KMC9 |
| 636 | B3KPL5 |
| 637 | B3KQF4 |
| 638 | B4DDN4 |
| 639 | B4DE01 |
| 640 | B4DEL3 |
| 641 | B4DH41 |
| 642 | B4DHK9 |
| 643 | B4DJA4 |
| 644 | B4DJB3 |
| 645 | B4DJJ5 |
| 646 | B4DJK3 |
| 647 | B4DKC9 |
| 648 | B4DNG6 |
| 649 | B4DVI2 |
| 650 | B4DW26 |
| 651 | B4DWB5 |
| 652 | B4DX85 |
| 653 | B4DYN5 |
| 654 | B4DZN4 |
| 655 | B4E1H7 |
| 656 | B4E201 |
| 657 | B4E2A3 |
| 658 | B4E2J2 |
| 659 | B4E394 |
| 660 | B5BU28 |
| 661 | B5MCV4 |
| 662 | B5MDV5 |
| 663 | B6VEX3 |
| 664 | B7Z2K1 |
| 665 | B7Z3E7 |
| 666 | B7Z4A9 |
| 667 | B7Z4X6 |
| 668 | B7Z523 |
| 669 | B7Z553 |
| 670 | B7Z5F6 |
| 671 | B7Z5K4 |
| 672 | B7Z7N3 |
| 673 | B7ZKX1 |
| 674 | B7ZLW3 |
| 675 | B7ZW00 |
| 676 | C9J941 |
| 677 | A0A024R9L9 |
| 678 | A0A024R9X5 |
| 679 | A0A087WV29 |
| 680 | A0A087WYS1 |
| 681 | A0A087X243 |
| 682 | A0A0C4DGA1 |
| 683 | A0A0E3MS57 |
| 684 | A0A0U1RR26 |
| 685 | A0A140T998 |
| 686 | A4QPE4 |
| 687 | A6NG45 |
| 688 | A6NLJ7 |
| 689 | A6QRH1 |
| 690 | A6YID4 |
| 691 | A8K2U2 |
| 692 | A8MXP8 |
| 693 | B2R8Y6 |
| 694 | B2RA03 |
| 695 | B2RMN7 |
| 696 | B3KNN9 |
| 697 | B3KQE1 |
| 698 | B3KT37 |
| 699 | B3KUI1 |
| 700 | B3KVX6 |
| 701 | B3KXB6 |
| 702 | B4DDN8 |
| 703 | B4DE23 |
| 704 | B4DE69 |
| 705 | B4DKE2 |
| 706 | B4DM63 |
| 707 | B4DN01 |
| 708 | B4DNL4 |
| 709 | B4DRE8 |
| 710 | B4DRR8 |
| 711 | B4DRY5 |
| 712 | B4E0Q9 |
| 713 | B7Z2S5 |
| 714 | B7Z8A8 |
| 715 | B7Z8C6 |
| 716 | B7Z994 |
| 717 | C9J5M1 |
| 718 | C9JE56 |
| 719 | C9JF79 |
| 720 | C9JFC0 |
| 721 | D3TTY5 |
| 722 | D6R9X8 |
| 723 | D6RBL6 |
| 724 | D6RBS1 |
| 725 | D6RBX4 |
| 726 | E5RFY0 |
| 727 | E7ERF2 |
| 728 | E7ERK4 |
| 729 | E7ES21 |
| 730 | E7ESA7 |
| 731 | E7ET40 |
| 732 | E9PBS1 |
| 733 | E9PC84 |
| 734 | E9PG15 |
| 735 | E9PKF6 |
| 736 | E9PKY7 |
| 737 | E9PNR9 |
| 738 | E9PP27 |
| 739 | E9PSF4 |
| 740 | F1T0J8 |
| 741 | F1T0K3 |
| 742 | F8W079 |
| 743 | F8W4S1 |
| 744 | F8W810 |
| 745 | F8WDG7 |
| 746 | G3V154 |
| 747 | G3V3Y5 |
| 748 | H0YB88 |
| 749 | H0YCC6 |
| 750 | H0YD69 |
| 751 | H0YI18 |
| 752 | H0YK69 |
| 753 | H3BMF9 |
| 754 | H3BUC1 |
| 755 | H3BVA8 |
| 756 | H7C0C4 |
| 757 | H7C298 |
| 758 | H7C2K7 |
| 759 | H7C300 |
| 760 | H7C4L5 |
| 761 | I3L2G5 |
| 762 | I3L3H7 |
| 763 | I3L504 |
| 764 | I6XKI8 |
| 765 | J3KN16 |
| 766 | J3KPY5 |
| 767 | J3QKW7 |
| 768 | J3QRG4 |
| 769 | K7EIE7 |
| 770 | K7EIT4 |
| 771 | K7EJ44 |
| 772 | K7EJB9 |
| 773 | K7EKQ5 |
| 774 | K7EPW7 |
| 775 | K7ERZ3 |
| 776 | M0QXZ3 |
| 777 | M0QY43 |
| 778 | M0R061 |
| 779 | A0A024RE10 |
| 780 | A0A0A0MTC8 |
| 781 | A0A0C4DGP0 |
| 782 | A0A0J9YXZ5 |
| 783 | A0A141PNN3 |

TABLE 4-continued

Proteins in both MSCEX and APEX

| | |
|---|---|
| 784 | A0PK02 |
| 785 | A1A4Z1 |
| 786 | A5GZ70 |
| 787 | A7E293 |
| 788 | A8K479 |
| 789 | A8K9B9 |
| 790 | A8K9V7 |
| 791 | A8KAY2 |
| 792 | A8MZG1 |
| 793 | B3KM68 |
| 794 | B3KQF5 |
| 795 | B3KSL2 |
| 796 | B4DEB4 |
| 797 | B4DJ78 |
| 798 | B4E3G9 |
| 799 | B7Z8F6 |
| 800 | B7ZC06 |
| 801 | C9J6N7 |
| 802 | E7EQL5 |
| 803 | E9PLY3 |
| 804 | H0Y5K2 |
| 805 | H0YI02 |
| 806 | H7C4W4 |
| 807 | J3QLH6 |
| 808 | B2RBH2 |
| 809 | A0A024R238 |
| 810 | A0A024R433 |
| 811 | A8K3W7 |
| 812 | B1Q3B4 |
| 813 | B2RBF4 |
| 814 | H0YKN4 |
| 815 | H0YL43 |
| 816 | H7C341 |
| 817 | H7C3S9 |
| 818 | I3NI29 |
| 819 | B4DM40 |
| 820 | B4DWQ3 |
| 821 | B4DWR3 |
| 822 | C9JSM2 |
| 823 | D6RAM7 |
| 824 | D6RD63 |
| 825 | D6W5E6 |
| 826 | F5GX75 |
| 827 | H0Y5N9 |
| 828 | H0YDZ9 |
| 829 | H0YEA0 |
| 830 | K4DI93 |
| 831 | A0A024R7E0 |
| 832 | A0A024R7P5 |
| 833 | A0A0E3DC72 |
| 834 | A0A0U1RQT3 |
| 835 | B2RBR9 |
| 836 | B3KU41 |
| 837 | B4DL19 |
| 838 | B4DNL9 |
| 839 | B4DPQ4 |
| 840 | B4DPU3 |
| 841 | B4DSX0 |
| 842 | B4DT47 |
| 843 | B4DTC0 |
| 844 | B4DTI0 |
| 845 | B4DYN7 |
| 846 | B4DZ41 |
| 847 | B7Z4E6 |
| 848 | A0A024R224 |
| 849 | A0A024R319 |
| 850 | A0A024R4H0 |
| 851 | A0A024R5Q7 |
| 852 | A0A024R771 |
| 853 | A0A024R872 |
| 854 | A0A024R983 |
| 855 | A0A024R9V5 |
| 856 | A0A024RDD7 |
| 857 | A0A075BW43 |
| 858 | A0A087WY35 |
| 859 | A0A087WZI0 |
| 860 | A0A090N8P3 |
| 861 | A0A096LNH1 |
| 862 | A0A0A0MSA3 |
| 863 | A0A0B4J1Y2 |
| 864 | A0A0G2JP44 |
| 865 | A0A0U1RRC3 |
| 866 | A0A0U1RRG3 |
| 867 | A0A140VKF3 |
| 868 | A2VDJ4 |
| 869 | A8K4A5 |
| 870 | A8K4C2 |
| 871 | A8MTM1 |
| 872 | B0AZU6 |
| 873 | B1AHM6 |
| 874 | B2R4P2 |
| 875 | B2R853 |
| 876 | B2RAX5 |
| 877 | B2RC37 |
| 878 | B2RCU2 |
| 879 | B3KN94 |
| 880 | B4DDN7 |
| 881 | B4DDQ2 |
| 882 | B4DDU2 |
| 883 | B4DEU0 |
| 884 | B4DFN9 |
| 885 | B4DFW2 |
| 886 | B4DGV4 |
| 887 | B4DIL5 |
| 888 | B4DKP9 |
| 889 | B4DMS0 |
| 890 | B4DNE1 |
| 891 | B4DNV4 |
| 892 | B4DPA0 |
| 893 | B4DPA3 |
| 894 | B4DPX5 |
| 895 | B4DQV1 |
| 896 | B4DR76 |
| 897 | B4DRB7 |
| 898 | B4DST8 |
| 899 | B4DSV2 |
| 900 | B4DT29 |
| 901 | B4DTA7 |
| 902 | B4DTG8 |
| 903 | B4DTK3 |
| 904 | B4DTK7 |
| 905 | B4DTS5 |
| 906 | B4DTX6 |
| 907 | B4DVX2 |
| 908 | B4DWI2 |
| 909 | B4DYC8 |
| 910 | B4DYZ8 |
| 911 | B4DZ90 |
| 912 | B4DZW8 |
| 913 | B4E0C7 |
| 914 | B4E104 |
| 915 | B4E1T8 |
| 916 | B4E2N1 |
| 917 | B4E2P8 |
| 918 | B4E2S7 |
| 919 | B4E2Z6 |
| 920 | B4E385 |
| 921 | B5A943 |
| 922 | B5MCJ9 |
| 923 | B7Z1C9 |
| 924 | B7Z1U8 |
| 925 | B7Z2Y7 |
| 926 | B7Z3Y2 |
| 927 | B7Z475 |
| 928 | B7Z5A2 |
| 929 | B7Z602 |
| 930 | B7Z7K9 |
| 931 | B7ZLY3 |
| 932 | C9J4D3 |
| 933 | C9JBB3 |
| 934 | C9JRL6 |
| 935 | C9JTV5 |
| 936 | D3DWB6 |
| 937 | D6RBZ4 |
| 938 | D6RFM2 |
| 939 | D6RGI3 |

TABLE 4-continued

Proteins in both MSCEX and APEX

| | |
|---|---|
| 940 | E1B4S5 |
| 941 | E7ESF4 |
| 942 | E7ESK7 |
| 943 | F5GXT7 |
| 944 | F5GZI0 |
| 945 | F5GZK1 |
| 946 | G8FSY7 |
| 947 | H0UI27 |
| 948 | H0Y8L3 |
| 949 | H0Y9D7 |
| 950 | H0YAR1 |
| 951 | H0YB80 |
| 952 | H0YF44 |
| 953 | H0YJC4 |
| 954 | H0YNJ8 |
| 955 | H3BM42 |
| 956 | H3BPE1 |
| 957 | H7BY98 |
| 958 | H7BZ76 |
| 959 | H7C0S0 |
| 960 | H7C0V2 |
| 961 | H7C3T4 |
| 962 | H7C4H6 |
| 963 | H7C4N2 |
| 964 | H9XGZ7 |
| 965 | I1Y8W7 |
| 966 | I3V9R4 |
| 967 | I6TRR8 |
| 968 | J3KR84 |
| 969 | J3QRU8 |
| 970 | J3QT73 |
| 971 | J7FK29 |
| 972 | K7EMQ1 |
| 973 | O14956 |
| 974 | O15050 |
| 975 | O15063 |
| 976 | A0A0J9YXB8 |
| 977 | A4D2Q0 |
| 978 | H3BQ34 |
| 979 | B7Z7M2 |
| 980 | G3V4U2 |
| 981 | H0YDG0 |
| 982 | H0YDG7 |
| 983 | B3KXY4 |
| 984 | B4DNP4 |
| 985 | B7Z230 |
| 986 | A0A024QZL1 |
| 987 | A0A024R6E0 |
| 988 | A0A024RAV0 |
| 989 | A0A087WYS9 |
| 990 | A0A096LPE1 |
| 991 | A0A0A0MSQ0 |
| 992 | A0A0G2JPI4 |
| 993 | A0A140VJI7 |
| 994 | A0A163HNC8 |
| 995 | A0A173GMX0 |
| 996 | A8K455 |
| 997 | B3KUR6 |
| 998 | B3KXA2 |
| 999 | B4DI30 |
| 1000 | B4DJN0 |
| 1001 | B4DKX5 |
| 1002 | B4DNG0 |
| 1003 | B4DNH2 |
| 1004 | B4DQ81 |
| 1005 | B4DTM7 |
| 1006 | B4DVB9 |
| 1007 | B4DVJ0 |
| 1008 | B4DY23 |
| 1009 | B4DYY1 |
| 1010 | B4E2Y9 |
| 1011 | B7Z2M8 |
| 1012 | B7Z9U8 |
| 1013 | C9J0J7 |
| 1014 | C9JC03 |
| 1015 | D6RAX0 |
| 1016 | D6REJ2 |
| 1017 | D6RGZ6 |
| 1018 | D6RH21 |
| 1019 | E5RGY4 |
| 1020 | E5RIA2 |
| 1021 | E5RJL2 |
| 1022 | E7EPG1 |
| 1023 | E9PKD3 |
| 1024 | F5GWX5 |
| 1025 | F5GXS2 |
| 1026 | F5H198 |
| 1027 | F5H2I0 |
| 1028 | F8W1U3 |
| 1029 | G3V3X6 |
| 1030 | H0YAJ5 |
| 1031 | H0YDX6 |
| 1032 | H0YJM8 |
| 1033 | H0YNA0 |
| 1034 | H1AE11 |
| 1035 | H3BR66 |
| 1036 | H3BTF6 |
| 1037 | H3BUK7 |
| 1038 | I3L4X5 |
| 1039 | I3QNU9 |
| 1040 | J3KSD8 |
| 1041 | K7EM49 |
| 1042 | K7ENJ2 |
| 1043 | M0R1X9 |
| 1044 | O15376 |
| 1045 | O60361 |
| 1046 | O60400 |
| 1047 | O76081 |
| 1048 | O95101 |
| 1049 | O95425 |
| 1050 | O95654 |
| 1051 | P01591 |
| 1052 | P05452 |
| 1053 | P08754 |
| 1054 | P0CG43 |
| 1055 | P11277 |
| 1056 | P25105 |
| 1057 | P30086 |
| 1058 | P42356 |
| 1059 | P49746 |
| 1060 | P61578 |
| 1061 | P83369 |
| 1062 | Q05BT9 |
| 1063 | Q05D06 |
| 1064 | Q05DE9 |
| 1065 | Q05DS6 |
| 1066 | Q0PHS6 |
| 1067 | Q0QEN7 |
| 1068 | Q0VGA5 |
| 1069 | Q0X0F2 |
| 1070 | Q12918 |
| 1071 | Q13070 |
| 1072 | Q13237 |
| 1073 | Q13876 |
| 1074 | Q14222 |
| 1075 | Q14400 |
| 1076 | Q14730 |
| 1077 | Q147W7 |
| 1078 | Q15036 |
| 1079 | Q15483 |
| 1080 | Q16768 |
| 1081 | Q17RA0 |
| 1082 | Q1JQ76 |
| 1083 | Q1P9K4 |
| 1084 | Q1XBU6 |
| 1085 | Q2F839 |
| 1086 | Q2M3G4 |
| 1087 | Q2MCL6 |
| 1088 | Q2TA90 |
| 1089 | Q2VJ45 |
| 1090 | Q3L3Q5 |
| 1091 | O3SY86 |
| 1092 | Q45KI0 |
| 1093 | Q495U0 |
| 1094 | Q49A78 |
| 1095 | Q49AI3 |

TABLE 4-continued

Proteins in both MSCEX and APEX

| | |
|---|---|
| 1096 | Q49IK8 |
| 1097 | Q4G7P9 |
| 1098 | Q4KMR2 |
| 1099 | Q4LE36 |
| 1100 | Q4LE49 |
| 1101 | Q52NV4 |
| 1102 | Q53ET2 |
| 1103 | Q53EX3 |
| 1104 | Q53EZ0 |
| 1105 | Q53FB0 |
| 1106 | Q53G95 |
| 1107 | Q53GB6 |
| 1108 | Q53GG0 |
| 1109 | Q53GQ8 |
| 1110 | Q53H72 |
| 1111 | Q53HF2 |
| 1112 | Q53HJ9 |
| 1113 | Q53HK9 |
| 1114 | Q53HL4 |
| 1115 | Q53HT9 |
| 1116 | Q53HU0 |
| 1117 | Q53HU8 |
| 1118 | Q53YY1 |
| 1119 | Q53Z63 |
| 1120 | Q567U8 |
| 1121 | Q58FF3 |
| 1122 | Q58FF4 |
| 1123 | Q59E93 |
| 1124 | Q59EB7 |
| 1125 | Q59EM4 |
| 1126 | Q59EP1 |
| 1127 | Q59ER6 |
| 1128 | Q59F25 |
| 1129 | Q59F63 |
| 1130 | Q59FE0 |
| 1131 | Q59FG9 |
| 1132 | Q59FI0 |
| 1133 | Q59FQ4 |
| 1134 | Q59FZ7 |
| 1135 | Q59G81 |
| 1136 | Q59GA0 |
| 1137 | Q59GD4 |
| 1138 | Q59GQ7 |
| 1139 | Q59GR8 |
| 1140 | Q59GT9 |
| 1141 | Q59GX5 |
| 1142 | Q59GX9 |
| 1143 | Q59H49 |
| 1144 | Q59H77 |
| 1145 | Q59H95 |
| 1146 | Q59HE5 |
| 1147 | Q5BJH1 |
| 1148 | Q5BKV1 |
| 1149 | Q5CAQ5 |
| 1150 | Q5D044 |
| 1151 | Q5EC54 |
| 1152 | Q5H924 |
| 1153 | Q5H9B4 |
| 1154 | Q5H9P1 |
| 1155 | Q5H9S4 |
| 1156 | Q5HYD8 |
| 1157 | Q5HYM2 |
| 1158 | Q5IBP5 |
| 1159 | Q5J7V8 |
| 1160 | Q5JNZ6 |
| 1161 | Q5JP01 |
| 1162 | Q5JPF7 |
| 1163 | Q5JRS3 |
| 1164 | Q5JT35 |
| 1165 | Q5JUQ1 |
| 1166 | Q5JWQ6 |
| 1167 | Q5JXB7 |
| 1168 | Q5QFB7 |
| 1169 | Q5RLJ0 |
| 1170 | Q5STK2 |
| 1171 | Q5SX87 |
| 1172 | Q5T0I0 |
| 1173 | Q5T244 |
| 1174 | Q5T670 |
| 1175 | Q5U8W9 |
| 1176 | Q5VSR5 |
| 1177 | Q5VU62 |
| 1178 | Q5VXX4 |
| 1179 | Q5XG79 |
| 1180 | Q5ZEY3 |
| 1181 | Q63HQ4 |
| 1182 | Q658U4 |
| 1183 | Q67AI3 |
| 1184 | Q68D25 |
| 1185 | Q68DU0 |
| 1186 | Q68DU4 |
| 1187 | Q69YV6 |
| 1188 | Q6FGE5 |
| 1189 | Q6FHE1 |
| 1190 | Q6FHK8 |
| 1191 | Q6FHL8 |
| 1192 | Q6FHW5 |
| 1193 | Q6FIE9 |
| 1194 | Q6IBG5 |
| 1195 | Q6IBT3 |
| 1196 | Q6J1Z9 |
| 1197 | Q6LAF9 |
| 1198 | Q6LBN5 |
| 1199 | Q6LCB5 |
| 1200 | Q6LDX7 |
| 1201 | Q6LET3 |
| 1202 | Q6MZE3 |
| 1203 | Q6MZE7 |
| 1204 | Q6MZL6 |
| 1205 | Q6MZR8 |
| 1206 | Q6NUQ1 |
| 1207 | Q6NX51 |
| 1208 | Q6NZX3 |
| 1209 | Q6P1J6 |
| 1210 | Q6P1N4 |
| 1211 | Q6P468 |
| 1212 | Q6PJ56 |
| 1213 | Q6PJK6 |
| 1214 | Q6PK82 |
| 1215 | O19760 |
| 1216 | P28072 |
| 1217 | P35556 |
| 1218 | Q05BN7 |
| 1219 | Q05D76 |
| 1220 | Q13041 |
| 1221 | Q13509 |
| 1222 | Q14006 |
| 1223 | Q1M0P4 |
| 1224 | Q2F831 |
| 1225 | Q2KQ74 |
| 1226 | Q2TAB6 |
| 1227 | Q3MIM8 |
| 1228 | Q3T7C5 |
| 1229 | Q4G0E1 |
| 1230 | Q4ZG85 |
| 1231 | Q53F60 |
| 1232 | Q53FC3 |
| 1233 | Q53GC9 |
| 1234 | Q53H91 |
| 1235 | Q53HF3 |
| 1236 | Q53RF4 |
| 1237 | Q59EE6 |
| 1238 | Q59GM1 |
| 1239 | Q5HYG5 |
| 1240 | Q5JXL7 |
| 1241 | Q5PR22 |
| 1242 | Q5S4N1 |
| 1243 | Q5T5N3 |
| 1244 | Q5URX0 |
| 1245 | Q5YLW1 |
| 1246 | Q6DHW5 |
| 1247 | Q6FHN3 |
| 1248 | Q6IE36 |
| 1249 | Q6IPN6 |
| 1250 | Q6MZG6 |
| 1251 | Q6MZT2 |

TABLE 4-continued

Proteins in both MSCEX and APEX

| | |
|---|---|
| 1252 | Q6PJJ3 |
| 1253 | Q6PRD1 |
| 1254 | A0A024RAY2 |
| 1255 | A0A087WXW9 |
| 1256 | A0A087WYG4 |
| 1257 | A0A087WZ47 |
| 1258 | A0A0A0MSA8 |
| 1259 | A0A0S2Z5C0 |
| 1260 | A0A0U1RQJ8 |
| 1261 | B4DFF0 |
| 1262 | A8K5A7 |
| 1263 | B2RBV7 |
| 1264 | B3KV72 |
| 1265 | B4DDH0 |
| 1266 | B4DDR8 |
| 1267 | B4DEF7 |
| 1268 | B4DHG3 |
| 1269 | B4DJT9 |
| 1270 | B4DS98 |
| 1271 | B4DTB1 |
| 1272 | B7Z752 |
| 1273 | B7Z7T1 |
| 1274 | C9J8I6 |
| 1275 | C9JYM4 |
| 1276 | D3DSS6 |
| 1277 | B3KRQ1 |
| 1278 | B3KS53 |
| 1279 | B4DF70 |
| 1280 | B4DKJ8 |
| 1281 | A0A087WVQ6 |
| 1282 | A0AUH1 |
| 1283 | A2IDB2 |
| 1284 | A5PLK9 |
| 1285 | B2R825 |
| 1286 | B2RBM1 |
| 1287 | B3KTS7 |
| 1288 | B4DHC4 |
| 1289 | B4DHL6 |
| 1290 | B4DYW5 |
| 1291 | B4E0I7 |
| 1292 | D6R917 |
| 1293 | A0A0D9SFK2 |
| 1294 | B2R951 |
| 1295 | B4DI06 |
| 1296 | B4DLF7 |
| 1297 | B4E1W8 |
| 1298 | B4E3A7 |
| 1299 | B4E3Q3 |
| 1300 | A0A024R7D5 |
| 1301 | A1YZ08 |
| 1302 | A8K259 |
| 1303 | B3KQJ7 |
| 1304 | B3KSZ4 |
| 1305 | B3KTR3 |
| 1306 | B3KXU8 |
| 1307 | B4DFG4 |
| 1308 | A0A024R6R3 |
| 1309 | A0A0S2Z3L8 |
| 1310 | A0A172Q3A1 |
| 1311 | A5Z217 |
| 1312 | A8KA64 |
| 1313 | B2R6U9 |
| 1314 | B4DI81 |
| 1315 | B4DZ47 |
| 1316 | C9JD84 |
| 1317 | C9JMX4 |
| 1318 | A0A140TA44 |
| 1319 | B4DF27 |
| 1320 | A0A024RDU0 |
| 1321 | A8K601 |
| 1322 | A0A024R254 |
| 1323 | A0A024R451 |
| 1324 | A0A140T9K2 |
| 1325 | A4UCS6 |
| 1326 | B0QYC8 |
| 1327 | B2RD89 |
| 1328 | B3KTX0 |
| 1329 | B3KTX3 |
| 1330 | B4DME4 |
| 1331 | B4DQX3 |
| 1332 | B7Z431 |
| 1333 | B7ZLP8 |
| 1334 | C9JKG1 |
| 1335 | C9JN42 |
| 1336 | E7ENL6 |
| 1337 | E7EP32 |
| 1338 | E7EQR6 |
| 1339 | F5GY03 |
| 1340 | G3V3A5 |
| 1341 | G3V3F4 |
| 1342 | G3V5M2 |
| 1343 | H0Y4P7 |
| 1344 | H0Y7F7 |
| 1345 | H0Y827 |
| 1346 | H0Y8V7 |
| 1347 | H0YH27 |
| 1348 | H3BRL3 |
| 1349 | H3BU53 |
| 1350 | H7C409 |
| 1351 | H7C538 |
| 3352 | H9C5C5 |
| 1353 | I3NI03 |
| 1354 | J3KMQ1 |
| 1355 | J3KRF8 |
| 1356 | K7ELN9 |
| 1357 | K7ESG8 |
| 1358 | B4E205 |
| 1359 | B7Z5D9 |
| 1360 | B7Z2A1 |
| 1361 | B1AK85 |
| 1362 | B4DP54 |
| 1363 | B7Z4B2 |
| 1364 | E9PIA2 |
| 1365 | F8VQ14 |
| 1366 | H0YI43 |
| 1367 | H7C034 |
| 1368 | J3KT25 |
| 1369 | K7EIV0 |
| 1370 | K7ES31 |
| 1371 | A0A024R5F8 |
| 1372 | A0A024RAK9 |
| 1373 | A0A024RDS2 |
| 1374 | A0A0S2Z5B1 |
| 1375 | A0A120HV04 |
| 1376 | A0A140T8Z6 |
| 1377 | B1APN9 |
| 1378 | B3KMI7 |
| 1379 | B4DEW0 |
| 1380 | B4DJN9 |
| 1381 | B4DQD6 |
| 1382 | B4DTH9 |
| 1383 | B4DYS5 |
| 1384 | B4E1E0 |
| 1385 | B7Z2B6 |
| 1386 | B7Z4S4 |
| 1387 | B7Z6T6 |
| 1388 | B7Z998 |
| 1389 | B7ZLK3 |
| 1390 | C9JLV5 |
| 1391 | C9JTN9 |
| 1392 | D3DPH5 |
| 1393 | A8K1M2 |
| 1394 | B0I1S1 |
| 1395 | B3KN63 |
| 1396 | B3KQQ9 |
| 1397 | C9K052 |
| 1398 | E9PLT3 |
| 1399 | E9PQ34 |
| 1400 | H0Y3V4 |
| 1401 | H7C556 |
| 1402 | H7C5L0 |
| 1403 | I3L1H5 |
| 1404 | J3KRF5 |
| 1405 | J3KSI6 |
| 1406 | J3KSQ2 |
| 1407 | M0R1M5 |

TABLE 4-continued

Proteins in both MSCEX and APEX

| | |
|---|---|
| 1408 | A0A0A0MTJ5 |
| 1409 | B3KWQ6 |
| 1410 | E7EXA3 |
| 1411 | A0A140VKC3 |
| 1412 | H7BXG7 |
| 1413 | A8K548 |
| 1414 | A0A024QZ34 |
| 1415 | A0A087WZ27 |
| 1416 | A0A0S2Z5H5 |
| 1417 | A0PJG0 |
| 1418 | A1L0V1 |
| 1419 | B2R5H0 |
| 1420 | B3KQM9 |
| 1421 | B3KV07 |
| 1422 | B4DEK5 |
| 1423 | B4DHT9 |
| 1424 | B4DN99 |
| 1425 | B4DQ93 |
| 1426 | B4DRN5 |
| 1427 | B4DUP0 |
| 1428 | B4DXF3 |
| 1429 | B4E027 |
| 1430 | B7Z471 |
| 1431 | D6RD66 |
| 1432 | H0Y8Q2 |
| 1433 | H0YKZ6 |
| 1434 | H7BY97 |
| 1435 | H7C381 |
| 1436 | H7C5R6 |
| 1437 | M0R2L7 |
| 1438 | A0A024QZM6 |
| 1439 | A0A024R5U5 |
| 1440 | A0A087WSW9 |
| 1441 | B3KQQ3 |
| 1442 | C9JHZ6 |
| 1443 | H0YAS8 |
| 1444 | H3BR68 |
| 1445 | Q0Z8D6 |
| 1446 | Q10567 |
| 1447 | Q53HA4 |
| 1448 | Q59EE7 |
| 1449 | Q59F55 |
| 1450 | Q59GY9 |
| 1451 | Q59HB9 |
| 1452 | Q5JRS1 |
| 1453 | Q5QPQ1 |
| 1454 | Q5T987 |
| 1455 | Q5U0A0 |
| 1456 | Q68CX0 |
| 1457 | Q6DK41 |
| 1458 | Q6IN67 |
| 1459 | Q6IT96 |
| 1460 | Q6MZZ3 |
| 1461 | Q6NS35 |
| 1462 | Q6P602 |
| 1463 | Q6P6D7 |
| 1464 | Q6PJ44 |
| 1465 | Q12986 |
| 1466 | Q562S2 |
| 1467 | Q59GK6 |
| 1468 | Q6PL18 |
| 1469 | Q6T4R5 |
| 1470 | A0A024RAV2 |
| 1471 | A0A087WXC2 |
| 1472 | A4D1M6 |
| 1473 | A5GZ69 |
| 1474 | A8K088 |
| 1475 | A8K0V5 |
| 1476 | B3KSS4 |
| 1477 | B3KY38 |
| 1478 | B4DDM1 |
| 1479 | A0A140VK57 |
| 1480 | A8K3T7 |
| 1481 | B2R6X5 |
| 1482 | B4DX81 |
| 1483 | C9JIS1 |
| 1484 | A0A0R4J2E1 |
| 1485 | A0A140VJE4 |
| 1486 | B4DNV6 |
| 1487 | A0A0A0MRL0 |
| 1488 | A0A0B4J269 |
| 1489 | A8KAL1 |
| 1490 | A8MUN2 |
| 1495 | B2RDY9 |
| 1492 | B3GQS7 |
| 1493 | B3KXR4 |
| 1494 | B4DLN6 |
| 1495 | B7Z1Q4 |
| 1496 | B7Z4R8 |
| 1497 | B7Z7L7 |
| 1498 | B9EJB8 |
| 1499 | C9JIX5 |
| 1500 | C9JVS8 |
| 1501 | D3DUW5 |
| 1502 | A0A087WTQ3 |
| 1503 | B4DLR2 |
| 1504 | B4DT32 |
| 1505 | B4DTV1 |
| 1506 | B4DX93 |
| 1507 | B7Z1Y5 |
| 1508 | B7Z556 |
| 1509 | C9JD75 |
| 1510 | A0A024R7A8 |
| 1511 | A0A087WT27 |
| 1512 | A0A140VK58 |
| 1513 | A5YM51 |
| 1514 | A8K270 |
| 1515 | B2RE43 |
| 1516 | B3KRA9 |
| 1517 | B4DDL4 |
| 1518 | B4DFW6 |
| 1519 | B4DHN1 |
| 1520 | B4DL49 |
| 1521 | A0A0G2JMS6 |
| 1522 | A0A140VJS7 |
| 1523 | A6YID5 |
| 1524 | A8K333 |
| 1525 | B2R918 |
| 1526 | B4DIE5 |
| 1527 | B4DS71 |
| 1528 | B4DWW8 |
| 1529 | B4E357 |
| 1530 | C9JCK5 |
| 1531 | D6RAK7 |
| 1532 | D6RGG3 |
| 1533 | A0A0G2JND4 |
| 1534 | A8K7Q2 |
| 1535 | A0A024RDA6 |
| 1536 | A0A075BTL2 |
| 1537 | A0A087X1W2 |
| 1538 | A0A0D9SFH4 |
| 1539 | A0A140VK80 |
| 1540 | A4D1Y2 |
| 1541 | A6XND9 |
| 1542 | B3KMV2 |
| 1543 | B3KUH4 |
| 1544 | B3KWK5 |
| 1545 | B4E320 |
| 1546 | C9JB25 |
| 1547 | D3DSM7 |
| 1548 | D3VVH7 |
| 1549 | E9PH62 |
| 1550 | E9PIG4 |
| 1551 | E9PJR2 |
| 1552 | F5GZS6 |
| 1553 | F5H157 |
| 1554 | F5H5N6 |
| 1555 | F6XY72 |
| 1556 | F8VX58 |
| 1557 | F8W1K6 |
| 1558 | F8W6C1 |
| 1559 | F8WD80 |
| 1560 | F8WDD7 |
| 1561 | G3V4Q1 |
| 1562 | G5EA09 |
| 1563 | H0UI22 |

TABLE 4-continued

Proteins in both MSCEX and APEX

| | |
|---|---|
| 1564 | H0Y5J5 |
| 1565 | H0Y8H4 |
| 1566 | H0YAI1 |
| 1567 | H0YCQ2 |
| 1568 | H0YDJ9 |
| 1569 | H0YDP9 |
| 1570 | H0YEB7 |
| 1571 | H0YFT8 |
| 1572 | H0YNV5 |
| 1573 | H7C457 |
| 1574 | I3V9V3 |
| 1575 | I6L984 |
| 1576 | J3KS15 |
| 1577 | K7EJJ5 |
| 1578 | K7EQX3 |
| 1579 | B3KR26 |
| 1580 | B4DVD7 |
| 1581 | A0A087WWW9 |
| 1582 | A0A140T9B7 |
| 1583 | B1APP6 |
| 1584 | B2R960 |
| 1585 | B4E2F9 |
| 1586 | B7Z582 |
| 1587 | F5GY34 |
| 1588 | F8VZH8 |
| 1589 | G3V361 |
| 1590 | H0YB61 |
| 1591 | H0YBH9 |
| 1592 | H0YD93 |
| 1593 | H7BXZ5 |
| 1594 | H7C3V5 |
| 1595 | K7EM73 |
| 1596 | A8K8D9 |
| 1597 | A8K8S6 |
| 1598 | B3KWT5 |
| 1599 | B4E0H6 |
| 1600 | H7BXV5 |
| 1601 | I3L3X7 |
| 1602 | B7ZLZ7 |
| 1603 | F8W692 |
| 1604 | F8WC54 |
| 1605 | H0UI83 |
| 1606 | H0YA75 |
| 1607 | H0YI37 |
| 1608 | A0A024R0A9 |
| 1609 | A8K912 |
| 1610 | B4DH11 |
| 1611 | A0A024R4I7 |
| 1612 | A0A024R688 |
| 1613 | A0A024R6D1 |
| 1614 | A0A024RC87 |
| 1615 | A0A087X0M0 |
| 1616 | A0A0A0MS98 |
| 1617 | A0A0U1RRM8 |
| 1618 | A0A140VJM1 |
| 1619 | A1A5B0 |
| 1620 | A8K9E1 |
| 1621 | A8KA75 |
| 1622 | B2R7T8 |
| 1623 | B2R995 |
| 1624 | B3KND4 |
| 1625 | B3KSM5 |
| 1626 | B3KXY0 |
| 1627 | B4DJS0 |
| 1628 | B4DM61 |
| 1629 | B4DMH3 |
| 1630 | B4DPS8 |
| 1631 | B4DPX8 |
| 1632 | B4DPZ4 |
| 1633 | B4DTH4 |
| 1634 | B4DTN7 |
| 1635 | B4DXW2 |
| 1636 | B4DYM0 |
| 1637 | B4DZB4 |
| 1638 | B4DZP5 |
| 1639 | B4E0L1 |
| 1640 | B4E1R7 |
| 1641 | B7Z1F8 |
| 1642 | B7Z4V4 |
| 1643 | B7Z577 |
| 1644 | B7Z9L0 |
| 1645 | C9J296 |
| 1646 | C9JTX5 |
| 1647 | E5RG28 |
| 1648 | E9PJ32 |
| 1649 | E9PQ98 |
| 1650 | F5H136 |
| 1651 | F8VZB4 |
| 1652 | F8WD59 |
| 1653 | F8WEB3 |
| 1654 | G3V3U4 |
| 1655 | G9K388 |
| 1656 | H0YEP3 |
| 1657 | H0YFX4 |
| 1658 | H0YKV8 |
| 1659 | H0YLS6 |
| 1660 | H7BY18 |
| 1661 | H7C144 |
| 1662 | H7C2W6 |
| 1663 | J3KNL1 |
| 1664 | M0QZG6 |
| 1665 | M0R3C9 |
| 1666 | P29279 |
| 1667 | Q0P5U8 |
| 1668 | Q14215 |
| 1669 | Q14DR2 |
| 1670 | Q1RMC8 |
| 1671 | Q2TU64 |
| 1672 | Q2VIM7 |
| 1673 | Q4ZF95 |
| 1674 | Q504U3 |
| 1675 | Q53FR4 |
| 1676 | Q53GR3 |
| 1677 | Q53H39 |
| 1678 | Q56CY1 |
| 1679 | Q59G97 |
| 1680 | Q59H37 |
| 1681 | Q5JVS8 |
| 1682 | Q5SX86 |
| 1683 | Q5SXM2 |
| 1684 | Q5T0S3 |
| 1685 | Q5U0B9 |
| 1686 | Q5VVQ1 |
| 1687 | Q6DC98 |
| 1688 | Q6NSG7 |
| 1689 | Q6PJT4 |
| 1690 | A0A024R060 |
| 1691 | A0A024R498 |
| 1692 | A0A024R599 |
| 1693 | A0A024R8B2 |
| 1694 | A0A024R9F3 |
| 1695 | A0A024R9Y3 |
| 1696 | A0A087WTP5 |
| 1697 | A0A087WU93 |
| 1698 | A0A087WW43 |
| 1699 | A0A087WXX1 |
| 1700 | A0A087WYV8 |
| 1701 | A0A087WYX9 |
| 1702 | A0A087X080 |
| 1703 | A0A087X271 |
| 1704 | A0A087X2I4 |
| 1705 | A0A090N7V0 |
| 1706 | A0A0A0MR56 |
| 1707 | A0A0B4J1R7 |
| 1708 | A0A0B6XK25 |
| 1709 | A0A0C4DFW8 |
| 1710 | A0A0D9SET8 |
| 1711 | A0A0D9SG79 |
| 1712 | A0A0G2JPA8 |
| 1713 | A0A0J9YWE8 |
| 1714 | A0A0J9YX86 |
| 1715 | A0A0K0Q0G7 |
| 1716 | A0A0R4J2G7 |
| 1717 | A0A0S2Z3X3 |
| 1718 | A0A0S2Z3X8 |
| 1719 | A0A0U1RR07 |

TABLE 4-continued

Proteins in both MSCEX and APEX

| | |
|---|---|
| 1720 | A0A126GWA0 |
| 1721 | A0A140T936 |
| 1722 | A0A140VJT0 |
| 1723 | A0A140VK45 |
| 1724 | A0A173GMX4 |
| 1725 | A4D1J9 |
| 1726 | A4QPA1 |
| 1727 | A4UCT1 |
| 1728 | A4UCT9 |
| 1729 | A5YM53 |
| 1730 | A6NDY9 |
| 1731 | A8K1S0 |
| 1732 | A8K2I0 |
| 1733 | A8K477 |
| 1734 | A8K4G9 |
| 1735 | A8K590 |
| 1736 | A8K5T0 |
| 1737 | A8K690 |
| 1738 | A8K6S3 |
| 1739 | A8K7F7 |
| 1740 | A8K7Q1 |
| 1741 | A8K7T8 |
| 1742 | A8K8A4 |
| 1743 | A8K900 |
| 1744 | A8K979 |
| 1745 | A8MXT2 |
| 1746 | B0YJC4 |
| 1747 | B2R932 |
| 1748 | B2RBP3 |
| 1749 | B3KMH6 |
| 1750 | B3KMM7 |
| 1751 | B3KNB9 |
| 1752 | B3KNF2 |
| 1753 | B3KNF9 |
| 1754 | B3KRK8 |
| 1755 | B3KT98 |
| 1756 | B3KTM1 |
| 1757 | B3KU27 |
| 1758 | B3KU60 |
| 1759 | B3KUY5 |
| 1760 | B3KX16 |
| 1761 | B3W6H4 |
| 1762 | B4DG55 |
| 1763 | B4DG73 |
| 1764 | B4DGT1 |
| 1765 | B4DGX9 |
| 1766 | B4DI19 |
| 1767 | B4DID6 |
| 1768 | B4DIW2 |
| 1769 | B4DJ06 |
| 1770 | B4DJ44 |
| 1771 | B4DMJ0 |
| 1772 | B4DN77 |
| 1773 | B4DND6 |
| 1774 | B4DQQ2 |
| 1775 | B4DQX0 |
| 1776 | B4DQZ0 |
| 1777 | B4DSF8 |
| 1778 | B4DT18 |
| 1779 | B4DW31 |
| 1780 | B4DX43 |
| 1781 | B4DYA7 |
| 1782 | B4DZX4 |
| 1783 | B4E392 |
| 1784 | B4E3Q9 |
| 1785 | B5MDS3 |
| 1786 | B7Z5H9 |
| 1787 | B7Z6E5 |
| 1788 | B7Z6L5 |
| 1789 | B7Z7W6 |
| 1790 | B7Z822 |
| 1791 | B7Z842 |
| 1792 | B7Z8E7 |
| 1793 | B7ZAE8 |
| 1794 | B7ZAP6 |
| 1795 | B7ZAX6 |
| 1796 | B7ZKR5 |
| 1797 | C6GLZ1 |
| 1798 | C9J7B7 |
| 1799 | C9JBU9 |
| 1800 | C9JIF9 |
| 1801 | C9JMZ3 |
| 1802 | C9JQJ4 |
| 1803 | C9JSL4 |
| 1804 | C9JT74 |
| 1805 | C9JU11 |
| 1806 | C9K0H9 |
| 1807 | D0V481 |
| 1808 | D3DT96 |
| 1809 | D3DUT5 |
| 1810 | D6R904 |
| 1811 | D6RJI2 |
| 1812 | E0Z3H2 |
| 1813 | E2QRI1 |
| 1814 | E5RG57 |
| 1815 | E5RGA2 |
| 1816 | E7EPM4 |
| 1817 | E7EU13 |
| 1818 | E7EUI6 |
| 1819 | E9PCC8 |
| 1820 | E9PF58 |
| 1821 | E9PL37 |
| 1822 | E9PLD0 |
| 1823 | E9PLK3 |
| 1824 | E9PLY5 |
| 1825 | E9PMN5 |
| 1826 | E9PPQ4 |
| 1827 | E9PQK6 |
| 1828 | E9PRR2 |
| 1829 | F1BXA6 |
| 1830 | F1D8R6 |
| 1831 | F5H6W8 |
| 1832 | F8VP67 |
| 1833 | F8VWV4 |
| 1834 | F8WE98 |
| 1835 | G3V2E8 |
| 1836 | G3V2W4 |
| 1837 | G3V380 |
| 1838 | G3V393 |
| 1839 | G3V511 |
| 1840 | G3XL79 |
| 1841 | G5E9Z2 |
| 1842 | H0Y400 |
| 1843 | H0Y897 |
| 1844 | H0YAB0 |
| 1845 | H0YAH8 |
| 1846 | H0YBW3 |
| 1847 | H0YCK7 |
| 1848 | H0YEG8 |
| 1849 | H0YEP8 |
| 1850 | H0YET5 |
| 1851 | H0YGZ3 |
| 1852 | H0YI33 |
| 1853 | H0YKU5 |
| 1854 | H0YLD1 |
| 1855 | H0YLJ1 |
| 1856 | H0YLM2 |
| 1857 | B3BN34 |
| 1858 | H3BN75 |
| 1859 | H3BNR4 |
| 1860 | H3BNT7 |
| 1861 | H3BPG7 |
| 1862 | H3BQA8 |
| 1863 | H3BRL2 |
| 1864 | H3BRV9 |
| 1865 | H3BU24 |
| 1866 | H3BUU9 |
| 1867 | H3BUV8 |
| 1868 | H3BV30 |
| 1869 | H7BZE9 |
| 1870 | H7C0M5 |
| 1871 | H7C0V9 |
| 1872 | H7C278 |
| 1873 | H7C531 |
| 1874 | H7C543 |
| 1875 | H7C5J5 |

TABLE 4-continued

Proteins in both MSCEX and APEX

| | |
|---|---|
| 1876 | I3L2R7 |
| 1877 | I3L3Q7 |
| 1878 | I3L3Z3 |
| 1879 | I3V9T1 |
| 1880 | J3QS16 |
| 1881 | J3QTJ6 |
| 1882 | K4RH61 |
| 1883 | K7ENH5 |
| 1884 | K7EPG3 |
| 1885 | K7ERA3 |
| 1886 | K7ERX2 |
| 1887 | L8E758 |
| 1888 | A0A087WT80 |
| 1889 | A0A087WUR8 |
| 1890 | A0A024RA94 |
| 1891 | A0A087WYP2 |
| 1892 | A0A096LPA6 |
| 1893 | A0A0A1HAN9 |
| 1894 | A0A0C4DGH2 |
| 1895 | A0A0G2JP90 |
| 1896 | A0A0S2Z3H5 |
| 1897 | A0A0S2Z476 |
| 1898 | A0A0U1RRI8 |
| 1899 | A0A0U5BLD0 |
| 1900 | A0A0U5EM55 |
| 1901 | A0A140VK69 |
| 1902 | A0A140VK70 |
| 1903 | A8K309 |
| 1904 | A8K3Q7 |
| 1905 | A8K4W8 |
| 1906 | A8K8U1 |
| 1907 | A8K9X5 |
| 1908 | A8MV29 |
| 1909 | A8YQF3 |
| 1910 | B2RD14 |
| 1911 | B2RDI5 |
| 1912 | B3KQM1 |
| 1913 | B3KRK1 |
| 1914 | B3KXF2 |
| 1915 | B4DFF9 |
| 1916 | B4DFG7 |
| 1917 | B4DHC3 |
| 1918 | B4DHQ7 |
| 1919 | B4DJQ5 |
| 1920 | B4DMB6 |
| 1921 | B4DMT4 |
| 1922 | B4DN21 |
| 1923 | B4DN30 |
| 1924 | B4DN32 |
| 1925 | B4DN78 |
| 1926 | B4DNM8 |
| 1927 | B4DPP0 |
| 1928 | B4DQK5 |
| 1929 | B4DR44 |
| 1930 | B4DRF7 |
| 1931 | B4DRX1 |
| 1932 | B4DSD3 |
| 1933 | B4DSQ5 |
| 1934 | B4DUK1 |
| 1935 | B4DUM2 |
| 1936 | B4DVL8 |
| 1937 | B4DWA8 |
| 1938 | B4DXJ6 |
| 1939 | B4DYU2 |
| 1940 | B4E163 |
| 1941 | B4E190 |
| 1942 | B4E1H9 |
| 1943 | B4E2V8 |
| 1944 | B4E356 |
| 1945 | B5A941 |
| 1946 | B7Z237 |
| 1947 | B7Z6I3 |
| 1948 | B7Z766 |
| 1949 | B7Z9C4 |
| 1950 | B7ZAB0 |
| 1951 | C6ZGX2 |
| 1952 | C9JAM8 |
| 1953 | C9JEG3 |
| 1954 | C9K0C5 |
| 1955 | D3DPU0 |
| 1956 | D6REX0 |
| 1957 | D6RFX4 |
| 1958 | D6RIR7 |
| 1959 | E5KRG5 |
| 1960 | E5RFS1 |
| 1961 | E9PK25 |
| 1962 | E9PKK9 |
| 1963 | E9PMR4 |
| 1964 | E9PNW5 |
| 1965 | E9PQH6 |
| 1966 | F5GYU2 |
| 1967 | F8VP03 |
| 1968 | G1UD79 |
| 1969 | H0YA83 |
| 1970 | H0YBG6 |
| 1971 | H0YIK3 |
| 1972 | H0YMD9 |
| 1973 | H0YN52 |
| 1974 | H3BLS7 |
| 1975 | H7C183 |
| 1976 | I3L0S0 |
| 1977 | I3L3P9 |
| 1978 | I3L3W3 |
| 1979 | I4AY87 |
| 1980 | J3KQ66 |
| 1981 | J3KTI8 |
| 1982 | J3QKQ5 |
| 1983 | J3QT34 |
| 1984 | J9R021 |
| 1985 | K7EP68 |
| 1986 | L7RSL3 |
| 1987 | M0R0W6 |
| 1988 | M0R2Z9 |
| 1989 | O14549 |
| 1990 | O15018 |
| 1991 | O15289 |
| 1992 | P07195 |
| 1993 | P0C221 |
| 1994 | P11217 |
| 1995 | P17032 |
| 1996 | P18669 |
| 1997 | P21912 |
| 1998 | P47871 |
| 1999 | P48741 |
| 2000 | P53675 |
| 2001 | P61201 |
| 2002 | Q0PNF2 |
| 2003 | Q14329 |
| 2004 | Q14769 |
| 2005 | Q1HA41 |
| 2006 | Q1LZN2 |
| 2007 | Q2I0A6 |
| 2008 | Q2PUK1 |
| 2009 | Q2V4X9 |
| 2010 | Q2VPA1 |
| 2011 | Q3B787 |
| 2012 | Q3MIC3 |
| 2013 | Q4G1B8 |
| 2014 | Q4JCP9 |
| 2015 | Q4LE33 |
| 2016 | Q4LE71 |
| 2017 | Q4V347 |
| 2018 | Q4W5E0 |
| 2019 | Q53F79 |
| 2020 | Q53FX5 |
| 2021 | Q53G35 |
| 2022 | Q53G83 |
| 2023 | Q53GG3 |
| 2024 | Q53GZ2 |
| 2025 | Q53HB6 |
| 2026 | Q53RS1 |
| 2027 | Q53SM6 |
| 2028 | Q53TA7 |
| 2029 | Q53TY1 |
| 2030 | Q53X91 |
| 2031 | Q562U1 |

TABLE 4-continued

Proteins in both MSCEX and APEX

| | |
|---|---|
| 2032 | Q562X2 |
| 2033 | Q56VW8 |
| 2034 | Q58I23 |
| 2035 | Q59E90 |
| 2036 | Q59EB3 |
| 2037 | Q59EL5 |
| 2038 | Q59F04 |
| 2039 | Q59FC6 |
| 2040 | Q59FD0 |
| 2041 | Q59FF0 |
| 2042 | Q59FJ0 |
| 2043 | Q59FK6 |
| 2044 | Q59GI7 |
| 2045 | Q59GI8 |
| 2046 | Q59GL1 |
| 2047 | Q59GS3 |
| 2048 | Q59H74 |
| 2049 | Q59HA6 |
| 2050 | Q5CZ99 |
| 2051 | Q5JPB8 |
| 2052 | Q5JPE4 |
| 2053 | Q5JTH9 |
| 2054 | Q5QNZ2 |
| 2055 | Q5SUI8 |
| 2056 | Q5T3N0 |
| 2057 | Q5TA01 |
| 2058 | Q5TBG5 |
| 2059 | Q5TEK2 |
| 2060 | Q5TZP0 |
| 2061 | Q68D23 |
| 2062 | Q69YT6 |
| 2063 | Q6DHY5 |
| 2064 | Q6FGL0 |
| 2065 | Q6FHZ0 |
| 2066 | Q6FI97 |
| 2067 | Q6I7N8 |
| 2068 | Q6IB71 |
| 2069 | Q6IC76 |
| 2070 | Q6IPN0 |
| 2071 | Q6LCH2 |
| 2072 | Q6MZF4 |
| 2073 | A0A024R411 |
| 2074 | A0A024R3H2 |
| 2075 | A0A024R3V8 |
| 2076 | A0A024R5L0 |
| 2077 | A0A024RAM4 |
| 2078 | A0A087WYF2 |
| 2079 | A0A097EV82 |
| 2080 | A0A0G2JRF9 |
| 2081 | A0A125S6H6 |
| 2082 | A0A140VK56 |
| 2083 | A0PJ81 |
| 2084 | A8K8B0 |
| 2085 | A8KAK1 |
| 2086 | A8MXH5 |
| 2087 | B2R8G3 |
| 2088 | B2R921 |
| 2089 | B4DE40 |
| 2090 | B4DIX1 |
| 2091 | B4DSW9 |
| 2092 | B4DX08 |
| 2093 | B4E0B4 |
| 2094 | B4E0X6 |
| 2095 | B5MD23 |
| 2096 | B7Z2Z0 |
| 2097 | B7Z3Z2 |
| 2098 | B7Z4G0 |
| 2099 | B7ZMJ0 |
| 2100 | C9JHG2 |
| 2101 | C9JK86 |
| 2102 | C9JKQ7 |
| 2103 | C9JPC3 |
| 2104 | D6RIA0 |
| 2105 | E5RJ43 |
| 2106 | E9PRU1 |
| 2107 | F5GXU1 |
| 2108 | F8WAA0 |
| 2109 | H0Y5C6 |
| 2110 | H0Y875 |
| 2111 | H0Y9P0 |
| 2112 | H0YAF9 |
| 2113 | H0YIB2 |
| 2114 | H0YN01 |
| 2115 | H7C3F9 |
| 2116 | H7C4Y7 |
| 2117 | J3QRA5 |
| 2118 | J3QS88 |
| 2119 | P19022 |
| 2120 | Q05BR9 |
| 2121 | Q14568 |
| 2122 | Q53SM9 |
| 2123 | Q59F65 |
| 2124 | Q5FWG8 |
| 2125 | Q6FH10 |
| 2126 | Q6M1B8 |
| 2127 | Q6MZT4 |
| 2128 | Q6NZ44 |
| 2129 | A0A024R084 |
| 2130 | A0A024R5W3 |
| 2131 | A0A024R6B5 |
| 2132 | A0A024RDG6 |
| 2133 | A0A024RDY3 |
| 2134 | A0A087X0M6 |
| 2135 | A0A0A0MRQ5 |
| 2136 | A0A0U1RR39 |
| 2137 | A0A140VJR3 |
| 2138 | A7MBM6 |
| 2139 | A8K1Y7 |
| 2140 | A8K781 |
| 2141 | B3KUE5 |
| 2142 | B3KVI8 |
| 2143 | B4DQH3 |
| 2144 | B4DRT3 |
| 2145 | B4DWQ5 |
| 2146 | B4DY05 |
| 2147 | B4DY98 |
| 2148 | F5H2L3 |
| 2149 | F8W787 |
| 2150 | H0YMC2 |
| 2151 | H7C2S8 |
| 2152 | Q14918 |
| 2153 | Q49A43 |
| 2154 | Q4W5D3 |
| 2155 | Q53FG3 |
| 2156 | Q53H18 |
| 2157 | Q53HJ0 |
| 2158 | Q59ET0 |
| 2159 | F6S8N6 |
| 2160 | F6X2W2 |
| 2161 | H0Y8I3 |
| 2162 | H0YCR7 |
| 2163 | H0YMM1 |
| 2164 | J3KQ42 |
| 2165 | M1LAK4 |
| 2166 | Q43532 |
| 2167 | Q0P682 |
| 2168 | Q59FU7 |
| 2169 | Q59GT2 |
| 2170 | Q5T4U8 |
| 2171 | Q5T9S5 |
| 2172 | Q5TCI8 |
| 2173 | A0A024R7C7 |
| 2174 | A0A087WWU3 |
| 2175 | A0A0A0MSV3 |
| 2176 | A0A140GPP7 |
| 2177 | A0A140VJX3 |
| 2178 | A2VCK8 |
| 2179 | A7E2S2 |
| 2180 | B2R708 |
| 2181 | B3KPG0 |
| 2182 | B3KQK1 |
| 2183 | B3KTJ9 |
| 2184 | B3KWY2 |
| 2185 | B4DDG4 |
| 2186 | B4DMK2 |
| 2187 | B4DP06 |

TABLE 4-continued

Proteins in both MSCEX and APEX

| | |
|---|---|
| 2188 | B4DT73 |
| 2189 | B4DU71 |
| 2190 | B7Z4C7 |
| 2191 | B9VPB4 |
| 2192 | C9JPC0 |
| 2193 | C9JUU5 |
| 2194 | C9K055 |
| 2195 | D3DSM4 |
| 2196 | E7ER45 |
| 2197 | E9PCH4 |
| 2198 | E9PN91 |
| 2199 | E9PNX1 |
| 2200 | F6XZQ7 |
| 2201 | F8WC37 |
| 2202 | G3V295 |
| 2203 | H0UI49 |
| 2204 | H0Y4E8 |
| 2205 | H0Y789 |
| 2206 | H0Y8F1 |
| 2207 | H0YMJ5 |
| 2208 | H3BV48 |
| 2209 | H7C3T2 |
| 2210 | A0A024QYX7 |
| 2211 | A0A024R017 |
| 2212 | A0A024R1D0 |
| 2213 | A0A024R2W4 |
| 2214 | A0A024R321 |
| 2215 | A0A024R4K5 |
| 2216 | A0A024R7J0 |
| 2217 | A0A024R8K6 |
| 2218 | A0A024R8Q1 |
| 2219 | A0A024R8U1 |
| 2220 | A0A024RAB2 |
| 2221 | A0A024RAJ6 |
| 2222 | A0A024RCA7 |
| 2221 | A0A024RDW8 |
| 2224 | A0A075EKM8 |
| 2225 | A0A087WT21 |
| 2226 | A0A087WU05 |
| 2227 | A0A087WW79 |
| 2228 | A0A087WWP7 |
| 2229 | A0A087WWY3 |
| 2230 | A0A0S7WY61 |
| 2231 | A0A087WZM5 |
| 2232 | A0A087WZN9 |
| 2233 | A0A087X1J2 |
| 2234 | A0A0A0MQX7 |
| 2235 | A0A0A0MRF9 |
| 2236 | A0A0A0MRH2 |
| 2237 | A0A0A0MTC1 |
| 2238 | A0A0A7M1X5 |
| 2239 | A0A0B6XK12 |
| 2240 | A0A0C4DFS1 |
| 2241 | A0A0G2JJ52 |
| 2242 | A0A0G2JN90 |
| 2243 | A0A0G2JNE7 |
| 2244 | A0A0G2JQ91 |
| 2245 | A0A0S2Z487 |
| 2246 | AGA0S2Z4T2 |
| 2247 | A2RUE7 |
| 2248 | A6XMV8 |
| 2249 | A6YID7 |
| 2250 | A8K0T9 |
| 2251 | A8K126 |
| 2252 | A8K168 |
| 2253 | A8K335 |
| 2254 | A8K6D3 |
| 2255 | A8K849 |
| 2256 | B0I1S3 |
| 2257 | B3KS68 |
| 2258 | B3KS71 |
| 2259 | B3KT0 |
| 2260 | B3KU58 |
| 2261 | B4DDF3 |
| 2262 | B4DE78 |
| 2263 | B4DF49 |
| 2264 | B4DG47 |
| 2265 | B4DHV7 |
| 2266 | B4DJJ9 |
| 2267 | B4DMB5 |
| 2268 | B4DNH1 |
| 2269 | B4DP69 |
| 2270 | B4DPW9 |
| 2271 | B4DTA8 |
| 2272 | B4DTH2 |
| 2273 | B4DYM7 |
| 2274 | B4E1B0 |
| 2275 | B4E284 |
| 2276 | B7Z2F0 |
| 2277 | B7Z2I6 |
| 2278 | B7Z597 |
| 2279 | B7Z754 |
| 2280 | B7Z924 |
| 2281 | B7Z9B8 |
| 2282 | B7ZA28 |
| 2283 | B7ZAG1 |
| 2284 | B7ZAY4 |
| 2285 | B7ZML4 |
| 2286 | C9IY79 |
| 2287 | C9JKZ2 |
| 2288 | D6RHZ5 |
| 2289 | D9ZGF8 |
| 2290 | E2ITE0 |
| 2291 | E5RGZ4 |
| 2292 | E5RH50 |
| 2293 | E5RII0 |
| 2294 | E5RJ14 |
| 2295 | E5RK62 |
| 2296 | E5RK63 |
| 2297 | E7EMB3 |
| 2298 | E7EMF1 |
| 2299 | E9KL30 |
| 2300 | E9PD53 |
| 2301 | E9PIA9 |
| 2302 | E9PJF9 |
| 2303 | E9PKH0 |
| 2304 | E9PM19 |
| 2305 | E9PM22 |
| 2306 | E9PMC9 |
| 2307 | E9PNQ9 |
| 2308 | E9PPD2 |
| 2309 | E9PPK9 |
| 2310 | E9PPR9 |
| 2311 | E9PQ70 |
| 2312 | E9PR84 |
| 2313 | E9PRJ8 |
| 2314 | F2Z3H1 |
| 2315 | F4ZW63 |
| 2316 | F5GWI0 |
| 2317 | F5H3N3 |
| 2318 | F5H4N4 |
| 2319 | F5H4Z8 |
| 2320 | F8VR50 |
| 2321 | F8VRX1 |
| 2322 | F8VXW2 |
| 2323 | F8W1A0 |
| 2324 | F8W1H8 |
| 2325 | F8W1K5 |
| 2326 | F8W9J4 |
| 2327 | F8WAE6 |
| 2328 | F8WD26 |
| 2329 | F8WDY7 |
| 2330 | G1EPL1 |
| 2331 | G3V1E2 |
| 2332 | G3V2H3 |
| 2333 | G3V2X9 |
| 2334 | G3V4U0 |
| 2335 | G3V5X8 |
| 2336 | G5EA44 |
| 2337 | G8XWS8 |
| 2338 | H0UI76 |
| 2339 | H0Y351 |
| 2340 | H0Y3A8 |
| 2341 | H0Y4K8 |
| 2342 | H0Y4R1 |
| 2343 | H0Y554 |

TABLE 4-continued

Proteins in both MSCEX and APEX

| | |
|---|---|
| 2344 | H0Y586 |
| 2345 | H0Y5C0 |
| 2346 | H0Y5F3 |
| 2347 | H0Y5U0 |
| 2348 | H0Y8S0 |
| 2349 | H0Y987 |
| 2350 | H0Y998 |
| 2351 | H0Y9C2 |
| 2352 | H0YAM7 |
| 2353 | H0YAP9 |
| 2354 | H0YC35 |
| 2355 | H0YC94 |
| 2356 | H0YCR9 |
| 2357 | H0YEM3 |
| 2358 | H0YET2 |
| 2359 | H0YIH3 |
| 2360 | H0YJ03 |
| 2361 | H0YJD3 |
| 2362 | H0YKB3 |
| 2363 | H0YKS8 |
| 2364 | H0YL50 |
| 2365 | H0YM03 |
| 2366 | H0YM92 |
| 2367 | H3BPF6 |
| 2368 | H3BTD4 |
| 2369 | H3BTN5 |
| 2370 | H3BU78 |
| 2371 | H3BUH7 |
| 2372 | H7BY82 |
| 2373 | H7C1M6 |
| 2374 | H7C2H7 |
| 2375 | H7C2Q8 |
| 2376 | H7C2U0 |
| 2377 | H7C2Y0 |
| 2378 | H7C4X4 |
| 2379 | I3L4F9 |
| 2380 | I3L4N7 |
| 2381 | J3K000 |
| 2382 | K7EKL3 |
| 2383 | K7EKS1 |
| 2384 | K7EM90 |
| 2385 | K7EMN2 |
| 2386 | K7EPL0 |
| 2387 | K7ERF7 |
| 2388 | M0R0U4 |
| 2389 | M1VKI9 |
| 2390 | O94985 |
| 2391 | O95617 |
| 2392 | P30419 |
| 2393 | P98174 |
| 2394 | Q00839 |
| 2395 | Q05BW8 |
| 2396 | Q05DA4 |
| 2397 | Q05DS5 |
| 2398 | Q14650 |
| 2399 | Q1RMZ5 |
| 2400 | Q2EF79 |
| 2401 | Q2VP91 |
| 2402 | Q2YD88 |
| 2403 | Q3B7A7 |
| 2404 | Q4G0Q4 |
| 2405 | Q4LE57 |
| 2406 | Q4VC00 |
| 2407 | Q504V9 |
| 2408 | Q508I7 |
| 2409 | Q53F09 |
| 2410 | Q53FI4 |
| 2411 | Q53FK2 |
| 2412 | Q53FU5 |
| 2413 | Q53GU8 |
| 2414 | Q53GW3 |
| 2415 | Q53HE2 |
| 2416 | Q53HU7 |
| 2417 | Q53S41 |
| 2418 | Q58FF2 |
| 2419 | Q59EG5 |
| 2420 | Q59EZ1 |
| 2421 | Q59F71 |
| 2422 | Q59FD9 |
| 2423 | Q59GH5 |
| 2424 | Q59GK2 |
| 2425 | Q59GZ8 |
| 2426 | Q59HA3 |
| 2427 | Q59HB3 |
| 2428 | Q59HB5 |
| 2429 | Q5FC05 |
| 2430 | Q5HYA2 |
| 2431 | Q5JPH6 |
| 2432 | Q5JQ13 |
| 2433 | Q5QNY5 |
| 2434 | Q5T0F3 |
| 2435 | Q5TA02 |
| 2436 | Q5TFM2 |
| 2437 | Q60FE5 |
| 2438 | Q658J0 |
| 2439 | Q68CW0 |
| 2440 | Q68CX6 |
| 2441 | Q6AI13 |
| 2442 | Q6EHZ3 |
| 2443 | Q6PEG1 |
| 2444 | Q6PK56 |
| 2445 | Q6PKD2 |
| 2446 | Q6PQ81 |
| 2447 | Q6S4P3 |
| 2448 | Q6U2L6 |
| 2449 | Q6U8A4 |
| 2450 | Q6UQL6 |
| 2451 | Q6UUU9 |
| 2452 | Q6W6M8 |
| 2453 | Q6XYD2 |
| 2454 | Q6ZMY0 |
| 2455 | Q6ZMY3 |
| 2456 | Q6ZN49 |
| 2457 | Q6ZNB8 |
| 2458 | Q6ZNL4 |
| 2459 | Q6ZNU3 |
| 2460 | Q6ZP35 |
| 2461 | Q6ZP53 |
| 2462 | Q6ZR44 |
| 2463 | Q6ZRZ8 |
| 2464 | Q6ZS01 |
| 2465 | Q6ZS03 |
| 2466 | Q6ZS14 |
| 2467 | Q6ZSD7 |
| 2468 | Q6ZSL4 |
| 2469 | Q6ZT31 |
| 2470 | Q6ZT94 |
| 2471 | Q6ZTY7 |
| 2472 | Q6ZVC6 |
| 2473 | Q71RC2 |
| 2474 | Q71S06 |
| 2475 | Q71SW6 |
| 2476 | Q71UD4 |
| 2477 | Q71UM7 |
| 2478 | Q75MN1 |
| 2479 | Q75MY0 |
| 2480 | Q75N18 |
| 2481 | Q75N89 |
| 2482 | Q7KZ71 |
| 2483 | Q7L4M3 |
| 2484 | Q7L4N0 |
| 2485 | Q7L8K0 |
| 2486 | Q7RTQ9 |
| 2487 | Q7RU04 |
| 2488 | Q7Z2F6 |
| 2489 | Q7Z2X7 |
| 2490 | Q7Z355 |
| 2491 | Q7Z3G7 |
| 2492 | Q7Z3T9 |
| 2493 | Q7Z427 |
| 2494 | Q7Z487 |
| 2495 | Q7Z497 |
| 2496 | Q7Z4Z1 |
| 2497 | Q7Z6M3 |
| 2498 | Q7Z738 |
| 2499 | Q7Z757 |

TABLE 4-continued

Proteins in both MSCEX and APEX

| | |
|---|---|
| 2500 | Q7Z7K9 |
| 2501 | Q7Z7R0 |
| 2502 | Q86TQ3 |
| 2503 | Q86TX4 |
| 2504 | Q86U12 |
| 2505 | Q86U75 |
| 2506 | Q86U79 |
| 2507 | Q86UP3 |
| 2508 | Q86V48 |
| 2509 | Q86W61 |
| 2510 | Q86WD0 |
| 2511 | Q86XU5 |
| 2512 | Q86YN0 |
| 2513 | Q8IVF4 |
| 2514 | Q8IWC8 |
| 2515 | Q8IWL5 |
| 2516 | Q8IXX0 |
| 2517 | Q8IY44 |
| 2518 | Q8IY97 |
| 2519 | Q8IY98 |
| 2520 | Q8IYQ9 |
| 2521 | Q8IZD4 |
| 2522 | Q8N1I1 |
| 2523 | Q8N1I8 |
| 2524 | Q8N274 |
| 2525 | Q8N294 |
| 2526 | QSN4Z1 |
| 2527 | Q8N505 |
| 2528 | Q8N5L9 |
| 2529 | Q8N6NS |
| 2530 | Q8N6P3 |
| 2531 | Q8N7Y3 |
| 2532 | Q8N7Z5 |
| 2533 | Q8N9C4 |
| 2534 | Q8N9F8 |
| 2535 | Q8N9K4 |
| 2536 | Q8N9Q8 |
| 2537 | Q8NA68 |
| 2538 | Q8NB89 |
| 2539 | Q8NBH6 |
| 2540 | Q8NCJ3 |
| 2541 | Q8NE02 |
| 2542 | Q8NF03 |
| 2543 | Q8NF19 |
| 2544 | Q8NF24 |
| 2545 | Q8NF60 |
| 2546 | Q8NG20 |
| 2547 | Q8NH73 |
| 2548 | Q8NI27 |
| 2549 | Q8TAS1 |
| 2550 | Q8TAT5 |
| 2551 | Q8TB01 |
| 2552 | Q8TB95 |
| 2553 | Q8TBN2 |
| 2554 | Q8TDG6 |
| 2555 | Q8TDS4 |
| 2556 | Q8TEP3 |
| 2557 | Q8TES4 |
| 2558 | Q8WTY5 |
| 2559 | Q8WU03 |
| 2560 | Q8WUI6 |
| 2561 | Q8WVX2 |
| 2562 | Q8WW96 |
| 2563 | Q8WWB2 |
| 2564 | Q8WX69 |
| 2565 | Q8WZ56 |
| 2566 | Q92468 |
| 2567 | Q92547 |
| 2568 | Q92681 |
| 2569 | Q92945 |
| 2570 | Q93063 |
| 2571 | Q93093 |
| 2572 | Q969I5 |
| 2573 | Q96AA2 |
| 2574 | Q96AQ0 |
| 2575 | Q96AR9 |
| 2576 | Q96AX1 |
| 2577 | Q96B07 |
| 2578 | Q96B60 |
| 2579 | Q96BA4 |
| 2580 | Q96BG6 |
| 2581 | Q96C61 |
| 2582 | Q96CD8 |
| 2583 | Q96CV8 |
| 2584 | Q96D30 |
| 2585 | Q96DQ5 |
| 2586 | Q96DZ4 |
| 2587 | Q96EB3 |
| 2588 | Q96G38 |
| 2589 | Q96GF5 |
| 2590 | Q96GW1 |
| 2591 | Q96HC2 |
| 2592 | Q96HF4 |
| 2593 | Q96HI1 |
| 2594 | Q96HN5 |
| 2595 | Q96IE3 |
| 2596 | O96JJ7 |
| 2597 | Q96K48 |
| 2598 | Q96K89 |
| 2599 | Q96KC0 |
| 2600 | Q96LJ7 |
| 2601 | Q96LN7 |
| 2602 | Q96LR2 |
| 2603 | Q96MN8 |
| 2604 | Q96N76 |
| 2605 | Q96NB3 |
| 2606 | Q96NX2 |
| 2607 | Q96PA3 |
| 2608 | Q96PJ0 |
| 2609 | Q96PV0 |
| 2610 | Q96Q06 |
| 2611 | Q96QU5 |
| 2612 | Q96RL8 |
| 2613 | Q96RP4 |
| 2614 | Q96RS2 |
| 2615 | Q96RZ7 |
| 2616 | Q96SE4 |
| 2617 | Q99435 |
| 2618 | Q99529 |
| 2619 | Q99538 |
| 2620 | Q99666 |
| 2621 | Q9BR56 |
| 2622 | Q9BR60 |
| 2623 | Q9BS14 |
| 2624 | Q9BS75 |
| 2625 | Q9BSD0 |
| 2626 | Q9BTL0 |
| 2627 | Q9BVS9 |
| 2628 | Q9BW34 |
| 2629 | Q9BXG2 |
| 2630 | Q9BXV5 |
| 2631 | Q9BZ93 |
| 2632 | Q9BZQ0 |
| 2633 | Q9H049 |
| 2634 | Q9H0M4 |
| 2635 | Q9B2E0 |
| 2636 | Q9H2E1 |
| 2637 | Q9H369 |
| 2638 | Q9H3B0 |
| 2639 | Q9H3R3 |
| 2640 | Q9H3U3 |
| 2641 | Q9H511 |
| 2642 | Q9H5S1 |
| 2643 | Q9H5T0 |
| 2644 | Q9H717 |
| 2645 | Q9H7J0 |
| 2646 | Q9H8J8 |
| 2647 | Q9HAP0 |
| 2648 | Q9HAP1 |
| 2649 | Q9HB74 |
| 2650 | Q9HBB2 |
| 2651 | Q9HBP0 |
| 2652 | Q9HC77 |
| 2653 | Q9HCI6 |
| 2654 | Q9NP01 |
| 2655 | Q9NPA9 |

TABLE 4-continued

Proteins in both MSCEX and APEX

| | |
|---|---|
| 2656 | Q9NPM2 |
| 2657 | Q9NQG5 |
| 2658 | Q9NRE2 |
| 2659 | Q9NRY4 |
| 2660 | Q9NS89 |
| 2661 | Q9NSH2 |
| 2662 | Q9NSK3 |
| 2663 | Q9NSM5 |
| 2664 | Q9NT11 |
| 2665 | Q9NTC4 |
| 2666 | Q9NTU6 |
| 2667 | Q9NV59 |
| 2668 | Q9NVF8 |
| 2669 | Q9NVY6 |
| 2670 | Q9NW05 |
| 2671 | Q9NW43 |
| 2672 | Q9NWD6 |
| 2673 | Q9NWP5 |
| 2674 | Q9NWW3 |
| 2675 | Q9P0V0 |
| 2676 | Q9P1C5 |
| 2677 | Q9P1G4 |
| 2678 | Q9P1N9 |
| 2679 | Q9P1Y0 |
| 2680 | Q9P262 |
| 2681 | Q9P2G7 |
| 2682 | Q9UBC7 |
| 2683 | Q9UD42 |
| 2684 | Q9UD69 |
| 2685 | Q9UDE8 |
| 2686 | Q9UDY3 |
| 2687 | Q9UDZ8 |
| 2688 | Q9UE33 |
| 2689 | Q9UE89 |
| 2690 | Q9UES0 |
| 2691 | Q9UFZ4 |
| 2692 | Q9UG85 |
| 2693 | Q9UGU0 |
| 2694 | Q9UIU0 |
| 2695 | Q9UJ56 |
| 2696 | Q9UJM0 |
| 2697 | Q9UJM1 |
| 2698 | Q9UJN9 |
| 2699 | Q9UJZ2 |
| 2700 | Q9UJZ7 |
| 2701 | Q9UM89 |
| 2702 | Q9UMB3 |
| 2703 | Q9UMN4 |
| 2704 | Q9UNF3 |
| 2705 | Q9UNU2 |
| 2706 | Q9UPH5 |
| 2707 | Q9UQC1 |
| 2708 | Q9UQS6 |
| 2709 | Q9Y267 |
| 2710 | Q9Y2Q2 |
| 2711 | Q9Y4R1 |
| 2712 | Q9Y546 |
| 2713 | Q9Y5E1 |
| 2714 | Q9Y623 |
| 2715 | Q9Y6D3 |
| 2716 | Q9Y6N6 |
| 2717 | Q9Y6U3 |
| 2718 | R4GMY1 |
| 2719 | R4GNC2 |
| 2720 | R4GNC7 |
| 2721 | R4RWV3 |
| 2722 | S4R328 |
| 2723 | S4R3E9 |
| 2724 | S4R3G7 |
| 2725 | S4R451 |
| 2726 | S5FMV1 |
| 2727 | U3KPX5 |
| 2728 | U3KQA9 |
| 2729 | U3KQE2 |
| 2730 | U3KQI3 |
| 2731 | U3KQK2 |
| 2732 | U3KQK8 |
| 2733 | U3KQP1 |
| 2734 | U3PXP0 |
| 2735 | U3REJ1 |
| 2736 | V5QSK8 |
| 2737 | V9GYK3 |
| 2738 | V9GYL0 |
| 2739 | V9GYV7 |
| 2740 | V9GZ17 |
| 2741 | V9GZ54 |
| 2742 | V9GZ76 |
| 2743 | V9GZR9 |
| 2744 | V9H0H3 |
| 2745 | V9H1C1 |
| 2746 | V9H1D9 |
| 2747 | V9HVZ6 |
| 2748 | V9HVZ7 |
| 2749 | V9HW24 |
| 2750 | V9HW31 |
| 2751 | V9HW35 |
| 2752 | V9HW55 |
| 2753 | V9HW63 |
| 2754 | V9HW80 |
| 2755 | V9HW89 |
| 2756 | V9HW90 |
| 2757 | V9HW95 |
| 2758 | V9HWA6 |
| 2759 | V9HWA9 |
| 2760 | V9HWC0 |
| 2761 | V9HWC1 |
| 2762 | V9HWC6 |
| 2763 | V9HWC7 |
| 2764 | V9HWE9 |
| 2765 | V9HWF4 |
| 2766 | V9HWF5 |
| 2767 | V9HWG9 |
| 2768 | V9HWH6 |
| 2769 | V9HWH9 |
| 2770 | W5X314 |
| 2771 | W6I206 |
| 2772 | W6MEN4 |
| 2773 | W8QEH3 |
| 2774 | W8QRJ0 |
| 2775 | X5D2F4 |
| 2776 | X5D2Z4 |
| 2777 | X5D784 |
| 2778 | X5D7K9 |
| 2779 | X5D7R7 |
| 2780 | X5DQS5 |
| 2781 | X5DQV1 |
| 2782 | X5DR74 |
| 2783 | X6R3R3 |
| 2784 | X6R6Z1 |
| 2785 | X6RJP6 |
| 2786 | X6RLX0 |

TABLE 5

Proteins in both NPEX and MSCEX

| | |
|---|---|
| 1 | A0A024RBF5 |
| 2 | A0A087WTU5 |
| 3 | A0A087WTY5 |
| 4 | A0A087WZY3 |
| 5 | A0A0A0MSD7 |
| 6 | A0A0U1RQQ9 |
| 7 | A8K457 |
| 8 | B0YIW5 |
| 9 | B2R6M6 |
| 10 | B2RWN5 |
| 11 | B3KM34 |
| 12 | B3KS32 |
| 13 | B4DK21 |
| 14 | B4DLA8 |
| 15 | B4DM04 |
| 16 | B4DYP3 |
| 17 | B7Z220 |

TABLE 5-continued

Proteins in both NPEX and MSCEX

| | |
|---|---|
| 18 | B7Z3F8 |
| 19 | A0A0A0MRE5 |
| 20 | A8K5A6 |
| 21 | B2RWN8 |
| 22 | B3KQE6 |
| 23 | B4DIY9 |
| 24 | F2Z2Y4 |
| 25 | I7GY12 |
| 26 | K7EIZ7 |
| 27 | A1DRY3 |
| 28 | A8K2S5 |
| 29 | B4DJ85 |
| 30 | D3DSZ2 |
| 31 | D6RHJ6 |
| 32 | E5RK22 |
| 33 | A0A090N7W7 |
| 34 | A0A024R9U8 |
| 35 | A0A087WTQ1 |
| 36 | A0A0A0MTS5 |
| 37 | A0A0J9YWF7 |
| 38 | A0A0S2Z5A6 |
| 39 | A0A140G945 |
| 40 | A0PJA6 |
| 41 | A8MYA2 |
| 42 | B3KY01 |
| 43 | B4DDZ2 |
| 44 | B4DJ87 |
| 45 | B4DN40 |
| 46 | B4DPI7 |
| 47 | B4DQJ6 |
| 48 | B7WNR7 |
| 49 | B7ZAV4 |
| 50 | C9J4J0 |
| 51 | D1CS68 |
| 52 | E9PR32 |
| 53 | H0Y4V9 |
| 54 | H0YE86 |
| 55 | H3BM13 |
| 56 | H7C124 |
| 57 | J3KNF5 |
| 58 | J3KTE8 |
| 59 | J3QQZ1 |
| 60 | K7EMU5 |
| 61 | A0A087X1K6 |
| 62 | B9EK65 |
| 63 | D2CPJ9 |
| 64 | A8K9G8 |
| 65 | E9PDY4 |
| 66 | E9PKB7 |
| 67 | F5GWB9 |
| 68 | H0Y5A3 |
| 69 | H0YDX7 |
| 70 | H0YGC5 |
| 71 | I3L2H2 |
| 72 | K7ENM8 |
| 73 | A0A024R2Q7 |
| 74 | A0A024RAC9 |
| 75 | A0A087X043 |
| 76 | A1L497 |
| 77 | A8K5C2 |
| 78 | B2R7A1 |
| 79 | B3KML1 |
| 80 | B4DPN0 |
| 81 | B4DPP6 |
| 82 | B4DSG6 |
| 83 | B4DW61 |
| 84 | B4DY21 |
| 85 | B4E1C1 |
| 86 | B7Z3E5 |
| 87 | B7Z8R2 |
| 88 | B7ZM83 |
| 89 | C9JUF9 |
| 90 | A0A0S2SW46 |
| 91 | A0A140G961 |
| 92 | A5YM44 |
| 93 | A8K3I0 |
| 94 | B2RCM2 |
| 95 | B2RD90 |
| 96 | B2RDH6 |
| 97 | B2RUU6 |
| 98 | B3KPC9 |
| 99 | B4DKV6 |
| 100 | C7FEB0 |
| 101 | E7EUN2 |
| 102 | F2Z2C0 |
| 103 | G3F4G3 |
| 104 | H3BUZ9 |
| 105 | I3L2G4 |
| 106 | J3KST4 |
| 107 | L0R875 |
| 108 | M0QY24 |
| 109 | M0QY93 |
| 110 | M0R167 |
| 111 | A0A140T9N1 |
| 112 | B3KV66 |
| 113 | B2RN10 |
| 114 | B4DX19 |
| 115 | A0A087WTM7 |
| 116 | A0A087WVZ9 |
| 117 | A0A087WZI7 |
| 118 | A0A0C4DGZ0 |
| 119 | A0A0F7T737 |
| 120 | A0A126GW30 |
| 121 | A8K5R3 |
| 122 | B1AA16 |
| 123 | B2RD71 |
| 124 | B4DQ03 |
| 125 | B4DRU3 |
| 126 | B4E1H3 |
| 127 | B4E3L4 |
| 128 | B5A930 |
| 129 | G1UI21 |
| 130 | H7C5E8 |
| 131 | I3L0S6 |
| 132 | K7ELE6 |
| 133 | K7ERU1 |
| 134 | O00303 |
| 135 | O15232 |
| 136 | O75144 |
| 137 | O75643 |
| 138 | O95757 |
| 139 | O95816 |
| 140 | P00390 |
| 141 | P04406 |
| 142 | P05455 |
| 143 | P06576 |
| 144 | P11908 |
| 145 | P12277 |
| 146 | P13010 |
| 147 | P13797 |
| 148 | P13798 |
| 149 | P14625 |
| 150 | P17787 |
| 151 | P18206 |
| 152 | P20592 |
| 153 | P20618 |
| 154 | P21399 |
| 155 | P23381 |
| 156 | P24534 |
| 157 | P25787 |
| 158 | P30520 |
| 159 | P30566 |
| 160 | P35052 |
| 161 | P37837 |
| 162 | P40925 |
| 163 | P43490 |
| 164 | P43699 |
| 165 | P48723 |
| 166 | P49721 |
| 167 | P49916 |
| 168 | P50991 |
| 169 | P55290 |
| 170 | P60842 |
| 171 | P61158 |
| 172 | P61970 |
| 173 | P78357 |

TABLE 5-continued

Proteins in both NPEX and MSCEX

| | |
|---|---|
| 174 | P78371 |
| 175 | Q02809 |
| 176 | Q04446 |
| 177 | Q05BW9 |
| 178 | Q05CU5 |
| 179 | Q05DQ6 |
| 180 | Q08431 |
| 181 | Q13191 |
| 182 | Q14397 |
| 183 | Q14974 |
| 184 | Q16555 |
| 185 | Q4G0U7 |
| 186 | Q4LE70 |
| 187 | Q4QQP8 |
| 188 | Q56A80 |
| 189 | Q58F05 |
| 190 | Q59GL5 |
| 191 | Q59H14 |
| 192 | Q5SRE5 |
| 193 | Q5VTG7 |
| 194 | Q6P1A2 |
| 195 | Q6P668 |
| 196 | B4DVZ8 |
| 197 | E9PN76 |
| 198 | A0A0A0MS56 |
| 199 | A8K228 |
| 200 | B4DHL3 |
| 201 | A0A024R0V9 |
| 202 | A0A024R2F7 |
| 203 | B2RB99 |
| 204 | B3KVJ8 |
| 205 | B4DL71 |
| 206 | B7Z5Q5 |
| 207 | F8WCB0 |
| 208 | G3V470 |
| 209 | H0YGP2 |
| 210 | H7BXX0 |
| 211 | P11310 |
| 212 | P13639 |
| 213 | P22234 |
| 214 | P41250 |
| 215 | P52209 |
| 216 | P98095 |
| 217 | Q00610 |
| 218 | Q04760 |
| 219 | Q1JQ81 |
| 220 | Q4LE34 |
| 221 | Q4ZG60 |
| 222 | Q562P0 |
| 223 | Q5SZP4 |
| 224 | Q5T7Q5 |
| 225 | Q6NR85 |
| 226 | Q6PKB2 |
| 227 | A0A024RDI0 |
| 228 | B3KVT0 |
| 229 | B3KW08 |
| 230 | B5BU64 |
| 231 | F8VTS6 |
| 232 | Q17RV3 |
| 233 | Q4LE35 |
| 234 | Q53ZD9 |
| 235 | H7BZ78 |
| 236 | P20700 |
| 237 | P23528 |
| 238 | P28066 |
| 239 | P43686 |
| 240 | P51665 |
| 241 | P63241 |
| 242 | Q12765 |
| 243 | Q14666 |
| 244 | Q5T9B7 |
| 245 | A0A024R0F1 |
| 246 | A6NNK5 |
| 247 | A7Y9J9 |
| 248 | B2RCN5 |
| 249 | B3KNG8 |
| 250 | B3KW67 |
| 251 | B4DJ43 |
| 252 | B7ZBJ6 |
| 253 | E5RGB1 |
| 254 | E9PNV8 |
| 255 | G5E9C5 |
| 256 | H0YD68 |
| 257 | O15020 |
| 258 | A0A024R3W8 |
| 259 | A0A024R4E7 |
| 260 | A0A024R7L2 |
| 261 | A0A024R8K8 |
| 262 | A0A024R8L5 |
| 263 | A0A024R8U4 |
| 264 | A0A024R9F1 |
| 265 | A0A087WVC6 |
| 266 | A0A087WW67 |
| 267 | A0A087WYA1 |
| 268 | A0A0C4DFY7 |
| 269 | A0A0G2JNI0 |
| 270 | A0A0J9YY10 |
| 271 | A0A126GVS6 |
| 272 | A2RTX5 |
| 273 | A6NF36 |
| 274 | A8K324 |
| 275 | A8K4N3 |
| 276 | A8K8J5 |
| 277 | A8K8R2 |
| 278 | B3KQ44 |
| 279 | B3KWP3 |
| 280 | B3KXW2 |
| 281 | B4DEL6 |
| 282 | B4DH82 |
| 283 | B4DJT2 |
| 284 | B4DLC6 |
| 285 | B4DNG2 |
| 286 | B4DS99 |
| 287 | B4DWK2 |
| 288 | B4DYK9 |
| 289 | B4DYX8 |
| 290 | B4E303 |
| 291 | B4E367 |
| 292 | B7Z1P9 |
| 293 | B7Z671 |
| 294 | C9JDR5 |
| 295 | C9JVG0 |
| 296 | D3DTQ7 |
| 297 | D3DXG8 |
| 298 | D4PHA4 |
| 299 | E3W983 |
| 300 | E5G743 |
| 301 | E5RG96 |
| 302 | E5RGT3 |
| 303 | E7EVQ3 |
| 304 | E9JVC4 |
| 305 | E9PH60 |
| 306 | E9PK12 |
| 307 | F5GXY0 |
| 308 | F5GY37 |
| 309 | F5H2D1 |
| 310 | F5H8J8 |
| 311 | F8UU18 |
| 312 | F8VWL0 |
| 313 | F8W7F7 |
| 314 | G3V5M4 |
| 315 | H0Y3H6 |
| 316 | H0Y6A5 |
| 317 | H0YBF7 |
| 318 | H0YF13 |
| 319 | H0YGG5 |
| 320 | H0YL42 |
| 321 | H3BRY5 |
| 322 | H7C463 |
| 323 | I6NLS4 |
| 324 | J3QKX5 |
| 325 | O00410 |
| 326 | O14943 |
| 327 | O15067 |
| 328 | O95996 |
| 329 | O96005 |

TABLE 5-continued

Proteins in both NPEX and MSCEX

| | |
|---|---|
| 330 | P05386 |
| 331 | P06744 |
| 332 | P08069 |
| 333 | P12956 |
| 334 | P22102 |
| 335 | P29401 |
| 336 | P30153 |
| 337 | P32119 |
| 338 | P42785 |
| 339 | P50747 |
| 340 | P53396 |
| 341 | P62314 |
| 342 | Q06323 |
| 343 | Q06AH7 |
| 344 | Q08629 |
| 345 | Q13393 |
| 346 | Q13616 |
| 347 | Q14563 |
| 348 | Q15828 |
| 349 | Q1KLZ0 |
| 350 | Q29RF7 |
| 351 | Q210A9 |
| 352 | Q32Q12 |
| 353 | Q495G0 |
| 354 | Q53R19 |
| 355 | Q59E15 |
| 356 | Q59ET3 |
| 357 | Q59GA8 |
| 358 | Q5SYQ9 |
| 359 | Q5XUU0 |
| 360 | Q6FH47 |
| 361 | Q6IFB0 |
| 362 | Q6LAP8 |
| 363 | Q6W4X9 |
| 364 | Q6XYC2 |
| 365 | Q6ZMN7 |
| 366 | Q6ZS81 |
| 367 | Q6ZTQ4 |
| 368 | Q6ZWK7 |
| 369 | Q7L2H7 |
| 370 | Q7Z3Y4 |
| 371 | Q7Z3Z0 |
| 372 | Q7Z442 |
| 373 | Q7Z4C2 |
| 374 | Q7Z534 |
| 375 | Q7Z5C1 |
| 376 | Q7Z6C1 |
| 377 | Q86T01 |
| 378 | Q86T64 |
| 379 | Q86VU1 |
| 380 | Q86X45 |
| 381 | Q86XV5 |
| 382 | Q86YS3 |
| 383 | Q8IVC0 |
| 384 | Q8IVV2 |
| 385 | Q8IWJ2 |
| 386 | Q8IXV0 |
| 387 | Q8IYT4 |
| 388 | Q8IZ41 |
| 389 | Q8IZC6 |
| 390 | Q8N303 |
| 391 | Q8N3N3 |
| 392 | Q8N3T6 |
| 393 | Q8N696 |
| 394 | Q8N8W4 |
| 395 | Q8NAD5 |
| 396 | Q8NBX0 |
| 397 | Q8NFN8 |
| 398 | Q8NG11 |
| 399 | Q8TA92 |
| 400 | Q8TAK2 |
| 401 | Q8TCE1 |
| 402 | Q8TDJ6 |
| 403 | Q8TDW7 |
| 404 | Q8TEU7 |
| 405 | Q8WUM4 |
| 406 | Q8WVV7 |
| 407 | Q8WVW5 |
| 408 | Q8WY27 |
| 409 | Q92484 |
| 410 | Q92820 |
| 411 | Q92863 |
| 412 | Q92905 |
| 413 | Q92973 |
| 414 | Q96AA1 |
| 415 | Q96HI4 |
| 416 | Q96I12 |
| 417 | Q96KR9 |
| 418 | Q96LC1 |
| 419 | Q96P44 |
| 420 | Q96RY7 |
| 421 | Q96SM3 |
| 422 | Q96ST3 |
| 423 | Q99436 |
| 424 | Q99598 |
| 425 | Q99707 |
| 426 | Q99832 |
| 427 | Q9BT36 |
| 428 | Q9BT78 |
| 429 | Q9BTY9 |
| 430 | Q9BWV3 |
| 431 | Q9BX63 |
| 432 | Q9BXS5 |
| 433 | Q9BXT5 |
| 434 | Q9C0C2 |
| 435 | Q9H0G2 |
| 436 | Q9H1W6 |
| 437 | Q9H3E1 |
| 438 | Q9H3Q7 |
| 439 | Q9HC03 |
| 440 | Q9NR71 |
| 441 | Q9NU86 |
| 442 | Q9NWN9 |
| 443 | Q9NYC9 |
| 444 | Q9P0S0 |
| 445 | Q9UCB0 |
| 446 | Q9UCS3 |
| 447 | Q9UE54 |
| 448 | Q9UF55 |
| 449 | Q9UGA0 |
| 450 | Q9UHV7 |
| 451 | Q9UIW2 |
| 452 | Q9UKP4 |
| 453 | Q9UKU9 |
| 454 | Q9ULC4 |
| 455 | Q9ULJ3 |
| 456 | Q9UNA2 |
| 457 | Q9UNM6 |
| 458 | Q9UPV8 |
| 459 | Q9Y266 |
| 460 | S4R3N1 |
| 461 | S4R3S7 |
| 462 | S4R400 |
| 463 | T1S9D5 |
| 464 | V9HWF8 |
| 465 | W4VSQ3 |
| 466 | W8SJH0 |
| 467 | X6R6S3 |

TABLE 6

Proteins in NPEX and APEX

| | |
|---|---|
| 1 | A0A024R3G7 |
| 2 | A0A024R8E2 |
| 3 | A0A087WTU9 |
| 4 | A0A087X191 |
| 5 | A0A0A0MSS2 |
| 6 | A0A0A0MTL9 |
| 7 | A0A0A6YYJ5 |
| 8 | A0A0J9YY72 |
| 9 | A4FTX9 |
| 10 | A5D906 |

TABLE 6-continued

Proteins in NPEX and APEX

| | |
|---|---|
| 11 | A5HML1 |
| 12 | B4DDH4 |
| 13 | B4DDI8 |
| 14 | B4DFH6 |
| 15 | B4DJQ7 |
| 16 | B4DV85 |
| 17 | B4DXB2 |
| 18 | B7Z7R2 |
| 19 | B7Z8P5 |
| 20 | B3KSE9 |
| 21 | B4DIA1 |
| 22 | B4DMS3 |
| 23 | B4E2P9 |
| 24 | B4E315 |
| 25 | B7Z380 |
| 26 | B7Z403 |
| 27 | B7Z625 |
| 28 | B7Z8W6 |
| 29 | B7ZLP5 |
| 30 | C9J2C0 |
| 31 | C9JER5 |
| 32 | E7EUT5 |
| 33 | E9PFH7 |
| 34 | E9PKG1 |
| 35 | G1UI17 |
| 36 | H0Y871 |
| 37 | H0YME5 |
| 38 | H3BMM5 |
| 39 | H9KV48 |
| 40 | J3QS51 |
| 41 | K7EIJ8 |
| 42 | K7ELF8 |
| 43 | K7ELK0 |
| 44 | A0A140CTX8 |
| 45 | A8K3Y5 |
| 46 | B4DFM5 |
| 47 | B4DGH0 |
| 48 | B4DWX3 |
| 49 | B4DXM1 |
| 50 | B7Z780 |
| 51 | C9JMY1 |
| 52 | A0A024R9W5 |
| 53 | A0A068F7M9 |
| 54 | A0A0A0MQZ2 |
| 55 | A0A0K0Q2Z1 |
| 56 | A8K719 |
| 57 | A8KAC4 |
| 58 | B2R6V9 |
| 59 | B3KW36 |
| 60 | B4DEN5 |
| 61 | B4DJX6 |
| 62 | B4DMD5 |
| 63 | B4DMN1 |
| 64 | B4DPD5 |
| 65 | B4DUJ5 |
| 66 | B4DZR3 |
| 67 | B7ZLC9 |
| 68 | B7ZLX9 |
| 69 | F5H6J0 |
| 70 | F8VV04 |
| 71 | H0YEZ5 |
| 72 | H7C1I7 |
| 73 | J3KS22 |
| 74 | K7ESP4 |
| 75 | A0A126GW47 |
| 76 | B3KVV6 |
| 77 | B4DEQ2 |
| 78 | B4DL70 |
| 79 | B4E3H4 |
| 80 | B9EK46 |
| 81 | C9JJE5 |
| 82 | C9K0S6 |
| 83 | A8K7H3 |
| 84 | A9UEZ6 |
| 85 | B3KNM0 |
| 86 | D4YW74 |
| 87 | F8W888 |
| 88 | G3V200 |
| 89 | G3V3A7 |
| 90 | H3BT58 |
| 91 | A0A024RAM0 |
| 92 | A0A0G2JS52 |
| 93 | A0A0U1ZI18 |
| 94 | A8K972 |
| 95 | A8K9U4 |
| 96 | A8KA50 |
| 97 | B2R6U8 |
| 98 | B3KMK2 |
| 99 | B4DV51 |
| 100 | B4DVV1 |
| 101 | B4DYQ4 |
| 102 | B4DZP8 |
| 103 | B5BUC0 |
| 104 | B7Z1E1 |
| 105 | B7Z7U9 |
| 106 | A0A024RA21 |
| 107 | A0A087X201 |
| 108 | A2MYD1 |
| 109 | A8K6R5 |
| 110 | A8K919 |
| 111 | B2R7E8 |
| 112 | B3KXS5 |
| 113 | B4DIX9 |
| 114 | C5J0G2 |
| 115 | C9J5X1 |
| 116 | E9PGN7 |
| 117 | F5H7S7 |
| 118 | H7BY57 |
| 119 | I3L2J8 |
| 120 | J3KR44 |
| 121 | A0A140VK43 |
| 122 | A8K2P6 |
| 123 | B7Z6W9 |
| 124 | A0A087WXD4 |
| 125 | B3KT18 |
| 126 | A0A024R333 |
| 127 | A0A024R637 |
| 128 | A0A059U7G5 |
| 129 | A0A0C4DGM5 |
| 130 | A0A0S2Z4F3 |
| 131 | A6NHN2 |
| 132 | A8K291 |
| 133 | B2R4S5 |
| 134 | B4DDN3 |
| 135 | B4DDS9 |
| 136 | B4DFK1 |
| 137 | B4DM68 |
| 138 | B4DNJ2 |
| 139 | B4DRC6 |
| 140 | B4DZV8 |
| 141 | B4DZW2 |
| 142 | B5A928 |
| 143 | D3DWL9 |
| 144 | E5RFX4 |
| 145 | E7ENU7 |
| 146 | F8WBE0 |
| 147 | H0YCC0 |
| 148 | H7BYM0 |
| 149 | I3NI20 |
| 150 | J3KP74 |
| 151 | J3KRC3 |
| 152 | O60391 |
| 153 | O60486 |
| 154 | O60760 |
| 155 | O75322 |
| 156 | O76061 |
| 157 | P02549 |
| 158 | P11216 |
| 159 | P20908 |
| 160 | P27105 |
| 161 | P42694 |
| 162 | P42702 |
| 163 | P48426 |
| 164 | P54578 |
| 165 | P59998 |
| 166 | P60660 |

TABLE 6-continued

Proteins in NPEX and APEX

| | |
|---|---|
| 167 | P61812 |
| 168 | Q01995 |
| 169 | Q0VAP0 |
| 170 | Q14571 |
| 171 | Q15181 |
| 172 | Q15670 |
| 173 | Q1WWK5 |
| 174 | Q1WWK6 |
| 175 | Q4LE40 |
| 176 | Q53EU0 |
| 177 | Q53GP3 |
| 178 | Q53H16 |
| 179 | Q562U0 |
| 180 | Q580X3 |
| 181 | Q59EA4 |
| 182 | Q59ES1 |
| 183 | Q59EY7 |
| 184 | Q59G44 |
| 185 | Q59G78 |
| 186 | Q59GJ6 |
| 187 | Q5GIA7 |
| 188 | Q5H9N4 |
| 189 | Q5T765 |
| 190 | Q5TDF0 |
| 191 | Q5VT06 |
| 192 | Q5W0B7 |
| 193 | Q5XJ04 |
| 194 | Q61N74 |
| 195 | Q6NSB2 |
| 196 | F8W9Z1 |
| 197 | H0YHD9 |
| 198 | F6TR53 |
| 199 | H0Y796 |
| 200 | A7E2C0 |
| 201 | B0I1R1 |
| 202 | A0A0G2JNC5 |
| 203 | B3KNW3 |
| 204 | B4DGV1 |
| 205 | D6RJD3 |
| 206 | E9PMI5 |
| 207 | H0YD65 |
| 208 | O43491 |
| 209 | O95782 |
| 210 | P16035 |
| 211 | P19320 |
| 212 | Q05D08 |
| 213 | Q12771 |
| 214 | Q2QD09 |
| 215 | Q2VPJ6 |
| 216 | Q59HC8 |
| 217 | Q5R210 |
| 218 | Q5VZB5 |
| 219 | Q68D26 |
| 220 | A0A024R566 |
| 221 | A0A024R899 |
| 222 | A0A087WTK0 |
| 223 | A0A087WWY8 |
| 224 | A0A0K0K1L8 |
| 225 | A0A0U1RRM0 |
| 226 | A0JLR0 |
| 227 | A4F4K4 |
| 228 | A4FVC3 |
| 229 | A6NLU0 |
| 230 | A8K1G1 |
| 231 | B4DEX9 |
| 232 | B4DF07 |
| 233 | B4DHL2 |
| 234 | B4DJ31 |
| 235 | B4DRK5 |
| 236 | B7Z6W5 |
| 237 | B7ZAG8 |
| 238 | C9JCJ5 |
| 239 | C9JQU8 |
| 240 | E5RIA9 |
| 241 | E9PI86 |
| 242 | F5H5K0 |
| 243 | F8W1A4 |
| 244 | H0Y831 |
| 245 | H0YF06 |
| 246 | H0YLN7 |
| 247 | H3BRP2 |
| 248 | H7BYJ9 |
| 249 | J3KR05 |
| 250 | J3KTP9 |
| 251 | K7EJ78 |
| 252 | A6MW40 |
| 253 | A6NIW5 |
| 254 | B3KM58 |
| 255 | B3KXP1 |
| 256 | B4DFC4 |
| 257 | B4DS57 |
| 258 | B4DVN5 |
| 259 | B7Z670 |
| 260 | J3QSF4 |
| 261 | O43242 |
| 262 | O75554 |
| 263 | P02771 |
| 264 | P07476 |
| 265 | P13521 |
| 266 | P52951 |
| 267 | Q53FB6 |
| 268 | Q53G25 |
| 269 | Q53GZ5 |
| 270 | Q53H60 |
| 271 | Q53HR1 |
| 272 | Q53SW3 |
| 273 | Q59FX3 |
| 274 | Q59GW6 |
| 275 | Q59H85 |
| 276 | Q5GJ68 |
| 277 | Q5U0Q1 |
| 278 | Q5VWT9 |
| 279 | Q68DF0 |
| 280 | Q6ICB4 |
| 281 | A0A0S2Z455 |
| 282 | B4DHJ3 |
| 283 | B4E354 |
| 284 | B5BTY4 |
| 285 | O75952 |
| 286 | A0A024R5W0 |
| 287 | A8K607 |
| 288 | B3KTA8 |
| 289 | Q16798 |
| 290 | B7Z7A4 |
| 291 | G3V504 |
| 292 | H0YCA1 |
| 293 | B3KS69 |
| 294 | F8W062 |
| 295 | A0A024QZ45 |
| 296 | A0A0A0MTE8 |
| 297 | A0A0A1TTP8 |
| 298 | A4FU65 |
| 299 | A8K8J2 |
| 300 | A8K9A5 |
| 301 | B3KQQ7 |
| 302 | B4DI59 |
| 303 | B4DNH7 |
| 304 | B4DVM1 |
| 305 | B4E2K5 |
| 306 | B4E3M8 |
| 307 | B7Z6H0 |
| 308 | B8XXQ3 |
| 309 | D6RBD3 |
| 310 | D6W632 |
| 311 | E5RI06 |
| 312 | E7EPB6 |
| 313 | E7ERH2 |
| 314 | E7ERU0 |
| 315 | E7ETU9 |
| 316 | E9PMI6 |
| 317 | F5GX94 |
| 318 | F5GYF1 |
| 319 | F8VRQ0 |
| 320 | F8VRZ4 |
| 321 | G3V2J8 |
| 322 | G3V595 |

TABLE 6-continued

Proteins in NPEX and APEX

| | |
|---|---|
| 323 | H0YAN8 |
| 324 | H0YCE8 |
| 325 | H0YJK0 |
| 326 | M0QXS6 |
| 327 | P08697 |
| 328 | P61604 |
| 329 | Q13415 |
| 330 | Q1L857 |
| 331 | Q4FEB4 |
| 332 | Q53FV3 |
| 333 | Q53G79 |
| 334 | Q5SPU2 |
| 335 | Q6IS14 |
| 336 | P29317 |
| 337 | B4DHN0 |
| 338 | A0A024QZL4 |
| 339 | A0A024R235 |
| 340 | A0A024R8H6 |
| 341 | A0A087WZX0 |
| 342 | A0A0G2JNJ8 |
| 343 | B4DFL3 |
| 344 | B4DVM7 |
| 345 | I6L9I5 |
| 346 | P84243 |
| 347 | Q0EFC9 |
| 348 | Q13787 |
| 349 | Q15102 |
| 350 | Q6PK50 |
| 351 | Q6PKT5 |
| 352 | Q6UVJ0 |
| 353 | Q6ZP82 |
| 354 | Q7Z3P6 |
| 355 | Q7Z5Q5 |
| 356 | Q7Z5V0 |
| 357 | Q7Z5V6 |
| 358 | Q86UF4 |
| 359 | Q86Y65 |
| 360 | Q8IY52 |
| 361 | Q8IYA8 |
| 362 | Q8IZ02 |
| 363 | Q8N754 |
| 364 | Q8N948 |
| 365 | Q8N959 |
| 366 | Q8N995 |
| 367 | Q8NEZ3 |
| 368 | Q8NHP6 |
| 369 | Q8NI77 |
| 370 | Q8TA90 |
| 371 | Q8TCL2 |
| 372 | Q8TE54 |
| 373 | Q8WU08 |
| 374 | Q8WXI3 |
| 375 | Q8WY81 |
| 376 | Q96AP5 |
| 377 | Q96DF0 |
| 378 | Q96M29 |
| 379 | Q9BZ26 |
| 380 | Q9H197 |
| 381 | Q9H3W5 |
| 382 | Q9H4B7 |
| 383 | Q9H5H4 |
| 384 | Q9H7K8 |
| 385 | Q9H853 |
| 386 | Q9NQY1 |
| 387 | Q9NS29 |
| 388 | Q9P019 |
| 389 | Q9P2Y4 |
| 390 | Q9UBV4 |
| 391 | Q9UEH4 |
| 392 | Q9UHV4 |
| 393 | Q9UKN7 |
| 394 | Q9UKV8 |
| 395 | Q9UKX3 |
| 396 | Q9UNP4 |
| 397 | Q9UQH3 |
| 398 | Q9UQM3 |
| 399 | Q9Y2D4 |
| 400 | Q9Y2I4 |
| 401 | Q9Y2J7 |
| 402 | Q9Y5T6 |
| 403 | Q9Y617 |
| 404 | S4R2Z6 |
| 405 | S4R3K3 |
| 406 | S4R457 |
| 407 | V5N4G2 |
| 408 | V9HW13 |
| 409 | V9HW39 |
| 410 | V9HW77 |
| 411 | V9HWD6 |
| 412 | X5D2V8 |
| 413 | Q7Z407 |
| 414 | Q86UP2 |
| 415 | Q8N3Y0 |
| 416 | Q8TB46 |
| 417 | Q8TBN9 |
| 418 | Q92736 |
| 419 | Q96QD5 |
| 420 | Q99698 |
| 421 | Q9H281 |
| 422 | Q9HCU0 |
| 423 | Q9UC36 |
| 424 | Q9UML6 |
| 425 | X5D9D6 |
| 426 | X6R3L3 |

TABLE 7

Proteins unique to MSCEX

| | |
|---|---|
| 1 | A0A024QYT5 |
| 2 | A0A024QZN8 |
| 3 | A0A024R059 |
| 4 | A0A024R1C3 |
| 5 | A0A024R241 |
| 6 | A0A024R2M8 |
| 7 | A0A024R407 |
| 8 | A0A024R4B7 |
| 9 | A0A024R4W0 |
| 10 | A0A024R5D9 |
| 11 | A0A024R5G9 |
| 12 | A0A024R5Z8 |
| 13 | A0A024R6C0 |
| 14 | A0A024R6F8 |
| 15 | A0A024R6I1 |
| 16 | A0A024R6L8 |
| 17 | A0A024R6X4 |
| 18 | A0A024R8B3 |
| 19 | A0A024R8V7 |
| 20 | A0A024R930 |
| 21 | A0A024R9X6 |
| 22 | A0A024RB85 |
| 23 | A0A024RCP3 |
| 24 | A0A068B0Y9 |
| 25 | A0A068BI38 |
| 26 | A0A087WSZ1 |
| 27 | A0A087WTU7 |
| 28 | A0A087WW54 |
| 29 | A0A087WXB0 |
| 30 | A0A087WY10 |
| 31 | A0A087WZV0 |
| 32 | A0A087X0V8 |
| 33 | A0A088QF11 |
| 34 | A0A0A0MRF6 |
| 35 | A0A0A0MRS7 |
| 36 | A0A0A0MRZ9 |
| 37 | A0A0A0MTE1 |
| 38 | A0A0A1TE42 |
| 39 | A0A0A6YY96 |
| 40 | A0A0B4J1S7 |
| 41 | A0A0C4DFX6 |
| 42 | A0A0C4ZN31 |
| 43 | A0A0G2JMD2 |
| 44 | A0A0G2JNH7 |

TABLE 7-continued

Proteins unique to MSCEX

| | |
|---|---|
| 45 | A0A0G2JNU3 |
| 46 | A0A0G2JQU7 |
| 47 | A0A0J9YY34 |
| 48 | A0A0K0KS85 |
| 49 | A0A0S2Z3G9 |
| 50 | A0A0S2Z645 |
| 51 | A0A0U1RQC7 |
| 52 | A0A0U1RRH9 |
| 53 | A0A140F1N4 |
| 54 | A0A140T9S2 |
| 55 | A0A140VK13 |
| 56 | A0AVL2 |
| 57 | A0PJ76 |
| 58 | A0PJM7 |
| 59 | A1KZ92 |
| 60 | A1L3V6 |
| 61 | A2I2N5 |
| 62 | A2RRC9 |
| 63 | A2VDK1 |
| 64 | A6NFQ2 |
| 65 | A6NFU0 |
| 66 | A7MAY2 |
| 67 | A8K0Z6 |
| 68 | A8K2M5 |
| 69 | A8K454 |
| 70 | A8K5X8 |
| 71 | A8K6R9 |
| 72 | A8K9U6 |
| 73 | A8MYV6 |
| 74 | A9YTQ3 |
| 75 | B0QYK4 |
| 76 | B1AHR3 |
| 77 | B1AJW0 |
| 78 | B1AUU8 |
| 79 | B2R6H3 |
| 80 | B2R6X6 |
| 81 | B2R6Y1 |
| 82 | B2R702 |
| 83 | B2R928 |
| 84 | B2R969 |
| 85 | B2RB72 |
| 86 | B2RC85 |
| 87 | B2RE36 |
| 88 | B2RWN6 |
| 89 | B3KQ04 |
| 90 | B3KR61 |
| 91 | B3KRU1 |
| 92 | B3KS75 |
| 93 | B3KSD8 |
| 94 | B3KTT6 |
| 95 | B3KU51 |
| 96 | B3KUR8 |
| 97 | B3KV69 |
| 98 | B3KW35 |
| 99 | B3KW47 |
| 100 | B3KXX8 |
| 101 | B4DDE5 |
| 102 | B4DE87 |
| 103 | B4DER4 |
| 104 | B4DEV8 |
| 105 | B4DFA5 |
| 106 | B4DFX9 |
| 107 | B4DHR9 |
| 108 | B4DIA7 |
| 109 | B4DIH7 |
| 110 | B4DNL5 |
| 111 | B4DNW7 |
| 112 | B4DPQ0 |
| 113 | B4DQI9 |
| 114 | B4DQQ0 |
| 115 | B4DR29 |
| 116 | B4DSP1 |
| 117 | B4DST5 |
| 118 | B4DTZ9 |
| 119 | B4DU14 |
| 120 | B4DWE2 |
| 121 | B4DWG5 |
| 122 | B4DWQ4 |
| 123 | B4DXC4 |
| 124 | B4DYB8 |
| 125 | B4DYX7 |
| 126 | B4DZK1 |
| 127 | B4DZP2 |
| 128 | B4E0I8 |
| 129 | B4E164 |
| 130 | B4E1Z4 |
| 131 | B4E295 |
| 132 | B4E3R6 |
| 133 | B4E3S9 |
| 134 | B5MCN7 |
| 135 | B7Z2D6 |
| 136 | B7Z2E6 |
| 137 | B7Z3I0 |
| 138 | B7Z3K9 |
| 139 | B7Z427 |
| 140 | B7Z4H0 |
| 141 | B7Z549 |
| 142 | B7Z5X3 |
| 143 | B7Z8B9 |
| 144 | B7Z9H7 |
| 145 | B7Z9J0 |
| 146 | B7ZAB8 |
| 147 | B7ZAL5 |
| 148 | B7ZL25 |
| 149 | B7ZMF3 |
| 150 | B8ZZH7 |
| 151 | C4B4C6 |
| 152 | C9J4M6 |
| 153 | C9J613 |
| 154 | C9JGT3 |
| 155 | C9JGV6 |
| 156 | C9JLB7 |
| 157 | C9JQI2 |
| 158 | C9JSI2 |
| 159 | C9JT28 |
| 160 | C9JYI9 |
| 161 | D2KTB5 |
| 162 | D2XBF0 |
| 163 | D3DV75 |
| 164 | D3DVD8 |
| 165 | D6R9U7 |
| 166 | D6RA00 |
| 167 | D6RF53 |
| 168 | D6RGY2 |
| 169 | D6W633 |
| 170 | E3W994 |
| 171 | E5KMI6 |
| 172 | E5KR05 |
| 173 | E5KRK5 |
| 174 | E5KTI5 |
| 175 | E5RGN8 |
| 176 | E5RHI0 |
| 177 | E7ENN3 |
| 178 | E7EUY3 |
| 179 | E7EWC2 |
| 180 | E7EX20 |
| 181 | E9PKT1 |
| 182 | E9PQI5 |
| 183 | E9PR16 |
| 184 | F2Z2C8 |
| 185 | F2Z2K5 |
| 186 | F5GX59 |
| 187 | F5GYJ8 |
| 188 | F5H065 |
| 189 | F5H226 |
| 190 | F5H432 |
| 191 | F5H4B6 |
| 192 | F6TLX2 |
| 193 | F8VU88 |
| 194 | F8VXG7 |
| 195 | F8VXL3 |
| 196 | F8VY04 |
| 197 | F8W0U9 |
| 198 | F8W9U4 |
| 199 | F8W9W0 |
| 200 | F8WCF6 |

TABLE 7-continued

Proteins unique to MSCEX

| | |
|---|---|
| 201 | G1UI33 |
| 202 | G5E971 |
| 203 | G5ELZ6 |
| 204 | H0Y468 |
| 205 | H0Y5R6 |
| 206 | H0Y6I0 |
| 207 | H0Y8G5 |
| 208 | H0YAN3 |
| 209 | H0YBI2 |
| 210 | H0YC83 |
| 211 | H0YCJ2 |
| 212 | H0YEL4 |
| 213 | H0YH65 |
| 214 | H0YL91 |
| 215 | H0YM70 |
| 216 | H3BP20 |
| 217 | H3BSC0 |
| 218 | H3BSE1 |
| 219 | H3BSM2 |
| 220 | H3BTW3 |
| 221 | H3BV41 |
| 222 | H7BYJ1 |
| 223 | H7BYX7 |
| 224 | H7C074 |
| 225 | H7C1W8 |
| 226 | I3L3E8 |
| 227 | I3L3P7 |
| 228 | J3KN38 |
| 229 | J3KNC6 |
| 230 | J3KPK1 |
| 231 | J3KQ09 |
| 232 | J3KTB8 |
| 233 | J3QL70 |
| 234 | K0I859 |
| 235 | K7EIS7 |
| 236 | K7EKQ3 |
| 237 | K7EL65 |
| 238 | K7ELC2 |
| 239 | K7ELW0 |
| 240 | K7EMJ5 |
| 241 | K7EMR1 |
| 242 | K7EPJ9 |
| 243 | K7ESE0 |
| 244 | L0R6V3 |
| 245 | L8E853 |
| 246 | M0R1K3 |
| 247 | M0R361 |
| 248 | O00469 |
| 249 | O00562 |
| 250 | O00592 |
| 251 | O14530 |
| 252 | O14879 |
| 253 | O15013 |
| 254 | O15042 |
| 255 | O15131 |
| 256 | O43505 |
| 257 | O43820 |
| 258 | O60245 |
| 259 | O60266 |
| 260 | O60294 |
| 261 | O60296 |
| 262 | O60343 |
| 263 | O60522 |
| 264 | O60543 |
| 265 | O60603 |
| 266 | O75161 |
| 267 | O75339 |
| 268 | O75390 |
| 269 | O75578 |
| 270 | O94844 |
| 271 | O94854 |
| 272 | O94925 |
| 273 | O95165 |
| 278 | P00519 |
| 279 | P02538 |
| 280 | P02786 |
| 281 | P04054 |
| 282 | P04075 |
| 283 | P04818 |
| 284 | P05091 |
| 285 | P05231 |
| 286 | P05937 |
| 287 | P06493 |
| 288 | P09622 |
| 289 | P09960 |
| 290 | P0DMV8 |
| 291 | P10398 |
| 292 | P13667 |
| 293 | P13807 |
| 294 | P15311 |
| 295 | P18065 |
| 296 | P22670 |
| 297 | P23109 |
| 298 | P28065 |
| 299 | P28482 |
| 300 | P29074 |
| 301 | P30532 |
| 302 | P31327 |
| 303 | P34932 |
| 304 | P35916 |
| 305 | P40189 |
| 306 | P42898 |
| 307 | P46782 |
| 308 | P47755 |
| 309 | P48058 |
| 310 | P48643 |
| 311 | P49863 |
| 312 | P50748 |
| 313 | P51828 |
| 314 | P61978 |
| 315 | P62701 |
| 316 | P63208 |
| 317 | P68104 |
| 318 | P78477 |
| 319 | Q10570 |
| 320 | Q10713 |
| 321 | Q12770 |
| 322 | Q12905 |
| 323 | Q12913 |
| 324 | Q13241 |
| 325 | Q13315 |
| 326 | Q13765 |
| 327 | Q13885 |
| 328 | Q14019 |
| 329 | Q14112 |
| 330 | Q14584 |
| 331 | Q14678 |
| 332 | Q14691 |
| 333 | Q14980 |
| 334 | Q149N5 |
| 335 | Q14CN4 |
| 336 | Q15274 |
| 337 | Q15431 |
| 338 | Q15751 |
| 339 | Q15878 |
| 340 | Q1L838 |
| 341 | Q1RMC9 |
| 342 | Q1W6H9 |
| 343 | Q20BJ8 |
| 344 | Q21096 |
| 345 | Q2TA76 |
| 346 | Q38SD2 |
| 347 | Q3KP44 |
| 348 | Q3KRB0 |
| 349 | Q3ZCN5 |
| 350 | Q3ZCT4 |
| 351 | Q495V9 |
| 352 | Q4G0L2 |
| 353 | Q4G192 |
| 354 | Q4QRK8 |
| 355 | Q4VNC1 |
| 356 | Q4W5F5 |
| 357 | Q53GQ2 |
| 358 | Q53HH4 |
| 359 | Q53QE9 |
| 360 | Q53Y51 |

TABLE 7-continued

Proteins unique to MSCEX

| | |
|---|---|
| 361 | Q58P21 |
| 362 | Q59E87 |
| 363 | Q59G22 |
| 364 | Q59G34 |
| 365 | Q59GT7 |
| 366 | Q59GW5 |
| 367 | Q59GX6 |
| 368 | Q59HG1 |
| 369 | Q5CCK6 |
| 370 | Q5EBN2 |
| 371 | Q5F0I5 |
| 372 | Q5I0G3 |
| 373 | Q5J9B1 |
| 374 | Q5NV87 |
| 375 | Q5STU8 |
| 376 | Q5SVJ3 |
| 377 | Q5T764 |
| 378 | Q5TEJ7 |
| 379 | Q5U608 |
| 380 | Q5VU34 |
| 381 | Q5VUJ6 |
| 382 | Q5VYI1 |
| 383 | Q5VYS4 |
| 384 | Q5VZ00 |
| 385 | Q5VZB4 |
| 386 | Q5VZL5 |
| 387 | Q68CZ1 |
| 388 | Q68DA4 |
| 389 | Q68DB7 |
| 390 | Q6EKJ0 |
| 391 | Q6FI27 |
| 392 | Q6NT96 |
| 393 | Q6P0N9 |
| 394 | Q6P1K8 |
| 395 | Q6P2S1 |
| 396 | Q6P4R9 |
| 397 | Q6P6D5 |
| 398 | Q6PD62 |
| 399 | Q6UWZ7 |
| 400 | Q6UXN9 |
| 401 | Q70IA8 |
| 402 | Q71U36 |
| 403 | Q75MN6 |
| 404 | Q7L6B3 |
| 405 | Q7Z3Z1 |
| 406 | Q7Z4W1 |
| 407 | Q7Z6M0 |
| 408 | Q86T35 |
| 409 | Q86U18 |
| 410 | Q86UU0 |
| 411 | Q86UW9 |
| 412 | Q86V60 |
| 413 | Q86XL3 |
| 414 | Q86YL5 |
| 415 | Q8IVH2 |
| 416 | Q8IWP9 |
| 417 | Q8IYA6 |
| 418 | Q8N304 |
| 419 | Q8N3P5 |
| 420 | Q8N4P6 |
| 421 | Q8N5U0 |
| 422 | Q8N7F5 |
| 423 | Q8NBB8 |
| 424 | Q8NE35 |
| 425 | Q8NES3 |
| 426 | Q8NFP9 |
| 427 | Q8NFQ8 |
| 428 | Q8NGS8 |
| 429 | Q8TAA3 |
| 430 | Q8TC08 |
| 431 | Q8TEQ6 |
| 432 | Q8WVC6 |
| 433 | Q8WVJ9 |
| 434 | Q8WWJ6 |
| 435 | Q8WWL7 |
| 436 | Q8WXI9 |
| 437 | Q8WYG9 |
| 438 | Q8WYJ0 |
| 439 | Q92530 |
| 440 | Q92539 |
| 441 | Q92823 |
| 442 | Q969U7 |
| 443 | Q96A69 |
| 444 | Q96B09 |
| 445 | Q96B65 |
| 446 | Q96CU9 |
| 447 | Q96CZ8 |
| 448 | Q96F45 |
| 449 | Q96FJ0 |
| 450 | Q96GE4 |
| 451 | Q96HY6 |
| 452 | Q96JB2 |
| 453 | Q96JM4 |
| 454 | Q96MM8 |
| 455 | Q96N57 |
| 456 | Q96PX1 |
| 457 | Q96QF4 |
| 458 | Q96QI5 |
| 459 | Q96S69 |
| 460 | Q99539 |
| 461 | Q99574 |
| 462 | Q9BPU6 |
| 463 | Q9BQN1 |
| 464 | Q9BQS2 |
| 465 | Q9BS61 |
| 466 | Q9BSD7 |
| 467 | Q9BW71 |
| 468 | Q9BWD1 |
| 469 | Q9BWT3 |
| 470 | Q9BXB5 |
| 471 | Q9BXT8 |
| 472 | Q9BYF1 |
| 473 | Q9C091 |
| 474 | Q9H0Q0 |
| 475 | Q9H2E5 |
| 476 | Q9H2I8 |
| 477 | Q9H2Z3 |
| 478 | Q9H7U7 |
| 479 | Q9H7W5 |
| 480 | Q9H8N6 |
| 481 | Q9H8Q1 |
| 482 | Q9HA17 |
| 483 | Q9HAR0 |
| 484 | Q9HD74 |
| 485 | Q9NP17 |
| 486 | Q9NPU7 |
| 487 | Q9NR45 |
| 488 | Q9NRD1 |
| 489 | Q9NT26 |
| 490 | Q9NTG1 |
| 491 | Q9NW02 |
| 492 | Q9NX58 |
| 493 | Q9NX91 |
| 494 | Q9NZF5 |
| 495 | Q9P283 |
| 496 | Q9P291 |
| 497 | Q9P2M7 |
| 498 | Q9P2N1 |
| 499 | Q9UBG9 |
| 500 | Q9UBL0 |
| 501 | Q9UC78 |
| 502 | Q9UEH6 |
| 503 | Q9UF08 |
| 504 | Q9UFA7 |
| 505 | Q9UIA9 |
| 506 | Q9UJD0 |
| 507 | Q9UJT0 |
| 508 | Q9UL70 |
| 509 | Q9ULJ7 |
| 510 | Q9ULW6 |
| 511 | Q9UME3 |
| 512 | Q9UNM1 |
| 513 | Q9UNS1 |
| 514 | Q9UPN4 |
| 515 | Q9UPV0 |
| 516 | Q9Y216 |

TABLE 7-continued

| | Proteins unique to MSCEX |
|---|---|
| 517 | Q9Y4L1 |
| 518 | Q9Y613 |
| 519 | Q9Y696 |
| 520 | Q9Y6K1 |
| 521 | Q9Y6S7 |
| 522 | Q9Y6U9 |
| 523 | R4GMT0 |
| 524 | S4R2X0 |
| 525 | S4R314 |
| 526 | S4R3C8 |
| 527 | U3KQK0 |
| 528 | U5YBI9 |
| 529 | V9GY77 |
| 530 | V9GYE3 |
| 531 | V9HW26 |
| 532 | V9HWC4 |
| 533 | V9HWH0 |
| 534 | X5D7Q2 |
| 535 | X5D9D2 |
| 536 | X6RL08 |

TABLE 8

| | Proteins unique to APEX |
|---|---|
| 1 | A0A087WXN9 |
| 2 | A0A0A0MTD1 |
| 3 | A0A0C4DFS8 |
| 4 | A0A0J9YX41 |
| 5 | A0A140VJI6 |
| 6 | A2VED2 |
| 7 | B0YJ74 |
| 8 | A0A0B4J1X7 |
| 9 | A0A5A9 |
| 10 | A8K1P5 |
| 11 | B3KMN2 |
| 12 | B5A934 |
| 13 | B7Z9C0 |
| 14 | A0A087X1U1 |
| 15 | A8K0G7 |
| 16 | B7ZLC4 |
| 17 | A0A140VKF7 |
| 18 | B4DY95 |
| 19 | A0A024R1K7 |
| 20 | A0A024RCS3 |
| 21 | A0A0G2JPN1 |
| 22 | A0A140VJP0 |
| 23 | B3KR94 |
| 24 | B3KSB6 |
| 25 | B4DET1 |
| 26 | B4DG15 |
| 27 | B4DJI2 |
| 28 | B7Z919 |
| 29 | C9J3L8 |
| 30 | A0A087X298 |
| 31 | B4DG65 |
| 32 | A0A0C4DH13 |
| 33 | B4DSP4 |
| 34 | B4DSR4 |
| 35 | C9J826 |
| 36 | A0A024RBC0 |
| 37 | A0A087X120 |
| 38 | A0A0C4DGC5 |
| 39 | A0A0U1WUY1 |
| 40 | A1L196 |
| 41 | A9CQZ2 |
| 42 | B3KX52 |
| 43 | A0A087X0D8 |
| 44 | B2RCJ5 |
| 45 | B4DN90 |
| 46 | B4DNZ9 |
| 47 | B4DZG1 |
| 48 | B7Z6I1 |
| 49 | C9J1D9 |
| 50 | C9J1K7 |

TABLE 8-continued

| | Proteins unique to APEX |
|---|---|
| 51 | A0AV47 |
| 52 | B3KNC3 |
| 53 | A0A024R120 |
| 54 | A0A087WUL9 |
| 55 | B3KMX4 |
| 56 | B3KNL6 |
| 57 | B3KPZ7 |
| 58 | B3KWB6 |
| 59 | B3KWC4 |
| 60 | D1CS35 |
| 61 | D2CPK5 |
| 62 | D3DUJ0 |
| 63 | D6REL5 |
| 64 | E5RHP0 |
| 65 | E9PCP0 |
| 66 | E9PJL7 |
| 67 | E9PNX2 |
| 68 | F5H0Y9 |
| 69 | F6QTA4 |
| 70 | F8W026 |
| 71 | G3V5R6 |
| 72 | G5E9J0 |
| 73 | H0Y757 |
| 74 | H0Y9N5 |
| 75 | H0YDE4 |
| 76 | H0YGV8 |
| 77 | H3BTQ9 |
| 78 | H7BZZ8 |
| 79 | H7C0D9 |
| 80 | J3KPD9 |
| 81 | J3KTL9 |
| 82 | K7EL58 |
| 83 | K7EMM9 |
| 84 | K7EQR9 |
| 85 | A2RRR7 |
| 86 | B4DFQ9 |
| 87 | B4DWW6 |
| 88 | A8MT18 |
| 89 | A0A024R461 |
| 90 | B4DZ23 |
| 91 | B7ZMJ6 |
| 92 | E5RJD0 |
| 93 | I7HAS0 |
| 94 | A0A075B610 |
| 95 | A0A087WU14 |
| 96 | A0A0U1ZBR1 |
| 97 | A0A140TA43 |
| 98 | A0A140VK41 |
| 99 | B2RA91 |
| 100 | B3KNB4 |
| 101 | B4DMA2 |
| 102 | B4DTA5 |
| 103 | B4DUF8 |
| 104 | A0A0C4DGH5 |
| 105 | A6NEP9 |
| 106 | A8K0K0 |
| 107 | B3KMS6 |
| 108 | B3KY88 |
| 109 | B7Z4X0 |
| 110 | E7ETB4 |
| 111 | E9PGC0 |
| 112 | F5H0M4 |
| 113 | F5H5D3 |
| 114 | H0Y463 |
| 115 | H7C080 |
| 116 | I3L0G6 |
| 117 | I3L1K1 |
| 118 | K7EJX8 |
| 119 | K7EK57 |
| 120 | A0A024R283 |
| 121 | A0A0C4DGB8 |
| 122 | A0A140VK27 |
| 123 | B4DY04 |
| 124 | B7ZM05 |
| 125 | K7ENN8 |
| 126 | B2R8P5 |
| 127 | H0Y873 |
| 128 | A0A024R542 |

TABLE 8-continued

Proteins unique to APEX

| | |
|---|---|
| 129 | A0A024R7E1 |
| 130 | A0A0M4FNU3 |
| 131 | B4DUC5 |
| 132 | B4DZ03 |
| 133 | A0A024R957 |
| 134 | A0A0A0MRY9 |
| 135 | A0A140VK76 |
| 136 | B0YJ32 |
| 137 | B3KPK8 |
| 138 | B4DEY4 |
| 139 | B4DMJ7 |
| 140 | B4DNX8 |
| 141 | B4DQY2 |
| 142 | B4DR52 |
| 143 | B4DR67 |
| 144 | B4DTA9 |
| 145 | B4E058 |
| 146 | B7ZAW7 |
| 147 | B7ZLB7 |
| 148 | E9PNS9 |
| 149 | H7BXG6 |
| 150 | H7C520 |
| 151 | I3L466 |
| 152 | A0A0A0MRM2 |
| 153 | A4FU77 |
| 154 | A0A024QZ75 |
| 155 | A0A024R674 |
| 156 | A0A0A0MRH0 |
| 157 | A8K4M1 |
| 158 | B3KTQ2 |
| 159 | B4DJ21 |
| 160 | B4DMJ5 |
| 161 | B4DV55 |
| 162 | D3DSV6 |
| 163 | D6R9D5 |
| 164 | E9PP50 |
| 165 | H0Y2M6 |
| 166 | H0YCV9 |
| 167 | H0YJ91 |
| 168 | H7C5H1 |
| 169 | J3QRV6 |
| 170 | L8E9P0 |
| 171 | M0R120 |
| 172 | O00512 |
| 173 | O00763 |
| 174 | O14524 |
| 175 | O15078 |
| 176 | O15090 |
| 177 | O15244 |
| 178 | O43570 |
| 179 | O60291 |
| 180 | O75094 |
| 181 | O75600 |
| 182 | P00352 |
| 183 | P02749 |
| 184 | P05546 |
| 185 | P08910 |
| 186 | P10916 |
| 187 | P17927 |
| 188 | P27169 |
| 189 | P29400 |
| 190 | P35499 |
| 191 | P35749 |
| 192 | P39023 |
| 193 | P40939 |
| 194 | P46059 |
| 195 | P50225 |
| 196 | P54756 |
| 197 | P61964 |
| 198 | P84085 |
| 199 | Q003V9 |
| 200 | Q01831 |
| 201 | Q0VAI6 |
| 202 | Q12873 |
| 203 | Q12980 |
| 204 | Q13349 |
| 205 | Q14145 |
| 206 | Q14469 |
| 207 | Q15238 |
| 208 | Q15697 |
| 209 | Q15762 |
| 210 | Q16820 |
| 211 | Q2TSD0 |
| 212 | Q32Q67 |
| 213 | Q3SY52 |
| 214 | Q53G92 |
| 215 | Q53GF5 |
| 216 | Q53HR5 |
| 217 | Q53SE2 |
| 218 | Q58DX5 |
| 219 | Q59EF3 |
| 220 | Q59HA9 |
| 221 | Q5GJ67 |
| 222 | Q5TEU4 |
| 223 | Q68DP4 |
| 224 | Q69YH5 |
| 225 | Q6FHK0 |
| 226 | Q6FHK9 |
| 227 | Q6FHU3 |
| 228 | Q6FI03 |
| 229 | Q6IFE0 |
| 230 | Q6JH03 |
| 231 | Q6NUI8 |
| 232 | O15123 |
| 233 | O43301 |
| 234 | O43424 |
| 235 | O95239 |
| 236 | P02533 |
| 237 | P55283 |
| 238 | Q15142 |
| 239 | Q1HP67 |
| 240 | Q562N6 |
| 241 | Q5H9B5 |
| 242 | Q5HY54 |
| 243 | Q5HYL7 |
| 244 | Q5VUA0 |
| 245 | Q6IAX6 |
| 246 | Q6P1L4 |
| 247 | Q6P5Q4 |
| 248 | B3KXC1 |
| 249 | B3KP29 |
| 250 | B7Z7C2 |
| 251 | A0A024RDT3 |
| 252 | A8K990 |
| 253 | E5RGT9 |
| 254 | E9PMW9 |
| 255 | G3V174 |
| 256 | H7BXS7 |
| 257 | H7C402 |
| 258 | H9A532 |
| 259 | H3BP35 |
| 260 | A0A024RDR3 |
| 261 | B4DEW9 |
| 262 | C9J3M5 |
| 263 | I0CMK4 |
| 264 | K7ENA0 |
| 265 | B3KNV9 |
| 266 | B4DUK7 |
| 267 | K7EPF6 |
| 268 | A0A024QZF7 |
| 269 | A0A024R5V2 |
| 270 | M0QY71 |
| 271 | O75843 |
| 272 | O95905 |
| 273 | O96011 |
| 274 | P07585 |
| 275 | Q0VD99 |
| 276 | Q15374 |
| 277 | Q5VX85 |
| 278 | Q61C98 |
| 279 | P30405 |
| 280 | Q5VIR6 |
| 281 | A0A0C4DFQ8 |
| 282 | B1AMW3 |
| 283 | A0A087WUF5 |
| 284 | A0A024R6K8 |

TABLE 8-continued

Proteins unique to APEX

| | |
|---|---|
| 285 | B2R9P0 |
| 286 | A0A087WSV7 |
| 287 | A0A0K0KR34 |
| 288 | A6NFY4 |
| 289 | A0A024RD47 |
| 290 | B2RTX2 |
| 291 | E9PFF2 |
| 292 | F2Z2G2 |
| 293 | F5GWA7 |
| 294 | F5GXC7 |
| 295 | F5GYF8 |
| 296 | F5H3Q5 |
| 297 | H9C875 |
| 298 | B7Z2E2 |
| 299 | J3KQ72 |
| 300 | A0A024R909 |
| 301 | F5GXR6 |
| 302 | J3KS93 |
| 303 | A0A126GVW7 |
| 304 | B4E266 |
| 305 | A0A024R2H7 |
| 306 | A0A097CK88 |
| 307 | A0A140T999 |
| 308 | A8K8H7 |
| 309 | B4DND2 |
| 310 | B4DQM1 |
| 311 | B4DZ35 |
| 312 | E7ERI8 |
| 313 | F5GZQ4 |
| 314 | F8WFC4 |
| 315 | H0Y9E9 |
| 316 | H7C1T2 |
| 317 | K7EPY4 |
| 318 | M0R2D3 |
| 319 | O76074 |
| 320 | P15085 |
| 321 | Q3YA63 |
| 322 | Q5MNZ6 |
| 323 | Q6IPX8 |
| 324 | A0A087X2E5 |
| 325 | A0A0A0MQR7 |
| 326 | A0A0C4DGY8 |
| 327 | A0A0D9SF28 |
| 328 | A0A0S2Z333 |
| 329 | A0A0S2Z366 |
| 330 | A4D202 |
| 331 | A8K731 |
| 332 | B3KX01 |
| 333 | B3KX41 |
| 334 | B4DEM5 |
| 335 | B4DK22 |
| 336 | B4E337 |
| 337 | B7Z4N1 |
| 338 | C9J8U1 |
| 339 | D6R9E4 |
| 340 | E7EP61 |
| 341 | E7EWZ1 |
| 342 | E9KL23 |
| 343 | E9PJK2 |
| 344 | F5GXY2 |
| 345 | F5H032 |
| 346 | G3V454 |
| 347 | H0YF19 |
| 348 | H0YGH1 |
| 349 | H3BRL9 |
| 350 | K0A7K7 |
| 351 | A0A0G2JN61 |
| 352 | A0A0M4FEM1 |
| 353 | A0A0U1RQL8 |
| 354 | A8K6X5 |
| 355 | B3KW51 |
| 356 | B4DQG4 |
| 357 | B4DW50 |
| 358 | B4DZY4 |
| 359 | B4E1S5 |
| 360 | B4E1T9 |
| 361 | B4E3A4 |
| 362 | B7Z1Y2 |
| 363 | C9JUE0 |
| 364 | D6RDI0 |
| 365 | F8VUX9 |
| 366 | J9UPX7 |
| 367 | K7ENE1 |
| 368 | P13637 |
| 369 | P28827 |
| 370 | P31150 |
| 371 | P31946 |
| 372 | Q12769 |
| 373 | Q13841 |
| 374 | Q20BG7 |
| 375 | Q2F838 |
| 376 | Q58FF6 |
| 377 | Q658X2 |
| 378 | Q659A9 |
| 379 | Q6FGX9 |
| 380 | A0A024R3D4 |
| 381 | A0A024RAM6 |
| 382 | A0A0G2JP38 |
| 383 | A0A140VJV9 |
| 384 | A0A140VKF6 |
| 385 | B4DLH5 |
| 386 | D6RHE5 |
| 387 | O14777 |
| 388 | Q6IBD2 |
| 389 | A0A024R684 |
| 390 | A8K5F3 |
| 391 | B3KU50 |
| 392 | B4DUZ8 |
| 393 | K7EQ48 |
| 394 | O75665 |
| 395 | Q59EK9 |
| 396 | A0A024R7D2 |
| 397 | A3KFK1 |
| 398 | G3V0E6 |
| 399 | A0A024QYZ8 |
| 400 | A0A024RAM1 |
| 401 | A0A087WWI0 |
| 402 | A0A0A0MQR2 |
| 403 | A4D0S8 |
| 404 | A4FU51 |
| 405 | A4QMW8 |
| 406 | A8K4Q4 |
| 407 | C9JVG3 |
| 408 | D6RC52 |
| 409 | E7ENJ7 |
| 410 | E9PHK0 |
| 411 | E9PQV8 |
| 412 | F5GZI5 |
| 413 | F5GZK2 |
| 414 | F5H2D0 |
| 415 | F5H6I7 |
| 416 | F6U236 |
| 417 | F8WAS2 |
| 418 | F8WAX8 |
| 419 | F8WCJ1 |
| 420 | H3BTW5 |
| 421 | H3BUA3 |
| 422 | K7EJH1 |
| 423 | M5EDK8 |
| 424 | O00160 |
| 425 | O15054 |
| 426 | P48444 |
| 427 | Q14258 |
| 428 | Q14434 |
| 429 | Q14690 |
| 430 | Q549N0 |
| 431 | Q6FH62 |
| 432 | A0A024RB92 |
| 433 | A0A087WW76 |
| 434 | B4DI80 |
| 435 | B4DTQ1 |
| 436 | B4E0B2 |
| 437 | D6RE83 |
| 438 | D9HTE9 |
| 439 | E9PMM8 |
| 440 | E9PNE6 |

TABLE 8-continued

Proteins unique to APEX

| | |
|---|---|
| 441 | F2Z393 |
| 442 | F5H0P4 |
| 443 | H0Y476 |
| 444 | H0YCK3 |
| 445 | J3KRJ6 |
| 446 | J3QS44 |
| 447 | O75077 |
| 448 | P06727 |
| 449 | P20062 |
| 450 | Q09472 |
| 451 | Q14643 |
| 452 | Q6PKD3 |
| 453 | Q6QWC0 |
| 454 | Q6RBX8 |
| 455 | Q6UW88 |
| 456 | Q6UX71 |
| 457 | Q6ZMU5 |
| 458 | Q6ZP56 |
| 459 | Q6ZPD6 |
| 460 | Q6ZR36 |
| 461 | Q6ZU35 |
| 462 | Q6ZVM7 |
| 463 | Q709C8 |
| 464 | Q7M4R4 |
| 465 | Q7Z2V5 |
| 466 | Q7Z606 |
| 467 | Q7Z612 |
| 468 | Q7Z668 |
| 469 | Q7Z7H5 |
| 470 | Q7Z7P9 |
| 471 | Q86SG7 |
| 472 | Q86TE2 |
| 473 | Q86TI0 |
| 474 | Q86UE3 |
| 475 | Q86X82 |
| 476 | Q86XM6 |
| 477 | Q86XQ3 |
| 478 | Q86YC4 |
| 479 | Q8IUN7 |
| 480 | Q8IUQ0 |
| 481 | Q8IV08 |
| 482 | Q8IWJ6 |
| 483 | Q8IXA4 |
| 484 | Q8IYT1 |
| 485 | Q8N1M4 |
| 486 | Q8N1Y9 |
| 487 | Q8N4M9 |
| 488 | Q8NC18 |
| 489 | Q8NCS7 |
| 490 | Q8NGA0 |
| 491 | Q8TBG4 |
| 492 | Q8TCC9 |
| 493 | Q8WLP1 |
| 494 | Q8WV67 |
| 495 | Q8WVV4 |
| 496 | Q8WYB5 |
| 497 | Q92574 |
| 498 | Q92615 |
| 499 | Q92932 |
| 500 | Q92990 |
| 501 | Q969V5 |
| 502 | Q96FW1 |
| 503 | Q96G03 |
| 504 | Q96HX7 |
| 505 | Q96KR4 |
| 506 | Q96MY1 |
| 507 | Q99062 |
| 508 | Q99440 |
| 509 | Q99973 |
| 510 | Q99989 |
| 511 | Q9BT21 |
| 512 | Q9BT27 |
| 513 | Q9BVJ8 |
| 514 | Q9BWT2 |
| 515 | Q9BZF9 |
| 516 | Q9C0A1 |
| 517 | Q9H295 |
| 518 | Q9H2M9 |
| 519 | Q9H4N8 |
| 520 | Q9H6A9 |
| 521 | Q9H6L3 |
| 522 | Q9H6Z9 |
| 523 | Q9H769 |
| 524 | Q9H995 |
| 525 | Q9HBM3 |
| 526 | Q9NPL4 |
| 527 | Q9NS28 |
| 528 | Q9NUJ7 |
| 529 | Q9NWV8 |
| 530 | Q9NX81 |
| 531 | Q9NX98 |
| 532 | Q9NXP1 |
| 533 | Q9NYK1 |
| 534 | Q9NZ52 |
| 535 | Q9P0C1 |
| 536 | Q9P0P1 |
| 537 | Q9P2H3 |
| 538 | Q9UBK7 |
| 539 | Q9UDV6 |
| 540 | Q9UDX4 |
| 541 | Q9UFP2 |
| 542 | Q9UFU2 |
| 543 | Q9UG36 |
| 544 | Q9UG64 |
| 545 | Q9UGU8 |
| 546 | Q9UH61 |
| 547 | Q9UHC1 |
| 548 | Q9UHC9 |
| 549 | Q9ULH1 |
| 550 | Q9UNX4 |
| 551 | Q9UPS8 |
| 552 | Q9Y287 |
| 553 | Q9Y4G6 |
| 554 | S4R3L5 |
| 555 | T1WFC1 |
| 556 | U3KPS2 |
| 557 | U5YEI7 |
| 558 | V9GYM3 |
| 559 | V9HW42 |
| 560 | V9HWC2 |
| 561 | V9HWC3 |
| 562 | V9HWG1 |
| 563 | W6JLH6 |
| 564 | W8SBA0 |
| 565 | Q6ZNY8 |
| 566 | Q6ZP01 |
| 567 | Q7Z5U6 |
| 568 | Q86TA0 |
| 569 | Q86VI3 |
| 570 | Q86WN1 |
| 571 | Q86YG0 |
| 572 | Q8IWK6 |
| 573 | Q8IXR5 |
| 574 | Q8N111 |
| 575 | Q8N976 |
| 576 | Q8NG48 |
| 577 | Q8TCU4 |
| 578 | Q8WYK0 |
| 579 | Q99994 |
| 580 | Q9BRL4 |
| 581 | Q9BS12 |
| 582 | Q9BTS8 |
| 583 | Q9C0K3 |
| 584 | Q9H583 |
| 585 | Q9HBG7 |
| 586 | Q9P2H0 |
| 587 | Q9UF83 |
| 588 | Q9UHP3 |
| 589 | Q9UIT6 |
| 590 | Q9UJ65 |
| 591 | Q9UN47 |
| 592 | Q9UNY4 |

TABLE 8-continued

| | Proteins unique to APEX |
|---|---|
| 593 | U3KQU8 |
| 594 | X5D5A9 |
| 595 | X5D7Z6 |
| 596 | X5DNR2 |

TABLE 9

| | Proteins unique to NPEX |
|---|---|
| 1 | A0A024DAK3 |
| 2 | A0A024QYX2 |
| 3 | A0A024QZJ1 |
| 4 | A0A024QZM2 |
| 5 | A0A024QZW5 |
| 6 | A0A024QZX5 |
| 7 | A0A024R095 |
| 8 | A0A024R0A0 |
| 9 | A0A024R233 |
| 10 | A0A024R2G9 |
| 11 | A0A024R2K1 |
| 12 | A0A024R301 |
| 13 | A0A024R4A0 |
| 14 | A0A024R4D1 |
| 15 | A0A024R4F1 |
| 16 | A0A024R4Z0 |
| 17 | A0A024R4Z5 |
| 18 | A0A024R5M9 |
| 19 | A0A024R5U3 |
| 20 | A0A024R5V6 |
| 21 | A0A024R5Y2 |
| 22 | A0A024R6G3 |
| 23 | A0A024R701 |
| 24 | A0A024R7B6 |
| 25 | A0A024R7L5 |
| 26 | A0A024R7T7 |
| 27 | A0A024R884 |
| 28 | A0A024R8F4 |
| 29 | A0A024R814 |
| 30 | A0A024R936 |
| 31 | A0A024R944 |
| 32 | A0A024RAF7 |
| 33 | A0A024RAS2 |
| 34 | A0A024RB01 |
| 35 | A0A024RBE5 |
| 36 | A0A024RBT9 |
| 37 | A0A024RCB7 |
| 38 | A0A024RCE1 |
| 39 | A0A024RCT0 |
| 40 | A0A024RD04 |
| 41 | A0A024RD09 |
| 42 | A0A024RD36 |
| 43 | A0A024RD77 |
| 44 | A0A024RDM3 |
| 45 | A0A024RDV8 |
| 46 | A0A024RDW5 |
| 47 | A0A075B6S4 |
| 48 | A0A075B734 |
| 49 | A0A087WSW7 |
| 50 | A0A087WT58 |
| 51 | A0A087WTH0 |
| 52 | A0A087WTK9 |
| 53 | A0A087WU78 |
| 54 | A0A087WUK8 |
| 55 | A0A087WUM0 |
| 56 | A0A087WVI0 |
| 57 | A0A087WW59 |
| 58 | A0A087WWE7 |
| 59 | A0A087WXK5 |
| 60 | A0A087WXM9 |
| 61 | A0A087WXX8 |
| 62 | A0A087WYC6 |
| 63 | A0A087WYK9 |
| 64 | A0A087WYW3 |
| 65 | A0A087WZ40 |
| 66 | A0A087WZC4 |

TABLE 9-continued

| | Proteins unique to NPEX |
|---|---|
| 67 | A0A087WZR8 |
| 68 | A0A087WZZ7 |
| 69 | A0A087X052 |
| 70 | A0A087X0D6 |
| 71 | A0A087X176 |
| 72 | A0A087X1Z6 |
| 73 | A0A087X250 |
| 74 | A0A087X2B0 |
| 75 | A0A090N8H8 |
| 76 | A0A097IQZ3 |
| 77 | A0A0A0MQS0 |
| 78 | A0A0A0MRP0 |
| 79 | A0A0A0MRT2 |
| 80 | A0A0A0MRV0 |
| 81 | A0A0A0MRX4 |
| 82 | A0A0A0MS45 |
| 83 | A0A0A0MS53 |
| 84 | A0A0A0MS59 |
| 85 | A0A0A0MS84 |
| 86 | A0A0A0MSA7 |
| 87 | A0A0A0MSU4 |
| 88 | A0A0A0MT74 |
| 89 | A0A0A0MTC4 |
| 90 | A0A0A0MTD9 |
| 91 | A0A0A0MTQ1 |
| 92 | A0A0A0MTQ8 |
| 93 | A0A0A0N0L2 |
| 94 | A0A0A0N0M1 |
| 95 | A0A0B4J1R2 |
| 96 | A0A0B4J210 |
| 97 | A0A0B4J212 |
| 98 | A0A0B4J223 |
| 99 | A0A0B4J2C3 |
| 100 | A0A0C4DFX7 |
| 101 | A0A0C4DG17 |
| 102 | A0A0C4DG82 |
| 103 | A0A0C4DGA6 |
| 104 | A0A0C4DGI2 |
| 105 | A0A0C7DW92 |
| 106 | A0A0D9SF54 |
| 107 | A0A0D9SF63 |
| 108 | A0A0D9SG17 |
| 109 | A0A0E3JG42 |
| 110 | A0A0G2JHI3 |
| 111 | A0A0G2JI86 |
| 112 | A0A0G2JM47 |
| 113 | A0A0G2JNH0 |
| 114 | A0A0G2JP14 |
| 115 | A0A0G2JP37 |
| 116 | A0A0G2JRM9 |
| 117 | A0A0G2JRN3 |
| 118 | A0A0J9YVY3 |
| 119 | A0A0J9YVZ3 |
| 120 | A0A0J9YWL0 |
| 121 | A0A0J9YWY2 |
| 122 | A0A0K1JS24 |
| 123 | A0A0K2GMW5 |
| 124 | A0A0S2Z3P7 |
| 125 | A0A0S2Z451 |
| 126 | A0A0S2Z489 |
| 127 | A0A0S2Z4F1 |
| 128 | A0A0S2Z4H6 |
| 129 | A0A0S2Z419 |
| 130 | A0A0S2Z4R1 |
| 131 | A0A0S2Z4Y4 |
| 132 | A0A0S2Z4Y6 |
| 133 | A0A0S2Z563 |
| 134 | A0A0S2Z5B0 |
| 135 | A0A0S2Z5Z7 |
| 136 | A0A0S2Z618 |
| 137 | A0A0U1RQH4 |
| 138 | A0A0U1RQP0 |
| 139 | A0A0U1RQR9 |
| 140 | A0A0U1RRM1 |
| 141 | A0A126GVG1 |
| 142 | A0A126GWA2 |
| 143 | A0A126LAY8 |
| 144 | A0A126LB32 |

TABLE 9-continued

Proteins unique to NPEX

| | |
|---|---|
| 145 | A0A140HDC1 |
| 146 | A0A140T8X2 |
| 147 | A0A140T9Y3 |
| 148 | A0A140TA40 |
| 149 | A0A140TA77 |
| 150 | A0A140VJC9 |
| 151 | A0A140VJI0 |
| 152 | A0A140VJL3 |
| 153 | A0A140VJN8 |
| 154 | A0A140VJP5 |
| 155 | A0A140VJU3 |
| 156 | A0A140VK35 |
| 157 | A0A141PNN4 |
| 158 | A0A146IHP0 |
| 159 | A0A158T700 |
| 160 | A0JLR2 |
| 161 | A0PJY9 |
| 162 | A1A512 |
| 163 | A1L3A3 |
| 164 | A2A2M0 |
| 165 | A2A368 |
| 166 | A2ADX3 |
| 167 | A2NX49 |
| 168 | A2PYH4 |
| 169 | A2RUH7 |
| 170 | A2VCK2 |
| 171 | A4D126 |
| 172 | A4D1B7 |
| 173 | A4D1P7 |
| 174 | A4D1R1 |
| 175 | A4FU69 |
| 176 | A4FUA2 |
| 177 | A4QPE5 |
| 178 | A6H8W6 |
| 179 | A6NC48 |
| 180 | A6NC78 |
| 181 | A6NED2 |
| 182 | A6NF31 |
| 183 | A6NGH7 |
| 184 | A6NGQ3 |
| 185 | A6NHN7 |
| 186 | A6NHT5 |
| 187 | A6NM62 |
| 188 | A6NN40 |
| 189 | A6NP61 |
| 190 | A6QRJ1 |
| 191 | A6XAA7 |
| 192 | A7E294 |
| 193 | A7E2X7 |
| 194 | A7J1R0 |
| 195 | A8E631 |
| 196 | A8K0E1 |
| 197 | A8K146 |
| 198 | A8K1W3 |
| 199 | A8K3A3 |
| 200 | A8K3L7 |
| 201 | A8K3X2 |
| 202 | A8K4F0 |
| 203 | A8K4I1 |
| 204 | A8K525 |
| 205 | A8K594 |
| 206 | A8K5E6 |
| 207 | A8K5H7 |
| 208 | A8K5J8 |
| 209 | A8K6K4 |
| 210 | A8K6V3 |
| 211 | A8K7K0 |
| 212 | A8K855 |
| 213 | A8K8K1 |
| 214 | A8K8T9 |
| 215 | A8MX12 |
| 216 | A9QM74 |
| 217 | A9UK01 |
| 218 | B0QY51 |
| 219 | B0QY53 |
| 220 | B0QYP5 |
| 221 | B1AKL4 |
| 222 | B1AKN6 |
| 223 | B1AKN8 |
| 224 | B1ALU6 |
| 225 | B1B5Q8 |
| 226 | B2R5U7 |
| 227 | B2R694 |
| 228 | B2R6V2 |
| 229 | B2R6X2 |
| 230 | B2R734 |
| 231 | B2R736 |
| 232 | B2R7D2 |
| 233 | B2R7I3 |
| 234 | B2R7S8 |
| 235 | B2R7W6 |
| 236 | B2R7Z4 |
| 237 | B2R892 |
| 238 | B2R9P8 |
| 239 | B2R9S6 |
| 240 | B2RA29 |
| 241 | B2RAN2 |
| 242 | B2RB27 |
| 243 | B2RC06 |
| 244 | B2RCB8 |
| 245 | B2RCD2 |
| 246 | B2RCG9 |
| 247 | B2RD40 |
| 248 | B2RDD7 |
| 249 | B2RDT9 |
| 250 | B2RNB2 |
| 251 | B2RNT9 |
| 252 | B2RUU1 |
| 253 | B3FR89 |
| 254 | B3KM41 |
| 255 | B3KM42 |
| 256 | B3KMB1 |
| 257 | B3KMB8 |
| 258 | B3KMD2 |
| 259 | B3KMJ7 |
| 260 | B3KMZ6 |
| 261 | B3KN57 |
| 262 | B3KP18 |
| 263 | B3KPA6 |
| 264 | B3KPD7 |
| 265 | B3KPK9 |
| 266 | B3KPM6 |
| 267 | B3KQ65 |
| 268 | B3KQZ8 |
| 269 | B3KR52 |
| 270 | B3KRY3 |
| 271 | B3KS09 |
| 272 | B3KS20 |
| 273 | B3KS48 |
| 274 | B3KS82 |
| 275 | B3KSV0 |
| 276 | B3KSW4 |
| 277 | B3KSZ3 |
| 278 | B3KTD8 |
| 279 | B3KTM6 |
| 280 | B3KTR4 |
| 281 | B3KU97 |
| 282 | B3KUG5 |
| 283 | B3KUL9 |
| 284 | B3KUN1 |
| 285 | B3KUR9 |
| 286 | B3KUU1 |
| 287 | B3KVI1 |
| 288 | B3KVH9 |
| 289 | B3KVJ1 |
| 290 | B3KVN4 |
| 291 | B3KVP2 |
| 292 | B3KVU9 |
| 293 | B3KW07 |
| 294 | B3KW31 |
| 295 | B3KW52 |
| 296 | B3KWI5 |
| 297 | B3KWS8 |
| 298 | B3KX72 |
| 299 | B3KXH9 |
| 300 | B3KXW5 |

TABLE 9-continued

Proteins unique to NPEX

| | |
|---|---|
| 301 | B3KXX5 |
| 302 | B3KY97 |
| 303 | B4DE05 |
| 304 | B4DE48 |
| 305 | B4DE80 |
| 306 | B4DEI6 |
| 307 | B4DEX7 |
| 308 | B4DF38 |
| 309 | B4DFB6 |
| 310 | B4DFF1 |
| 311 | B4DFN8 |
| 312 | B4DG42 |
| 313 | B4DGF4 |
| 314 | B4DHN5 |
| 315 | B4DHX3 |
| 316 | B4DI94 |
| 317 | B4DIB9 |
| 318 | B4DIC2 |
| 319 | B4DJ53 |
| 320 | B4DKC2 |
| 321 | B4DKX2 |
| 322 | B4DL63 |
| 323 | B4DLP0 |
| 324 | B4DM77 |
| 325 | B4DMQ1 |
| 326 | B4DND4 |
| 327 | B4DP10 |
| 328 | B4DP52 |
| 329 | B4DQ24 |
| 330 | B4DQ80 |
| 331 | B4DQD4 |
| 332 | B4DRG0 |
| 333 | B4DRG2 |
| 334 | B4DRT4 |
| 335 | B4DS66 |
| 336 | B4DSA0 |
| 337 | B4DSC7 |
| 338 | B4DSC8 |
| 339 | B4DT06 |
| 340 | B4DTQ9 |
| 341 | B4DUB2 |
| 342 | B4DUY8 |
| 343 | B4DV73 |
| 344 | B4DVA7 |
| 345 | B4DWE9 |
| 346 | B4DWF9 |
| 347 | B4DWY2 |
| 348 | B4DWZ8 |
| 349 | B4DX03 |
| 350 | B4DXP2 |
| 351 | B4DXR7 |
| 352 | B4DXR8 |
| 353 | B4DY09 |
| 354 | B4DYD2 |
| 355 | B4DYE6 |
| 356 | B4DZ04 |
| 357 | B4DZ99 |
| 358 | B4DZC2 |
| 359 | B4DZC3 |
| 360 | B4DZC9 |
| 361 | B4DZD2 |
| 362 | B4DZS8 |
| 363 | B4E0B7 |
| 364 | B4E0E1 |
| 365 | B4E0J9 |
| 366 | B4E0Q4 |
| 367 | B4E143 |
| 368 | B4E173 |
| 369 | B4E282 |
| 370 | B4E2E2 |
| 371 | B4E2F7 |
| 372 | B4E2W8 |
| 373 | B4E2X3 |
| 374 | B4E3A8 |
| 375 | B4E3M6 |
| 376 | B5A954 |
| 377 | B5BU72 |
| 378 | B5MBY4 |
| 379 | B5TYJ1 |
| 380 | B7Z1G4 |
| 381 | B7Z282 |
| 382 | B7Z2F7 |
| 383 | B7Z2X2 |
| 384 | B7Z2Z2 |
| 385 | B7Z321 |
| 386 | B7Z3A3 |
| 387 | B7Z5H2 |
| 388 | B7Z5N6 |
| 389 | B7Z6E2 |
| 390 | B7Z6K2 |
| 391 | B7Z6P1 |
| 392 | B7Z6R5 |
| 393 | B7Z6T0 |
| 394 | B7Z6X5 |
| 395 | B7Z7R8 |
| 396 | B7Z7W2 |
| 397 | B7Z942 |
| 398 | B7Z970 |
| 399 | B7Z971 |
| 400 | B7Z9C6 |
| 401 | B7ZAR1 |
| 402 | B7ZAV2 |
| 403 | B7ZB07 |
| 404 | B7ZB16 |
| 405 | B7ZBD5 |
| 406 | B7ZBH1 |
| 407 | B7ZL21 |
| 408 | B7ZLC8 |
| 409 | B7ZMI2 |
| 410 | B7ZMM1 |
| 411 | B8ZZA5 |
| 412 | B9A6J2 |
| 413 | B9EG68 |
| 414 | B9EG95 |
| 415 | B9TWZ8 |
| 416 | C4IXU6 |
| 417 | C6ZGQ9 |
| 418 | C7S316 |
| 419 | C9J0Q5 |
| 420 | C9J268 |
| 421 | C9J408 |
| 422 | C9J524 |
| 423 | C9J712 |
| 424 | C9J7G0 |
| 425 | C9J8V3 |
| 426 | C9JBE8 |
| 427 | C9JCQ9 |
| 428 | C9JEN8 |
| 429 | C9JH19 |
| 430 | C9JSK8 |
| 431 | C9JYQ2 |
| 432 | D3DPF8 |
| 433 | D3DS02 |
| 434 | D3DSB5 |
| 435 | D3DVJ3 |
| 436 | D3DVS8 |
| 437 | D3DVT0 |
| 438 | D3DXI8 |
| 439 | D3DXI9 |
| 440 | D3TTY9 |
| 441 | D4IH22 |
| 442 | D5KMU6 |
| 443 | D6R921 |
| 444 | D6R936 |
| 445 | D6R938 |
| 446 | D6R9C2 |
| 447 | D6R9E3 |
| 448 | D6R9V7 |
| 449 | D6R9W4 |
| 450 | D6RB55 |
| 451 | D6RC76 |
| 452 | D6RD46 |
| 453 | D6RD74 |
| 454 | D6RE68 |
| 455 | D6RFH3 |
| 456 | D6RGK7 |

TABLE 9-continued

Proteins unique to NPEX

| | |
|---|---|
| 457 | D6RIC7 |
| 458 | D6RTK6 |
| 459 | D7NTU0 |
| 460 | E0Z3H0 |
| 461 | E2RYF6 |
| 462 | E5RFZ0 |
| 463 | E5RG94 |
| 464 | E5RHK2 |
| 465 | E5RJ52 |
| 466 | E6Y365 |
| 467 | E6Y3F9 |
| 468 | E7EME3 |
| 469 | E7EMS9 |
| 470 | E7ENT8 |
| 471 | E7EP60 |
| 472 | E7EPN9 |
| 473 | E7ERS3 |
| 474 | E7ESK9 |
| 475 | E7ET15 |
| 476 | E7ETR9 |
| 477 | E7EU35 |
| 478 | E7EUC7 |
| 479 | E7EV71 |
| 480 | E7EV99 |
| 481 | E7EVX8 |
| 482 | E9PB18 |
| 483 | E9PB90 |
| 484 | E9PCY5 |
| 485 | E9PDF5 |
| 486 | E9PEW0 |
| 487 | E9PF18 |
| 488 | E9PG59 |
| 489 | E9PGK7 |
| 490 | E9PGW9 |
| 491 | E9PIT3 |
| 492 | E9PK85 |
| 493 | E9PL71 |
| 494 | E9PLE2 |
| 495 | E9PLF1 |
| 496 | E9PMF9 |
| 497 | E9PMH3 |
| 498 | E9PMP7 |
| 499 | E9PNL2 |
| 500 | E9PPT0 |
| 501 | E9PQ63 |
| 502 | E9PQ78 |
| 503 | E9PQR7 |
| 504 | E9PS38 |
| 505 | E9PSI1 |
| 506 | F1D8R5 |
| 507 | F2FB34 |
| 508 | F2Z2C9 |
| 509 | F2Z2V2 |
| 510 | F5GXE6 |
| 511 | F5GXV7 |
| 512 | F5GY90 |
| 513 | F5GYI5 |
| 514 | F5H081 |
| 515 | F5H0Q0 |
| 516 | F5H1B0 |
| 517 | F5H248 |
| 518 | F5H269 |
| 519 | F5H2B9 |
| 520 | F5H3F0 |
| 521 | F5H4R4 |
| 522 | F5H5L5 |
| 523 | F5H5P4 |
| 524 | F5H6T1 |
| 525 | F5H7H1 |
| 526 | F6SS63 |
| 527 | F8LFZ0 |
| 528 | F8VPW7 |
| 529 | F8VS27 |
| 530 | F8VXU5 |
| 531 | F8VZR8 |
| 532 | F8W0I7 |
| 533 | F8W0P6 |
| 534 | F8W1Y6 |
| 535 | F8W6X9 |
| 536 | F8W8W4 |
| 537 | F8WBD4 |
| 538 | F8WEE2 |
| 539 | G1UD80 |
| 540 | G2XKQ0 |
| 541 | G3V119 |
| 542 | G3V1R5 |
| 543 | G3V2T5 |
| 544 | G3V3H3 |
| 545 | G3V5A2 |
| 546 | G3V5B2 |
| 547 | G4V217 |
| 548 | G5E9U2 |
| 549 | G5E9W5 |
| 550 | G5E9X1 |
| 551 | G8JLD5 |
| 552 | G9HZ40 |
| 553 | G9LIE3 |
| 554 | H0UI21 |
| 555 | H0Y2R3 |
| 556 | H0Y494 |
| 557 | H0Y5G0 |
| 558 | H0Y626 |
| 559 | H0Y6T7 |
| 560 | H0Y7U8 |
| 561 | H0Y8A5 |
| 562 | H0Y8J2 |
| 563 | H0YA41 |
| 564 | H0YA82 |
| 565 | H0YAN2 |
| 566 | H0YC24 |
| 567 | H0YC74 |
| 568 | H0YDG2 |
| 569 | H0YDS4 |
| 570 | H0YE28 |
| 571 | H0YGQ5 |
| 572 | H0YGS7 |
| 573 | H0YI92 |
| 574 | H0YIC9 |
| 575 | H0YJN7 |
| 576 | H0YKE9 |
| 577 | H0YKJ0 |
| 578 | H0YKU1 |
| 579 | H0YL26 |
| 580 | H0YLC7 |
| 581 | H0YMT1 |
| 582 | H0YNC2 |
| 583 | H3BMQ0 |
| 584 | H3BMX7 |
| 585 | H3BN32 |
| 586 | H3BNJ0 |
| 587 | H3BPD5 |
| 588 | H3BPM0 |
| 589 | H3BQH0 |
| 590 | H3BRR1 |
| 591 | H3BRT3 |
| 592 | H3BRW2 |
| 593 | H3BS46 |
| 594 | H3BSK8 |
| 595 | H3BT65 |
| 596 | H3BTA7 |
| 597 | H3BTB7 |
| 598 | H3BTQ7 |
| 599 | H3BTZ4 |
| 600 | H3BUN2 |
| 601 | H3BUQ6 |
| 602 | H3BV12 |
| 603 | H6WCP5 |
| 604 | H7BXH2 |
| 605 | H7BY59 |
| 606 | H7BYG4 |
| 607 | H7BZR8 |
| 608 | H7BZR9 |
| 609 | H7BZS7 |
| 610 | H7C0N2 |
| 611 | H7C150 |
| 612 | H7C276 |

TABLE 9-continued

Proteins unique to NPEX

| | |
|---|---|
| 613 | H7C2M1 |
| 614 | H7C2Q0 |
| 615 | H7C2T4 |
| 616 | H7C2Y1 |
| 617 | H7C354 |
| 618 | H7C3W2 |
| 619 | H7C440 |
| 620 | H7C4T1 |
| 621 | H7C525 |
| 622 | H7C5Q0 |
| 623 | H9C3J9 |
| 624 | H9PCV7 |
| 625 | I1VYG6 |
| 626 | I3L0A5 |
| 627 | I3L194 |
| 628 | I3L1M7 |
| 629 | I3L305 |
| 630 | I3L3Z0 |
| 631 | I6L9F7 |
| 632 | I6T4L2 |
| 633 | J3KP02 |
| 634 | J3KQA9 |
| 635 | J3KQJ9 |
| 636 | J3KR49 |
| 637 | J3KRL2 |
| 638 | J3KRL5 |
| 639 | J3KS17 |
| 640 | J3KS19 |
| 641 | J3KSU0 |
| 642 | J3KSZ0 |
| 643 | J3KTE6 |
| 644 | J3KTF8 |
| 645 | J3KTH2 |
| 646 | J3QLL3 |
| 647 | J3QQW1 |
| 648 | J3QQX3 |
| 649 | J3QS13 |
| 650 | J3QSU0 |
| 651 | J3QT83 |
| 652 | J7M5B9 |
| 653 | K0IIP4 |
| 654 | K7EID4 |
| 655 | K7EIY4 |
| 656 | K7EJZ2 |
| 657 | K7EL35 |
| 658 | K7ELW4 |
| 659 | K7EM44 |
| 660 | K7EMC6 |
| 661 | K7EMK6 |
| 662 | K7ENP1 |
| 663 | K7EQK2 |
| 664 | K7EQR0 |
| 665 | K7ERD4 |
| 666 | K7ERV2 |
| 667 | K7ES09 |
| 668 | K7ESB7 |
| 669 | M0QXU3 |
| 670 | M0QZB5 |
| 671 | M0R165 |
| 672 | M0R3B5 |
| 673 | M0R312 |
| 674 | M1V481 |
| 675 | M4QHP2 |
| 676 | O00299 |
| 677 | O00363 |
| 678 | O00443 |
| 679 | O00444 |
| 680 | O00451 |
| 681 | O00462 |
| 682 | O00471 |
| 683 | O00505 |
| 684 | O00571 |
| 685 | O00754 |
| 686 | O14579 |
| 687 | O14617 |
| 688 | O14672 |
| 689 | O14715 |
| 690 | O14757 |
| 691 | O14773 |
| 692 | O14792 |
| 693 | O14818 |
| 694 | O14950 |
| 695 | O15016 |
| 696 | O15021 |
| 697 | O15040 |
| 698 | O15075 |
| 699 | O15117 |
| 700 | O15145 |
| 701 | O15212 |
| 702 | O15372 |
| 703 | O15397 |
| 704 | O15427 |
| 705 | O15460 |
| 706 | O15498 |
| 707 | O15511 |
| 708 | O43143 |
| 709 | O43151 |
| 710 | O43323 |
| 711 | O43396 |
| 712 | O43464 |
| 713 | O43823 |
| 714 | O43865 |
| 715 | O60229 |
| 716 | O60279 |
| 717 | O60281 |
| 718 | O60423 |
| 719 | O60456 |
| 720 | O60500 |
| 721 | O60518 |
| 722 | O60673 |
| 723 | O60759 |
| 724 | O60763 |
| 725 | O60784 |
| 726 | O60890 |
| 727 | O75083 |
| 728 | O75326 |
| 729 | O75340 |
| 730 | O75376 |
| 731 | O75417 |
| 732 | O75508 |
| 733 | O75533 |
| 734 | O75616 |
| 735 | O75718 |
| 736 | O75792 |
| 737 | O75937 |
| 738 | O75954 |
| 739 | O75962 |
| 740 | O94855 |
| 741 | O94973 |
| 742 | O94986 |
| 743 | O95084 |
| 744 | O95147 |
| 745 | O95201 |
| 746 | O95202 |
| 747 | O95391 |
| 748 | O95447 |
| 749 | O95486 |
| 750 | O95633 |
| 751 | O95786 |
| 752 | O95965 |
| 753 | O95967 |
| 754 | O95999 |
| 755 | O96019 |
| 756 | P00367 |
| 757 | P00491 |
| 758 | P00505 |
| 759 | P00558 |
| 760 | P00918 |
| 761 | P01033 |
| 762 | P01137 |
| 763 | P01601 |
| 764 | P01613 |
| 765 | P02511 |
| 766 | P02649 |
| 767 | P02765 |
| 768 | P02787 |

TABLE 9-continued

Proteins unique to NPEX

| | |
|---|---|
| 769 | P02794 |
| 770 | P03956 |
| 771 | P04004 |
| 772 | P04083 |
| 773 | P04216 |
| 774 | P04424 |
| 775 | P04632 |
| 776 | P04899 |
| 777 | P05114 |
| 778 | P05121 |
| 779 | P05166 |
| 780 | P05387 |
| 781 | P05783 |
| 782 | P06132 |
| 783 | P06703 |
| 784 | P07093 |
| 785 | P07237 |
| 786 | P07355 |
| 787 | P07384 |
| 788 | P07437 |
| 789 | P07686 |
| 790 | P07858 |
| 791 | P07954 |
| 792 | P08100 |
| 793 | P08133 |
| 794 | P08195 |
| 795 | P08476 |
| 796 | P08590 |
| 797 | P08758 |
| 798 | P09211 |
| 799 | P09238 |
| 800 | P09543 |
| 801 | P09603 |
| 802 | P09936 |
| 803 | P09972 |
| 804 | P0CG42 |
| 805 | P0CI25 |
| 806 | P10124 |
| 807 | P10646 |
| 808 | P10809 |
| 809 | P10915 |
| 810 | P11142 |
| 811 | P11166 |
| 812 | P11413 |
| 813 | P11717 |
| 814 | P11766 |
| 815 | P11940 |
| 816 | P12081 |
| 817 | P13473 |
| 818 | P13489 |
| 819 | P13569 |
| 820 | P13646 |
| 821 | P13674 |
| 822 | P13716 |
| 823 | P13987 |
| 824 | P14174 |
| 825 | P14209 |
| 826 | P14324 |
| 827 | P14735 |
| 828 | P15121 |
| 829 | P15144 |
| 830 | P15586 |
| 831 | P16278 |
| 832 | P16520 |
| 833 | P16885 |
| 834 | P17035 |
| 835 | P17174 |
| 836 | P17342 |
| 837 | P17655 |
| 838 | P17812 |
| 839 | P17931 |
| 840 | P17936 |
| 841 | P17980 |
| 842 | P17987 |
| 843 | P19113 |
| 844 | P19623 |
| 845 | P19823 |
| 846 | P19883 |
| 847 | P20929 |
| 848 | P21266 |
| 849 | P21333 |
| 850 | P21397 |
| 851 | P21439 |
| 852 | P21589 |
| 853 | P21810 |
| 854 | P21817 |
| 855 | P21926 |
| 856 | P21980 |
| 857 | P22304 |
| 858 | P22681 |
| 859 | P22897 |
| 860 | P23276 |
| 861 | P23284 |
| 862 | P23396 |
| 863 | P23470 |
| 864 | P24043 |
| 865 | P24539 |
| 866 | P24593 |
| 867 | P25092 |
| 868 | P25325 |
| 869 | P25789 |
| 870 | P26006 |
| 871 | P26038 |
| 872 | P26599 |
| 873 | P26639 |
| 874 | P26640 |
| 875 | P27658 |
| 876 | P28062 |
| 877 | P30085 |
| 878 | P30530 |
| 879 | P30622 |
| 880 | P31937 |
| 881 | P31939 |
| 882 | P31948 |
| 883 | P31949 |
| 884 | P32926 |
| 885 | P33402 |
| 886 | P35221 |
| 887 | P35222 |
| 888 | P35250 |
| 889 | P35579 |
| 890 | P35913 |
| 891 | P35998 |
| 892 | P36954 |
| 893 | P37802 |
| 894 | P40199 |
| 895 | P40818 |
| 896 | P40855 |
| 897 | P40926 |
| 898 | P41091 |
| 899 | P41221 |
| 900 | P41252 |
| 901 | P42336 |
| 902 | P46063 |
| 903 | P46821 |
| 904 | P46926 |
| 905 | P46939 |
| 906 | P47756 |
| 907 | P48509 |
| 908 | P49189 |
| 909 | P49368 |
| 910 | P49589 |
| 911 | P49591 |
| 912 | P49888 |
| 913 | P50135 |
| 914 | P50213 |
| 915 | P50219 |
| 916 | P50281 |
| 917 | P50395 |
| 918 | P50591 |
| 919 | P50990 |
| 920 | P51397 |
| 921 | P51610 |
| 922 | P51813 |
| 923 | P51948 |
| 924 | P52788 |

TABLE 9-continued

Proteins unique to NPEX

| | |
|---|---|
| 925 | P52848 |
| 926 | P52888 |
| 927 | P52907 |
| 928 | P53611 |
| 929 | P53992 |
| 930 | P54289 |
| 931 | P54296 |
| 932 | P54687 |
| 933 | P54802 |
| 934 | P55001 |
| 935 | P55008 |
| 936 | P55072 |
| 937 | P55083 |
| 938 | P55268 |
| 939 | P55285 |
| 940 | P55287 |
| 941 | P55884 |
| 942 | P56159 |
| 943 | P56559 |
| 944 | P57075 |
| 945 | P58215 |
| 946 | P59817 |
| 947 | P60900 |
| 948 | P60903 |
| 949 | P60953 |
| 950 | P60981 |
| 951 | P61011 |
| 952 | P61163 |
| 953 | P61586 |
| 954 | P61758 |
| 955 | P61769 |
| 956 | P62140 |
| 957 | P62166 |
| 958 | P62195 |
| 959 | P62249 |
| 960 | P62280 |
| 961 | P62328 |
| 962 | P62333 |
| 963 | P62873 |
| 964 | P62906 |
| 965 | P62942 |
| 966 | P63135 |
| 967 | P63151 |
| 968 | P68366 |
| 969 | P68543 |
| 970 | P69849 |
| 971 | P78315 |
| 972 | P78316 |
| 973 | P78368 |
| 974 | P78417 |
| 975 | P78424 |
| 976 | P78504 |
| 977 | P80303 |
| 978 | P84077 |
| 979 | Q00266 |
| 980 | Q00341 |
| 981 | Q00587 |
| 982 | Q00796 |
| 983 | Q01082 |
| 984 | Q01518 |
| 985 | Q01650 |
| 986 | Q01746 |
| 987 | Q01813 |
| 988 | Q01973 |
| 989 | Q02045 |
| 990 | Q02818 |
| 991 | Q02846 |
| 992 | Q06033 |
| 993 | Q06830 |
| 994 | Q06HC4 |
| 995 | Q07021 |
| 996 | Q07065 |
| 997 | Q07343 |
| 998 | Q07666 |
| 999 | Q07960 |
| 1000 | Q08378 |
| 1001 | Q08379 |
| 1002 | Q08397 |
| 1003 | Q09328 |
| 1004 | Q0R2U2 |
| 1005 | Q0VFZ6 |
| 1006 | Q108H6 |
| 1007 | Q12830 |
| 1008 | Q12884 |
| 1009 | Q12889 |
| 1010 | Q12907 |
| 1011 | Q13045 |
| 1012 | Q13069 |
| 1013 | Q13098 |
| 1014 | Q13155 |
| 1015 | Q13283 |
| 1016 | Q13347 |
| 1017 | Q13362 |
| 1018 | Q13416 |
| 1019 | Q13443 |
| 1020 | Q13464 |
| 1021 | Q13478 |
| 1022 | Q13564 |
| 1023 | Q13591 |
| 1024 | Q13596 |
| 1025 | Q13682 |
| 1026 | Q13823 |
| 1027 | Q13939 |
| 1028 | Q14055 |
| 1029 | Q14108 |
| 1030 | Q14118 |
| 1031 | Q14126 |
| 1032 | Q14197 |
| 1033 | Q14257 |
| 1034 | Q14442 |
| 1035 | Q14444 |
| 1036 | Q14523 |
| 1037 | Q14651 |
| 1038 | Q14683 |
| 1039 | Q14689 |
| 1040 | Q14699 |
| 1041 | Q14764 |
| 1042 | Q14767 |
| 1043 | Q14839 |
| 1044 | Q14868 |
| 1045 | Q14CZ0 |
| 1046 | Q15008 |
| 1047 | Q15019 |
| 1048 | Q15024 |
| 1049 | Q15029 |
| 1050 | Q15136 |
| 1051 | Q15228 |
| 1052 | Q15256 |
| 1053 | Q15262 |
| 1054 | Q15413 |
| 1055 | Q15424 |
| 1056 | Q15464 |
| 1057 | Q15465 |
| 1058 | Q15526 |
| 1059 | Q15596 |
| 1060 | Q15648 |
| 1061 | Q15753 |
| 1062 | Q15904 |
| 1063 | Q16181 |
| 1064 | Q16204 |
| 1065 | Q16270 |
| 1066 | Q16531 |
| 1067 | Q16576 |
| 1068 | Q16832 |
| 1069 | Q1KMD3 |
| 1070 | Q1WIS0 |
| 1071 | Q24JU4 |
| 1072 | Q2KHR2 |
| 1073 | Q2LAE2 |
| 1074 | Q2M2A7 |
| 1075 | Q2TAZ0 |
| 1076 | Q2UY09 |
| 1077 | Q2VIQ3 |
| 1078 | Q2VIR3 |
| 1079 | Q2VPA4 |
| 1080 | Q2VPJ0 |

TABLE 9-continued

Proteins unique to NPEX

| | |
|---|---|
| 1081 | Q2YDB1 |
| 1082 | Q32ND0 |
| 1083 | Q3B7X1 |
| 1084 | Q3KNR5 |
| 1085 | Q3KNT2 |
| 1086 | Q3LIF6 |
| 1087 | Q3SXZ7 |
| 1088 | Q3ZCM1 |
| 1089 | Q3ZLR7 |
| 1090 | Q3ZTS5 |
| 1091 | Q461N2 |
| 1092 | Q494Z1 |
| 1093 | Q495C1 |
| 1094 | Q495F8 |
| 1095 | Q496J3 |
| 1096 | Q4G0H8 |
| 1097 | Q4KMZ1 |
| 1098 | Q4QRJ3 |
| 1099 | Q4VAN1 |
| 1100 | Q4VY13 |
| 1101 | Q502X7 |
| 1102 | Q504U6 |
| 1103 | Q53EL0 |
| 1104 | Q53F80 |
| 1105 | Q53FN7 |
| 1106 | Q53FW8 |
| 1107 | Q53H08 |
| 1108 | Q53H26 |
| 1109 | Q53HA9 |
| 1110 | Q53QV8 |
| 1111 | Q53SB6 |
| 1112 | Q53XL7 |
| 1113 | Q53Y83 |
| 1114 | Q53Y86 |
| 1115 | Q53YD7 |
| 1116 | Q53ZX7 |
| 1117 | Q540U8 |
| 1118 | Q548T7 |
| 1119 | Q549N7 |
| 1120 | Q54A51 |
| 1121 | Q569L6 |
| 1122 | Q56N19 |
| 1123 | Q587J7 |
| 1124 | Q58F26 |
| 1125 | Q59ED9 |
| 1126 | Q59EU4 |
| 1127 | Q59F19 |
| 1128 | Q59FL3 |
| 1129 | Q59GL0 |
| 1130 | Q5BJE1 |
| 1131 | Q5CZ70 |
| 1132 | Q5CZA0 |
| 1133 | Q5CZC0 |
| 1134 | Q5EBM7 |
| 1135 | Q5HYB0 |
| 1136 | Q5HYG7 |
| 1137 | Q5JC44 |
| 1138 | Q5JPA7 |
| 1139 | Q5JRW7 |
| 1140 | Q5JTN6 |
| 1141 | Q5JTW6 |
| 1142 | Q5JUQ2 |
| 1143 | Q5JWF2 |
| 1144 | Q5JXX7 |
| 1145 | Q5JZ08 |
| 1146 | Q5M8T4 |
| 1147 | Q5PY49 |
| 1148 | Q5QJU3 |
| 1149 | Q5STV5 |
| 1150 | Q5T0U0 |
| 1151 | Q5T160 |
| 1152 | Q5T427 |
| 1153 | Q5T655 |
| 1154 | Q5T6L9 |
| 1155 | Q5T7B3 |
| 1156 | Q5T7W0 |
| 1157 | Q5T9L3 |
| 1158 | Q5TB52 |
| 1159 | Q5TCJ2 |
| 1160 | Q5TCX8 |
| 1161 | Q5TEZ5 |
| 1162 | Q5TGS1 |
| 1163 | Q5TH69 |
| 1164 | Q5U0F2 |
| 1165 | Q5VT97 |
| 1166 | Q5VV63 |
| 1167 | Q5VWT5 |
| 1168 | Q5VYK3 |
| 1169 | Q5VZK9 |
| 1170 | Q5VZV1 |
| 1171 | Q63HP0 |
| 1172 | Q643R0 |
| 1173 | Q658R0 |
| 1174 | Q659E8 |
| 1175 | Q659F6 |
| 1176 | Q659F8 |
| 1177 | Q68D86 |
| 1178 | Q68DA7 |
| 1179 | Q68DM7 |
| 1180 | Q68DN3 |
| 1181 | Q68DS2 |
| 1182 | Q68DS3 |
| 1183 | Q6AZY7 |
| 1184 | Q6FGL8 |
| 1185 | Q6FI91 |
| 1186 | Q6IAT7 |
| 1187 | Q6IAX5 |
| 1188 | Q6IB29 |
| 1189 | Q6IBR6 |
| 1190 | Q6ICD2 |
| 1191 | Q6IE37 |
| 1192 | Q6IPS9 |
| 1193 | Q6K0P9 |
| 1194 | Q6MZF2 |
| 1195 | Q6MZM3 |
| 1196 | Q6NSC9 |
| 1197 | Q6NTE8 |
| 1198 | Q6NV74 |
| 1199 | Q6NX68 |
| 1200 | Q6NZ83 |
| 1201 | Q6P0Q8 |
| 1202 | Q6P2D0 |
| 1203 | Q6P3W7 |
| 1204 | Q6P528 |
| 1205 | Q6P5Z4 |
| 1206 | Q6PCE3 |
| 1207 | Q6PEW0 |
| 1208 | Q6PIK3 |
| 1209 | Q6PIW4 |
| 1210 | Q6PJ36 |
| 1211 | Q6PKF2 |
| 1212 | Q6Q4G3 |
| 1213 | Q6Q759 |
| 1214 | Q6UWP2 |
| 1215 | Q6UWW8 |
| 1216 | Q6UXE8 |
| 1217 | Q6UXH8 |
| 1218 | Q6WCQ1 |
| 1219 | Q6WRI0 |
| 1220 | Q6XZE5 |
| 1221 | Q6YNQ1 |
| 1222 | Q6ZMW9 |
| 1223 | Q6ZN06 |
| 1224 | Q6ZN13 |
| 1225 | Q6ZNK6 |
| 1226 | Q6ZNS6 |
| 1227 | Q6ZPB4 |
| 1228 | Q6ZR08 |
| 1229 | Q6ZR62 |
| 1230 | Q6ZR81 |
| 1231 | Q6ZRR7 |
| 1232 | Q6ZRR9 |
| 1233 | Q6ZS30 |
| 1234 | Q6ZSA3 |
| 1235 | Q6ZUX3 |
| 1236 | Q6ZVH7 |

TABLE 9-continued

Proteins unique to NPEX

| | |
|---|---|
| 1237 | Q6ZVJ0 |
| 1238 | Q6ZWD7 |
| 1239 | Q70Q86 |
| 1240 | Q76KX8 |
| 1241 | Q76M96 |
| 1242 | Q76N11 |
| 1243 | Q7KZF4 |
| 1244 | Q7L112 |
| 1245 | Q7L2K0 |
| 1246 | Q7L5A8 |
| 1247 | Q7L5N1 |
| 1248 | Q7LBC6 |
| 1249 | Q7LBX6 |
| 1250 | Q7LFX5 |
| 1251 | Q7RTM4 |
| 1252 | Q7RTU9 |
| 1253 | Q7RTV5 |
| 1254 | Q7Z304 |
| 1255 | Q7Z3G2 |
| 1256 | Q7Z3L3 |
| 1257 | Q7Z410 |
| 1258 | Q7Z4H8 |
| 1259 | Q7Z4L4 |
| 1260 | Q7Z4X1 |
| 1261 | Q7Z583 |
| 1262 | Q7Z5L2 |
| 1263 | Q7Z5M5 |
| 1264 | Q7Z5X8 |
| 1265 | Q7Z679 |
| 1266 | Q7Z7G0 |
| 1267 | Q85ZX8 |
| 1268 | Q86SG6 |
| 1269 | Q86SJ2 |
| 1270 | Q86T20 |
| 1271 | Q86TS1 |
| 1272 | Q86U45 |
| 1273 | Q86U53 |
| 1274 | Q86UB2 |
| 1275 | Q86UE9 |
| 1276 | Q86VS8 |
| 1277 | Q86W50 |
| 1278 | Q86W67 |
| 1279 | Q86WT6 |
| 1280 | Q86XA9 |
| 1281 | Q86YW9 |
| 1282 | Q8IU62 |
| 1283 | Q8IUU5 |
| 1284 | Q8IUX7 |
| 1285 | Q8IVB1 |
| 1286 | Q8IVL5 |
| 1287 | Q8IW47 |
| 1288 | Q8IWB6 |
| 1289 | Q8IWE2 |
| 1290 | Q8IYT3 |
| 1291 | Q8IZF3 |
| 1292 | Q8IZG2 |
| 1293 | Q8IZP2 |
| 1294 | Q8IZZ8 |
| 1295 | Q8N137 |
| 1296 | Q8N248 |
| 1297 | Q8N212 |
| 1298 | Q8N2S1 |
| 1299 | Q8N412 |
| 1300 | Q8N414 |
| 1301 | Q8N427 |
| 1302 | Q8N474 |
| 1303 | Q8N4E4 |
| 1304 | Q8N508 |
| 1305 | Q8N6J3 |
| 1306 | Q8N7D9 |
| 1307 | Q8N7X0 |
| 1308 | Q8N822 |
| 1309 | Q8N8F1 |
| 1310 | Q8N961 |
| 1311 | Q8N9D1 |
| 1312 | Q8NA02 |
| 1313 | Q8NA54 |
| 1314 | Q8NBJ4 |
| 1315 | Q8NBS9 |
| 1316 | Q8NCC3 |
| 1317 | Q8NDD5 |
| 1318 | Q8NDM7 |
| 1319 | Q8NE71 |
| 1320 | Q8NEL0 |
| 1321 | Q8NEN0 |
| 1322 | Q8NEP9 |
| 1323 | Q8NEZ5 |
| 1324 | Q8NFF3 |
| 1325 | Q8NFW1 |
| 1326 | Q8NFZ4 |
| 1327 | Q8NHX6 |
| 1328 | Q8TB37 |
| 1329 | Q8TB73 |
| 1330 | Q8TBC4 |
| 1331 | Q8TBW1 |
| 1332 | Q8TCE6 |
| 1333 | Q8TCU5 |
| 1334 | Q8TCY9 |
| 1335 | Q8TD47 |
| 1336 | Q8TDD1 |
| 1337 | Q8TDD2 |
| 1338 | Q8TDR4 |
| 1339 | Q8TEC9 |
| 1340 | Q8TEF5 |
| 1341 | Q8TF27 |
| 1342 | Q8TF62 |
| 1343 | Q8WUQ3 |
| 1344 | Q8WUS6 |
| 1345 | Q8WV16 |
| 1346 | Q8WW02 |
| 1347 | Q8WWH5 |
| 1348 | Q8WWI5 |
| 1349 | Q8WWN8 |
| 1350 | Q8WWV3 |
| 1351 | Q8WXA3 |
| 1352 | Q8WXG9 |
| 1353 | Q8WXJ2 |
| 1354 | Q8WY19 |
| 1355 | Q8WZ74 |
| 1356 | Q8WZ99 |
| 1357 | Q8WZA0 |
| 1358 | Q92545 |
| 1359 | Q92598 |
| 1360 | Q92614 |
| 1361 | Q92621 |
| 1362 | Q92667 |
| 1363 | Q92673 |
| 1364 | Q92777 |
| 1365 | Q92791 |
| 1366 | Q92794 |
| 1367 | Q92878 |
| 1368 | Q92896 |
| 1369 | Q92913 |
| 1370 | Q93008 |
| 1371 | Q93009 |
| 1372 | Q969J2 |
| 1373 | Q969P5 |
| 1374 | Q969X0 |
| 1375 | Q96AB3 |
| 1376 | Q96AC1 |
| 1377 | Q96AG3 |
| 1378 | Q96AL5 |
| 1379 | Q96AW4 |
| 1380 | Q96AY3 |
| 1381 | Q96B45 |
| 1382 | Q96B70 |
| 1383 | Q96C11 |
| 1384 | Q96C57 |
| 1385 | Q96CP2 |
| 1386 | Q96CW1 |
| 1387 | Q96DX8 |
| 1388 | Q96EB6 |
| 1389 | Q96ES0 |
| 1390 | Q96HK3 |
| 1391 | Q96I86 |
| 1392 | Q96IC2 |

TABLE 9-continued

Proteins unique to NPEX

| | |
|---|---|
| 1393 | Q96I19 |
| 1394 | Q96J40 |
| 1395 | Q96J66 |
| 1396 | Q96J72 |
| 1397 | Q96JC1 |
| 1398 | Q96JH7 |
| 1399 | Q96JM2 |
| 1400 | Q96JP2 |
| 1401 | Q96L42 |
| 1402 | Q96M20 |
| 1403 | Q96M97 |
| 1404 | Q96MC4 |
| 1405 | Q96MY7 |
| 1406 | Q96N32 |
| 1407 | Q96N83 |
| 1408 | Q96NX8 |
| 1409 | Q96Q42 |
| 1410 | Q96QB0 |
| 1411 | Q96QF1 |
| 1412 | Q96RE7 |
| 1413 | Q96RT7 |
| 1414 | Q96RZ6 |
| 1415 | Q96T23 |
| 1416 | Q96T70 |
| 1417 | Q96TA1 |
| 1418 | Q96TC7 |
| 1419 | Q96TG0 |
| 1420 | Q99422 |
| 1421 | Q99471 |
| 1422 | Q99497 |
| 1423 | Q99525 |
| 1424 | Q99608 |
| 1425 | Q99613 |
| 1426 | Q99623 |
| 1427 | Q99626 |
| 1428 | Q99712 |
| 1429 | Q99767 |
| 1430 | Q99868 |
| 1431 | Q99874 |
| 1432 | Q9BR76 |
| 1433 | Q9BRM9 |
| 1434 | Q9BSH8 |
| 1435 | Q9BSJ5 |
| 1436 | Q9BSK1 |
| 1437 | Q9BT66 |
| 1438 | Q9BTF5 |
| 1439 | Q9BTG3 |
| 1440 | Q9BTN2 |
| 1441 | Q9BTZ8 |
| 1442 | Q9BU99 |
| 1443 | Q9BUB5 |
| 1444 | Q9BV90 |
| 1445 | Q9BW52 |
| 1446 | Q9BW58 |
| 1447 | Q9BWZ5 |
| 1448 | Q9BXF1 |
| 1449 | Q9BXF3 |
| 1450 | Q9BXL5 |
| 1451 | Q9BYT8 |
| 1452 | Q9BZ74 |
| 1453 | Q9BZE3 |
| 1454 | Q9BZQ4 |
| 1455 | Q9C040 |
| 1456 | Q9GZP4 |
| 1457 | Q9GZT8 |
| 1458 | Q9GZV3 |
| 1459 | Q9H0A0 |
| 1460 | Q9H0B8 |
| 1461 | Q9H0E2 |
| 1462 | Q9H0H0 |
| 1463 | Q9H0I3 |
| 1464 | Q9H0P5 |
| 1465 | Q9H106 |
| 1466 | Q9H128 |
| 1467 | Q9H156 |
| 1468 | Q9H173 |
| 1469 | Q9H1J1 |
| 1470 | Q9H1J7 |
| 1471 | Q9H1Z3 |
| 1472 | Q9H1Z5 |
| 1473 | Q9H299 |
| 1474 | Q9H2J7 |
| 1475 | Q9H2K3 |
| 1476 | Q9H2P8 |
| 1477 | Q9H3P9 |
| 1478 | Q9H3S7 |
| 1479 | Q9H4A4 |
| 1480 | Q9H4D0 |
| 1481 | Q9H4F8 |
| 1482 | Q9H4M9 |
| 1483 | Q9H515 |
| 1484 | Q9H5L6 |
| 1485 | Q9H5R6 |
| 1486 | Q9H6D4 |
| 1487 | Q9H7D0 |
| 1488 | Q9H7H0 |
| 1489 | Q9H7H5 |
| 1490 | Q9H7P3 |
| 1491 | Q9H8E8 |
| 1492 | Q9H8G5 |
| 1493 | Q9H8H3 |
| 1494 | Q9H8S9 |
| 1495 | Q9H8V8 |
| 1496 | Q9H903 |
| 1497 | Q9H9Q2 |
| 1498 | Q9HA51 |
| 1499 | Q9HB40 |
| 1500 | Q9HBH9 |
| 1501 | Q9HC39 |
| 1502 | Q9HC87 |
| 1503 | Q9HCC0 |
| 1504 | Q9HCF4 |
| 1505 | Q9HCG1 |
| 1506 | Q9HCM1 |
| 1507 | Q9HCN6 |
| 1508 | Q9HD26 |
| 1509 | Q9NNZ5 |
| 1510 | Q9NPK3 |
| 1511 | Q9NPW9 |
| 1512 | Q9NQW6 |
| 1513 | Q9NR18 |
| 1514 | Q9NRA1 |
| 1515 | Q9NRN5 |
| 1516 | Q9NRY6 |
| 1517 | Q9NS13 |
| 1518 | Q9NS15 |
| 1519 | Q9NS87 |
| 1520 | Q9NSJ3 |
| 1521 | Q9NTH6 |
| 1522 | Q9NUY8 |
| 1523 | Q9NVA2 |
| 1524 | Q9NVE4 |
| 1525 | Q9NVE5 |
| 1526 | Q9NVR2 |
| 1527 | Q9NWL6 |
| 1528 | Q9NXA5 |
| 1529 | Q9NXC3 |
| 1530 | Q9NXZ1 |
| 1531 | Q9NY33 |
| 1532 | Q9NYM2 |
| 1533 | Q9NYQ7 |
| 1534 | Q9NZ08 |
| 1535 | Q9NZN4 |
| 1536 | Q9NZP2 |
| 1537 | Q9NZQ9 |
| 1538 | Q9NZU1 |
| 1539 | Q9NZV1 |
| 1540 | Q9P0K1 |
| 1541 | Q9P1S5 |
| 1542 | Q9P1W9 |
| 1543 | Q9P246 |
| 1544 | Q9P2L0 |
| 1545 | Q9P2W4 |
| 1546 | Q9P2X3 |
| 1547 | Q9TQL1 |
| 1548 | Q9UBC0 |

TABLE 9-continued

Proteins unique to NPEX

| | |
|---|---|
| 1549 | Q9UBF2 |
| 1550 | Q9UBP4 |
| 1551 | Q9UBQ5 |
| 1552 | Q9UBU7 |
| 1553 | Q9UC56 |
| 1554 | Q9UCV3 |
| 1555 | Q9UDG3 |
| 1556 | Q9UDL5 |
| 1557 | Q9UEB7 |
| 1558 | Q9UF52 |
| 1559 | Q9UF61 |
| 1560 | Q9UFC6 |
| 1561 | Q9UFT4 |
| 1562 | Q9UFW3 |
| 1563 | Q9UGJ1 |
| 1564 | Q9UHY1 |
| 1565 | Q9U142 |
| 1566 | Q9UIF8 |
| 1567 | Q9UIY4 |
| 1568 | Q9UJ70 |
| 1569 | Q9UJ71 |
| 1570 | Q9UJC6 |
| 1571 | Q9UJF2 |
| 1572 | Q9UJJ2 |
| 1573 | Q9UJJ9 |
| 1574 | Q9UJU4 |
| 1575 | Q9UKA4 |
| 1576 | Q9UKJ8 |
| 1577 | Q9UL63 |
| 1578 | Q9UL95 |
| 1579 | Q9ULA0 |
| 1580 | Q9ULD6 |
| 1581 | Q9ULG3 |
| 1582 | Q9ULJ9 |
| 1583 | Q9ULT8 |
| 1584 | Q9ULU8 |
| 1585 | Q9ULY4 |
| 1586 | Q9UM21 |
| 1587 | Q9UMG6 |
| 1588 | Q9UMG7 |
| 1589 | Q9UMN6 |
| 1590 | Q9UMV8 |
| 1591 | Q9UN71 |
| 1592 | Q9UNN5 |
| 1593 | Q9UNP5 |
| 1594 | Q9UNS2 |
| 1595 | Q9UP50 |
| 1596 | Q9UPJ7 |
| 1597 | Q9UQP3 |
| 1598 | Q9UQR1 |
| 1599 | Q9UQR9 |
| 1600 | Q9Y224 |
| 1601 | Q9Y234 |
| 1602 | Q9Y240 |
| 1603 | Q9Y264 |
| 1604 | Q9Y2B0 |
| 1605 | Q9Y2E5 |
| 1606 | Q9Y2G5 |
| 1607 | Q9Y2H8 |
| 1608 | Q9Y2M5 |
| 1609 | Q9Y2S0 |
| 1610 | Q9Y2T6 |
| 1611 | Q9Y2X7 |
| 1612 | Q9Y3I1 |
| 1613 | Q9Y3R5 |
| 1614 | Q9Y3X0 |
| 1615 | Q9Y423 |
| 1616 | Q9Y450 |
| 1617 | Q9Y467 |
| 1618 | Q9Y4C4 |
| 1619 | Q9Y4E8 |
| 1620 | Q9Y4G2 |
| 1621 | Q9Y4G8 |
| 1622 | Q9Y4M4 |
| 1623 | Q9Y5E6 |
| 1624 | Q9Y5S2 |
| 1625 | Q9Y5V3 |
| 1626 | Q9Y5Z7 |
| 1627 | Q9Y687 |
| 1628 | Q9Y6B7 |
| 1629 | Q9Y6D5 |
| 1630 | Q9Y6N7 |
| 1631 | Q9Y6V7 |
| 1632 | R4GNE8 |
| 1633 | R4GNI9 |
| 1634 | S4R2Z0 |
| 1635 | S4R354 |
| 1636 | S4R3N6 |
| 1637 | S4R3P9 |
| 1638 | T2FFJ4 |
| 1639 | U3KQ69 |
| 1640 | U3KQL2 |
| 1641 | U5TP13 |
| 1642 | V9GYP9 |
| 1643 | V9HVU7 |
| 1644 | V9HW54 |
| 1645 | V9HWB9 |
| 1646 | W8JD10 |
| 1647 | X5D2S9 |
| 1648 | X5DNF2 |
| 1649 | X6R3I0 |
| 1650 | X6R772 |
| 1651 | X6R8W7 |
| 1652 | X6R922 |
| 1653 | X6RLN4 |

Therefore, the disclosed EVs are unique based on the source of cells from which they are derived. Moreover, these proteins can be used as a signature to identify the EVs.

DISCUSSION

This is the first documentation that we are aware of on a scale that requires the Amicon stirred-cell ultrafiltration units, allowing filtration and EV enrichment from 24 liters of media within one week, an amount of media that could not logistically be purified by ultracentrifuge, and would require intense manpower and multiple centrifuges using the smaller Centricon/Amicon centrifugal filter units.

The inclusion of hFGF2 from cell culture media in NPEX™, combined with the ability of NPEX EVs to distribute to targets within the CNS (as demonstrated in biodistribution section), suggests that these EVs can potentially deliver hFGF2 across the blood brain barrier to target CNS tissue. These results suggest that a potential method for delivering large molecules including proteins (hFGF2 in the example above) to targets in vivo, including the CNS, using extracellular vesicles (NPEX™ by supplementing the EV source cell (hNP1™ in example above) culture media with the molecule of interest.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of reducing inflammation in the brain of a subject, comprising administering to the subject an effective amount of a pharmaceutical composition comprising isolated extracellular vesicles (EVs) derived from non-transformed human neural progenitor cells that are capable of differentiating into neurons, astrocytes and oligodendrocytes in vitro, wherein the EVs are produced from neural progenitor cells derived in vitro from pluripotent stem cells, or from neural cells derived in vitro from the neural progenitor cells or the pluripotent stem cells, and wherein the EVs comprise one or more of melanoma-associated chondroitin sulfate proteoglycan (MCSP), pentraxin-3 (PTX3), angiopoietin-1, insulin-like growth factor-binding protein 2 (IGFBP2), macrophage colony-stimulating factor, and ecto-5'-nucleotidase (NT5E).

2. The method of claim 1, wherein administering the pharmaceutical composition increases the number of regulatory T cells in the circulation of the subject.

3. The method of claim 1, wherein administering the pharmaceutical composition reduces the number of T helper cells in the circulation of the subject.

4. The method of claim 1, wherein administering the pharmaceutical composition increases the number of M2 macrophages in the circulation of the subject.

5. The method of claim 1, wherein administering the pharmaceutical composition suppresses an inflammatory response of M1 macrophages in the subject.

6. The method of claim 1, wherein administering the pharmaceutical composition enhances an anti-inflammatory response of M2 macrophages in the subject.

7. The method of claim 1, wherein administering the pharmaceutical composition reduces a level of IL-17 in the subject.

8. The method of claim 1, wherein administering the pharmaceutical composition increases a level of IL-10 in the subject.

9. The method of claim 1, wherein the neural progenitor cells are derived from human induced pluripotent stem cells.

10. The method of claim 1, wherein the neural progenitor cells are derived from human embryonic stem cells.

11. The method of claim 1, wherein the neural progenitor cells express one or more markers selected from the group consisting of nestin, SOX1, and SOX2, and do not express OCT4.

12. The method of claim 1, wherein the pharmaceutical composition comprises about 1 mg to about 750 mg of EVs.

13. The method of claim 1, wherein the EVs comprise exosomes.

14. The method of claim 1, wherein the EVs are about 20 nm to 10 μm in size.

15. The method of claim 1, wherein the EVs are about 25 nm to about 250 nm in size.

16. The method of claim 1, wherein the pharmaceutical composition is administered intravenously.

17. The method of claim 1, wherein the pharmaceutical composition is administered intranasally.

18. The method of claim 1, wherein the pharmaceutical composition is administered via a route of delivery selected from intrathecal, intraperitoneal (IP), oral, or direct delivery into the brain.

19. The method of claim 1, wherein the EVs further comprise an siRNA or an antisense oligonucleotide.

20. The method of claim 1, wherein the EVs further comprise an exogenous peptide or an exogenous protein.

21. The method of claim 1, wherein the EVs further comprise a small molecule.

22. The method of claim 1, wherein the EVs further comprise an antibody.

23. The method of claim 1, wherein the subject has a traumatic brain injury.

24. The method of claim 1, wherein the subject has a neurodegenerative disease.

25. The method of claim 24, wherein the neurodegenerative disease is one or more of Alzheimer's disease, Parkinson's disease, a Parkinson's-related disorder, Huntington's disease, amyotrophic lateral sclerosis, prion disease, motor neuron disease (MND), spinocerebellar ataxia (SCA), or spinal muscular atrophy (SMA).

26. The method of claim 1, wherein the subject has swelling in the brain, and wherein the method reduces the swelling in the brain.

* * * * *